(12) United States Patent
Cohet et al.

(10) Patent No.: US 11,167,022 B2
(45) Date of Patent: Nov. 9, 2021

(54) IMMUNOGENIC COMPOSITION, USE AND METHOD OF TREATMENT

(71) Applicants: GLAXOSMITHKLINE INTELLECTUAL PROPERTY DEVELOPMENT LIMITED, Brentford (GB); GLAXOSMITHKLINE BIOLOGICALS S.A., Rixensart (BE)

(72) Inventors: Catherine Cohet, Wavre (BE); Jeanne-Marie Josephine Devaster, Rixensart (BE); David Mayhew, Collegeville, PA (US); Bruce Miller, Collegeville, PA (US); Ruth Tal-Singer, Collegeville, PA (US); Vincent Weynants, Wavre (BE); Thomas Wilkinson, Southampton (GB)

(73) Assignees: GLAXOSMITHKLINE INTELLECTUAL PROPERTY DEVELOPMENT LIMITED, Brentford (GB); GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 16/499,001

(22) PCT Filed: Mar. 29, 2018

(86) PCT No.: PCT/EP2018/058130
§ 371 (c)(1),
(2) Date: Sep. 27, 2019

(87) PCT Pub. No.: WO2018/178264
PCT Pub. Date: Oct. 4, 2018

(65) Prior Publication Data
US 2020/0046823 A1 Feb. 13, 2020

Related U.S. Application Data

(60) Provisional application No. 62/479,550, filed on Mar. 31, 2017.

(51) Int. Cl.
*A61K 39/104* (2006.01)
*A61P 31/04* (2006.01)
*A61P 11/00* (2006.01)
*A61K 39/102* (2006.01)

(52) U.S. Cl.
CPC ........ *A61K 39/1045* (2013.01); *A61K 39/102* (2013.01); *A61P 11/00* (2018.01); *A61P 31/04* (2018.01)

(58) Field of Classification Search
None
See application file for complete search history.

(56) References Cited

FOREIGN PATENT DOCUMENTS

WO     WO 01/05424 A2     1/2001
WO     WO 2015/125118 A1     8/2015

OTHER PUBLICATIONS

Andrade et al., "Effect of Pneumococcal Conjugate Vaccine on the Natural Antibodies and Antibody Responses Against Protein Antigens From *Streptococcus pneumoniae*, Haemophilus influenzae and Moraxella catarrhalis in Children With Community-acquired Pneumonia", *Pediatric Infectious Disease Journal*, vol. 35, No. 6, pp. 683-689 (2016).

Mawas et al., "Physico-chemical characterisation and immunogenicity of a multi-valent candidate vaccine against non-typeable Haemophilus influenzae and Moraxella catarrhalis", *Vaccine*, vol. 25, No. 25, pp. 4801-4808 (2007).

Ruedl, et al., "Immune Response in the Lungs following Oral Immunization with Bacterial Lysates of Respiratory Pathogens", *Clinical and Diagnostic Laboratory Immunology*, vol. 1, No. 2, pp. 150-154 (1994).

Shelley R. Salpeter, "Bronchodilators in COPD: Impact of β-agonists and anticholinergics on severe exacerbations and mortality", *International Journal of Chronic Obstructive Pulmonary Disease*, vol. 2, No. 1, pp. 11-18 (2007).

*Primary Examiner* — Padmavathi Baskar

(57) ABSTRACT

The present invention relates to immunogenic compositions comprising an immunogenic polypeptide from *Haemophilus influenzae* or an immunogenic fragment thereof and/or an immunogenic polypeptide from *Moraxella catarrhalis* or an immunogenic fragment thereof, for use in the treatment or prevention of a recurrence of an acute exacerbation of chronic obstructive pulmonary disease (AECOPD) resulting from a bacterial infection in a subject.

17 Claims, 11 Drawing Sheets

Specification includes a Sequence Listing.

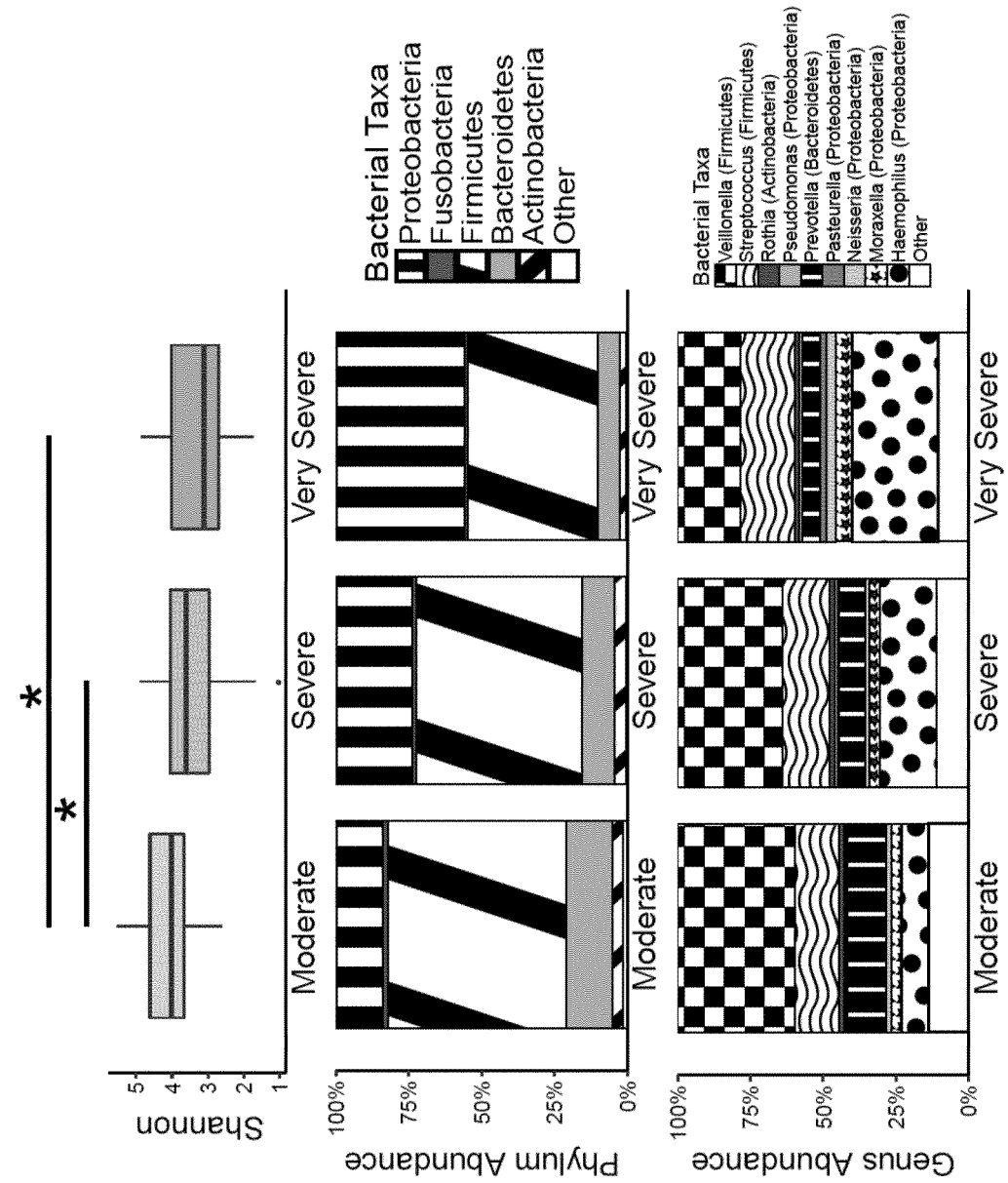
FIGURE 2A(1)

|  | Severe vs Moderate | Very Severe vs Moderate | Very Severe vs Severe |
|---|---|---|---|
| % Proteobacteria | ←* | ←* | ←* |
| % Bacteroidetes | →* | →* |  |
| % Firmicutes |  | →* | →* |
| % Haemophilus | ←* | ←* |  |
| % Prevotella | →* | →* |  |
| % Veillonella |  | →* | →* |
| % Streptococcus |  |  |  |
| % Moraxella |  |  |  |

\* : P-value < 0.05

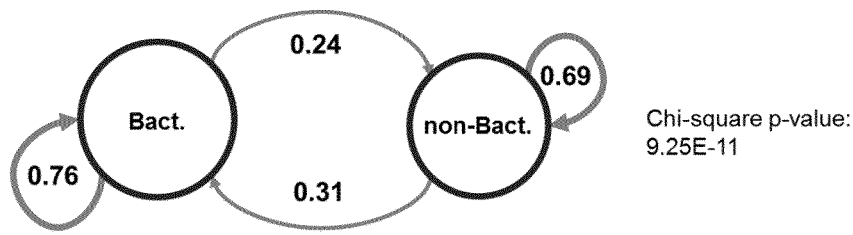

Independent probability of all samples:
57% Bacterial
43% non-Bacterial

Chi-square p-value: 9.25E-11

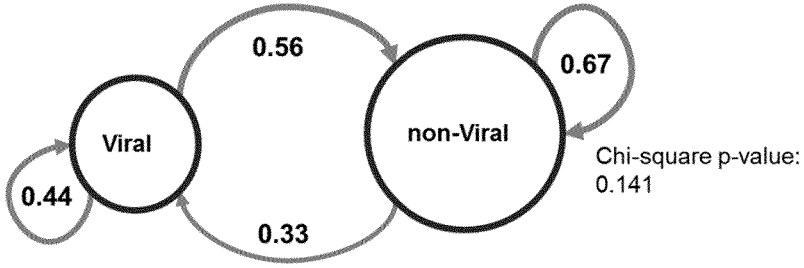

Independent probability of all samples:
36% Viral
64% non-Viral

Chi-square p-value: 0.141

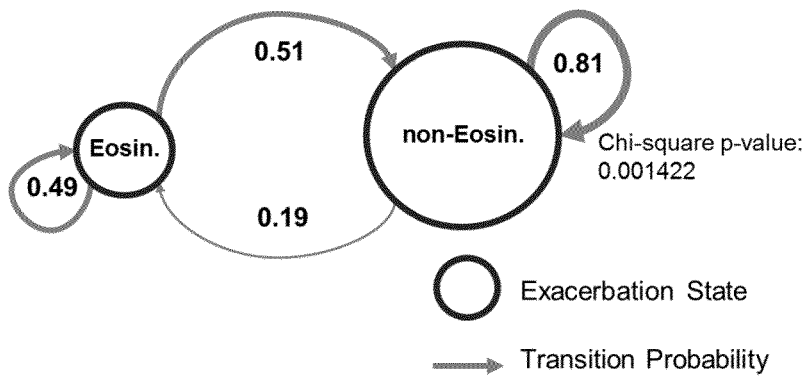

Independent probability of all samples:
24% Eosinophilic
76% non-Eosinophilic

Chi-square p-value: 0.001422

○ Exacerbation State
⟶ Transition Probability

B

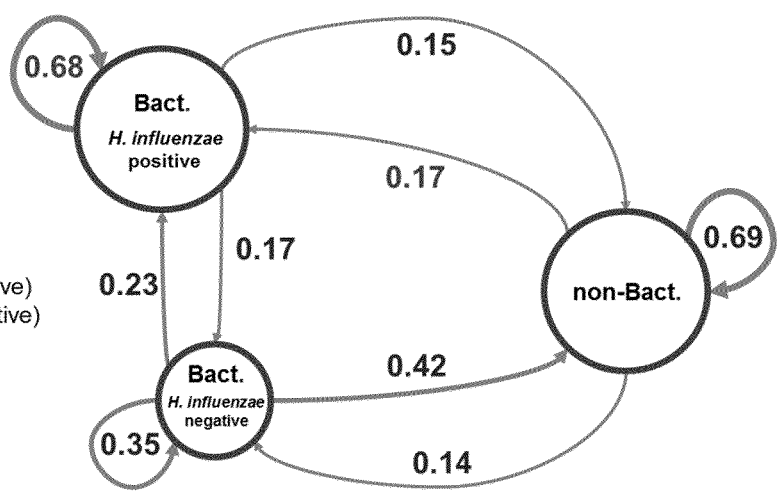

Independent probability of all samples:

40.3% Bacterial (*Hi* positive)
18.4% Bacterial (*Hi* negative)
41.3% non-Bacterial

IMMUNOGENIC COMPOSITION, USE AND METHOD OF TREATMENT

CROSS-REFERENCE TO RELATED APPLICATIONS

This application is filed pursuant to 35 U.S.C. § 371 as a United States National Phase Application of International Application No. PCT/EP2018/058130 filed Mar. 29, 2018 which claims priority from U.S. 62/479,550 filed Mar. 31, 2017.

SEQUENCE LISTING

A sequence listing filed herewith, entitled "PB66320 National Stage seq listing", prepared Sep. 26, 2019, 274 KB in size, is hereby incorporated by reference herein.

TECHNICAL FIELD

The present invention relates to the field of immunogenic compositions and the use of such compositions in medicine. More particularly, it relates to immunogenic compositions comprising an immunogenic polypeptide from *Haemophilus influenzae* or an immunogenic fragment thereof and/or an immunogenic polypeptide from *Moraxella catarrhalis* or an immunogenic fragment thereof, for use in the treatment or prevention of a recurrence of an acute exacerbation of chronic obstructive pulmonary disease (AECOPD) associated with a bacterial infection in a subject.

BACKGROUND TO THE INVENTION

Chronic Obstructive Pulmonary Disease (COPD) is a chronic inflammatory disorder resulting in irreversible decline in lung function as a consequence of inhalation of tobacco smoke or other irritants. Chronic obstructive pulmonary disease (COPD) is recognised as encompassing several conditions (airflow obstruction, chronic bronchitis, bronchiolitis or small airways disease and emphysema) that often coexist (Wilson et al., Eur. Respir. J. 2001; 17: 995-1007). Patients suffer exacerbations of their condition that are usually associated with increased breathlessness, and often have increased cough that may be productive of mucus or purulent sputum (Wilson, Eur Respir J 2001 17:995-1007). COPD is defined physiologically by the presence of irreversible or partially reversible airway obstruction in patients with chronic bronchitis and/or emphysema (Standards for the diagnosis and care of patients with chronic obstructive pulmonary disease. American Thoracic Society. Am J Respir Crit Care Med. 1995 November; 152(5 Pt 2):577-121).

COPD is a major cause of morbidity and mortality worldwide. Approximately one in 20 deaths in 2005 in the US had COPD as the underlying cause. (Drugs and Aging 26:985-999 (2009)). It is projected that in 2020 COPD will rise to the fifth leading cause of disability adjusted life years, chronic invalidating diseases, and to the third most important cause of mortality (Lancet 349:1498-1504 (1997)). The course of COPD is characterized by progressive worsening of airflow limitation and a decline in pulmonary function. COPD may be complicated by frequent and recurrent acute exacerbations (AE), which are associated with enormous health care expenditure and high morbidity. (Proceedings of the American Thoracic Society 4:554-564 (2007)). One study suggests that approximately 50% of acute exacerbations of symptoms in COPD are caused by non-typeable *Haemophilus influenzae*, *Moraxella catarrhalis*, *Streptococcus pneumoniae*, and *Pseudomonas aeruginosa*. (Drugs and Aging 26:985-999 (2009)). *Haemophilus influenzae* (*H. influenzae*) is found in 20-30% of exacerbations of COPD; *Streptococcus pneumoniae*, in 10-15% of exacerbations of COPD; and *Moraxella catarrhalis*, in 10-15% of exacerbations of COPD. (New England Journal of Medicine 359: 2355-2365 (2008)). *Haemophilus influenzae*, *Streptococcus pneumoniae*, and *Moraxella catarrhalis* have been shown to be the primary pathogens in acute exacerbations of bronchitis in Hong Kong, South Korea, and the Phillipines, while *Klebsiella* spp., *Pseudomonas aeruginosa* and *Acinetobacter* spp. constitute a large proportion of pathogens in other Asian countries/regions including Indonesia, Thailand, Malaysia and Taiwan (Respirology, (2011) 16, 532-539; doi:10.1111/j.1440-1843.2011.01943.x). In Bangladesh, 20% of patients with COPD showed positive sputum culture for *Pseudomonas*, *Klebsiella*, *Streptococcus pneumoniae* and *Haemophilus influenzae*, while 65% of patients with AECOPD (acute exacerbation of COPD) showed positive cultures for *Pseudomonas*, *Klebsiella*, *Acinetobacter*, *Enterobacter*, *Moraxella catarrhalis* and combinations thereof. (Mymensingh Medical Journal 19:576-585 (2010)). However, it has been suggested that the two most important measures to prevent COPD exacerbation are active immunizations and chronic maintenance of pharmacotherapy. (Proceedings of the American Thoracic Society 4:554-564 (2007)).

One of the difficulties in treating and managing COPD is the heterogeneity of this complex disease in terms of severity, progression, exercise tolerance, and nature of symptoms. This complexity is also evident in acute exacerbations of COPD (AECOPD), which are transient and apparently stochastic periods of increased COPD symptoms requiring additional medical treatment and often hospitalization (Sethi et al., N Eng J Med 2008; 359:2355-65). Known subtypes of exacerbations are defined by the nature of key triggers including bacterial or viral infections, and/or high eosinophil levels, and these events are typically treated with a combination of antibiotics and steroids in a non-specific manner (Bafadhel et al., Am J Respir Crit Care Med 2011; 184:662).

There exists a need for improved uses of immunogenic compositions and methods for the prevention and/or treatment of AECOPD.

SUMMARY OF THE INVENTION

According to the present invention, it has been surprisingly found that bacterial exacerbations are more likely to be repeated in subsequent exacerbations within a subject and that this finding can be used to determine appropriate treatments for a given subject (e.g. a COPD patient).

Accordingly, there is provided in one aspect of the present invention an immunogenic composition comprising an immunogenic polypeptide from *Haemophilus influenzae* or an immunogenic fragment thereof and/or an immunogenic polypeptide from *Moraxella catarrhalis* or an immunogenic fragment thereof, for use in the treatment or prevention of a recurrence of an acute exacerbation of chronic obstructive pulmonary disease (AECOPD) associated with a bacterial infection in a subject.

In another aspect of the present invention there is provided an immunogenic composition comprising an immunogenic polypeptide from *Haemophilus influenzae* or an immunogenic fragment thereof and/or an immunogenic polypeptide from *Moraxella catarrhalis* or an immunogenic fragment thereof, for use in a method of treating or preventing a recurrence of an acute exacerbation of chronic obstructive pulmonary disease (AECOPD) resulting from a bacterial infection in a subject, wherein the method comprises identifying that the subject has previously had an acute exacerbation of chronic obstructive pulmonary disease (AECOPD) associated with a bacterial infection and then administering the immunogenic composition to the subject.

In another aspect of the present invention there is provided the use of an immunogenic composition comprising an immunogenic polypeptide from *Haemophilus influenzae* or an immunogenic fragment thereof and/or an immunogenic polypeptide from *Moraxella catarrhalis* or an immunogenic fragment thereof, in the manufacture of a medicament for the treatment or prevention of a recurrence of an acute exacerbation of chronic obstructive pulmonary disease (AECOPD) associated with a bacterial infection in a subject.

In another aspect of the present invention there is provided the use of an immunogenic composition comprising an immunogenic polypeptide from *Haemophilus influenzae* or an immunogenic fragment thereof and/or an immunogenic polypeptide from *Moraxella catarrhalis* or an immunogenic fragment thereof, in the manufacture of a medicament for use in a method of treating or preventing a recurrence of an acute exacerbation of chronic obstructive pulmonary disease (AECOPD) associated with a bacterial infection in a subject, wherein the method comprises identifying that the subject has previously had an acute exacerbation of chronic obstructive pulmonary disease (AECOPD) associated with a bacterial infection and then administering the immunogenic composition to the subject.

In another aspect of the present invention there is provided a method of treatment or prevention of a recurrence of an acute exacerbation of chronic obstructive pulmonary disease (AECOPD) associated with a bacterial infection in a subject at risk of developing an acute exacerbation of chronic obstructive pulmonary disease (AECOPD) recurrence, said method comprising administering to said subject, a therapeutically effective amount of an immunogenic composition comprising an immunogenic polypeptide from *Haemophilus influenzae* or an immunogenic fragment thereof and/or an immunogenic polypeptide from *Moraxella catarrhalis* or an immunogenic fragment thereof.

In another aspect of the present invention there is provided a method of treatment or prevention of a recurrence of an acute exacerbation of chronic obstructive pulmonary disease (AECOPD) associated with a bacterial infection in a subject at risk of developing an acute exacerbation of chronic obstructive pulmonary disease (AECOPD) recurrence, said method comprising administering to said subject, a therapeutically effective amount of an immunogenic composition comprising an immunogenic polypeptide from *Haemophilus influenzae* or an immunogenic fragment thereof and/or an immunogenic polypeptide from *Moraxella catarrhalis* or an immunogenic fragment thereof, wherein the method comprises identifying that the subject has previously had an acute exacerbation of chronic obstructive pulmonary disease (AECOPD) associated with a bacterial infection and then administering the immunogenic composition to the subject.

DETAILED DESCRIPTION

Terminology

A "subject" as used herein is a mammal, including humans, non-human primates, and non-primate mammals such as members of the rodent genus (including but not limited to mice and rats) and members of the order Lagomorpha (including but not limited to rabbits). In one embodiment, the subject is a human.

As used herein, "adjuvant" means a compound or substance that, when administered to a subject in conjunction with a vaccine, immunotherapeutic, or other antigen- or immunogen-containing composition, increases or enhances the subject's immune response to the administered antigen or immunogen (as compared to the immune response that would be obtained in the absence of adjuvant).

As used herein, the term "immunogenic fragment" is a portion of an antigen smaller than the whole, that is capable of eliciting a humoral and/or cellular immune response in a host animal, e.g. human, specific for that fragment. Fragments of a protein can be produced using techniques known in the art, e.g. recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide.

As used herein, the term "conservative amino acid substitution" involves substitution of a native amino acid residue with a non-native residue such that there is little or no effect on the size, polarity, charge, hydrophobicity, or hydrophilicity of the amino acid residue at that position, and without resulting in decreased immunogenicity. For example, these may be substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Conservative amino acid modifications to the sequence of a polypeptide (and the corresponding modifications to the encoding nucleotides) may produce polypeptides having functional and chemical characteristics similar to those of a reference polypeptide.

As used herein "signal peptide" refers to a short (less than 60 amino acids, for example, 3 to 60 amino acids) polypeptide present on precursor proteins (typically at the N terminus), and which is typically absent from the mature protein. The signal peptide (sp) is typically rich in hydrophobic amino acids. The signal peptide directs the transport and/or secretion of the translated protein through the membrane. Signal peptides may also be called targeting signals, transit peptides, localization signals, or signal sequences. For example, the signal sequence may be a co-translational or post-translational signal peptide.

Chronic obstructive pulmonary disease (COPD) is a lung disease characterized by chronic obstruction of lung airflow that interferes with normal breathing and is not fully reversible.

A COPD diagnosis is confirmed by a simple test called spirometry, which measures how deeply a person can breathe and how fast air can move into and out of the lungs. Such a diagnosis should be considered in any patient who has symptoms of cough, sputum production, or dyspnea (difficult or labored breathing), and/or a history of exposure to risk factors for the disease. Where spirometry is unavailable, the diagnosis of COPD should be made using all available tools. Clinical symptoms and signs, such as abnormal shortness of breath and increased forced expiratory time, can be used to help with the diagnosis. A low peak flow is consistent with COPD, but may not be specific to COPD because it can be caused by other lung diseases and by poor performance during testing. Chronic cough and sputum production often precede the development of airflow limitation by many years, although not all individuals with cough and sputum production go on to develop COPD.

An acute exacerbation of COPD (AECOPD) is an acute event characterised by a worsening of the patient's respiratory symptoms that is beyond normal day-to-day variations. Typically an AECOPD leads to a change in medication.

For the purposes of this invention, "treatment of a recurrence of an acute exacerbation of COPD" means ameliorating, stabilising, reducing or eliminating the increased symptoms that are a feature of an acute exacerbation in a subject, wherein the subject has experienced one or more past exacerbations of the same phenotype (e.g. bacterial phenotype associated with a bacterial infection by *Haemophilus influenza* (e.g. non-typeable *H. influenzae* (NTHi) and/or *Moraxella catarrhalis*). As used herein, the phrase "prevention of a recurrence of an acute exacerbation of COPD" means preventing, reducing the incidence or frequency, or reducing the severity of future acute exacerbations of a particular phenotype (e.g. bacterial phenotype associated with a bacterial infection by *Haemophilus influenza* (e.g. non-typeable *H. influenzae* (NTHi) and/or *Moraxella catarrhalis*)) in a subject who has experienced one or more past exacerbations of the same phenotype. In one embodiment, an immunogenic composition according to the present invention is for the reduction of the frequency of acute exacerbations of chronic obstructive pulmonary disease (AECOPD) in a subject. In another embodiment, an immunogenic composition according to the present invention is for the reduction of the frequency of acute exacerbations of chronic obstructive pulmonary disease (AECOPD) resulting from a bacterial infection in a subject.

In one embodiment, an immunogenic composition according to the present invention is for the prevention of a recurrence of an acute exacerbation of chronic obstructive pulmonary disease (AECOPD) resulting from a bacterial infection in a subject.

In a further embodiment, an immunogenic composition according to the present invention is for the treatment of a recurrence of an acute exacerbation of chronic obstructive pulmonary disease (AECOPD) resulting from a bacterial infection in a subject.

DESCRIPTION OF FIGURES

FIG. 4: Markov chain analysis of transitions between exacerbation states (A) Markov chain analysis from longitudinal exacerbation sampling within individuals identifies non-random transition probabilities for bacterial and eosinophilic exacerbations, but not viral. The size of each node is proportional to abundance of that exacerbation type and the width of the edges are proportional to the transition probabilities. (B) Markov chain analysis of the bacterial exacerbation identifies significantly different transition probabilities for bacterial exacerbations which were positive and negative for the presence of *H. influenzae*.

Figure 1:
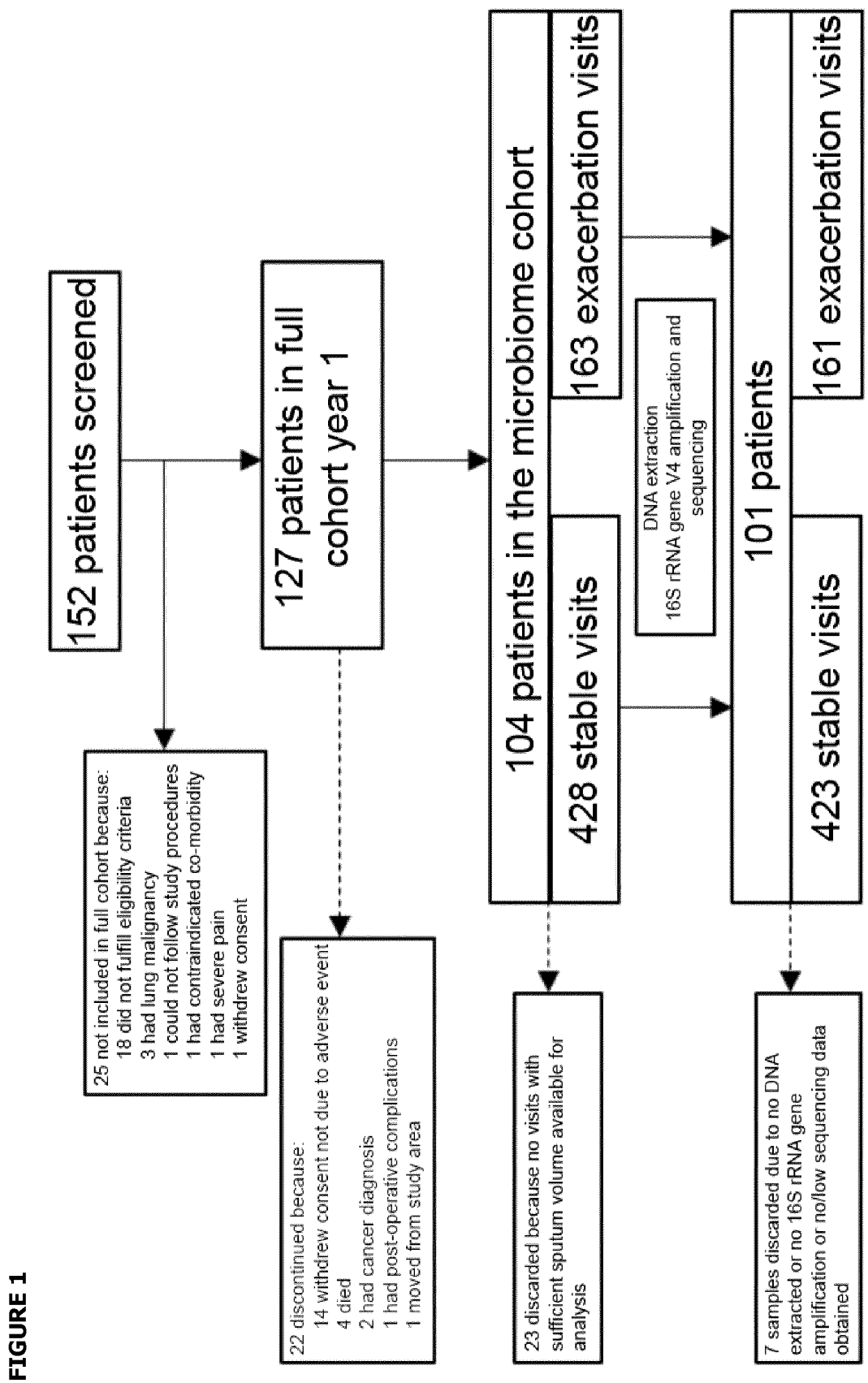
FIG. 1: Flow chart of subject enrollment, sputum sampling, and selection samples for microbiome analysis for AERIS

COPD is characterised by progressive worsening of airflow limitation and a decline in pulmonary function. The disease is complicated by acute exacerbations (AECOPD), which are transient and apparently stochastic periods of increased COPD symptoms requiring additional medical treatment and often hospitalisation. The present inventors have now surprisingly found that an understanding of a subject's exacerbation history (i.e. previous exacerbation phenotype) can be used to guide future therapeutic strategies. Clinical data from a previous exacerbation can be used to inform the likely phenotype of the next acute exacerbation, enabling administration of preventative/prophylactic treatment and/or a more rapid administration of appropriate therapy on presentation of an acute exacerbation.

The present inventors have found, in particular, that bacterial exacerbations are more likely to be repeated in subsequent exacerbations within a subject (e.g. a COPD patient). Thus, COPD patients with a documented history of one or more bacterial exacerbations represent a high-risk sub-population of COPD patients that would benefit from preventive therapy with an immunogenic composition.

As used herein, the term "bacterial exacerbation" refers to an exacerbation associated with a positive bacterial pathogen on routine culture (*Haemophilus influenza, Moraxella catarrhalis, Streptococcus pneumoniae, Staphylococcus aureus* or *Pseudomonas aeruginosa*) or a total aerobic CFU count greater than or equal to $10^7$ cells. In one embodiment, the bacterial exacerbation is associated with a positive bacterial culture for a) *Haemophilus influenza* (e.g. non-typeable *H. influenzae* (NTHi));

b) *Moraxella catarrhalis*; or c) *Haemophilus influenzae* (e.g. non-typeable *H. influenzae* (NTHi)) and *Moraxella catarrhalis*

In one aspect there is provided an immunogenic composition for use, use of an immunogenic composition or method of treatment or prevention according to the present invention, wherein the acute exacerbation of chronic obstructive pulmonary disease (AECOPD) associated with a bacterial infection is defined by:

a) a positive bacterial pathogen on culture of an induced or spontaneous sputum sample obtained from a subject; and/or b) a total aerobic CFU count greater than or equal to $10^7$ cells; and/or c) the presence of increased sputum purulence.

In a further aspect there is provided an immunogenic composition for use, use of an immunogenic composition or method of treatment or prevention according to the present invention, wherein the acute exacerbation of chronic obstructive pulmonary disease (AECOPD) associated with a bacterial infection is defined by a positive bacterial pathogen on culture of an induced or spontaneous sputum sample obtained from a subject.

In a further aspect there is provided an immunogenic composition for use, use of an immunogenic composition or method of treatment or prevention according to the present invention, wherein the acute exacerbation of chronic obstructive pulmonary disease (AECOPD) associated with a bacterial infection is defined by a total aerobic CFU count greater than or equal to $10^7$ cells.

In a further aspect, the bacterial infection is present in the lung(s) of a subject.

In a further aspect there is provided an immunogenic composition for use, use of an immunogenic composition or method of treatment or prevention according to the present invention, wherein the bacterial infection occurred in the presence of *Haemophilus influenza* (e.g. non-typeable *H. influenzae* (NTHi)) and/or *Moraxella catarrhalis*. In one aspect, the bacterial infection occurred in the presence of *Haemophilus influenza* (e.g. non-typeable *H. influenzae* (NTHi)). In another aspect, the bacterial infection occurred in the presence of *Moraxella catarrhalis*.

In one aspect there is provided an immunogenic composition for use, use of an immunogenic composition or method of treatment or prevention according to the present invention, wherein the subject is at risk for developing an acute exacerbation of chronic obstructive pulmonary disease (AECOPD) resulting from a bacterial infection.

In particular, the present inventors found that a significant decrease in entropy of the microbiome (Shannon diviersity index; $P_{adj}<0.05$) and an increase in the relative abundance of Proteobacteria, such as *Haemophilus*, is associated with an increase in disease severity. Furthermore, *Moraxella* showed a significant increase in exacerbation (P=0.0153). Thus, in one aspect there is provided an immunogenic composition for use, use of an immunogenic composition or method of treatment or prevention according to the present invention, wherein the subject has a decreased entropy of the lung microbiome as measured according to the Shannon diversity index ($P_{adj}<0.05$) compared to a measurement taken during a previous acute exacerbation in COPD (AECOPD) in the same subject. In another aspect, there is provided an immunogenic composition for use, use of an immunogenic composition or method of treatment or prevention according to the present invention, wherein the subject has a Shannon diversity index less than 3.0.

In another aspect there is provided an immunogenic composition for use, use of an immunogenic composition or method of treatment or prevention according to the present invention, wherein the subject has an increased abundance of Proteobacteria, e.g. *Haemophilus* and/or *Moraxella*.

The present inventors assessed the contribution of changes in the COPD airway microbiome to the incidence of AECOPD in patients aged 40-85 years with a confirmed diagnosis of COPD, categorised as moderate, severe, or very severe according to the Global Initiative for Chronic Obstructive Lung Disease (GOLD) classification.

The Global Strategy for the Diagnosis, Management and Prevention of COPD prepared by GOLD state that COPD should be considered in any patient with dyspnea, chronic cough or sputum production, and/or a history of exposure to risk factors for the disease, such as tobacco smoking, occupation, or pollutants. A spirometry assessment, measuring airflow limitation, is required to establish diagnosis. The classification of airflow limitation severity in COPD outlined in the GOLD strategy is shown in Table 1.

TABLE 1

Classification of airflow limitation severity in COPD (Based on post-bronchodilator $FEV_1$) In patients with $FEV_1/FVC < 0.70$

| GOLD 1 | Mild | $FEV_1 \geq 80\%$ predicted |
| GOLD 2 | Moderate | $50\% \leq FEV_1 < 80\%$ predicted |
| GOLD 3 | Severe | $30\% \leq FEV_1 < 50\%$ predicted |
| GOLD 4 | Very Severe | $FEV_1 < 30\%$ predicted |

COPD assessment also includes analysis of patient symptoms, and this can be performed using comprehensive disease-specific health status questionnaires such as the Chronic Respiratory Questionnaire (CRQ) and St. George's Respiratory Questionnaire (SGRQ). For routine practice the COPD Assessment Test (CAT™) and The COPD Control Questionnaire (The CCQ©) have been developed. The CAT™ and CCQ© tests do not categorise patients for the purpose of treatment, however for the SRGQ assessment a symptom score ≥25 may be used as the threshold for considered regular treatment for breathlessness. The equivalent threshold for the CAT™ is 10. A simple assessment of breathlessness is the Modified British Medical Research Council (mMRC) Questionnaire.

According to the GOLD strategy, of the patients classified at the GOLD 2 (moderate) stage, approximately 20% may experience frequent exacerbations requiring antibiotic and/or systemic corticosteroid therapy in addition to regular maintenance therapy. The risk of exacerbations is significantly higher for patients classified as GOLD 3 (severe) and GOLD 4 (very severe).

Figure 5:
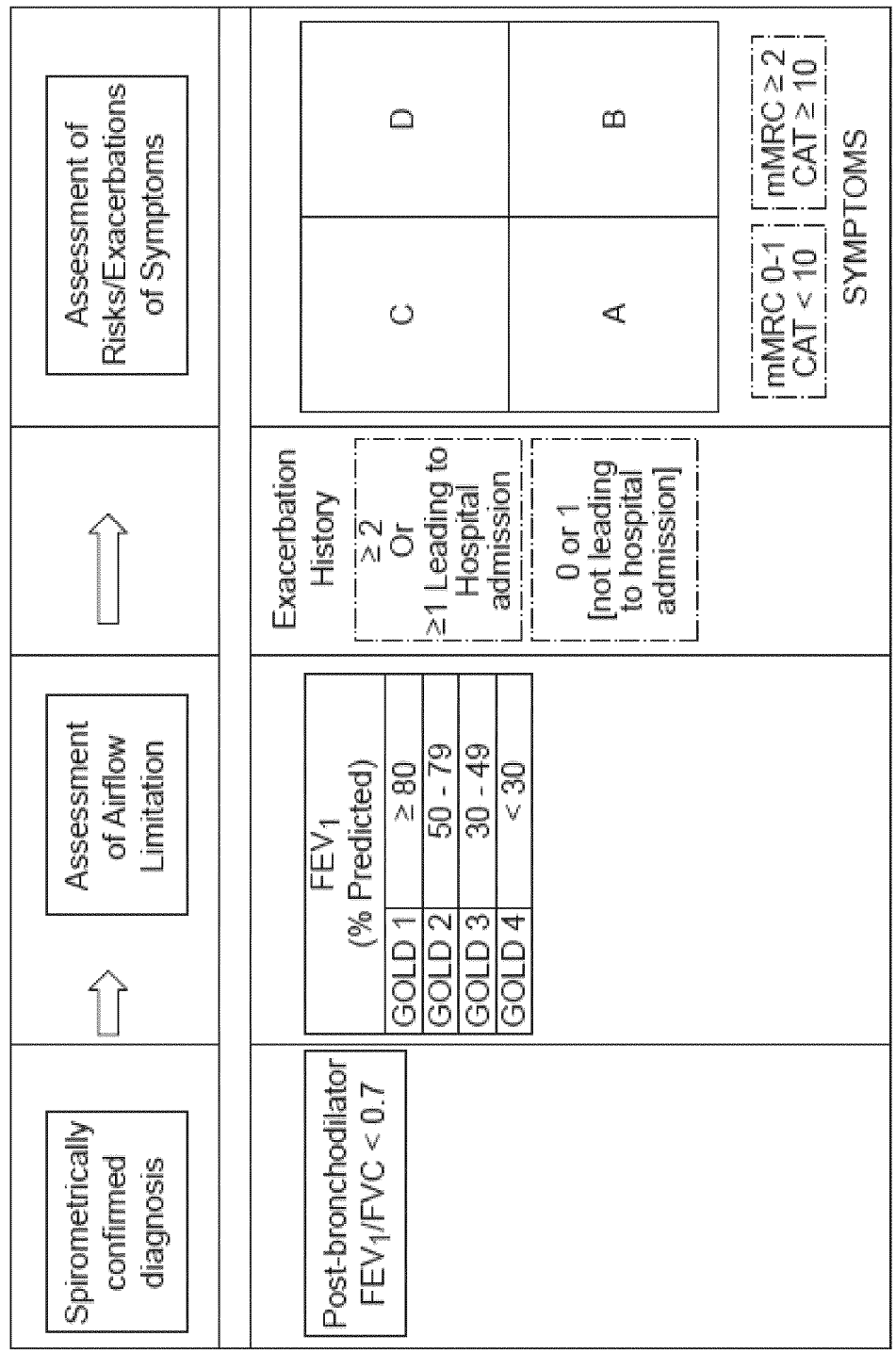
FIG. 5: ABCD Assessment Tool for COPD

The "ABCD" assessment tool is further used to understand a COPD patient's severity of disease. This assessment combines the patient's spirometry analysis with their exacerbation history and symptom assessment to give a spirometric grade combined with an "ABCD" group. The ABCD assessment tool is shown in FIG. 5.

In another aspect there is provided an immunogenic composition for use, use of an immunogenic composition or method of treatment or prevention according to the present invention, wherein the subject has GOLD 2 (moderate), GOLD 3 (severe) or GOLD 4 (very severe) COPD status.

In one aspect there is provided an immunogenic composition, use or method of treatment or prevention according to the present invention, wherein the subject is an adult aged 40-85 years old.

In another aspect there is provided an immunogenic composition for use, use of an immunogenic composition or method of treatment or prevention according to the present invention, wherein the subject is a tobacco smoker.

In one aspect, the present invention provides an immunogenic composition for use, use of an immunogenic composition or method of treatment or prevention according to the present invention, wherein the subject has experienced at least one (e.g. 2 or more, 3 or more) episodes of acute exacerbation in chronic obstructive pulmonary disease (AECOPD) resulting from a bacterial infection. In another aspect, the present invention provides an immunogenic composition for use, use of an immunogenic composition or method of treatment or prevention according to the present invention, wherein the subject has experienced at least one (e.g. 2 or more, 3 or more) episodes of acute exacerbation in chronic obstructive pulmonary disease (AECOPD) associated with a bacterial infection within a period of 12 months.

In a further aspect there is provided an immunogenic composition for use, use of an immunogenic composition or method of treatment or prevention according to the present invention, wherein the subject has experienced at least one (e.g. 2 or more, 3 or more) episodes of acute exacerbation in chronic obstructive pulmonary disease (AECOPD) resulting from a bacterial infection in the preceding 12 months.

The present inventors also found that in patients with bronchiectasis, a substantial increase in *Haemophilus* was observed which was evident in both stable and exacerbation events. Bronchiectasis is a condition in which an area of the bronchial tubes is permanently and abnormally widened (dilated), with accompanying infection. Types include cylindrical, follicular, fusiform, saccular, and varicose, named according to the nature of the dilatations. Examination of the walls of the bronchial tubes reveals destruction of the normal structural elements, with replacement by scar tissue. Pus collects within the bronchi, and the normal flow of oxygen into the lungs, and carbon dioxide out of the lungs (air exchange) is impaired. The bronchi show signs of inflammation, with swelling and invasion by a variety of immune cells. The inflamed areas show signs of increased growth of blood vessels. The area of the lung which should be served by a diseased bronchial tube is also prone to inflammation and infection. The most immediate symptom is persistent coughing with sputum production.

Thus, in another aspect there is provided an immunogenic composition for use, use of an immunogenic composition or method of treatment or prevention according to the present invention, wherein the subject has bronchiectasis.

The present invention also provides an immunogenic composition for use, use of an immunogenic composition or method of treatment or prevention according to the present invention, wherein the subject has experienced an acute exacerbation of chronic obstructive pulmonary disease (AECOPD) resulting from a bacterial infection and failed to achieve resolution of symptoms after antibiotic therapy.

Additional Pharmacologic Therapy

The present invention further provides an immunogenic composition for use, use of an immunogenic composition or method of treatment or prevention according to the present invention, wherein the subject is taking one or more other therapeutic agents for COPD. In a further embodiment, the present invention also provides an immunogenic composition, use or method of treatment or prevention according to the present invention, wherein the subject has been prescribed one or more other therapeutic agents for COPD.

Pharmacologic therapy for COPD is utilised to control and reduce symptoms, reduce the frequency and severity of exacerbations and improve tolerance to exercise. Classes of therapeutic agents that can be used to treat COPD include, but are not limited to, beta$_2$-agonists, anticholinergics, methylxanthines and phosphodiesterase-4 (PDE-4) inhibitors. Anti-inflammatory agents, such as inhaled corticosteroids are also used, typically in combination with a beta$_2$-agonist and/or an antibcholinergic.

Beta$_2$agonists include, but are not limited to, short-acting beta$_2$-agonists such as fenoterol, levalbuterol, salbutamol, terbutaline, and long-acting beta$_2$-agonists such as arformoterol, formoterol, indacaterol, vilanterol (e.g. vilanterol as the acetate, 1-naphthoate, (R)-mandelate, α-phenylcinnamate or triphenylacetate (trifenatate) salt), olodaterol and salmeterol (e.g. salmeterol xinafoate).

Anticholinergics include, but are not limited to, short-acting anticholinergics such as ipratropium (e.g. ipratropium bromide), oxitropium (e.g. oxitropium bromide), and long-acting anticholinergics such as aclidinium (e.g. aclidinium bromide, glycopyrronium (e.g. glycopyrronium bromide), tiotropium (e.g. tiotropium bromide) and umeclidinium (e.g. umeclidinium bromide).

Methylxanthines include, but are not limited to, aminophylline and theophylline (SR).

It will be clear to the person skilled in the art that, where appropriate, the other therapeutic agents may be used in the form of salts, prodrugs, esters, or solvates (e.g. hydrates) to optimise the activity and/or stability and/or physical characteristics (e.g. solubility) of the therapeutic agent. The additional therapeutic agents may be used in optically pure form and in either amorphous or crystalline form.

In one embodiment, the present invention provides an immunogenic composition for use, use of an immunogenic composition or method of treatment or prevention according to the present invention, wherein the subject is taking an anticholinergic therapy, for example umeclidinium (e.g. umeclidinium bromide), for COPD.

Combinations of pharmacologic therapies may also be used for the treatment of COPD. In one embodiment, the therapy is a dual combination of a beta$_2$-agonist and an anticholinergic, such as the combination of vilanterol, or a pharmaceutically acceptable salt or solvate thereof, and umeclidinium, or a pharmaceutically acceptable salt or solvate thereof. In one embodiment, the therapy is a combination of vilanterol trifenatate and umeclidinium bromide.

In a further embodiment, the therapy is a dual combination of a beta$_2$-agonist and an inhaled corticosteroid, such as the combination of vilanterol, or a pharmaceutically acceptable salt or solvate thereof, and fluticasone furoate. In one embodiment, the therapy is a combination of vilanterol trifenatate and fluticasone furoate.

Pharmacologic therapy may also include the combination of three classes of therapeutic agents, such as the combination of a beta$_2$-agonist, an anticholinergic and an inhaled corticosteroid. In one embodiment, the therapy is a combination of vilanterol, or a pharmaceutically acceptable salt or solvate thereof, umeclidinium, or a pharmaceutically acceptable salt or solvate thereof, and fluticasone furoate. In a further embodiment, the therapy is a combination of vilanterol trifenatate, umeclidinium bromide and fluticasone furoate.

In one embodiment, the present invention provides an immunogenic composition for use, use of an immunogenic composition or method of treatment or prevention according to the present invention, wherein the subject is taking one or more other therapeutic agents for COPD selected from the group consisting of beta$_2$-agonists, anticholinergics, methylxanthines, phosphodiesterase-4 (PDE-4) inhibitors and inhaled corticosteroids.

In one embodiment, the present invention provides an immunogenic composition for use, use of an immunogenic composition or method of treatment or prevention according to the present invention, wherein the subject is taking a combination of a beta$_2$-agonist, for example vilanterol (e.g. vilanterol trifenatate), and an anticholinergic, for example umeclidinium (e.g. umeclidinium bromide), for COPD.

In one embodiment, the present invention provides an immunogenic composition for use, use of an immunogenic composition or method of treatment or prevention according to the present invention, wherein the subject is taking a combination of a beta$_2$-agonist, for example vilanterol (e.g. vilanterol trifenatate), and an inhaled corticosteroid, for example fluticasone furoate, for COPD.

In one embodiment, the present invention provides an immunogenic composition for use, use of an immunogenic composition or method of treatment or prevention according to the present invention, wherein the subject is taking a combination of a beta$_2$-agonist, for example vilanterol (e.g. vilanterol trifenatate), an anticholinergic, for example umeclidinium (e.g. umeclidinium bromide), and an inhaled corticosteroid, for example fluticasone furoate, for COPD.

Pharmacologic therapy may be formulated as solutions, suspensions or as dry powder compositions typically for inhalation via a reservoir dry powder inhaler, unit-dose dry powder inhaler, per-metered multi-dose dry powder inhaler, nasal inhaler, pressurised metered dose inhaler, or nebuliser. Representative dry powder inhalers are the DISKHALER™ inhaler device, the DISKUS™ inhalation device, and the ELLIPTA™ inhalation device, marketed by GlaxoSmithKline. The DISKUS™ inhalation device is, for example, described in GB 2242134A, and the ELLIPTA™ inhalation device is, for example, described in WO 2003/061743 A1, WO 2007/012871 A1 and/or WO 2007/068896 A1.

Dry powder compositions may be presented in unit dose form, as capsules, cartridges or commonly blisters. Umeclidinium, for example umeclidinium bromide, may be formulated as a dry powder composition, wherein umeclidinium is to be administered at a dose of 62.5 mcg or 125 mcg once daily, wherein the dose is the amount of the free cation (i.e. umeclidinium).

Vilanterol, for example vilanterol trifenatate, may be formulated as a dry powder composition, wherein vilanterol is to be administered at a dose of 25 mcg once daily, wherein the dose is the amount of the free base (i.e. vilanterol).

Fluticasone furoate may be formulated as a dry powder composition, wherein fluticasone furoate is to be administered at a dose of 50 mcg, 100 mcg, or 200 mcg once daily. In one embodiment, the dose is 100 mcg once daily.

Individual therapeutic agents may be administered sequentially or simultaneously in separate or combined pharmaceutical formulations/compositions. Where appropriate, the individual therapeutic agents may be admixed within the same formulation, and presented as a fixed pharmaceutical combination. In general such formulations/compositions will include pharmaceutical carriers or excipients.

In one embodiment, the present invention provides an immunogenic composition for use, use of an immunogenic composition or method of treatment or prevention according to the present invention, wherein the subject is taking an anticholinergic therapy, for example umeclidinium bromide at a dose of 62.5 mcg once daily, for COPD. In a further embodiment, the subject is taking the product Incruse™.

In one embodiment, the present invention provides an immunogenic composition for use, use of an immunogenic composition or method of treatment or prevention according to the present invention, wherein the subject is taking a combination of a beta$_2$-agonist, for example vilanterol trifenatate at a dose of 25 mcg once daily, and an anticholinergic, for example umeclidinium bromide at a dose of 62.5 mcg once daily, for COPD. In a further embodiment, the subject is taking the product Anoro™.

In one embodiment, the present invention provides an immunogenic composition for use, use of an immunogenic composition or method of treatment or prevention according to the present invention, wherein the subject is taking a combination of a vilanterol trifenatate and umeclidinium bromide for COPD, and wherein umeclidinium bromide and vilanterol trifenatate are contained within the same dry powder inhaler device (e.g. the Ellipta™ Inhaler), wherein the dry powder inhaler device contains two blister strips, wherein one strip contains a blend of micronised umeclidinium bromide (approximately 125 or 62.5 mcg per blister of umeclidinium), lactose monohydrate and magnesium stearate (for example at about 0.6% w/w of the total weight of the dry powder composition), and a second strip contains vilanterol trifenatate (approximately 25 mcg per blister of vilanterol), lactose monohydrate and magnesium stearate (for example at about 1.0% w/w/based on the total weight of the dry powder composition).

In one embodiment, the present invention provides an immunogenic composition for use, use of an immunogenic composition or method of treatment or prevention according to the present invention, wherein the subject is taking a combination of a beta$_2$-agonist, for example vilanterol trifenatate at a dose of 25 mcg once daily, and an inhaled corticosteroid, for example fluticasone furoate at a dose of 100 mcg once daily, for COPD. In a further embodiment, the subject is taking the product Breo™.

In one embodiment, the present invention provides an immunogenic composition for use, use of an immunogenic composition or method of treatment or prevention according to the present invention, wherein the subject is taking a combination of vilanterol trifenatate and fluticasone furoate for COPD, wherein vilanterol trifenatate and fluticasone furoate are contained within the same dry powder inhaler device (e.g. the Ellipta™ Inhaler), wherein the dry powder inhaler device contains two blister strips, wherein one strip contains a blend of micronised fluticasone furoate (approximately 100 mcg per blister) and lactose monohydrate, and a second strip contains vilanterol trifenatate (approximately 25 mcg per blister of vilanterol), lactose monohydrate and magnesium stearate (for example at about 1.0% w/w/based on the total weight of the dry powder composition).

In one embodiment, the present invention provides an immunogenic composition for use, use of an immunogenic composition or method of treatment or prevention according to the present invention, wherein the subject is taking a combination of a beta$_2$-agonist, for example vilanterol trifenatate at a dose of 25 mcg once daily, an anticholinergic, for example umeclidinium bromide at a dose of 62.5 mcg once daily, and an inhaled corticosteroid, for example fluticasone furoate at a dose of 100 mcg once daily, for COPD.

In one embodiment, the present invention provides an immunogenic composition for use, use of an immunogenic composition or method of treatment or prevention according to the present invention, wherein the subject is taking a combination of a vilanterol trifenatate, umeclidinium bromide and fluticasone furoate for COPD, wherein umeclidinium bromide, vilanterol trifenatate and fluticasone furoate are contained within the same dry powder inhaler device (e.g. the Ellipta™ Inhaler), wherein the dry powder inhaler device contains two blister strips, wherein one strip contains a blend of micronised umeclidinium bromide (approximately 125 or 62.5 mcg per blister of umeclidinium), vilanterol trifenatate (approximately 25 mcg per blister of vilanterol), magnesium stearate (for example at about 1.0% w/w/based on the total weight of the dry powder composition) and lactose monohydrate, and a second strip contains a blend of micronized fluticasone furoate (approximately 100 mcg per blister) and lactose monohydrate.

The inhaler device may deliver, when actuated, the contents of a single blister simultaneously from each of the two blister strips. Each blister strip may be a double foil laminate containing 7, 14 or 30 filled blisters per strip.

All COPD patients, in particular those with moderate to severe persistant airflow obstruction classified as either GOLD 2, GOLD 3 or GOLD 4, are prone to bacterial exacerbations and thus may benefit from treatment or prevention with an immunogenic composition of the present invention when added to existing maintenance therapy for COPD. In one embodiment, an immunogenic composition of the present invention may be used in the treatment of human subjects (e.g. patients) with moderate to severe COPD with a previous history of acute exacerbations (AECOPD), for example at least one (e.g. 2 or more, 3 or more) episodes of moderate to severe AECOPD within the last 12 months. In another embodiment, combination of an immunogenic composition of the present invention with existing maintenance therapy may be used in the treatment of human subjects (e.g. patients) with moderate to severe COPD with a previous history of acute exacerbations (AECOPD), for example at least one (e.g. 2 or more, 3 or more) episodes of moderate to severe AECOPD within the last 12 months. Exacerbations are predominantly triggered by viral infections although bacterial infections such as those that occurred in the presence of *Haemophilus influenzae* and/or *Moraxella catarrhalis* may also initiate and/or amplify exacerbations.

The addition of an immunogenic composition according to the present invention to a patient's existing maintenance therapy may be complementary, and, for example, may reduce the frequency and/or severity (i.e. mild, moderate or severe) of AECOPD.

Thus, in a further aspect of the invention there is provided a combination therapy comprising:
  (i) one or more therapeutic agents selected from the group consisting of beta$_2$-agonists, anticholinergics, methylxanthines, phosphodiesterase-4 (PDE-4) inhibitors and inhaled corticosteroids; and
  (ii) an immunogenic composition comprising an immunogenic polypeptide from *Haemophilus influenzae* or an immunogenic fragment thereof and/or an immunogenic polypeptide from *Moraxella catarrhalis* or an immunogenic fragment thereof.

In a further aspect, there is provided a combination therapy for use in the treatment or prevention of COPD (e.g. moderate, severe or very severe COPD) comprising:
  (i) one or more therapeutic agents selected from the group consisting of beta$_2$-agonists, anticholinergics, methylxanthines, phosphodiesterase-4 (PDE-4) inhibitors and inhaled corticosteroids; and
  (ii) an immunogenic composition comprising an immunogenic polypeptide from *Haemophilus influenzae* or an immunogenic fragment thereof and/or an immunogenic polypeptide from *Moraxella catarrhalis* or an immunogenic fragment thereof.

In one embodiment, the combination therapy or combination therapy for use comprises an anticholinergic as the therapeutic agent.

In a further embodiment, the combination therapy or combination therapy for use comprises two therapeutic agents a beta$_2$-agonist and an anticholinergic.

In a further embodiment, the combination therapy or combination therapy for use comprises three therapeutic agents: a beta$_2$-agonist, an anticholinergic and an inhaled corticosteroid.

In a further embodiment, the combination therapy or combination therapy for use comprises two therapeutic agents: a beta$_2$-agonist and an inhaled corticosteroid.

In a further embodiment, the combination therapy or combination therapy for use comprises umeclidinium (e.g. umeclidinium bromide) as the anticholinergic, optionally at a dose of 62.5 mcg once daily.

In a further embodiment, the combination therapy or combination therapy for use comprises vilanterol (e.g. vilanterol trifenatate) as the beta$_2$-agonist, optionally at a dose of 25 mcg once daily.

In a further embodiment, the combination therapy or combination therapy for use comprises fluticasone furoate as the inhaled corticosteroid, optionally at a dose of 100 mcg once daily.

In a further embodiment, the combination therapy of combination therapy for use comprises vilanterol trifenatate at a dose of 25 mcg once daily and umeclidinium bromide at a dose of 62.5 mcg once daily.

In a further embodiment, the combination therapy of combination therapy for use comprises vilanterol trifenatate at a dose of 25 mcg once daily, and fluticasone furoate at a dose of 100 mcg once daily.

In a further embodiment, the combination therapy of combination therapy for use comprises vilanterol trifenatate at a dose of 25 mcg once daily, umeclidinium bromide at a dose of 62.5 mcg once daily, and fluticasone furoate at a dose of 100 mcg once daily.

In a further embodiment, in the combination therapy of combination therapy for use umeclidinium bromide, vilanterol trifenatate and/or fluticasone furoate are formulated at dry powder compositions with lactose monohydrate and optionally magnesium stearate and contained within the same dry powder inhaler device (e.g. the Ellipta™ Inhaler).

In a further embodiment, in the combination therapy of combination therapy for use umeclidinium bromide, vilanterol trifenatate and fluticasone furoate are contained within the same dry powder inhaler device (e.g. the Ellipta™ Inhaler), wherein the dry powder inhaler device contains two blister strips, wherein one strip contains a blend of micronised umeclidinium bromide (approximately 125 or 62.5 mcg per blister of umeclidinium), vilanterol trifenatate (approximately 25 mcg per blister of vilanterol), magnesium stearate (for example at about 1.0% w/w/based on the total weight of the dry powder composition) and lactose monohydrate, and a second strip contains a blend of micronized fluticasone furoate (approximately 100 mcg per blister) and lactose monohydrate.

In a further embodiment, in the combination therapy of combination therapy for use umeclidinium bromide and vilanterol trifenatate are contained within the same dry powder inhaler device (e.g. the Ellipta™ Inhaler), wherein the dry powder inhaler device contains two blister strips, wherein one strip contains a blend of micronised umeclidinium bromide (approximately 125 or 62.5 mcg per blister of umeclidinium), lactose monohydrate and magnesium stearate (for example at about 0.6% w/w of the total weight of the dry powder composition), and a second strip contains vilanterol trifenatate (approximately 25 mcg per blister of vilanterol), lactose monohydrate and magnesium stearate (for example at about 1.0% w/w/based on the total weight of the dry powder composition).

In a further embodiment, in the combination therapy of combination therapy for use vilanterol trifenatate and fluticasone furoate are contained within the same dry powder inhaler device (e.g. the Ellipta™ Inhaler), wherein the dry powder inhaler device contains two blister strips, wherein one strip contains a blend of micronised fluticasone furoate (approximately 100 mcg per blister) and lactose monohydrate, and a second strip contains vilanterol trifenatate (approximately 25 mcg per blister of vilanterol), lactose monohydrate and magnesium stearate (for example at about 1.0% w/w/based on the total weight of the dry powder composition).

The inhaler device may deliver, when actuated, the contents of a single blister simultaneously from each of the two blister strips. Each blister strip may be a double foil laminate containing 7, 14 or 30 filled blisters per strip.

Typically, the immunogenic composition, which forms part of the combination therapy along with the one or more therapeutic agents, is formulated as herein below described and packaged separately from the one or more therapeutic agents, for sequential or simultaneous administration.

In one embodiment, the combination therapy or combination therapy for use comprises an immunogenic composition comprising an immunogenic polypeptide from non-typeable *H. influenzae* (NTHi) or an immunogenic fragment thereof.

In a further embodiment, the combination therapy or combination therapy for use comprises an immunogenic composition comprising Protein D or an immunogenic fragment thereof, suitably an isolated immunogenic polypeptide with at least 70%, 80%, 85%, 90%, 91%, 92%, 93%, 94%, 95%, 96%, 97%, 98%, 99%, or 100% to Protein D sequence (SEQ ID NO. 1). In a further embodiment, the combination therapy or combination therapy for use comprises an immunogenic composition comprising Protein D or an immunogenic fragment thereof, suitably an isolated immunogenic polypeptide with at least 70%, 80%, 85%, 90%, 91%, 92%, 93%, 94%, 95%, 96%, 97%, 98%, 99%, or 100% to SEQ ID NO. 2.

In a further embodiment, the combination therapy or combination therapy for use comprises an immunogenic composition comprising Protein E or an immunogenic fragment thereof, suitably an isolated immunogenic polypeptide with at least 70%, 80%, 85%, 90%, 91%, 92%, 93%, 94%, 95%, 96%, 97%, 98%, 99%, or 100% to SEQ ID NO. 4. In a further embodiment, the combination therapy or combination therapy for use comprises an immunogenic composition comprising an immunogenic fragment of Protein E, suitably an isolated immunogenic polypeptide with at least 70%, 80%, 85%, 90%, 91%, 92%, 93%, 94%, 95%, 96%, 97%, 98%, 99%, or 100% to SEQ ID NO. 5.

In a further embodiment, the combination therapy or combination therapy for use comprises an immunogenic composition comprising PilA or an immunogenic fragment thereof, suitably an isolated immunogenic polypeptide with at least 70%, 80%, 85%, 90%, 91%, 92%, 93%, 94%, 95%, 96%, 97%, 98%, 99%, or 100% to SEQ ID NO. 6. In a further embodiment, the combination therapy or combination therapy for use comprises an immunogenic composition comprising an immunogenic fragment of PilA, suitably an isolated immunogenic polypeptide with at least 70%, 80%, 85%, 90%, 91%, 92%, 93%, 94%, 95%, 96%, 97%, 98%, 99%, or 100% to SEQ ID NO. 7.

In a further embodiment, the combination therapy or combination therapy for use comprises an immunogenic composition comprising Protein E and PilA, wherein Protein E and PilA are present as a fusion protein, suitably an isolated immunogenic polypeptide with at least 70%, 80%, 85%, 90%, 91%, 92%, 93%, 94%, 95%, 96%, 97%, 98%, 99%, or 100% to SEQ ID NO. 8. In a further embodiment, the combination therapy or combination therapy for use comprises an immunogenic composition comprising Protein E and PilA, wherein Protein E and PilA are present as a fusion protein, suitably an isolated immunogenic polypeptide with at least 70%, 80%, 85%, 90%, 91%, 92%, 93%, 94%, 95%, 96%, 97%, 98%, 99%, or 100% to SEQ ID NO. 9.

In a further embodiment, the combination therapy or combination therapy for use comprises an immunogenic composition comprising an immunogenic polypeptide from *M. catarrhalis* or an immunogenic fragment thereof.

In a further embodiment, the combination therapy or combination therapy for use comprises an immunogenic composition comprising UspA2 or an immunogenic fragment thereof.

In a further embodiment, the combination therapy or combination therapy for use comprises an immunogenic composition comprising an immunogenic fragment of UspA2, suitably an isolated immunogenic polypeptide with at least 70%, 80%, 85%, 90%, 91%, 92%, 93%, 94%, 95%, 96%, 97%, 98%, 99%, or 100% to a polypeptide selected from the group consisting of MC-001 (SEQ ID NO. 11), MC-002 (SEQ ID NO. 12), MC-003 (SEQ ID NO. 13), MC-004 (SEQ ID NO. 14), MC-005 (SEQ ID NO. 15), MC-006 (SEQ ID NO. 16), MC-007 (SEQ ID NO. 17), MC-008 (SEQ ID NO. 18), MC-009 (SEQ ID NO. 19), MC-010 (SEQ ID NO. 20) or MC-011 (SEQ ID NO. 21) e.g. MC009 SEQ ID NO. 19.

In a further embodiment, the combination therapy or combination therapy for use comprises an immunogenic composition comprising a pharmaceutically acceptable excipient or carrier.

In a further embodiment, the combination therapy or combination therapy for use comprises an immunogenic composition comprising an adjuvant, e.g. ASO1E.

Immunogenic Proteins and Immunogenic Fragments

Identity between polypeptides may be calculated by various algorithms. For example, the Needle program, from the EMBOSS package (Free software; EMBOSS: The European Molecular Biology Open Software Suite (2000). Trends in Genetics 16(6): 276-277) and the Gap program from the GCG® package (Accelrys Inc.) may be used. This Gap program is an implementation of the Needleman-Wunsch algorithm described in: Needleman, S. B. and Wunsch, C. D. (1970) J. Mol. Biol. 48, 443-453. The BLOSUM62 scoring matrix has been used, and the gap open and extension penalties were respectively 8 and 2.

Looking at the computed alignment, identical residues between two compared sequences can be observed. A percentage of identity can be computed by (1) calculating the number of identities divided by the length of the alignment, multiplied by 100 (for example, for the Needle program analysis), (2) calculating the number of identities divided by the length of the longest sequence, multiplied by 100, (3) calculating the number of identities divided by the length of the shortest sequence, multiplied by 100, or (4) calculating the number of identities divided by the number of aligned residues, multiplied by 100 (a residue is aligned if it is in front of another) (for example, for the Gap program analysis).

In one embodiment, sequence identity is calculated over the full length of the reference sequence (e.g. SEQ ID NO. 1 to 21 of the present invention). The immunogenic polypeptides and immunogenic fragments the invention may be derived from an amino acid sequence at least 70%, 80%, 85%, 90%, 91%, 92%, 93%, 94%, 95%, 96%, 97%, 98%, 99%, or 100% identical to a reference sequence (e.g. SEQ ID NO. 1 to 21 of the present invention) which has been modified by the deletion and/or addition and/or substitution of one or more amino acids (e.g. 1, 2, 3, 4, 5, 6, 7, 8, 9, 10, 11 or 12 amino acids). Amino acid substitution may be conservative or non-conservative. In one aspect, amino acid substitution is conservative. Substitutions, deletions, additions or any combination thereof may be combined in a single variant so long as the variant is an immunogenic polypeptide.

Immunogenic Polypeptides from Non-Typeable *H. Influenzae* (NTHi) and Immunogenic Fragments In one aspect of the invention, the immunogenic composition comprises an immunogenic polypeptide from non-typeable *H. influenzae* (NTHi) or an immunogenic fragment thereof. In another aspect of the invention, the immunogenic composition comprises an immunogenic fragment of a polypeptide from non-typeable *H. influenzae* (NTHi).

In one aspect of the invention, the immunogenic composition comprises Protein D or an immunogenic fragment thereof, suitably an isolated immunogenic polypeptide with at least 70%, 80%, 85%, 90%, 91%, 92%, 93%, 94%, 95%, 96%, 97%, 98%, 99%, or 100% to Protein D sequence.

Protein D may be as described in WO91/18926. In an embodiment, the immunogenic composition of the invention comprises protein D from *Haemophilus influenzae* (PD), for example, protein D sequence from FIG. 9 (FIGS. 9a and 9b together, 364 amino acids) of EP 0594610 (SEQ ID NO: 1). Inclusion of this protein in the immunogenic composition may provide a level of protection against *Haemophilus influenzae* related otitis media (Pyrmula et al Lancet 367; 740-748 (2006)). Protein D may be used as a full length protein or as a fragment (for example, Protein D may be as described in WO0056360). For example, a protein D sequence may comprise (or consist) of the protein D fragment described in EP0594610 which begins at the sequence SSHSSNMANT (SerSerHisSerSerAsnMetAlaAsnThr) (SEQ ID NO. 3), and lacks the 19 N-terminal amino acids from FIG. 9 of EP0594610, optionally with the tripeptide MDP from NS1 fused to the N-terminal of said protein D fragment (348 amino acids) (SEQ ID NO:2). In one aspect, the protein D or fragment of protein D is unlipidated.

In one aspect of the invention, the immunogenic composition comprises Protein D or an immunogenic fragment thereof, suitably an isolated immunogenic polypeptide with at least 70%, 80%, 85%, 90%, 91%, 92%, 93%, 94%, 95%, 96%, 97%, 98%, 99%, or 100% to SEQ ID NO. 1. Immunogenic fragments of Protein D comprise immunogenic fragments of at least 7, 10, 15, 20, 25, 30 or 50 contiguous amino acids of SEQ ID NO. 1. The immunogenic fragments may elicit antibodies which can bind SEQ ID NO. 1. In another aspect of the invention, the immunogenic composition comprises Protein D or an immunogenic fragment thereof, suitably an isolated immunogenic polypeptide with at least 70%, 80%, 85%, 90%, 91%, 92%, 93%, 94%, 95%, 96%, 97%, 98%, 99%, or 100% to SEQ ID NO. 2.

In one aspect of the invention, the immunogenic composition comprises Protein E or an immunogenic fragment thereof, suitably an isolated immunogenic polypeptide with at least 70%, 80%, 85%, 90%, 91%, 92%, 93%, 94%, 95%, 96%, 97%, 98%, 99%, or 100% to Protein E sequence. In another aspect of the invention, the immunogenic composition comprises an immunogenic fragment of Protein E, suitably an isolated immunogenic polypeptide with at least 70%, 80%, 85%, 90%, 91%, 92%, 93%, 94%, 95%, 96%, 97%, 98%, 99%, or 100% to Protein E sequence.

Protein E (PE) is an outer membrane lipoprotein with adhesive properties. It plays a role in the adhesion/invasion of non-typeable *Haemophilus influenzae* (NTHi) to epithelial cells. (J. Immunology 183: 2593-2601 (2009); The Journal of Infectious Diseases 199:522-531 (2009), Microbes and Infection 10:87-96 (2008)). It is highly conserved in both encapsulated *Haemophilus influenzae* and non-typeable *H. influenzae* and has a conserved epithelial binding domain. (The Journal of Infectious Diseases 201: 414-419 (2010)). Thirteen different point mutations have been described in different *Haemophilus* species when compared with *Haemophilus influenzae* Rd as a reference strain. Its expression is observed on both logarithmic growing and stationary phase bacteria. (WO2007/084053).

Protein E is also involved in human complement resistance through binding vitronectin. (Immunology 183: 2593-2601 (2009)). PE, by the binding domain PKRYARSVRQ YKILNCANYH LTQVR (SEQ ID NO. 1, corresponding to amino acids 84-108 of SEQ ID NO. 4), binds vitronectin which is an important inhibitor of the terminal complement pathway. (J. Immunology 183:2593-2601 (2009)).

As used herein "Protein E", "protein E", "Prot E", and "PE" mean Protein E from *H. influenzae*. Protein E may consist of or comprise the amino acid sequence of SEQ ID NO. 4 (corresponding to SEQ ID NO. 4 of WO2012/139225A1): (MKKIILTLSL GLLTACSAQI QKAEQNDVKL APPTDVRSGY IRLVKNVNYY IDSESIWVDN QEPQIVHFDA WNLDKGLYV YPEPKR-YARS VRQYKILNCA NYHLTQVRTD FYDEFWGQGL RAAPKKQKKH TLSLTPDTTL YNAAQIICAN YGEAFSVDKK) as well as sequences with at least or exactly 75%, 77%, 80%, 85%, 90%, 95%, 97%, 99% or 100% identity, over the entire length, to SEQ ID NO. 4. In an aspect of the invention, the immunogenic composition comprises Protein E or an immunogenic fragment thereof, suitably an isolated immunogenic polypeptide with at least 70%, 80%, 85%, 90%, 91%, 92%, 93%, 94%, 95%, 96%, 97%, 98%, 99%, or 100% to SEQ ID NO. 4. Immunogenic fragments of Protein E comprise immunogenic fragments of at least 7, 10, 15, 20, 25, 30 or 50 contiguous amino acids of SEQ ID NO. 4. The immunogenic fragments may elicit antibodies which can bind SEQ ID NO. 4.

In another aspect of the invention, the immunogenic composition comprises an immunogenic fragment of Protein E, suitably an isolated immunogenic polypeptide with at least 70%, 80%, 85%, 90%, 91%, 92%, 93%, 94%, 95%, 96%, 97%, 98%, 99%, or 100% to SEQ ID NO. 5 (corresponding to Seq ID No. 125 of WO2012/139225A1):

```
SEQ ID NO. 5: Amino acids 20-160 of Protein E
I QKAEQNDVKL APPTDVRSGY IRLVKNVNYY IDSESIWVDN

QEPQIVHFDA VVNLDKGLYV YPEPKRYARS VRQYKILNCA

NYHLTQVRTD FYDEFWGQGL RAAPKKQKKH TLSLTPDTTL

YNAAQIICAN YGEAFSVDKK
```

In one aspect of the invention, the immunogenic composition comprises PilA or an immunogenic fragment thereof, suitably an isolated immunogenic polypeptide with at least 70%, 80%, 85%, 90%, 91%, 92%, 93%, 94%, 95%, 96%, 97%, 98%, 99%, or 100% to PilA sequence. In another aspect of the invention, the immunogenic composition comprises an immunogenic fragment of PilA, suitably an isolated immunogenic polypeptide with at least 70%, 80%, 85%, 90%, 91%, 92%, 93%, 94%, 95%, 96%, 97%, 98%, 99%, or 100% to PilA sequence.

Pilin A (PilA) is likely the major pilin subunit of *H. influenzae* Type IV Pilus (Tfp) involved in twitching motility (Infection and Immunity, 73: 1635-1643 (2005)). NTHi PilA is a conserved adhesin expressed in vivo. It has been shown to be involved in NTHi adherence, colonization and biofilm formation. (Molecular Microbiology 65: 1288-1299 (2007)).

As used herein "PilA" means Pilin A from *H. influenzae*. PilA may consist of or comprise the protein sequence of SEQ ID NO. 6 (corresponding to SEQ ID NO. 58 of WO2012/139225A1) (MKLTTQQTLK KGFTLIELMI VIAIIAILAT IAIPSYQNYT KKAAVSELLQ ASAPY- KADVE LCVYSTNETT NCTGGKNGIA ADITTAKGYV KSVTTSNGAI TVKGDGTLAN MEYILQATGN AATGVTWTTT CKGTDASLFP ANFCGSVTQ) as well as sequences with 80% to 100% identity to SEQ ID NO. 6. For example, PilA may be at least 80%, 85%, 90%, 95%, 97% or 100% identical to SEQ ID NO. 6. In an aspect of the invention, the immunogenic composition comprises PilA or an immunogenic fragment thereof, suitably an isolated immunogenic polypeptide with at least 70%, 80%, 85%, 90%, 91%, 92%, 93%, 94%, 95%, 96%, 97%, 98%, 99%, or 100% to Seq ID NO. 6.

For example, immunogenic fragments of PilA comprise immunogenic fragments of at least 7, 10, 15, 20, 25, 30 or 50 contiguous amino acids of SEQ ID NO. 6. The immunogenic fragments may elicit antibodies which can bind SEQ ID NO. 6.

In another aspect of the invention, the immunogenic composition comprises an immunogenic fragment of PilA, suitably an isolated immunogenic polypeptide with at least 70%, 80%, 85%, 90%, 91%, 92%, 93%, 94%, 95%, 96%, 97%, 98%, 99%, or 100% to SEQ ID NO. 7 (corresponding to Seq ID No. 127 of WO2012/139225A1):

```
SEQ ID NO. 7 Amino acids 40-149 of PilA from H.
influenzae strain 86-028NP
T KKAAVSELLQ ASAPYKADVE LCVYSTNETT NCTGGKNGIA
ADITTAKGYV KSVTTSNGAI TVKGDGTLAN MEYILQATGN
AATGVTWTTT CKGTDASLFP ANFCGSVTQ.
```

Protein E and Pilin A may be presented as a fusion protein (PE-PilA). In another aspect of the invention, the immunogenic composition comprises Protein E and PilA, wherein Protein E and PilA are present as a fusion protein, suitably an isolated immunogenic polypeptide with at least 70%, 80%, 85%, 90%, 91%, 92%, 93%, 94%, 95%, 96%, 97%, 98%, 99%, or 100% to LVL-735 SEQ ID NO. 8 (corresponding to Seq ID No. 194 of WO2012/139225A1).

```
SEQ ID NO. 8: LVL735 (protein): (pelB sp)(ProtE
aa 20-160)(GG)(PilA aa40-149):
MKYLLPTAAA GLLLLAAQPA MAIQKAEQND VKLAPPTDVR

SGYIRLVKNV NYYIDSESIW VDNQEPQIVH FDAVVNLDKG

LYVYPEPKRY ARSVRQYKIL NCANYHLTQV RTDFYDEFWG

QGLRAAPKKQ KKHTLSLTPD TTLYNAAQII CANYGEAFSV

DKKGGTKKAA VSELLQASAP YKADVELCVY STNETTNCTG

GKNGIAADIT TAKGYVKSVT TSNGAITVKG DGTLANMEYI

LQATGNAATG VTWTTTCKGT DASLFPANFC GSVTQ
```

In another aspect of the invention, the immunogenic composition comprises Protein E and PilA, wherein Protein E and PilA are present as a fusion protein, suitably an isolated immunogenic polypeptide with at least 70%, 80%, 85%, 90%, 91%, 92%, 93%, 94%, 95%, 96%, 97%, 98%, 99%, or 100% to LVL-735, wherein the signal peptide has been removed, SEQ ID NO. 9 (Corresponding to Seq ID No. 219 of WO2012/139225A1).

```
SEQ ID NO. 9: PE-PilA fusion protein without
signal peptide
IQKAEQND VKLAPPTDVR SGYIRLVKNV NYYIDSESIW

VDNQEPQIVH FDAVVNLDKG LYVYPEPKRY ARSVRQYKIL

-continued
NCANYHLTQV RTDFYDEFWG QGLRAAPKKQ KKHTLSLTPD

TTLYNAAQII CANYGEAFSV DKKGGTKKAA VSELLQASAP

YKADVELCVY STNETTNCTG GKNGIAADIT TAKGYVKSVT

TSNGAITVKG DGTLANMEYI LQATGNAATG VTWTTTCKGT

DASLFPANFC GSVTQ
```

The immunogenicity of Protein E (PE) and Pilin A (PilA) polypeptides may be measured as described in WO2012/139225A1; the contents of which are incorporated herein by reference.

Immunogenic Polypeptides from *Moraxella Catarrhalis* and Immunogenic Fragments

In one aspect of the invention, the immunogenic composition comprises an immunogenic polypeptide from *M. catarrhalis* or an immunogenic fragment thereof.

In another aspect of the invention, the immunogenic composition comprises UspA2 or an immunogenic fragment thereof.

In one aspect of the invention, the immunogenic composition comprises UspA2 or an immunogenic fragment thereof, suitably an isolated immunogenic polypeptide with at least 70%, 80%, 85%, 90%, 91%, 92%, 93%, 94%, 95%, 96%, 97%, 98%, 99%, or 100% to UspA2 sequence. In another aspect of the invention, the immunogenic composition comprises an immunogenic fragment of UspA2, suitably an isolated immunogenic polypeptide with at least 70%, 80%, 85%, 90%, 91%, 92%, 93%, 94%, 95%, 96%, 97%, 98%, 99%, or 100% to UspA2 sequence.

Ubiquitous surface protein A2 (UspA2) is a trimeric autotransporter that appears as a lollipop-shared structure in electron micrographs (Hoiczyk et al. EMBO J. 19: 5989-5999 (2000)). It is composed of a N-terminal head, followed by a stalk which ends by an amphipathic helix and a C-terminal membrane domain. (Hoiczyk et al. EMBO J. 19: 5989-5999 (2000)). UspA2 contains a very well conserved domain (Aebi et al., Infection & Immunity 65(11) 4367-4377 (1997)), which is recognized by a monoclonal antibody that was shown protective upon passive transfer in a mouse *Moraxella catarrhalis* challenge model (Helminnen et al. J Infect Dis. 170(4): 867-72 (1994)).

UspA2 has been shown to interact with host structures and extracellular matrix proteins like fibronectin (Tan et al., J Infect Dis. 192(6): 1029-38 (2005)) and laminin (Tan et al., J Infect Dis. 194(4): 493-7 (2006)), suggesting it can play a role at an early stage of *Moraxella catarrhalis* infection.

UspA2 also seems to be involved in the ability of *Moraxella catarrhalis* to resist the bactericidal activity of normal human serum. (Attia A S et al. Infect Immun 73(4): 2400-2410 (2005)). It (i) binds the complement inhibitor C4bp, enabling *Moraxella catarrhalis* to inhibit the classical complement system, (ii) prevents activation of the alternative complement pathway by absorbing C3 from serum and (iii) interferes with the terminal stages of the complement system, the Membrane Attack Complex (MAC), by binding the complement regulator protein vitronectin. (de Vries et al., Microbiol Mol Biol Rev. 73(3): 389-406 (2009)).

As used herein "UspA2" means Ubiquitous surface protein A2 from *Moraxella catarrhalis*. UspA2 may consist of or comprise the amino acid sequence of SEQ ID NO: 10 from ATCC 25238:

```
                                                  (SEQ ID NO: 1)
MKTMKLLPLKIAVTSAMIIGLGAASTANAQAKNDITLEDLPYLIKKIDQN

ELEADIGDITALEKYLALSQYGNILALEELNKALEELDEDVGWNQNDIAN

LEDDVETLTKNQNALAEQGEAIKEDLQGLADFVEGQEGKILQNETSIKKN

TQRNLVNGFEIEKNKDAIAKNNESIEDLYDFGHEVAESIGEIHAHNEAQN

ETLKGLITNSIENTNNITKNKADIQALENNVVEELFNLSGRLIDQKADID

NNINNIYELAQQQDQHSSDIKTLKKNVEEGLLELSGHLIDQKTDIAQNQA

NIQDLATYNELQDQYAQKQTEAIDALNKASSENTQNIEDLAAYNELQDAY

AKQQTEAIDALNKASSENTQNIEDLAAYNELQDAYAKQQTEAIDALNKAS

SENTQNIAKNQADIANNINNIYELAQQQDQHSSDIKTLAKASAANTDRIA

KNKADADASFETLTKNQNTLIEKDKEHDKLITANKTAIDANKASADTKFA

ATADAITKNGNAITKNAKSITDLGTKVDGFDSRVTALDTKVNAFDGRITA

LDSKVENGMAAQAALSGLFQPYSVGKFNATAALGGYGSKSAVAIGAGYRV

NPNLAFKAGAAINTSGNKKGSYNIGVNYEF
``` as well as sequences with at least or exactly 63%, 66%, 70%, 72%, 74%, 75%, 77%, 80%, 84%, 85%, 90%, 95%, 96%, 97%, 98%, 99% or 100% identity, over the entire length, to SEQ ID NO: 10.

UspA2 as described in SEQ ID NO: 10 contains a signal peptide (for example, amino acids 1 to 29 of SEQ ID NO: 10), a laminin binding domain (for example, amino acids 30 to 177 of SEQ ID NO: 10), a fibronectin binding domain (for example, amino acids 165 to 318 of SEQ ID NO: 10) (Tan et al. JID 192: 1029-38 (2005)), a C3 binding domain (for example, amino acids 30 to 539 of SEQ ID NO: 10 (WO2007/018463), or a fragment of amino acids 30 to 539 of SEQ ID NO: 10, for example, amino acids 165 to 318 of SEQ ID NO: 1 (Hallström T et al. J. Immunol. 186: 3120-3129 (2011)), an amphipathic helix (for example, amino acids 519 to 564 of SEQ ID NO: 10 or amino acids 520-559 of SEQ ID NO:10, identified using different prediction methods) and a C terminal anchor domain (for example, amino acids 576 to 630 amino acids of SEQ ID NO: 10 (Brooks et al., Infection & Immunity, 76(11), 5330-5340 (2008)).

In an embodiment, an immunogenic fragment of UspA2 contains a laminin binding domain and a fibronectin binding domain. In an additional embodiment, an immunogenic fragment of UspA2 contains a laminin binding domain, a fibronectin binding domain and a C3 binding domain. In a further embodiment, an immunogenic fragment of UspA2 contains a laminin binding domain, a fibronectin binding domain, a C3 binding domain and an amphipathic helix.

UspA2 amino acid differences have been described for various *Moraxella catarrhalis* species. See for example, J Bacteriology 181(13):4026-34 (1999), Infection and Immunity 76(11):5330-40 (2008) and PLoS One 7(9):e45452 (2012).

UspA2 may consist of or comprise an amino acid sequence that differs from SEQ ID NO: 10 at any one or more amino acid selected from the group consisting of: AA (amino acid) 30 to 298, AA 299 to 302, AA 303 to 333, AA 334 to 339, AA 349, AA 352 to 354, AA 368 to 403, AA 441, AA 451 to 471, AA 472, AA 474 to 483, AA 487, AA 490, AA 493, AA 529, AA 532 or AA 543. UspA2 may consist of or comprise an amino acid sequence that differs from SEQ ID NO: 10 in that it contains an amino acid insertion in comparison to SEQ ID NO: 10. UspA2 may consists of or comprise an amino acid sequence that differs from SEQ ID NO. 10 at any one of the amino acid differences in SEQ ID NO: 22 through SEQ ID NO: 58. For example, SEQ ID NO. 10 may contain K instead of Q at amino acid 70, Q instead of G at amino acid 135 and/or D instead of N at amino acid 216.

TABLE 1

UspA2 amino acid sequences from 38 strains of *Moraxalla catarrhalis*
(SEQ ID NO: 10 and SEQ ID NO: 22-SEQ ID NO: 58).

| Strain | UspA2 sequences |
|---|---|
| ATCC 25238 (SEQ ID NO: 10) | MKTMKLLPLKIAVTSAMIIGLGAASTANAQAKNDITLEDLPYLIKKIDQNELEADIGDITALEK YLALSQYGNILALEELNKALEELDEDVGWNQNDIANLEDDVETLTKNQNALAEQGEAIKEDLQG LADFVEGQEGKILQNETSIKKNTQRNLVNGFEIEKNKDAIAKNNESIEDLYDFGHEVAESIGEI HAHNEAQNETLKGLITNSIENTNNITKNKADIQALENNVVEELFNLSGRLIDQKADIDNNINNI YELAQQQDQHSSDIKTLKKNVEEGLLELSGHLIDQKTDIAQNQANIQDLATYNELQDQYAQKQT EAIDALNKASSENTQNIEDLAAYNELQDAYAKQQTEAIDALNKASSENTQNIEDLAAYNELQDA YAKQQTEAIDALNKASSENTQNIAKNQADIANNINNIYELAQQQDQHSSDIKTLAKASAANTDR IAKNKADADASFETLTKNQNTLIEKDKEHDKLITANKTAIDANKASADTKFAATADAITKNGNA ITKNAKSITDLGTKVDGFDSRVTALDTKVNAFDGRITALDSKVENGMAAQAALSGLFQPYSVGK FNATAALGGYGSKSAVAIGAGYRVNPNLAFKAGAAINTSGNKKGSYNIGVNYEF (630 aa) |
| American 2933 (SEQ ID NO: 22) | MKTMKLLPLKIAVTSAMIIGLGAASTANAQSRDRSLEDIQDSISKLVQDDINTLKQDQQKMNKY LLLNQLANTLITDELNNNVIKNTNSIEALGDEIGWLENDIADLEEGVEELTKNQNTLIEKDEEH DRLIAQNQADIQTLENNVVEELFNLSGRLIDQEADIAKNNASIEELYDFDNEVAERIGEIHAYT EEVNKTLENLITNSVKNTDNIDKNKADIDNNINHIYELAQQQDQHSSDIKTLKNNVEEGLLELS GHLIDQKADLTKDIKALESNVEEGLLDLSGRLLDQKADLTKDIKALESNVEEGLLDLSGRLLDQ KADIAQNQTDIQDLAAYNELQDQYAQKQTEAIDALNKASSENTQNIEDLAAYNELQDAYAKQQT EAIDALNKASSENTQNIAKNQADIANNINNIYELAQQQDQHSSDIKTLAKASAANTNRIATAEL GIAENKKDAQIAKAQANANKTAIDENKASADTKFAATADAITKNGNAITKNAKSITDLGTKVDG FDGRVTALDTKVNAFDGRITALDSKVENGMAAQAALSGLFQPYSVGKFNATAALGGYGSKSAVA IGAGYRVNPNLAFKAGAAINTSGNKKGSYNIGVNYEF (613 aa) |
| American 2912 (SEQ ID NO: 23) | MKTMKLLPLKIAVTSALIIGLGAASTANAQQQLQTETFLPNFLSNDNYDLTDPFYHNMILGDTA LLDKQDGSQPQLKFYSNDKDSVPDSLLFSKLLHEQQLNGFKKGDTIIPLDKDGKPVYQVDYKLD GKGKKQKRRQVYSVTTKTATDDDVNSAYSRGILGKVDDLDDEMNFLNHDITSLYDVTANQQDAI KDLKKGVKGLNKELKELDKEVGVLSRDIGSLNDDVAQNNESIEDLYDFSQEVADSIGEIHAHNK AQNETLQDLITNSVENTNNITKNKADIQALENNVVEELFNLSGRLIDQKADLTKDIKTLESNVE EGLLELSGHLIDQKADIAKNQADIAQNQANIQDLAAYNELQDAYAKQQTEAIDALNKASSENTQ NIEDLAAYNELQDAYAKQQTEAIDALNKASSENTQNIAKNQADIANNINNIYELAQQQDQHSSD |

TABLE 1-continued

UspA2 amino acid sequences from 38 strains of *Moraxalla catarrhalis*
(SEQ ID NO: 10 and SEQ ID NO: 22-SEQ ID NO: 58).

| Strain | UspA2 sequences |
|---|---|
| | IKTLAKASAANTDRIAKNKADADASFETLTKNQNTLIEKDKEHDKLITANKTAIDENKASADTK FAATADAITKNGNAITKNAKSITDLGTKVDGFDSRVTALDTKVNAFDGRITALDSKVENGMAAQ AALSGLFQPYSVGKFNATAALGGYGSKSAVAIGAGYRVNPNLAFKAGAAINTSGNKKGSYNIGV NYEF (644 aa) |
| American 2908 (SEQ ID NO: 24) | MKTMKLLPLKIAVTSALIVGLGAASTANAQLVERFFPNIFLDKPLAKQHYHNVVVGDTSIVSDL QSNSDQLKFYSDDEGLVPDSLLFNKMLHEQLLNGFKEGDTIIPLDENGKPVYKVDYKLDGKEPR KVYSVTTKIATAEDVATSSYANGIQKDIDDLYDFDHQVTERLTQHGKTIYRNGERILANEESVQ YLNKEVQNNIEHIYELAQQQDQHSSDIKTLESNVEKGLLELSGHLIDQKADLTKDIKTLESNVE EGLLDLSGRLIDQKADLTKDIKTLESNVEEGLLDLSGRLIDQKADIAQNQANIQDLAAYNELQD QYAQKQTEAIDALNKASSENTQNIEDLAAYNELQDAYAKQQTEAIDALNKASSENTQNIAKNQA DIANNINNIYELAQQQDQHSSDIKTLAKASAANTNRIATAELGIAENKKDAQIAKAQANANKTA IDENKASADTKFAATADAITKNGNAITKNAKSITDLGTKVDGFDSRVTALDTKVNAFDGRITAL DSKVENGMAAQAALSGLFQPYSVGKFNATAALGGYGSKSAVAIGAGYRVNPNLAFKAGAAINTS GNKKGSYNIGVNYEF (591 aa) |
| Finnish 307 (SEQ ID NO: 25) | MKTMKLLPLKIAVTSAMIIGLGAASTANAQQQQQQQQQQSRTEIFFPNIFFNENHDELDDAYH NIILGDTALLDKQDGSQPQLKFYSNDKDSVPDSLLFSKLLHEQQLNGFKKGDTIIPLDKDGKPV YQVDYKLDGKGKKQKRRQVYSVTTKTATDDDVNSAYSRGILGKVDDLDDEMNFLNHDITSLYDV TANQQDAIKGLKKGVKGLNKELKELDKEVGVLSRDIGSLNDDVAQNNESIEDLYDFSQEVADSI GEIHAHNKAQNETLQDLITNSVENTNNITKNKADIQALENNVVEELFNLSGRLIDQKADLTKDI KTLESNVEEGLLELSGHLIDQKADIAKNQADIAQNQANIQDLAAYNELQDAYAKQQTEAIDALN KASSENTQNIEDLAAYNELQDAYAKQQTEAIDALNKASSENTQNIEDLAAYNELQDAYAKQQTE AIDALNKASSENTQNIAKNQADIANNINNIYELAQQQDQHSSDIKTLAKASAANTDRIAKNKAD ADASFETLTKNQNTLIEKDKEHDKLITANKTAIDENKASADTKFAATADAITKNGNAITKNAKS ITDLGTKVDAFDGRVTALDTKVNAFDGRITALDSKVENGMAAQAALSGLFQPYSVGKFNATAAL GGYGSKSAVAIGAGYRVNPNLAFKAGAAINTSGNKKGSYNIGVNYEF (687 aa) |
| Finnish 353 (SEQ ID NO: 26) | MKTMKLLPLKIAVTSAMIVGLGMASTANAQQQKSPKTETFLPNIFFNEYADDLDTLYHNMILGD TAITHDDQYKFYADDATEVPDSLFFNKILHDQLLYGFKEGDKIIPLDENGKPVYKLDKRLENGV QKTVYSVTTKTATADDVNSAYSRGIQGDIDDLYEANKENVNRLIEHGDKIFANEESVQYLNREV QNNIENIHELAQQQDQHSSDIKTLKKNVEKDLLDLSGRLIAQKEDIAQNQTDIQDLATYNELQD QYAQKQTEAIDALNKASSENTQNIAKNSNHIKTLENNIEEGLLELSGHLIDQKADLTKDIKALE SNVEEGLLDLSGRLIDQKADIAQNQANIQDLAAYNELQDAYAKQQTEAIDALNKASSENTQNIE DLAAYNELQDAYAKQQTEAIDALNKASSENTQNIEDLAAYNELQDAYAKQQTEAIDALNKASSE NTQNIAKNQADIANNINNIYELAQQQDQHSSDIKTLAKASAANTDRIAKNKADADASFETLTKN QNTLIEKDKEHDKLITANKTAIDANKASADTKFAATADAITKNGNAITKNAKSITDLGTKVDF DGRVTALDTKVNALDTKVNAFDGRITALDSKVENGMAAQAALSGLFQPYSVGKFNATAALGGYG SKSAVAIGAGYRVNPNLAFKAGAAINTSGNKKGSYNIGVNYEF (683 amino acids) |
| Finnish 358 (SEQ ID NO: 27) | MKTMKLLPLKIAVTSAMMVGLGMASTANAQQQKSPKTEIFLPNLFDNDNTELTDPLYHNMILGN TALLTQENQYKFYADDGNGVPDSLLFNKILHDQLLHGFKEGGTIIPLDENGKPVYKLDSIVEQG KTKTVYSVTTKTATADDVNSAYSRGIQGDIDDLYEANKENVNRLIEHGDKIFANEESVQYLNRE VQNNIENIHELAQQQDQHSSDIKTLKKNVEKDLLDLSGRLIAQKEDIAQNQTDIQDLATYNELQ DQYAQKQTEAIDALNKASSENTQNIAKNSNHIKTLENNIEEGLLELSGHLIDQKADLTKDIKAL ESNVEEGLLDLSGRLIDQKADIAQNQANIQDLAAYNELQDAYAKQQTEAIDALNKASSENTQNI EDLAAYNELQDAYAKQQTEAIDALNKASSENTQNIEDLAAYNELQDAYAKQQTEAIDALNKASS ENTQNIAKNQADIANNINNIYELAQQQDQHSSDIKTLAKASAANTDRIAKNKADADASFETLTK NQNTLIEKDKEHDKLITANKTAIDANKASADTKFAATADAITKNGNAITKNAKSITDLGTKVDG FDGRVTALDTKVNALDTKVNAFDGRITALDSKVENGMAAQAALSGLFQPYSVGKFNATAALGGY GSKSAVAIGAGYRVNPNLAFKAGAAINTSGNKKGSYNIGVNYEF (684 amino acids) |
| Finnish 216 (SEQ ID NO: 28) | MKTMKLLPLKIAVTSAMIIGLGAASTANAQQQKTKTEVFLPNLFDNDYYDLTDPLYHSMILGD TATLFDQQDNSKSQLKFYSNDKDSVPDSLLFSKLLHEQQLNGFKAGDTIIPLDKDGKPVYTQDT RTKDGKVETVYSVTTKIATQDDVEQSAYSRGIQGDIDDLYDINREVNEYLKATHDYNERQTEAI DALNKASSANTDRIDTAEERIDKNEYDIKALESNVGKDLLDLSGRLIAQKEDIDNNINHIYELA QQQDQHSSDIKTLKNNVEEGLLELSGHLIDQKADLTKDIKTLENNIEEGLLELSGHLIDQKADL TKDIKTLENNIEEGLLELSGHLIDQKADIAQNQANIQDLAAYNELQDAYAKQQTEAIDALNKAS SENTQNIEDLAAYNELQDAYAKQQTEAIDALNKASSENTQNIEDLAAYNELQDAYAKQQTEAID ALNKASSENTQNIAKNQADIANNINNIYELAQQQDQHSSDIKTLAKVSAANTDRIAKNKADADA SFETLTKNQNTLIEKDKEHDKLITANKTAIDANKASADTKFAATADAITKNGNAITKNAKSITD LGTKVDGFDGRVTALDTKVNAFDGRITALDSKVENGMAAQAALSGLFQPYSVGKFNATAALGGY GSKSAVAIGAGYRVNPNLAFKAGAAINTSGNKKGSYNIGVNYEF (684 amino acids) |
| Dutch H2 (SEQ ID NO: 29) | MKTMKLLPLKIAVTSAMMVGLGMASTANAQQQKSPKTEIFLPNLFDNDNTELTDPLYHNMILGN TALLTQENQYKFYADDGNGVPDSLLFNKILHDQLLHGFKKGDTIIPLDENGKPVYKLDSIVEQG KTKTVYSVTTKTATADDVNSAYSRGIQGDIDDLYEANKENVNRLIEHGDKIFANEESVQYLNRE VQNNIENIYELVQQQDQHSSDIKTLKKNVEKDLLDLSGRLIAQKEDIAQNQTDIQDLATYNELQ DQYAQKQTEAIDALNKASSENTQNIAKNSNHIKTLENNIEEGLLELSGHLIDQKADLTKDIKAL ESNVEEGLLDLSGRLIDQKADIAQNQANIQDLAAYNELQDAYAKQQTEAIDALNKASSENTQNI EDLAAYNELQDAYAKQQTEAIDALNKASSENTQNIEDLAAYNELQDAYAKQQTEAIDALNKASS ENTQNIAKNQADIANNINNIYELAQQQDQHSSDIKTLAKASAANTDRIAKNKADADASFETLTK NQNTLIEKDKEHDKLITANKTAIDANKASADTKFAATADAITKNGNAITKNAKSITDLGTKVDG FDGRVTALDTKVNALDTKVNAFDGRITALDSKVENGMAAQAALSGLFQPYSVGKFNATAALGGY GSKSAVAIGAGYRVNPNLAFKAGAAINTSGNKKGSYNIGVNYEF (684 amino acids) |

TABLE 1-continued

UspA2 amino acid sequences from 38 strains of *Moraxalla catarrhalis*
(SEQ ID NO: 10 and SEQ ID NO: 22-SEQ ID NO: 58).

| Strain | UspA2 sequences |
|---|---|
| Dutch F10 (SEQ ID NO: 30) | MKTMKLLPLKIAVTSAMIIGLGAASTANAQLAEQFFPNIFSNHAPVKQHYHNVVVGDTSIVENL QDSDDTQLKFYSNDEYSVPDSLLFNKMLHEQQLNGFKKGDTIIPLDENGKPVYKLDGQEP RRVYSVTTKIATQDDVDNSPYSRGIQGDIDDLYEANKENVNRLIEHGDKIFANEESVQYLNKEV QNNIENIYELAQQQDQHSSDIKTLKKNVEEGLLELSGHLIDQKADLTKDIKTLESNVEEGLLEL SGHLIDQKADIAKNQADIAQNQANIQDLAAYNELQDAYAKQQTEAIDALNKASSENTQNIEDLA AYNELQDAYAKQQTEAIDALNKASSENTQNIAKNQADIANNINNIYELAQQQDQHSSDIKTLAK ASAANTDRIAKNKADADASFETLTKNQNTLIEKDKEHDKLITANKTAIDANKASADTKFAATAD AITKNGNAITKNAKSITDLGTKVDAFDGRVTALDTKVNAFDGRITALDSKVENGMAAQAALSGL FQPYSVGKFNATAALGGYGSKSAVAIGAGYRVNPNLAFKAGAAINTSGNKKGSYNIGVNYEF (574 amino acids) |
| Norwegian 1 (SEQ ID NO: 31) | MKTMKLLPLKIAVTSALIVGLGAASTANAQQQPQTETFFPNIFFNENHDALDDVYHNMILGDTA ITQDNQYKFYADAISEVPDSLLFNKILHDQQLNGFKEGDTIIPLDENGKPVYKLDEKVENGVKK SVYSVTTKTATRADVEQSAYSRGIQGDIDDLYEANKENVNRLIEHGDKIFANEESVQYLNKEVQ NNIENIHELAQQQDQHSSDIKTLKKNVEEGLLELSGHLLDLSGHLIDQKADLTKDIKTLESNVEEGLLDLS GRLLDQKADIAQNQANIQDLAAYNELQDAYAKQQTEAIDALNKASSENTQNIEDLAAYNELQDA YAKQQTEAIDALNKASSENTQNIEDLAAYNELQDAYAKQQTEAIDALNKASSENTQNIEDLAAY NELQDAYAKQQTEAIDALNKASSENTQNIEDLAAYNELQDAYAKQQTEAIDALNKASSENTQNI AKNQADIANNINNIYELAQQQDQHSSDIKTLAKASAANTDRIAKNKADADASFETLTKNQNTLI EKDKEHDKLITANKTAIDANKASADTKFAATADAITKNGNAITKNAKSITDLGTKVDAFDGRVT ALDTKVNALDTKVNAFDGRITALDSKVENGMAAQAALSGLFQPYSVGKFNATAALGGYGSKSAV AIGAGYRVNPNLAFKAGAAINTSGNKKGSYNIGVNYEF (678 amino acids) |
| Norwegian 13 (SEQ ID NO: 32) | MKTMKLLPLKIAVTSAMIVGLGAASTANAQQQQQPRTETFFPNIFFNENHDALDDVYHNMILGD TAITQDNQYKFYADAISEVPDSLLFNKILHDQQLNGFKEGDTIIPLDENGKPVYKLDEKVENGV KKSVYSVTTKTATRADVEQSAYSRGIQGDIDDLYEANKENVNRLIEHGDKIFANEESVQYLNRE VQNNIENIHELAQQQDQHSSDIKTLKKNVEKDLLDLSGRLIAQKEDIAQNQTDIQDLATYNELQ DQYAQKQTEAIDALNKASSENTQNIAKNSNHIKTLENNIEEGLLELSGHLIDQKADLTKDIKTL ENNIEEGLLELSGHLIDQKADLTKDIKALESNVEEGLLDLSGRLLDQKADIAQNQANIQDLAAY NELQDQYAKQQTEAIDALNKASSENTQNIEDLAAYNELQDAYAKQQTEAIDALNKASSENTQNI AKNQADIANNINNIYELAQQQDQHSSDIKTLAKASAANTDRIAKNKADADASFETLTKNQNTLI EKDKEHDKLITANKTAIDTNKASADTKFAATADAITKNGNAITKNAKSITDLGTKVDFDGRVT ALDTKVNALDTKVNAFDGRITALDSKVENGMAAQAALSGLFQPYSVGKFNATAALGGYGSKSAV AIGAGYRVNPNLAFKAGAAINTSGNKKGSYNIGVNYEF (678 amino acids) |
| Norwegian 33 (SEQ ID NO: 33) | MKTMKLLPLKIAVTSALIVGLGAASTANAQLVERFFPNIFLDKPLAKQHYHNVVVGDTSIVSDL QSNSDQLKFYSDDEGLVPDSLLFNKMLHEQQLLNGFKEGDTIIPLDENGKPVYKVDYKLDGKEPR KVYSVTTKIATAEDVATSSYANGIQKDIDDLYDFDHQVTERLTQHGKTIYRNGERILANEESVQ YLNKEVQNNIEHIYELAQQQDQHSSDIKTLESNVEKGLLELSGHLIDQKADLTKDIKTLENNVE EGLLDLSGRLIDQKADIAQNQANIQDLAAYNELQDQYAQKQTEAIDALNKASSENTQNIEDLAA YNELQDAYAKQQTEAIDALNKASSENTQNIAKNQADIANNINNIYELAQQQDQHSSDIKTLAKA SAANTDRIAKNKADADASFETLTKNQNTLIEKDKEHDKLITANKTAIDTNKASADTKFAATADA ITKNGNAITKNAKSITDLGTKVDGFDSRVTALDTKVNALDTKVNALDTKVNAFDGRITALDSKV ENGMAAQAALSGLFQPYSVGKFNATAALGGYGSKSAVAIGAGYRVNPNLAFKAGAAINTSGNKK GSYNIGVNYEF (587 amino acids) |
| Norwegian 25 (SEQ ID NO: 34) | MKTMKLLPLKIAVTSAMIVGLGAASTANAQQQQQPRTETFFPNIFFNENHDALDDVYHNMILGD TAITQDNQYKFYADAISEVPDSLLFNKILHDQQLNGFKEGDTIIPLDENGKPVYKLDEKVENGV KKSVYSVTTKTATRADVEQSAYSRGIQGDIDDLYEANKENVNRLIEHGDKIFANEESVQYLNRE VQNNIENIHELAQQQDQHSSDIKTLKKNVEKDLLDLSGRLIAQKEDIAQNQTDIQDLATYNELQ DQYAQKQTEAIDALNKASSENTQNIAKNSNHIKTLENNIEEGLLELSGHLIDQKADLTKDIKTL ENNIEEGLLELSGHLIDQKADLTKDIKALESNVEEGLLDLSGRLLDQKADIAQNQANIQDLAAY NELQDQYAKQQTEAIDALNKASSENTQNIEDLAAYNELQDAYAKQQTEAIDALNKASSENTQNI AKNQADIANNINNIYELAQQQDQHSSDIKTLAKASAANTDRIAKNKADADASFETLTKNQNTLI EKDKEHDKLITANKTAIDTNKASADTKFAATADAITKNGNAITKNAKSITDLGTKVDGFDGRVT ALDTKVNALDTKVNAFDGRITALDSKVENGMAAQAALSGLFQPYSVGKFNATAALGGYGSKSAV AIGAGYRVNPNLAFKAGAAINTSGNKKGSYNIGVNYEF (678 amino acids) |
| Norwegian 27 (SEQ ID NO: 35) | MKTMKLLPLKIAVTSALIVGLGAASTANAQVRDKSLEDIEALLGKIDISKLEKEKKQQTELQKY LLLSQYANVLTMEELNKNVEKNTNSIEALGYEIGWLENDIADLEEGVEELTKNQNTLIEKDEEH DRLIAQNQADIKTLENNVVEELFNLSDRLIAQNQADIAKNNASIEKDLYDFDNEVAERIGEIHAYT EEVNKTLEKLITNSVKNTDNIDKNKADIQALENNVEEGLLELSGHLIDQKADLTKDIKALESNV EEGLLDLSGRLLDQKADIAKNQADIAQNQTDIQDLAAYNELQDQYAKQQTEAIDALNKASSENT QNIEDLAAYNELQDAYAKQQTEAIDALNKASSENTQNIEDLAAYNELQDAYAKQQTEAIDALNK ASSENTQNIAKNQADIANNINNIYELAQQQDQHSSDIKTLAKVSAANTDRIAKNKADADASFET LTKNQNTLIEKDKEHDKLITANKTAIDANKASADTKFAATADAITKNGNAITKNAKSITDLGTK VDGFDSRVTALDTKVNAFDGRITALDSKVENGMAAQAALSGLFQPYSVGKFNATAALGGYGSKS AVAIGAGYRVNPNLAFKAGAAINTSGNKKGSYNIGVNYEF (616 amino acids) |
| Norwegian 36 (SEQ ID NO: 36) | MKTMKLLPLKIAVTSALIVGLGAASTANAQATETFLPNLFDNDYTETTDPLYHGMILGNTAITQ DTQYKFYAENGNEVPDSLFFNKILHDQQLNGFKEGDTIIPLDENGKPVYKLDEITENGVKRKVY SVTTKTATREDVEQSAYSRGIQGDIDDLYEANKENVNRLIEHGDKIFANEESVQYLNKEVQNNI ENIHELAQQQDQHSSDIKTLKKNVEEGLLELSGHLIDQKADLTKDIKALESNVEEGLLDLSGHL IDQKADLTKDIKALESNVEEGLLDLSGRLLDQKADIAKNQADIAQNQTDIQDLAAYNELQDQYA |

TABLE 1-continued

UspA2 amino acid sequences from 38 strains of *Moraxalla catarrhalis*
(SEQ ID NO: 10 and SEQ ID NO: 22-SEQ ID NO: 58).

| Strain | UspA2 sequences |
|---|---|
| | QKQTEAIDALNKASSENTQNIEDLAAYNELQDYAQKQTEAIDALNKASSENTQNIEDLAAYNE
LQDYAQKQTEAIDALNKASSENTQNIEDLAAYNELQDYAQKQTEAIDALNKASSENTQNIAK
NQADIANNINNIYELAQQQDQHSSDIKTLAKASAANTDRIAKNKADADASFETLTKNQNTLIEK
DKEHDKLITANKTAIDANKASADTKFAATADAITKNGNAITKNAKSITDLGTKVDGFDGRVTAL
DTKVNALDTKVNAFDGRITALDSKVENGMAAQAALSGLFQPYSVGKFNATAALGGYGSKSAVAI
GAGYRVNPNLAFKAGAAINTSGNKKGSYNIGVNYEF (676 amino acids) |
| BC5SV (SEQ ID NO: 37) | MKTMKLLPLKIAVTSALIVGLGAASTANAQNGTSTKLKNLKEYAQYLDNYAQYLDDDIDDL
DKEVGELSQNIAKNQANIKDLNKKLSRDIDSLREDVYDNQYEIVNNQADIEKNQDDIKELE
NNVGKELLNLSGRLLDQKADIDNNINNIYELAQQQDQHSSDIKTLKKNVEEGLLELSGHLI
DQKSDIAQNQTDIQDLATYNELQDQYAQKQTEAIDALNKASSENTQNIEDLAAYNELQDAY
AKQQTEAIDALNKASSENTQNIQDLAAYNELQDAYAKQQTEAIDALNKASSENTQNIEDLA
AYNELQDAYAKQQTEAIDALNKASSENTQNIEDLAAYNELQDAYAKQQTEAIDALNKASSE
NTQNIEDLAAYNELQDAYAKQQTEAIDALNKASSENTQNIAKNQADIANNINNIYELAQQQ
DQHSSDIKTLAKASAANTDRIAKNKADADASFETLTKNQNTLIEKDKEHDKLITANKTAID
ANKASADTKFAATADAITKNGNAITKNAKSITDLGTKVDAFDGRVTALDTKVNAFDGRITA
LDSKVENGMAAQAALSGLFQPYSVGKFNATAALGGYGSKSAVAIGAGYRVNPNLAFKAGAA
INTSGNKKGSYNIGVNYEF (629 amino acids) |
| Norwegian 14 (SEQ ID NO: 38) | MKTMKLLPLKIAVTSAMIVGLGMASTANAQQQRSPKTETFLPNIFFNEYADDLDTLYHNMI
LGDTAITHDDQYKFYADDATEVPDSLFFNKILHDQLLYGFKEGDKIIPLDENGKPVYKLDK
RLDNGVQKTVYSVTTKTATADDVNSAYSRGIQGDIDDLYEANKENVNRLIEHGDKIFANEE
SVQYLNKEVQNNIENIHELAQQQDQHSSDIKTLKKNVEEGLLELSGHLIDQKTDIAQNQTD
IQDLATYNELQDQYAQKQTEAIDALNKASSENTQNIAKNSNRIKALENNIEEGLLELSGHL
IDQKADLTKDIKALESNVEEGLLDLSGRLIDQKADIAQNQANIQDLAAYNELQDAYAKQQT
EAIDALNKASSENTQNIEDLAAYNELQDAYAKQQTEAIDALNKASSENTQNIEDLAAYNEL
QDAYAKQQTEAIDALNKASSENTQNIAKNQADIANNINNIYELAQQQDQHSSDIKTLAKAS
AANTDRIAKNKADADASFETLTKNQNTLIEKDKEHDKLITANKTAIDANKASADTKFAATA
DAITKNGNAITKNAKSITDLGTKVDGFDGRVTALDTKVNALDTKVNAFDGRITALDSKVEN
GMAAQAALSGLFQPYSVGKFNATAALGGYGSKSAVAIGAGYRVNPNLAFKAGAAINTSGNK
KGSYNIGVNYEF (683 amino acids) |
| Norwegian 3 (SEQ ID NO: 39) | MKTMKLLPLKIAVTSAMIVGLGMASTANAQAQSNRSLDQVQALLRGIDETKIKKEIQQSQQ
PELNKYLTFNQLANALNIEELNNNVQKNTQRLDSAATLYGDLSKTVPKSIKENKESIKENK
ESIKENKESIKENKESIKENKESITTLTRKSFQNQVDIVRNNASIEDLYAYGQE
VAKSIGEIHAYTEEVNKTLENLITNSVENTNNITKNKADIQALENNVVEELFNLSGRLIDQ
KADINNNINNIYELAQQQDQHSSDIKTLKKNVEEGLLELSGHLIDQKADLTKDIKTLESNV
EEGLLDLSGRLLDQKADIAQNQANIQDLAAYNELQDAYAKQQTEAIDALNKASSENTQNIE
DLAAYNELQDAYAKQQTEAIDALNKASSENTQNIEDLAAYNELQDAYAKQQTEAIDALNKA
SSENTQNIEDLAAYNELQDAYAKQQTEAIDALNKASSENTQNIAKNQADIANNINNIYELA
QQQDQHSSDIKTLAKASAANTDRIAKNKADADASFETLTKNQNTLIEKDKEHDKLITANKT
VIDANKASADTKFAATADAITKNGNAITKNAKSITDLGTKVDGFDGRVTALDTKVNALDTK
VNAFDGRITALDSKVENGMAAQAALSGLFQPYSVGKFNATAALGGYGSKSAVAIGAGYRVN
PNLAFKAGAAINTSGNKKGSYNIGVNYEF (700 amino acids) |
| Finnish 414 (SEQ ID NO: 40) | MKTMKLLPLKIAVTSALIVGLGAASTANAQATETFLPNLFDNDYIETTDPLYHGMILGNTA
ITQDTQYKFYAENGNEVPDSLFFNKILHDQQLNGFKEGDTIIPLDENGKPVYKLDEITENG
VKRKVYSVTTKTATREDVEQSAYSRGIQGDIDDLYEANKENVNRLIEHGDKIFANEESVQY
LNKEVQNNIENIHELAQQQDQHSSDIKTLKKNVEEGLLELSGHLIDQKADLTKDIKTLENN
VEEGLLELSGHLIDQKADLTKDIKALESNVEEGLLDLSGRLIDQKADIAKNQADIAQNQTD
IQDLAAYNELQDQYAQKQTEAIDALNKASSENTQNIEDLAAYNELQDQYAQKQTEAIDALN
KASSENTQNIEDLAAYNELQDQYAQKQTEAIDALNKASSENTQNIEDLAAYNELQDQYAQK
QTEAIDALNKASSENTQNIAKNQADIANNINNIYELAQQQDQHSSDIKTLAKASAANTDRI
AKNKADADASFETLTKNQNTLIEKDKEHDKLITANKTAIDANKASADTKFAATADAITKNG
NAITKNAKSITDLGTKVDGFDGRVTALDTKVNALDTKVNAFDGRITALDSKVENGMAAQAA
LSGLFQPYSVGKFNATAALGGYGSKSAVAIGAGYRVNPNLAFKAGAAINTSGNKKGSYNIG
VNYEF (676 amino acids) |
| Japanese Z7476 (SEQ ID NO: 41) | MKTMKLLPLKIAVTSAMIIGLGAASTANAQLAEQFFPNIFSNHAPVKQHYHNVVVGDTSIV
ENLQDSDDTQLKFYSNDEYSVPDSLLFNKMLHEQQLNGFKKGDTIIPLDENGKPVYKVDYK
LDGQEPRRVYSVTTKIATQDDVDNSPYSRGIQGDIDDLYEANKENVNRLIEHGDKIFANEE
SVQYLNKEVQNNIENIYELAQQQDQHSSDIKTLKKNVEEGLLELSGRLIDQKADIAQNQAN
IQDLAAYNELQDQYAQKQTEAIDALNKASSENTQNIEDLAAYNELQDAYAKQQTEAIDALN
KASSENTQNIEDLAAYNELQDAYAKQQTEAIDALNKASSENTQNIEDLAAYNELQDAYAKQ
QTEAIDALNKASSENTQNIEDLAAYNELQDAYAKQQTEAIDALNKASSENTQNIEDLAAYN
ELQDAYAKQQTEAIDALNKASSENTQNIAKNQADIANNINNIYELAQQQDQHSSDIKTLAK
VSAANTDRIAKNKADADASFETLTKNQNTLIEKDKEHDKLITANKTAIDANKASADTKFAA
TADAITKNGNAITKNAKSITDLGTKVDGFDGRVTALDTKVNAFDGRITALDSKVENGMAAQ
AALSGLFQPYSVGKFNATAALGGYGSKSAVAIGAGYRVNPNLAFKAGAAINTSGNKKGSYN
IGVNYEF (678 amino acids) |
| Belgian Z7530 (SEQ ID NO: 42) | MKTMKLLPLKIAVTSAMIIGLGAASTANAQSRDRSLEDIQDSISKLVQDDINTLKQDQQKM
NKYLLLNQLANTLITDELNNNVIKNTNSIEALGDEIGWLENDIADLEEGVEELTKNQNTLI
EKDEEHDRLIAQNQADIQTLENNVVEELFNLSGRLIDQEADIAKNNASIEELYDFDNEVAE
RIGEIHAYTEEVNKTLENLITNSVKNTDNIDKNKADIDNNINHIYELAQQQDQHSSDIKTL |

TABLE 1-continued

UspA2 amino acid sequences from 38 strains of *Moraxalla catarrhalis*
(SEQ ID NO: 10 and SEQ ID NO: 22-SEQ ID NO: 58).

| Strain | UspA2 sequences |
|---|---|
| | KNNVEEGLLELSGHLIDQKADLTKDIKALESNVEEGLLDLSGRLLDQKADLTKDIKALESN VEEGLLDLSGRLLDQKADIAQNQTDIQDLAAYNELQDQYAQKQTEAIDALNKASSENTQNI EDLAAYNELQDAYAKQQTEAIDALNKASSENTQNIAKNQADIANNINNIYELAQQQDQHSS DIKTLAKASAANTNRIATAELGIAENKKDAQIAKAQANANKTAIDENKASADTKFAATADA ITKNGNAITKNAKSITDLGTKVDGFDGRVTALDTKVNAFDGRITALDSKVENGMAAQAALS GLFQPYSVGKFNATAALGGYGSKSAVAIGAGYRVNPNLAFKAGAAINTSGNKKGSYNIGVN YEF (613 amino acids) |
| German Z8063 (SEQ ID NO: 43) | MKTMKLLPLKIAVTSALIVGLGAASTANAQATNKDITLEDVLKSIEEIDPYELRDYIEYPT AIERFLLLSQYGNTLTLEEFDNDIELLDQDVEDLEESVTELAKNQNSLIEQGEAIKEDLQG LADFVERQEDKILQNETSIKKNTQRNLVNGFEIEKNKDAIAKNNESIEDLYDFGHEVAKSI GEIHAHNEAQNETLKDLITNSVKNTDNITNKNKADIQALESNVEKGLLELSGHLIDQKADID NNINNIHELAQQQDQHSSDIKTLKKNVEEGLLELSGHLIDQKSDIAQNQANIQDLATYNEL QDQYAQKQTEAIDALNKASSENTQNIEDLAAYNELQDAYAKQQTEAIDALNKASSENTQNI AKNQADIANNINNIYELAQQQDQHSSDIKTLAKASAANTDRIAKNKADADASFETLTKNQN TLIEKDKEHDKLITANKTAIDANKASADTKFAATADAITKNGNAITKNAKSITDLGTKVDG FDSRVTALDTKVNAFDGRITALDSKVENGMAAQAALSGLFQPYSVGKFNATAALGGYGSKS AVAIGAGYRVNPNLAFKAGAAINTSGNKKGSYNIGVNYEF (589 amino acids) |
| American O12E (SEQ ID NO: 44) | MKTMKLLPLKIAVTSAMMVGLGMASTANAQQQKSPKTEIFLPNLFDNDNTELTDPLYHNMI LGNTALLTQENQYKFYADDGNGVPDSLLFNKILHDQLLHGFKEGDTIIPLDENGKPVYKLD SIVEQGKTKTVYSVTTKTATADDVNSAYSRGIQGDIDDLYEANKENVNRLIEHGDKIFANE ESVQYLNREVQNNIENIHELAQQQDQHSSDIKTLKKNVEKDLLDLSGRLIAQKEDIAQNQT DIQDLATYNELQDQYAQKQTEAIDALNKASSENTQNIAKNSNHIKTLENNIEEGLLELSGH LIDQKADLTKDIKALESNVEEGLLDLSGRLIDQKADIAQNQANIQDLAAYNELQDAYAKQQ TEAIDALNKASSENTQNIEDLAAYNELQDAYAKQQTEAIDALNKASSENTQNIEDLAAYNE LQDAYAKQQTEAIDALNKASSENTQNIAKNQADIANNINNIYELAQQQDQHSSDIKTLAKA SAANTDRIAKNKADADASFETLTKNQNTLIEKDKEHDKLITANKTAIDANKASADTKFAAT ADAITKNGNAITKNAKSITDLGTKVDGFDGRVTALDTKVNALDTKVNAFDGRITALDSKVE NGMAAQAALSGLFQPYSVGKFNATAALGGYGSKSAVAIGAGYRVNPNLAFKAGAAINTSGN KKGSYNIGVNYEF (684 amino acids) |
| Greek MC317 (SEQ ID NO: 45) | MKTMKLLPLKIAVTSALIVGLGAASTANAQQQKTKTEVFLPNLFYNDYIEETDLLYHNMI LGDTAALVDRQNYSNSQLKFYSNDEESVPDSLLFSKMLNNQQLNGFKAGDIIIPVDANGQV IYQKDTRVEGGKTRTVLSVTTKIATQQDVDSAYSRGIQGKVNDLDDEMNFLNHDITSLYDV TANQQDDIKGLKKGVKDLKKGVKGLNKELKELDKEVGVLSRDIGSLNDDVAQNNESIEDLY DFSQEVADSIGEIHAHNKAQNETLQDLITNSVENTNNITKNKADIQALENNVVEELFNLSG RLIDQKADLTKDIKTLESNVEEGLLELSGHLIDQKADIAKNQADIAQNQANIQDLAAYNEL QDAYAKQQTEAIDALNKASSENTQNIEDLAAYNELQDAYAKQQTEAIDALNKASSENTQNI AKNQADIANNINNIYELAQQQDQHSSDIKTLAKASAANTDRIAKNKADADASFETLTKNQN TLIEKDKEHDKLITANKTAIDENKASADTKFAATADAITKNGNAITKNAKSITDLGTKVDG FDGRVTALDTKVNAFDGRITALDSKVENGMAAQAALSGLFQPYSVGKFNATAALGGYGSKS AVAIGAGYRVNPNLAFKAGAAINTSGNKKGSYNIGVNYEF (650 amino acids) |
| American V1122 (SEQ ID NO: 46) | MKTMKLLPLKIAVTSALIVGLGAVSTTNAQAQSRSLDQIQTKLADLAGKIAAGKNGGGQNN QNNQNDINKYLFLSQYANILTMEELNNNVVKNSSSIETLETDFGWLENDVADLEDGVEELT KNQNTLIEKDEEHDRLIAQNQADIQTLENNVVEELFNLSDRLIDQKADIAKNQADIAQNNE SIEELYDFDNEVAEKIGEIHAYTEEVNKTLQDLITNSVKNTDNIDKNKADIDNNINHIYEL AQQQDQHSSDIKTLKNNVEEGLLELSGHLLDQKADLTKDIKTLENNVEEGLLDLSGRLIDQ KADIAKNQADIAQNQTDIQDLAAYNELQDQYAQKQTEAIDALNKASSENTQNIEDLAAYNE LQDAYAKQQTEAIDALNKASSENTQNIAKNQADIANNINNIYELAQQQDQHSSDIKTLAKA SAANTDRIAKNKADADASFETLTKNQNTLIEKDKEHDKLITANKTAIDENKASADTKFAAT ADAITKNGNAITKNAKSITDLGTKVDGFDGRVTALDTKVNAFDGRITALDSKVENGMAAQA ALSGLFQPYSVGKFNATAALGGYGSKSAVAIGAGYRVNPNLAFKAGAAINTSGNKKGSYNI GVNYEF (616 amino acids) |
| American P44 (SEQ ID NO: 47) | MKTMKLLPLKIAVTSALIVGLGTASTANAQVASPANQKIQQKIKKVRKELRQDIKSLRNDI DSNTADIGSLNDDVADNQDDILDNQADIAKNQDDIEKNQADIKELDKEVGVLSREIGSLND DIADNYTDIIDNYTDIIDNQANIAKNQDDIEKNQADIKELDKEVGVLSREIGSLNDDVADN QDDIAKNQADIQTLENNVEEGLLELSGHLLDQKADIDNNINNIYELAQQQDQHSSDIKTLK KNVEEGLLELSGHLIDQKTDIAQNQANIQDLATYNELQDQYAQEQTEAIDALNKASSENTQ NIAKNSNRIKALESNVEEGLLELSGHLIDQKADLTKDIKALESNVEEGLLELSGHLIDQKA DIAQNQANIQDLAAYNELQDQYAQKQTEAIDALNKASSENTQNIEDLAAYNELQDAYAKQQ TEAIDALNKASSENTQNIAKNQADIANNINNIYELAQQQDQHSSDIKTLAKASAANTDRIA KNKADADASFETLTKNQNTLIEKDKEHDKLITANKTAIDANKVSADTKFAATADAITKNGN AITKNAKSITDLGTKVDAFDSRVTALDTKVNAFDGRITALDSKVENGMAAQAALSGLFQPY SVGKFNATAALGGYGSKSAVAIGAGYRVNPNLAFKAGAAINTSGNKKGSYNIGVNYEF (668 amino acids) |
| American V1171 (SEQ ID NO: 48) | MKTMKLLPLKIAVTSAMIVGLGATSTVNAQVVEQFFPNIFFNENHDELDDAYHNMILGDTA IVSNSQDNSTQLKFYSNDEDSVPDSLLFSKLLHEQQLNGFKAGDTIIPLDKDGKPVYTKDT RTKDGKVETVYSVTTKIATQDDVEQSAYSRGIQGDIDDLYDINREVNEYLKATHDYNERQT EAIDALNKASSANTDRIDTAEERIDKNEYDIKALESNVEEGLLELSGHLIDQKADLTKDIK ALESNVEEGLLELSGHLIDQKADLTKDIKALESNVEEGLLDLSGRLIDQKADIAQNQANIQ DLAAYNELQDAYAKQQTEAIDALNKASSENTQNIEDLAAYNELQDAYAKQQTEAIDALNKA |

TABLE 1-continued

UspA2 amino acid sequences from 38 strains of *Moraxalla catarrhalis*
(SEQ ID NO: 10 and SEQ ID NO: 22-SEQ ID NO: 58).

| Strain | UspA2 sequences |
|---|---|
| | SSENTQNIEDLAAYNELQDAYAKQQTEAIDALNKASSENTQNIEDLAAYNELQDAYAKQQT<br>EAIDALNKASSENTQNIAKNQADIANNINNIYELAQQQDQHSSDIKTLAKASAANTDRIAK<br>NKADADASFETLTKQNQTLIEKDKEHDKLITANKTAIDANKASADTKFAATADAITKNGNA<br>ITKNAKSITDLGTKVDGFDGRVTALDTKVNALDTKVNAFDGRITALDSKVENGMAAQAALS<br>GLFQPYSVGKFNATAALGGYGSKSAVAIGAGYRVNPNLAFKAGAAINTSGNKKGSYNIGVN<br>YEF (674 amino acids) |
| American<br>TTA24<br>(SEQ ID<br>NO: 49) | MKTMKLLPLKIAVTSAMIIGLGAASTANAQSRDRSLEDIQDSISKLVQDDIDTLKQDQQKM<br>NKYLLLNQLANTLITDELNNNVIKNTNSIEALGDEIGWLENDIADLEEGVEELTKNQNTLI<br>EKDEEHDRLIAQNQADIQTLENNVVEELFNLSGRLIDQEADIAKNNASIEELYDFDNEVAE<br>RIGEIHAYTEEVNKTLENLITNSVKNTDNIDKNKADIDNNINHIYELAQQQDQHSSDIKTL<br>KNNVEEGLLELSGHLIDQKADLTKDIKALESNVEEGLLDLSGRLLDQKADLTKDIKALESN<br>VEEGLLDLSGRLLDQKADIAQNQTDIQDLAAYNELQDQYAQKQTEAIDALNKASSENTQNI<br>EDLAAYNELQDAYAKQQTEAIDALNKASSENTQNIAKNQADIANNINNIYELAQQQDQHSS<br>DIKTLAKASAANTNRIATAELGIAENKKDAQIAKAQANANKTAIDENKASADTKFAATADA<br>ITKNGNAITKNAKSITDLGTKVDGFDGRVTALDTKVNAFDGRITALDSKVENGMAAQAALS<br>GLFQPYSVGKFNATAALGGYGSKSAVAIGAGYRVNPNLAFKAGAAINTSGNKKGSYNIGVN<br>YEF (613 amino acids) |
| American<br>O35E<br>(SEQ ID<br>NO: 50) | MKTMKLLPLKIAVTSAMIVGLGATSTVNAQVVEQFFPNIFFNENHDELDDAYHNMILGDTA<br>IVSNSQDNSTQLKFYSNDEDSVPDSLLFSKLLHEQQLNGFKAGDTIIPLDKDGKPVYTKDT<br>RTKDGKVETVYSVTTKIATQDDVEQSAYSRGIQGDIDDLYDINREVNEYLKATHDYNERQT<br>EAIDALNKASSANTDRIDTAEERIDKNEYDIKALESNVEEGLLELSGHLIDQKADLTKDIK<br>ALESNVEEGLLELSGHLIDQKADLTKDIKALESNVEEGLLDLSGRLLDQKADIAKNQADIA<br>QNQTDIQDLAAYNELQDAYAKQQTEAIDALNKASSENTQNIAKNQADIANNINNIYELAQQ<br>QDQHSSDIKTLAKASAANTDRIAKNKADADASFETLTKQNQTLIEKDKEHDKLITANKTAI<br>DANKASADTKFAATADAITKNGNAITKNAKSITDLGTKVDGFDGRVTALDTKVNALDTKVN<br>AFDGRITALDSKVENGMAAQAALSGLFQPYSVGKFNATAALGGYGSKSAVAIGAGYRVNPN<br>LAFKAGAAINTSGNKKGSYNIGVNYEF (576 amino acids) |
| American<br>SP12-6<br>(SEQ ID<br>NO: 51) | MKTMKLLPLKIAVTSAMMVGLGMASTANAQQQKSPKTEIFLPNLFDNDNTELTDPLYHNMI<br>LGNTALLTQENQYKFYADDGNGVPDSLLFNKILHDQLLHGFKEGDTIIPLDENGKPVYKLD<br>SIVEQGKTKTVYSVTTKTATADDVNSAYSRGIQGDIDDLYEANKENVNRLIEHGDKIFANE<br>ESVQYLNREVQNNIENIHELAQQQDQHSSDIKTLKKNVEKDLLDLSGRLIAQKEDIAQNQT<br>DIQDLATYNELQDQYAQKQTEAIDALNKASSENTQNIAKNSNHIKTLENNIEEGLLELSGH<br>LIDQKADLTKDIKALESNVEEGLLDLSGRLIDQKADIAQNQANIQDLAAYNELQDAYAKQQ<br>TEAIDALNKASSENTQNIEDLAAYNELQDAYAKQQTEAIDALNKASSENTQNIEDLAAYNE<br>LQDAYAKQQTEAIDALNKASSENTQNIAKNQADIANNINNIYELAQQQDQHSSDIKTLAKA<br>SAANTDRIAKNKADADASFETLTKQNQTLIEKDKEHDKLITANKTAIDANKASADTKFAAT<br>ADAITKNGNAITKNAKSITDLGTKVDGFDGRVTALDTKVNALDTKVNAFDGRITALDSKVE<br>NGMAAQAALSGLFQPYSVGKFNATAALGGYGSKSAVAIGAGYRVNPNLAFKAGAAINTSGN<br>KKGSYNIGVNYEF (684 amino acids) |
| American<br>SP12-5<br>(SEQ ID<br>NO: 52) | MKTMKLLPLKIAVTSAMIIGLGAASTANAQATETFLPNLFDNDYTETTDPLYHGMILGNTA<br>ITQDTQYKFYAENGNEVPDSLFFNKILHDQLLNGFKEGDTIIPLDENGKPVYKLDSITENG<br>VKRKVYSVTTKTATREDVEQSAYSRGIQGDIDDLYEANKENVNRLIEHGDKIFANEESVQY<br>LNKEVQNNIENIHELAQQQDQHSSDIKTLKKNVEEGLLELSGRLIAQKEDIAQNQTDIQDL<br>ATYNELQDQYAQKQTEAIDALNKASSENTQNIAKNSNHIKTLENNIEEGLLELSGHLIDQK<br>ADLTKDIKALESNVEEGLLDLSGRLLDQKADIAQNQTDIQDLAAYNELQDQYAQ<br>KQTEAIDALNKASSENTQNIEDLAAYNELQDAYAKQQTEAIDALNKASSENTQNIEDLAAY<br>NELQDAYAKQQTEAIDALNKASSENTQNIAKNQADIANNINNIYELAQQQDQHSSDIKTLA<br>KASAANTDRIAKNKADADASFETLTKQNQTLIEKDKEHDKLITANKTAIDANKASADTKFA<br>ATADAITKNGNAITKNAKSITDLGTKVDGFDGRVTALDTKVNALDTKVNAFDGRITALDSK<br>VENGMAAQAALSGLFQPYSVGKFNATAALGGYGSKSAVAIGAGYRVNPNLAFKAGAAINTS<br>GNKKGSYNIGVNYEF (686 amino acids) |
| Swedish<br>BC5<br>(SEQ ID<br>NO: 53) | MKTMKLLPLKIAVTSAMIIGLGAASTANAQAKNDITLEDLPYLIKKIDQNELEADIGDITALEK<br>YLALSQYGNILALEELNKALEELDEDVGWNQNDIANLEDDVETLTKNQNALAEQGEAIKEDLQG<br>LADFVEGQEGKILQNETSIKKNTQRNLVNGFEIEKNKDAIAKNNESIEDLYDFGHEVAESIGEI<br>HAHNEAQNETLKGLITNSIENTNNITKNKADIQALENNVVEELFNLSGRLIDQKADIDNNINNI<br>YELAQQQDQHSSDIKTLKKNVEEGLLELSGHLIDQKTDIAQNQANIQDLATYNELQDQYAQKQT<br>EAIDALNKASSENTQNIEDLAAYNELQDAYAKQQTEAIDALNKASSENTQNIEDLAAYNELQDA<br>YAKQQTEAIDALNKASSENTQNIAKNQADIANNINNIYELAQQQDQHSSDIKTLAKASAANTDR<br>IAKNKADADASFETLTKQNQTLIEKDKEHDKLITANKTAIDANKASADTKFAATADAITKNGNA<br>ITKNAKSITDLGTKVDGFDSRVTALDTKVNAFDGRITALDSKVENGMAAQAALSGLFQPYSVGK<br>FNATAALGGYGSKSAVAIGAGYRVNPNLAFKAGAAINTSGNKKGSYNIGVNYEF (630<br>amino acids) |
| American<br>7169<br>(SEQ ID<br>NO: 54) | MKTMKLLPLKIAVTSALIVGLGAASTANAQAQDRSLEQIQDKLANLVEKIEQAKSQNGQSQ<br>KDINQYLLLSQYANVLTMEELNNNVVKNSSSIETLDNDIAWLNDDLLDKEVGVLSRDIG<br>SLHDDVAQNQADIKTLKNNVEELFNLSDRLIDQEADIAQNNESIEDLYDFGREVAESIGE<br>IHAHNEAQNETLKDLITNSVKNTDNITKNKADIQALENDVGKELLNLSGRLIDQKADIDNN<br>INHIYELAQQQDQHSSDIKTLKNNVEEGLLELSGHLIDQKADLTKDIKALESNVEEGLLDL<br>SGRLLDQKADIAQNQANIQDLAAYNELQDAYAKQQTEAIDALNKASSENTQNIEDLAAYNE<br>LQDAYAKQQTEAIDALNKASSENTQNIAKNQADIANNINNIYELAQQQDQHSSDIKTLAKA |

TABLE 1-continued

UspA2 amino acid sequences from 38 strains of Moraxalla catarrhalis
(SEQ ID NO: 10 and SEQ ID NO: 22-SEQ ID NO: 58).

| Strain | UspA2 sequences |
|---|---|
| | SAANTDRIAKNKADADASFETLTKNQNTLIEKDKEHDKLITANKTAIDANKASADTKFAAT<br>ADAITKNGNAITKNAKSITDLGTKVDGFDSRVTALDTKVNAFDGRITALDSKVENGMAAQA<br>ALSGLFQPYSVGKFNATAALGGYGSKSAVAIGAGYRVNPNLAFKAGAAINTSGNKKGSYNI<br>GVNYEF (616 amino acids) |
| Finnish<br>FIN2344<br>(SEQ ID<br>NO: 55) | MKTMKLLPLKIAVTSAMIIGLGATSTVNAQVVEQFFPNIFFNENHDELDDAYHNMILGDTA<br>IVSNSQDNSTQLKFYSNDEDSVPDSLLFSKLLHEQQLNGFKAGDTIIPLDKDGKPVYTKDT<br>RTKDGKVETVYSVTTKIATQDDVEQSAYSRGIQGDIDDLYDINREVNEYLKATHDYNERQT<br>EAIDALNKASSANTDRIDTAEERIDKNEYDIKALESNVGKDLLDLSGRLIAQKEDIDNNIN<br>HIYELAQQQDQHSSDIKTLKNNVEEGLLELSGHLIDQKADLTKDIKTLESNVEEGLLDLSG<br>RLIDQKADIAQNQANIQDLAAYNELQDQYAQKQTEAIDALNKASSENTQNIEDLAAYNELQ<br>DAYAKQQTEAIDALNKASSENTQNIAKNQADIANNINNIYELAQQQDQHSSDIKTLAKVSA<br>ANTDRIAKNKADADASFETLTKNQNTLIEKDKEHDKLITANKTAIDANKASADTKFAATAD<br>AITKNGNAITKNAKSITDLGTKVDGFDGRVTALDTKVNAFDGRITALDSKVENGMAAQAAL<br>SGLFQPYSVGKFNATAALGGYGSKSAVAIGAGYRVNPNLAFKAGAAINTSGNKKGSYNIGV<br>NYEF (614 amino acids) |
| American<br>V1118<br>(SEQ ID<br>NO: 56) | MKTMKLPPLKIAVTSAMIIGLGAASTANAQTTETFLPNLFDNDYTETTDPLYHGMILGDTA<br>ITQDTQYKFYAENGNEVPDSLFFNKILHDQLLNGFKAGDTIIPLDENGKPVYKLDERTENG<br>VKRKVYSVTTKTATQADVEQSAYSRGIQGDIDDLYEANKENVNRLIEHGDKIFANEESVQY<br>LNREVQNNIENIHELAQQQDQHSSDIKTLKKNVEKDLLDLSGRLIAQKEDIAQNQTDIQDL<br>ATYNELQDQYAQKQTEAIDALNKASSENTQNIAKNSNHIKTLENNIEECLLELSGHLIDQK<br>ADLTKDIKALESNVEEGLLDLSGRLIDQKADIAQNQANIQDLAAYNELQDAYAKQQTEAID<br>ALNKASSENTQNIEDLAAYNELQDAYAKQQTEAIDALNKASSENTQNIEDLAAYNELQDAY<br>AKQQTEAIDALNKASSENTQNIAKNQADIANNINNIYELAQQQDQHSSDIKTLAKASAANT<br>DRIAKNKADADASFETLTKNQNTLIEKDKEHDKLITANKTAIDANKASADTKFAATADAIT<br>KNGNAITKNAKSITDLGTKVDGFDGRVTALDTKVNALDTKVNAFDGRITALDSKVENGMAA<br>QAALSGLFQPYSVGKFNATAALGYGSKSAVAIGAGYRVNPNLAFKAGAAINTSGNKKGSY<br>NIGVNYEF (679 amino acids) |
| American<br>V1145<br>(SEQ ID<br>NO: 57) | MKTMKLLPLKIAVTSALIVGLGAASTANAQETLEEVLESIKQINEQDLQDDIGYNSALDRY<br>LVLSQYGNLLIAKELNENVEKNSNSIAKNSNSIADLEADVGYLAENQNTLIEQNETINQEL<br>EGITHELESFIAYAHAQDQKNLVNEFEIEKNKDAIAKNNESIEDLYDFGHEVAESIGEIHA<br>YTEEVNKTLENLITNSVKNTDNITKNKADIQALESNVEKELLNLSGRLIDQKADIDNNINH<br>IYELAQQQDQHSSDIKTLKKNVEEGLLELSGHLIDQKSDIAQNQTDIQDLATYNELQDQYA<br>QKQTEAIDALNKASSENTQNIEDLAAYNELQDAYAKQQTEAIDALNKASSENTQNIEDLAA<br>YNELQDAYAKQQTEAIDALNKASSENTQNIEDLAAYNELQDAYAKQQTEAIDALNKASSEN<br>TQNIEDLAAYNELQDAYAKQQTEAIDALNKASSENTQNIEDLAAYNELQDAYAKQQTEAID<br>ALNKASSENTQNIAKNQADIANNINNIYELAQQQDQHSSDIKTLAKASAANTDRIAKNKAD<br>ADASFETLTKNQNTLIEKDKEHDKLITANKTAIDANKASADTKFAATADAITKNGNAITKN<br>AKSITDLGTKVDGFDSRVTALDTKVNAFDGRITALDSKVENGMAAQAALSGLFQPYSVGKF<br>NATAALGGYGSKSAVAIGAGYRVNPNLAFKAGAAINTSGNKKGSYNIGVNYEF (724<br>amino acids) |
| American<br>V1156<br>(SEQ ID<br>NO: 58) | MKTMKLLPLKIAVTSALIVGLGAASTANAQAQARDRSLEDIQALIGNIDVDKIRSQKQKNP<br>EIFQYLLLNQLSNTLITDELNNNVIKNTNSIETLDNDIAWLNDDLIDLDKEVGVLSRDIGS<br>LHDDVAQNQADIKTLENNVVEELFNLSDRLIDQEAEIAQNNESIEDLYDFGREVAESIGEI<br>HAHNEAQNETLKDLITNSVKNTDNIDKNKADIQALENNVEEGLLELSGHLIDQKADLTKDI<br>KALESNVEEGLLDLSGRLLDQKADIAKNQADIAQNQTDIQDLAAYNELQDQYAQKQTEAID<br>ALNKASSENTQNIEDLAAYNELQDAYAKQQTEAIDALNKASSENTQNIEDLAAYNELQDAY<br>AKQQTEAIDALNKASSENTQNIAKNQADIANNINNIYELAQQQDQHSSDIKTLAKVSAANT<br>DRIAKNKADADASFETLTKNQNTLIEKDKEHDKLITANKTAIDANKASADTKFAATADAIT<br>KNGNAITKNAKSITDLGTKVDGFDSRVTALDTKVNAFDGRITALDSKVENGMAAQAALSGL<br>FQPYSVGKFNATAALGGYGSKSAVAIGAGYRVNPNLAFKAGAAINTSGNKKGSYNIGVNYE<br>F (611 amino acids) |

UspA2 may be UspA2 from M. catarrhalis strain ATCC(a US registered trademark) 25238™, American 2933. American 2912, American 2908, Finnish 307, Finnish 353, Finnish 358, Finnish 216, Dutch H2, Dutch F10, Norwegian 1, Norwegian 13, Norwegian 20, Norwegian 25, Norwegian 27, Norwegian 36, BC5SV, Norwegian 14, Norwegian 3, Finish 414, Japanese Z7476, Belgium Z7530, German Z8063, American O12E, Greek MC317, American V1122, American P44, American V1171, American TTA24, American O35E, American SP12-6, American SP12-5, Swedish BC5, American 7169, Finnish FIN2344, American V1118, American V1145 or American V1156. UspA2 may be UspA2 as set forth in any of SEQ ID NO: 10 or SEQ ID NO: 22-SEQ ID NO: 38. UspA2 may be UspA2 from another source which corresponds to the sequence of UspA2 in any one of SEQ ID NO: 10 or SEQ ID NO: 22-SEQ ID NO: 58. Corresponding UspA2 sequences may be determined by one skilled in the art using various algorithms. For example, the Gap program or the Needle program may be used to determine UspA2 sequences corresponding to any one of SEQ ID NO: 10 or SEQ ID NO: 22-SEQ ID NO: 58.

UspA2 may be a sequence with at least 95% identity, over the entire length, to any of SEQ ID NO: 10 or SEQ ID NO: 22-SEQ ID NO: 58. In one embodiment, UspA2 may be a sequence as set forth in an amino acid sequence selected from the group consisting of SEQ ID NO: 10, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57 and SEQ ID NO: 58 or any subset of SEQ ID NO: 1 or SEQ ID NO. 22 through SEQ ID NO:58.

Immunogenic fragments of UspA2 comprise immunogenic fragments of at least 450 contiguous amino acids of SEQ ID NO: 1, 490 contiguous amino acids of SEQ ID NO: 10 (for example, the UspA2 fragment of MC-004 or MC-005), 511 contiguous amino acids of SEQ ID NO: 10 (for example, the UspA2 fragment of construct MC-001, MC-002, MC-003 or MC-004), 534 contiguous amino acids of SEQ ID NO: 10 (for example, the UspA2 fragment of MC-009 or MC-011) or 535 contiguous amino acids of SEQ ID NO: 10 (for example, the UspA2 fragment of MC-007, MC-008 or MC-010). The immunogenic fragments may elicit antibodies which can bind SEQ ID NO: 10.

Immunogenic fragments of UspA2 may comprise immunogenic fragments of at least 450, 490, 511, 534 or 535 contiguous amino acids of SEQ ID NO: 10. Immunogenic fragments of UspA2 may comprise immunogenic fragments of UspA2, for example any of the UspA2 constructs MC-001 (SEQ ID NO. 11), MC-002 (SEQ ID NO. 12), MC-003 (SEQ ID NO. 13), MC-004 (SEQ ID NO. 14), MC-005 (SEQ ID NO. 15), MC-006 (SEQ ID NO. 16), MC-007 (SEQ ID NO. 17), MC-008 (SEQ ID NO. 18), MC-009 (SEQ ID NO. 19), MC-010 (SEQ ID NO. 20) or MC-011 (SEQ ID NO. 21). The immunogenic fragments may elicit antibodies which can bind the full length sequence from which the fragment is derived.

In another aspect of the invention, the immunogenic composition comprises an immunogenic fragment of UspA2, suitably an isolated immunogenic polypeptide with at least 70%, 80%, 85%, 90%, 91%, 92%, 93%, 94%, 95%, 96%, 97%, 98%, 99%, or 100% to a polypeptide selected from the group consisting of MC-001 (SEQ ID NO. 11), MC-002 (SEQ ID NO. 12), MC-003 (SEQ ID NO. 13), MC-004 (SEQ ID NO. 14), MC-005 (SEQ ID NO. 15), MC-006 (SEQ ID NO. 16), MC-007 (SEQ ID NO. 17), MC-008 (SEQ ID NO. 18), MC-009 (SEQ ID NO. 19), MC-010 (SEQ ID NO. 20) or MC-011 (SEQ ID NO. 21) e.g. MC009 SEQ ID NO. 19 (corresponding to Seq ID No. 69 of WO2015/125118A1).

Immunogenicity of UspA2 polypeptides may be measured as described in WO2015/125118A1; the contents of which are incorporated herein by reference.

The immunogenic compositions of the present invention may comprise protein D, PE-PilA and UspA2 for example:
 PD 10 µg/PE-PilA (LVL735 construct, as described in WO2012/139225) 10 µg/UspA2 (MC009 construct, as described in WO2015125118) 10 µg/AS01$_E$
 PD 10 µg/PE-PilA (LVL735 construct, as described in WO2012/139225) 10 µg/UspA2 (MC009 construct, as described in WO2015125118) 3.3 µg/AS01$_E$ The above two specific immunogenic compositions were evaluated in a mouse *Moraxella catarrhalis* lung inflammation model in WO2015125118 (Example 14).

Dosage

The amount of the immunogenic composition which is required to achieve the desired therapeutic or biological effect will depend on a number of factors such as means of administration, the recipient and the type and severity of the condition being treated, and will be ultimately at the discretion of the attendant physician or veterinarian. The present invention provides an immunogenic composition comprising an immunogenic polypeptide from *Haemophilus influenzae* or an immunogenic fragment thereof and/or an immunogenic polypeptide from *Moraxella catarrhalis* or an immunogenic fragment thereof for use in the treatment or prevention of a recurrence of an acute exacerbation of chronic obstructive pulmonary disease (AECOPD) associated with a bacterial infection in a subject. In one embodiment, one or more previous exacerbations in the same subject were caused wholly or in part by *M. catarrhalis*. In a further embodiment, one or more previous exacerbations in the same subject were caused wholly or in part by *H. influenzae*. In general, a typical dose of the immunogenic polypeptide from *Moraxella catarrhalis* or an immunogenic fragment thereof may be expected to lie in the range of from about 0.001 mg-0.120 mg. More specifically, a typical dose in a human may lie in the range of from about 0.003 mg to about 0.03 mg of protein. In general, a typical dose of the immunogenic polypeptide from *H. influenzae* or an immunogenic fragment thereof may be expected to lie in the range of from about 0.005 mg to about 0.05 mg. This dose may be administered as a single unit dose. Several separate unit doses may also be administered. For example, separate unit doses may be administered as separate priming doses within the first year of life or as separate booster doses given at regular intervals (for example, every 1, 5 or 10 years).

In a further embodiment, two doses of an immunogenic composition according to the present invention are administered, optionally according to a 0, 2 month vaccination schedule, wherein the second dose is administered about two-months after the first dose (e.g. at the end of the second month or at the beginning or the third month, for example, the first dose on Day 1 and the second dose on Day 61).

Formulations and Adjuvants

Formulations comprising the immunogenic compositions of the invention may be adapted for administration by an appropriate route, for example, by the intramuscular, sublingual, transcutaneous, intradermal or intranasal route. In one embodiment, the immunogenic compositions of the present invention are administered intramuscularly. Such formulations may be prepared by any method known in the art.

The immunogenic compositions of the present invention may additionally comprise an adjuvant. When the term "adjuvant" is used in this specification, it refers to a substance that is administered in conjunction with the immunogenic composition to boost the patient's immune response to the immunogenic component of the composition.

Suitable adjuvants include an aluminum salt such as aluminum hydroxide gel or aluminum phosphate or alum, but may also be a salt of calcium, magnesium, iron or zinc, or may be an insoluble suspension of acylated tyrosine, or acylated sugars, cationically or anionically derivatized saccharides, or polyphosphazenes. In one embodiment, the protein may be adsorbed onto aluminium phosphate. In another embodiment, the protein may be adsorbed onto aluminium hydroxide. In a third embodiment, alum may be used as an adjuvant.

Suitable adjuvant systems which promote a predominantly Th1 response include: non-toxic derivatives of lipid A, Monophosphoryl lipid A (MPL) or a derivative thereof, particularly 3-de-O-acylated monophosphoryl lipid A (3D-MPL) (for its preparation see GB 2220211 A); and a combination of monophosphoryl lipid A, preferably 3-de-O-acylated monophosphoryl lipid A, together with either an aluminum salt (for instance aluminum phosphate or aluminum hydroxide) or an oil-in-water emulsion. In such combinations, antigen and 3D-MPL are contained in the same particulate structures, allowing for more efficient delivery of antigenic and immunostimulatory signals. Studies have shown that 3D-MPL is able to further enhance the immunogenicity of an alum-adsorbed antigen (Thoelen et al. Vaccine (1998) 16:708-14; EP 689454-B1).

AS01 is an Adjuvant System containing MPL (3-O-desacyl-4'-monophosphoryl lipid A), QS21 ((*Quillaja saponaria* Molina, fraction 21) Antigenics, New York, N.Y., USA) and liposomes. AS01B is an Adjuvant System containing MPL, QS21 and liposomes (50 µg MPL and 50 µg QS21). AS01E is an Adjuvant System containing MPL, QS21 and liposomes (25 µg MPL and 25 µg QS21). In one embodiment, the immunogenic composition or vaccine comprises AS01. In another embodiment, the immunogenic composition or vaccine comprises AS01B or AS01E. In a particular embodiment, the immunogenic composition or vaccine comprises AS01E.

AS02 is an Adjuvant System containing MPL and QS21 in an oil/water emulsion. AS02V is an Adjuvant System containing MPL and QS21 in an oil/water emulsion (50 µg MPL and 50 µg QS21).

AS03 is an Adjuvant System containing α-Tocopherol and squalene in an oil/water (o/w) emulsion. $AS03_A$ is an Adjuvant System containing α-Tocopherol and squalene in an o/w emulsion (11.86 mg tocopherol). $AS03_B$ is an Adjuvant System containing α-Tocopherol and squalene in an o/w emulsion (5.93 mg tocopherol). $AS03_C$ is an Adjuvant System containing α-Tocopherol and squalene in an o/w emulsion (2.97 mg tocopherol). In one embodiment, the immunogenic composition or vaccine comprises AS03.

AS04 is an Adjuvant System containing MPL (50 µg MPL) adsorbed on an aluminum salt (500 µg $Al^{3+}$). In one embodiment, the immunogenic composition or vaccine comprises AS04.

A system involving the use of QS21 and 3D-MPL is disclosed in WO 94/00153. A composition wherein the QS21 is quenched with cholesterol is disclosed in WO 96/33739. An additional adjuvant formulation involving QS21, 3D-MPL and tocopherol in an oil in water emulsion is described in WO 95/17210. In one embodiment the immunogenic composition additionally comprises a saponin, which may be QS21. The formulation may also comprise an oil in water emulsion and tocopherol (WO 95/17210). Unmethylated CpG containing oligonucleotides (WO 96/02555) and other immunomodulatory oligonucleotides (WO 0226757 and WO 03507822) are also preferential inducers of a TH1 response and are suitable for use in the present invention.

Additional adjuvants are those selected from the group of metal salts, oil in water emulsions, Toll like receptor agonists, (in particular Toll like receptor 2 agonist, Toll like receptor 3 agonist, Toll like receptor 4 agonist, Toll like receptor 7 agonist, Toll like receptor 8 agonist and Toll like receptor 9 agonist), saponins or combinations thereof.

Possible excipients include arginine, pluronic acid and/or polysorbate. In a preferred embodiment, polysorbate 80 (for example, TWEEN (a US registered trademark) 80) is used. In a further embodiment, a final concentration of about 0.03% to about 0.06% is used. Specifically, a final concentration of about 0.03%, 0.04%, 0.05% or 0.06% polysorbate 80 (w/v) may be used.

Thus, in one aspect of the invention, the immunogenic composition comprises a pharmaceutically acceptable excipient or carrier.

In another aspect of the invention, the immunogenic composition comprises an adjuvant, e.g. ASO1E.

The present invention provides a method for the treatment or prevention of exacerbations in chronic obstructive pulmonary disease. The exacerbation of COPD may be an acute exacerbation. The method comprises administering to a subject in need thereof a therapeutically effective amount of the immunogenic composition of the invention.

In an additional aspect, the present invention provides a method for the treatment or prevention of a condition or disease caused wholly or in part by *Moraxella catarrhalis* and/or *Haemophilus influenzae*.

EXAMPLES

Example 1: Lung Microbiome Analysis and Stochastic Modeling of COPD Exacerbations in the AERIS Study Chronic Obstructive Pulmonary Disease (COPD) is a chronic inflammatory disorder resulting in irreversible decline in lung function as a consequence of inhalation of tobacco smoke or other irritants (1). One of the difficulties in treating and managing COPD is the heterogeneity of this complex disease in terms of severity, progression, exercise tolerance, and nature of symptoms (2, 3). This complexity is also evident in acute exacerbations of COPD (AECOPD), which are transient and apparently stochastic periods of increased COPD symptoms requiring additional medical treatment and often hospitalization (4). Known subtypes of exacerbations are defined by the nature of key triggers including bacterial or viral infections, and/or high eosinophil levels, and these events are typically treated with a combination of antibiotics and steroids in a non-specific manner (5).

The lung microbiome represents an emerging opportunity to understand COPD heterogeneity and exacerbations. The healthy human lung contains a variety of commensal microbiota throughout the respiratory tract, and these bacteria can show substantial heterogeneity between individuals, across regions within the lung, and over time within an individual (6-8). Alterations in the taxonomic composition of the lung microbiome, known as dysbiosis, have been associated with multiple lung diseases and in particular may play a functional role in disease severity and exacerbations in COPD (6, 9).

Multiple studies have reported differences in the microbiome between healthy and disease states, differences correlated with COPD severity and associated with exacerbation states within an individual, and interactions between the microbiome and host immune response (7, 9-12). Notably, however, many lung microbiome studies have adopted a cross-sectional design which prevents a longitudinal examination of the microbiome to assess the stability of taxa and correlations with clinical traits monitored over long periods of time and covering multiple exacerbations.

The Acute Exacerbation and Respiratory InfectionS in COPD (AERIS) observational cohort study allows for a unique examination of the lung microbiome with a rich set of microbiology and clinical measurements longitudinally observed in stable time points and exacerbation events in 104 patients with COPD (a subset of the full cohort of 127 patients) (13).

Disclosed herein are data from the 16S rRNA sequencing analysis of the AERIS patient cohort. Through integrated analyses using the total AERIS dataset, the present inventors were able to explore the dynamics of the lung microbiome in COPD across multiple clinical visits and to determine the clinical associations of these changes in a deeply phenotyped cohort.

Methods

Study Design

The AERIS study (ClinicalTrials.gov: NCT01360398) was a prospective, observational cohort study based at University Hospital Southampton (UHS). The study protocol has been described in detail (13).

Processing of Sputum Samples

All study procedures for sputum sampling, the detection of exacerbations, and pathogen detection have been described previously (13). Briefly, patients were followed monthly in the stable state and reviewed within 72 hours of onset of AECOPD symptoms. Sputum samples were obtained by spontaneous expectoration or induced and were processed according to standard methods. COPD exacerbation subtypes were determined using previously-defined criteria (5).

16S rRNA Amplification and Sequencing

The V4 hypervariable region of the 16S rRNA gene was amplified with specific primers (515F/806R), including Illumina sequencing adapters and sample-specific barcodes, and sequenced on an Illumina MiSeq desktop sequencer. Sequence data are deposited in NCBI's Sequence Read Archive (PRJNA377739).

16S rRNA Sequence Analysis

Paired-end sequence reads were filtered for quality, assembled using PEAR (14), and then processed using the QIIME pipeline (15).

Statistical Analyses

Comparisons of bacterial taxonomic relative abundances and alpha diversities were performed with a linear mixed model controlling for gender, age, and repeated measures on the same subject within a group. Longitudinal comparisons of relative abundances between stable and exacerbations time points were performed with a paired t-test. Markov chain analysis was performed by counting transitions between adjacent exacerbations with the subtype of exacerbation classifying each state. Statistical analyses were performed using the 'R' language and environment (version 3.3.2).

Results

Population and Sampling

Samples for 16S rRNA sequencing were analyzed from 104 subjects with available sputum samples in the first year of the study (FIG. 1). Characteristics of the cohort used for microbiome analysis were similar to those of the full cohort (unpublished observations).

TABLE 2

Characteristics of the cohort for microbiome analysis

| Characteristic | N = 101 |
| --- | --- |
| Age (years) at enrolment, mean ± SD | 67.1 ± 8.4 |
| Female sex, n (%) | 42 (41.6%) |
| BMI at enrolment, mean ± SD | 27.6 ± 5.4 |
| Current smokers, n (%) | 40 (39.6%) |
| Medication for COPD, n (%) | 101 (100%) |
| Inhaled corticosteroids, n (%) | 94 (93.1%) |
| COPD status, GOLD stage, n (%) | |
| Mild | 0 (0%) |
| Moderate | 45 (44.6%) |
| Severe | 40 (39.6%) |
| Very severe | 16 (15.8%) |
| Bronchiectasis status, n (%) | 10 (9.9%) |
| Number of exacerbations experienced by subject in 12 months, n (%) | |
| One exacerbation | 31 (22.0%) |
| Two exacerbations | 23 (29.1%) |
| Three or more exacerbations | 47 (19.7%) |
| $FEV_1$ after bronchodilator use (% predicted), mean ± SD | 47.1 ± 12.8 |

Table abbreviations: N—number of subjects in the microbiome cohort, n—number of subjects corresponding to characteristic, SD—standard deviation, COPD—chronic obstructive pulmonary disease, GOLD—global initiative for chronic obstructive lung disease, FEV—forced expiratory volume in 1 second.

Lung Microbiome Composition in Stable State

An analysis of the relative abundances of bacterial taxa identified in the set of 584 microbiome samples passing quality control revealed bacteria commonly observed in the lung microbiome with Firmicutes, Proteobacteria, and Bacteroidetes representing the three most abundant phyla and *Veillonella, Haemophilus, Streptococcus, Prevotella*, and *Moraxella* representing the five most abundant genera. The number of successfully sequenced microbiome sputum samples averaged 5.7 per subject with 2.1 collected during an exacerbation. The relative abundances of Firmicutes and Bacteroides correlated with higher alpha diversity, while the abundance Proteobacteria had a negative correlation with other taxa and alpha diversity.

We first compared the composition and diversity of the lung microbiome to trends observed in previous studies. As described in other studies describing the lung microbiome in COPD, we observed a shift towards increasing Proteobacteria with increasing disease severity (16,17). More specifically this shift included a significant increase in *Haemophilus* (Proteobacteria) and decreases in *Prevotella* (Bacteroidetes) and *Veillonella* (Firmicutes), as well as decreased Shannon's entropy ($P_{adj}$<0.05 for each) with increasing disease severity (FIG. 2A).

Changes in the Lung Microbiome in Exacerbation States

Figure 2B:
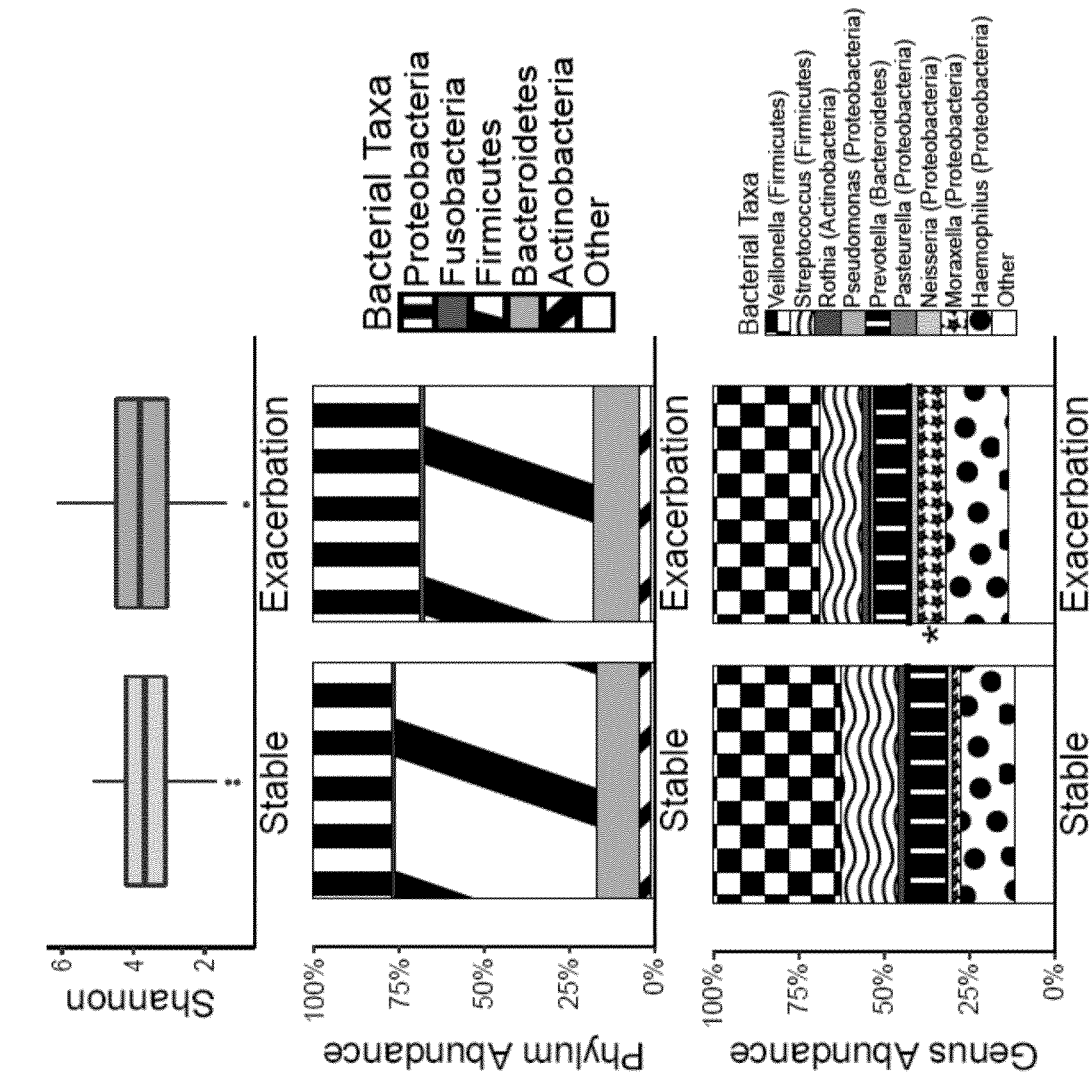
FIG. 2: Microbiome differences in disease severity and stable or exacerbation visits (A) The Shannon diversity index and relative abundances of bacteria labeled at the phylum and genus level of samples grouped by COPD disease severity. Significant differences in relative abundances between groups are labeled with arrows indicating the relative change in abundance; *$P<0.05$. (B) The same alpha diversity and relative abundances grouped by stable or exacerbation status. (C) Paired analysis of changes in relative abundances of key genera between matched stable and subsequent exacerbation events; *$P<0.05$.
Figure 2C:
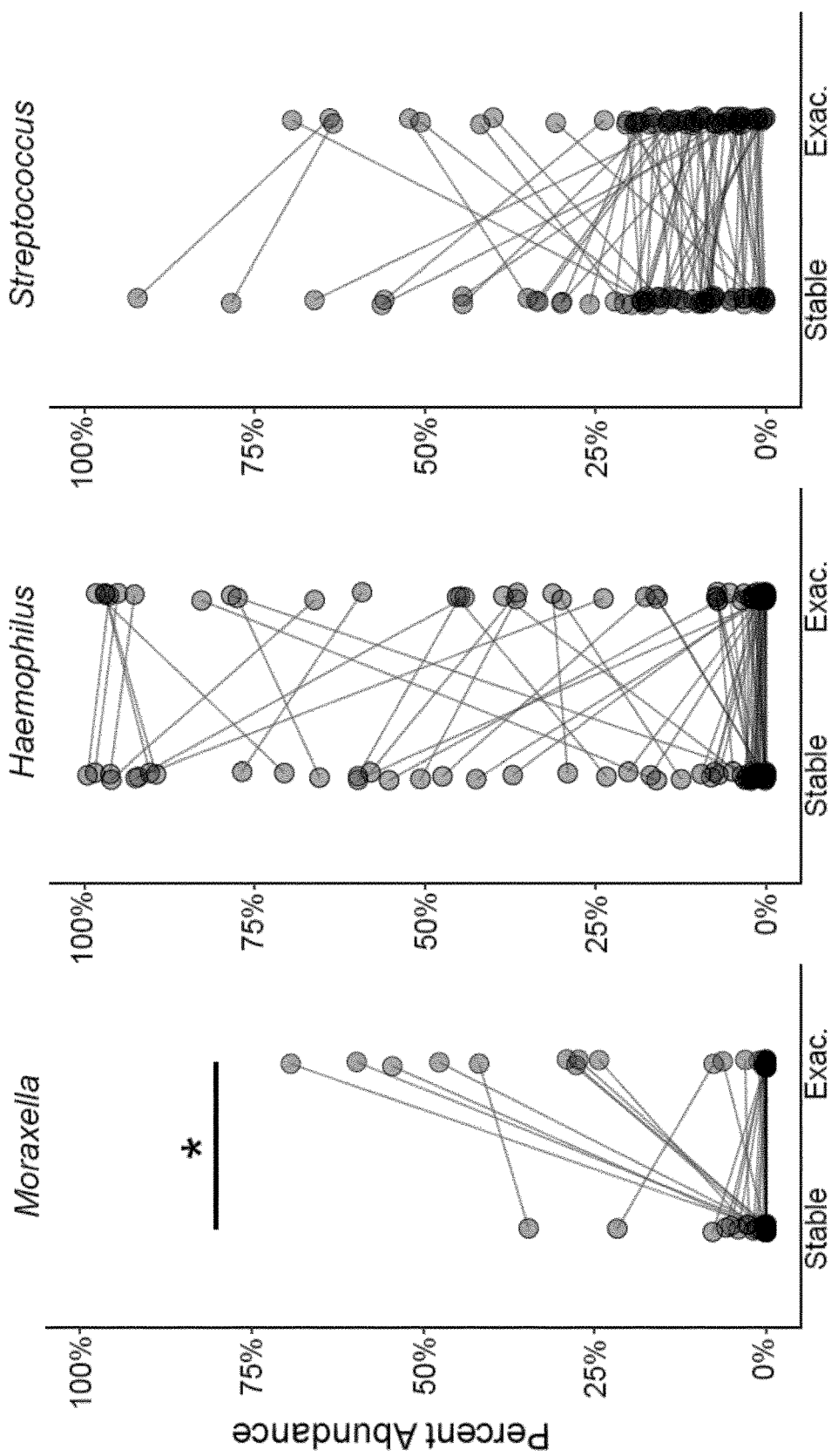

When comparing stable and exacerbation samples across all individuals, the differences were less pronounced than differences between disease severities, with no significant changes in alpha diversity measures or main taxa relative abundances with the exception of the genus *Moraxella* (Proteobacteria) which showed a significant increase in relative abundance in exacerbations (P=0.0134) (FIG. 2B). To confirm these results within longitudinally-sampled individuals we also used a paired t-test to compare matched stable and exacerbation events within an individual. Again, *Moraxella* showed a significant increase in exacerbation (P=0.0153) (FIG. 2C).

Clinical and microbiology data have been used as biomarkers to stratify subtypes of COPD and AECOPD (5) and some of these have revealed distinct lung microbiome profiles (9). We compared the composition of previously defined exacerbation subtypes characterized by sputum potentially-pathogenic bacterial culture, viral-PCR, or eosinophil percentage. The two most dissimilar exacerbation signatures were bacterial and eosinophilic. Another classification of COPD with a unique microbiome profile is that of bronchiectasis, where we observed a substantial increase in *Haemophilus* (P=1.2E-5) which was evident in both stable and exacerbation events.

Longitudinal Stability of the Lung Microbiome

Figure 3A:
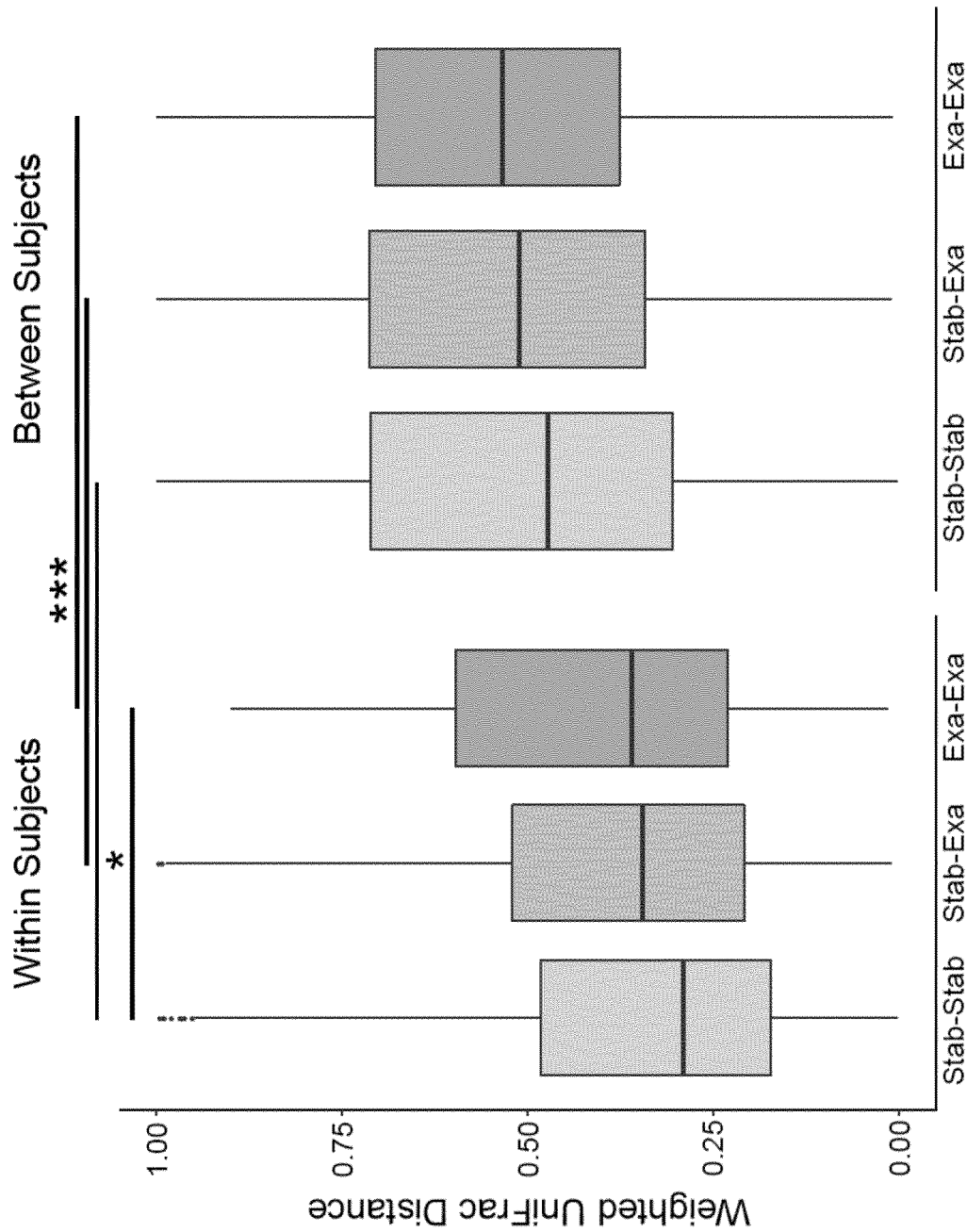
FIG. 3: Lung microbiome stability (A) Weighted UniFrac distances measured within and between subjects and comparing stable and exacerbation events; *$P<0.001$, $P<0.0001$. (B) Unweighted UniFrac distances measured within and between subjects and comparing stable and exacerbation events; **$P<0.0001$. (C) Weighted UniFrac distances for all within subject samples as a function of exacerbation frequency defined by number of exacerbation event and the fraction of samples within an individual taken during an exacerbation. (D) Paired weighted UniFrac distances between exacerbation sample and its previous stable sample from that subject. Exacerbation subtypes labelled as B-Bacterial, V-Viral, E-Eosinophilic, Other, or mixed, *$P<0.05$.
Figure 3B:
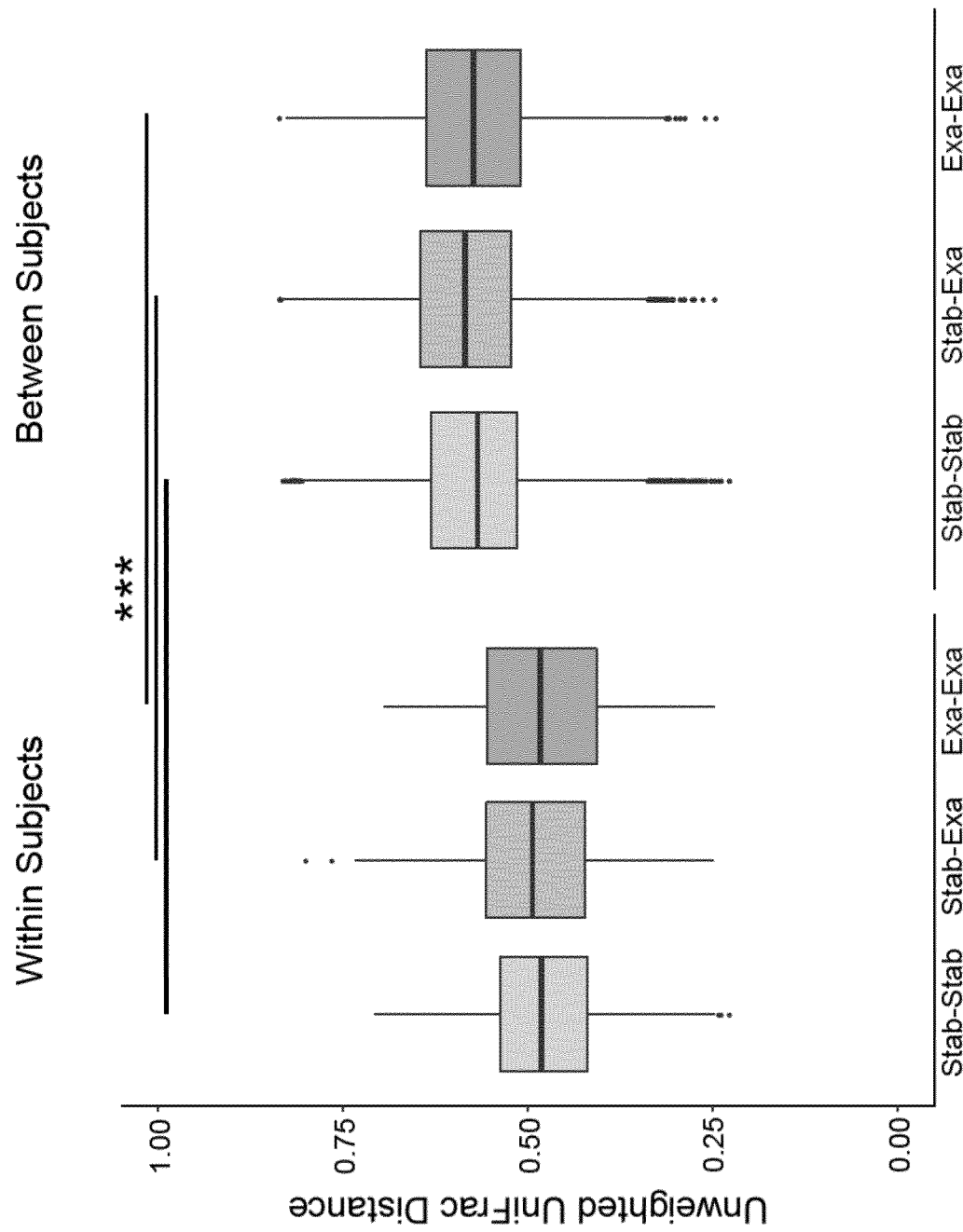

Intensive longitudinal sampling within the AERIS study allowed us to assess the relative stability of the lung microbiome within an individual. To analyze temporal microbiome stability, we computed UniFrac distance (weighted and unweighted) between all pairs of microbiome profiles within a subject, and stratified results based on comparisons between stable-stable, stable-exacerbation, and exacerbation-exacerbation comparisons. In all groups, we found UniFrac distance to be significantly lower within an individual compared to distances between individuals (FIG. 3A-B). This result suggests that individuals have somewhat distinct lung microbiomes from each other. Moreover, weighted UniFrac distances were significantly higher for stable-exacerbation and exacerbation-exacerbation comparisons relative to stable-stable comparisons (P<1.0E-3) (comparisons using unweighted UniFrac distance not significant) (FIG. 3B). This measure-specific result suggests that dysbiosis events in the lung may typically result from changes in the relative abundance of pre-existing bacteria (detected by weighted UniFrac) rather than complete removal or appearance of novel species (detected by unweighted UniFrac).

Figure 3C:
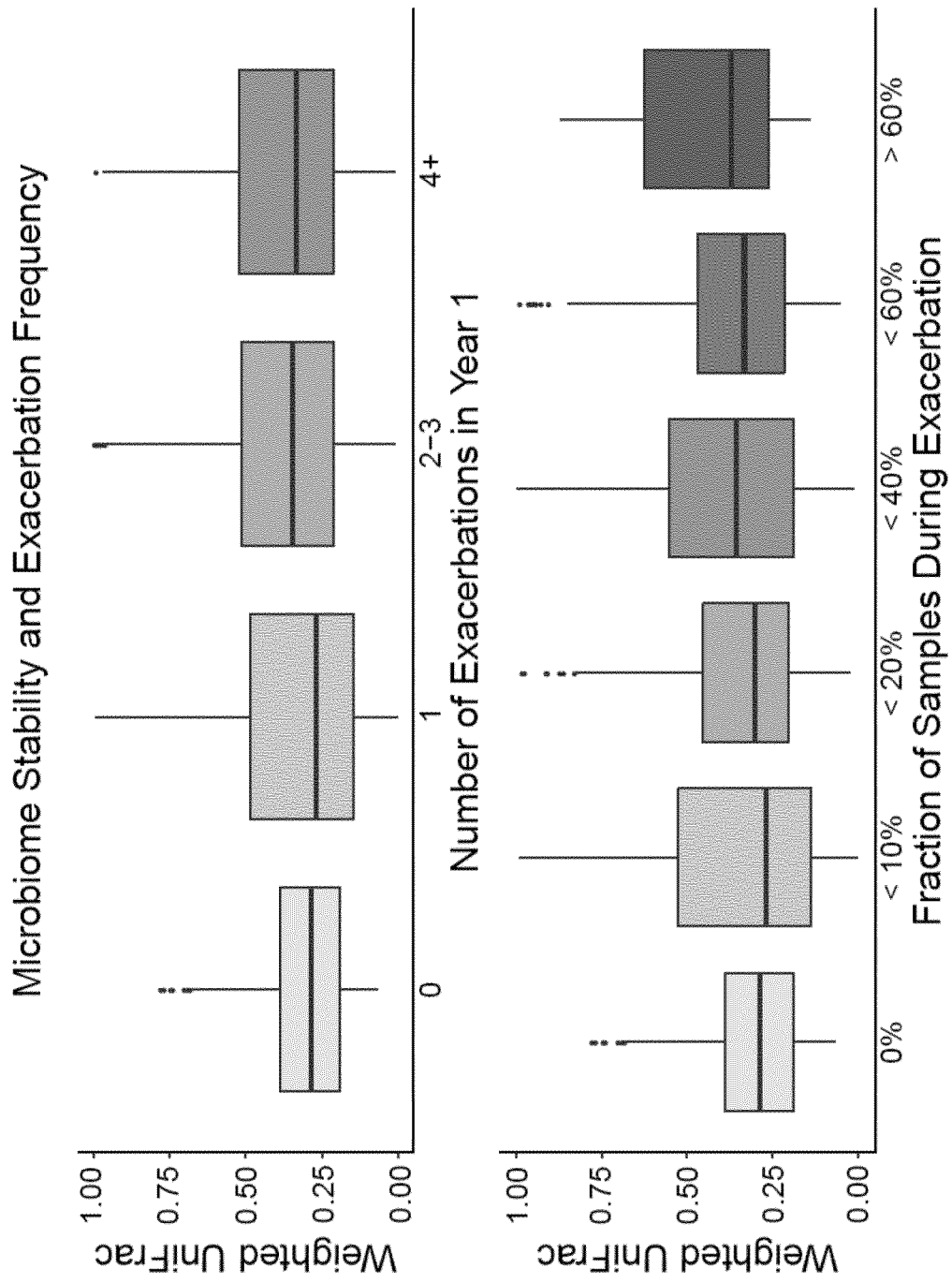

Moreover, given that weighted UniFrac distances involving exacerbations (stable-exacerbation and exacerbation-exacerbation) were higher than stable-stable, it appears exacerbation events are most likely to be associated with dysbiosis within an individual. While the lung microbiome may have a degree of within-subject stability, there remains a large degree of variation between longitudinal samples, especially when comparing an individual's exacerbation events. One possible explanation is that the frequency of exacerbation events experienced by an individual may contribute to destabilization of the lung microbiome, such that frequent exacerbators may be associated with greater dysbiosis than infrequent exacerbators. To evaluate this hypothesis, we analyzed an individual's UniFrac distance as a function of exacerbation frequency. Because of incomplete sampling of all exacerbation events, we conservatively estimated exacerbation frequency in two ways, by counting total reported exacerbation events and by the proportion of microbiome samples obtained from an exacerbation event relative to the total number of microbiome samples obtained for that individual. We found that the lung microbiome became more distinct with greater exacerbation frequency using either definition, affecting bacterial abundance in both stable and exacerbation states (P<1.0E-5, ANOVA) (FIG. 3C). To identify specific taxa associated with exacerbation frequency, we computed the correlation between each taxon's average abundance with exacerbation frequency across subjects. The genus with the highest positive correlation was *Moraxella* (R=0.23, P=0.016, Pearson), consistent with our observation of its increased abundance in exacerbations relative to stable states. In contrast, the genus *Lactobacillus* showed the strongest negative correlation with exacerbation frequency (R=-0.37, P=0.02, Pearson).

Figure 3D:
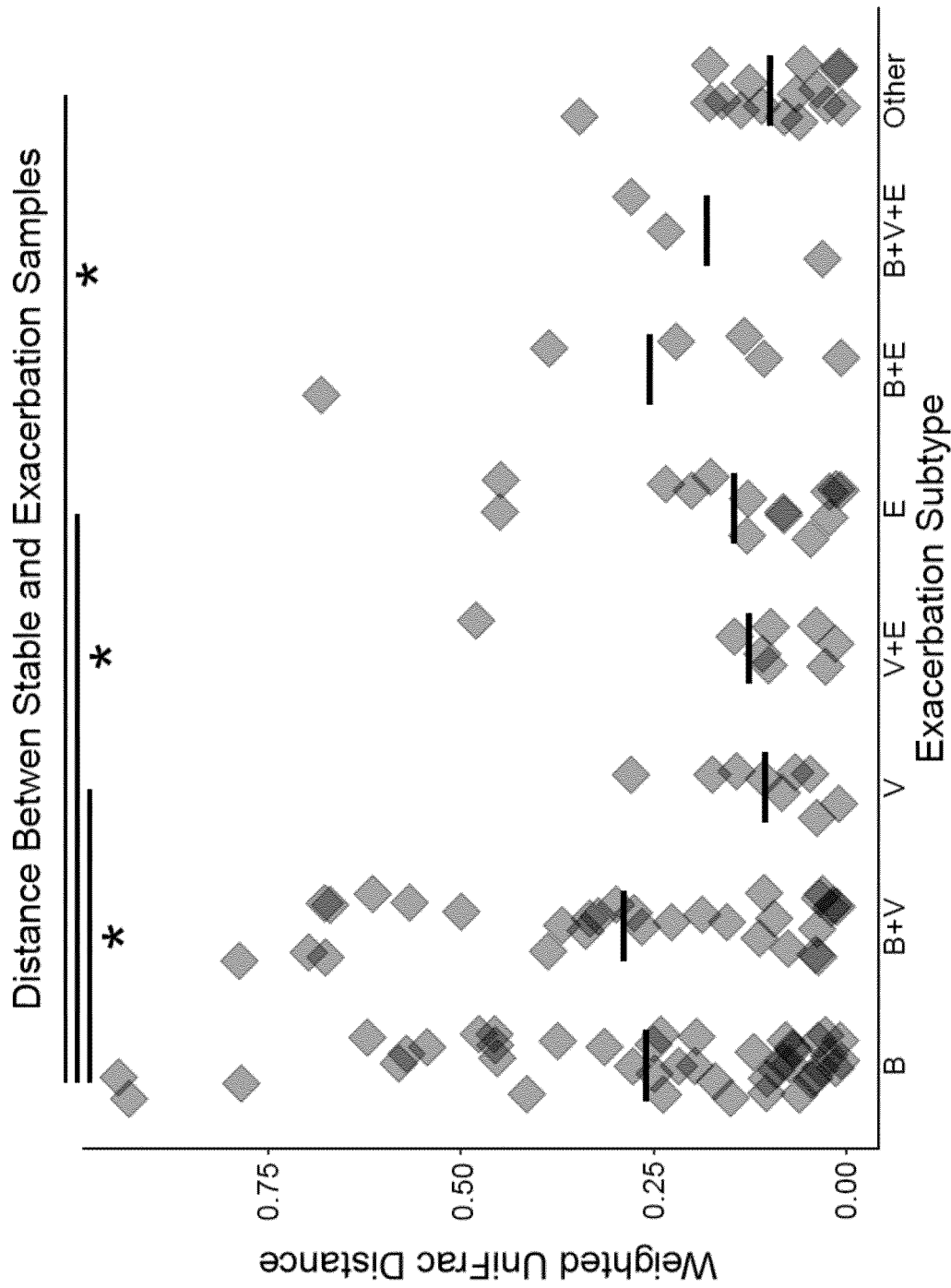

To test whether any of the AECOPD phenotypes are more likely to experience dysbiosis, we performed a paired analysis comparing the weighted UniFrac distance between each exacerbation type and its previous stable event. Exacerbations with a bacterial component had significantly higher distance compared to viral, eosinophilic, or other exacerbations (P<0.05 for each) (FIG. 3D). These results suggest that dysbiosis is more likely to occur in bacterial exacerbations compared to stable COPD; however, it is not a required characteristic, as many exacerbations show no detectable evidence of dysbiosis.

Stochastic Modeling of COPD Exacerbation Phenotypes

Having observed that some COPD exacerbation phenotypes had different lung microbiome profiles, we utilized the longitudinal attributes of the AERIS study to model the exacerbations experienced by an individual over time as a stochastic process. We employed a Markov chain analysis and defined each exacerbation event as a discrete state of being positive or negative for bacterial, viral, or eosinophilic status independently for each type (inclusive of mixed-type exacerbations). To estimate the state transition probabilities for each Markov model, we counted the number of exacerbations of a given phenotype which were chronologically followed by another exacerbation with the same phenotype (FIG. 4A). We found significantly non-random transition probabilities for the bacterial and eosinophilic Markov models with p-values of 9.25E-11 and 1.42E-3 (chi-square test, df=3), respectively. In contrast, the viral Markov model was not significant (P=0.141). These results indicate that for bacterial and eosinophilic exacerbations, the phenotype of the next exacerbation experienced by an individual may be more likely to repeat the prior exacerbation phenotype than expected by chance. Interestingly, we did not detect a significant difference in the times between exacerbations for any of the Markov transitions.

Next, a Markov model of bacterial exacerbation phenotype was built to examine the potential role of *Haemophilus influenzae* (Hi). Most of the *Haemophilus* observed from sputum is likely non-typeable *Haemophilus influenzae* (NTHi) a non-capsulated bacterium which commonly infects the airways and whose carriage is commonly associated with COPD and inflammation (12). In our analysis of microbiome profiles in different COPD phenotypes, *Haemophilus* was the dominant genus observed in patients with bronchiectasis, both in stable and exacerbation events. We hypothesized that patients with a positive Hi culture in a positive bacterial exacerbation may be even more likely to repeat an Hi-positive culture in their next exacerbation. The Markov chain of bacterial exacerbations was modified by dividing the bacterial-positive exacerbation state in two separate states of positive and negative Hi. After calculating the new transition probabilities, this Markov chain was non-random (P=1.42E-12, chi-square test, df=5) and the Hi-positive bacterial exacerbations were most likely to repeat a subsequent Hi-positive exacerbation and less likely to transition non-bacterial exacerbation compared to Hi-negative bacterial exacerbations (P=2.62E-4, Fisher's exact test) (FIG. 4B). The repetition of Hi-positive exacerbations suggests a persistence of *Haemophilus* in certain subtypes of COPD over time and observed through multiple exacerbations. We also expanded the Markov chain analysis of eosinophilic exacerbations by dividing the eosinophilic-positive state into high eosinophilic (>6% in sputum) and moderate eosinophilic (>3% and <6%) positive exacerbations (18). The revised model showed that the higher the eosinophil levels in the exacerbation the more likely it was to repeat the same high eosinophil phenotype (P=0.02, Fisher's exact test).

Discussion

This study has confirmed previous findings of lung microbiome heterogeneity with distinct patterns of bacterial abundance in COPD subtypes (9, 16-17) and for the first time described the stability of the lung microbiome in COPD and the non-random nature of exacerbations experienced by an individual over time. Our analysis shows that grouping samples by specific phenotypes could yield distinct microbiome populations or probabilities of repeating that type of exacerbation. These subtypes underscore the importance of sample size and stratification in generating reproducible results in studying the microbiome of a heterogeneous disease.

Utilizing the unique repeated longitudinal sampling of the AERIS study design, we found that the lung microbiome shows significantly less variation within an individual than between individuals, indicating some degree of temporal stability of an individual's lung microbiome. Nevertheless, we also observed large dysbiosis events within an individual. To characterize these dysbiotic events, we identified individuals with bacterial exacerbations as well as frequent exacerbations as more likely to experience significant changes in lung microbiome patterns. These findings will require further examination to determine the causes and consequences of lung dysbiosis. One appealing model is that lung microbiome composition can functionally drive host inflammatory signals via bacterial proteins or metabolites; specific examples have already been identified and models for their mechanism are being created and tested (9, 11, 19-20).

An appreciation of an individual's lung microbiome may influence the future clinician's choice of appropriate therapy, especially for exacerbations which are commonly treated with antibiotics. The increasing prevalence of recurrent Clostridium difficile infections after antibiotic use has highlighted the risks of disrupting the healthy microbiome when treating primary infections (21). Therefore a move towards selective-spectrum antimicrobials which may be less likely to disturb commensal species and hence minimize treatment-related risk of future infection or exacerbations needs to be explored. The relationship of NTHi with bronchiectasis and its association with repeating bacterial exacerbations may represent a unique treatment challenge. *Haemophilus* is known to produce biofilms (22) protecting it from the immune system and antibiotics, which may explain its persistence in these COPD subtypes and may offer another avenue for a therapeutic target. Biofilm formation is a component of antibiotic resistance in *Moraxella catarrhalis* and *Pseudomonas aeruginosa*, as well (23), indicating potentially common difficulties in eliminating pathogenic bacteria in the lung. The recurring motifs of key pathogenic bacteria such as *Moraxella* and NTHi identified in this and other COPD lung microbiome studies support the potential of a vaccine or targeted anti-bacterial drug against these pathogens in order to minimize a wider disruption of the lung microbiome.

The ability to model exacerbation phenotypes as stochastic processes has important implications for diagnosis and treatment of AECOPD if the phenotypes of future clinical events can be accurately predicted. Exacerbation events are typically diagnosed and treated as independent phenomena, as and when they are experienced by a patient with COPD (24). If clinical data from the previous exacerbation can inform the likely phenotype of the next event, it can enable a more rapid administration of the appropriate therapy (25). While bacterial and eosinophilic exacerbations are most likely to repeat the same phenotype in our Markov chain model, there is also evidence from other studies that viral infections may predispose the respiratory tract to subsequent secondary bacterial infections (26) indicating additional longitudinal relationships between the infections and colonization of viruses and bacteria.

REFERENCES (CITED IN EXAMPLE 1)

1. Vestbo J, Hurd S S, Agusti A G, Jones P W, Vogelmeier C, Anzueto A, Barnes B J, Fabbri L M, Martinez F J, Nishimura M, Stockley R A, Sin D D, Rodriguez-Roisin R. Global strategy for the diagnosis, management, and prevention of chronic obstructive pulmonary disease: GOLD executive summary. *Am J Respir Crit Care Med* 2013; 187:347-365.

2. Roca J, Vargas C, Cano I, Selivanov V, Barreiro E, Maier D, Falciani F, Wagner P, Cascante M, Garcia-Aymerich J, Kalko S, De Mas I, Tegner J, Escarrabill J, Agusti A, Gomez-Cabrero D; Synergy-COPD consortium. Chronic obstructive pulmonary disease heterogeneity: challenges for health risk assessment, stratification and management. *J Trans Med* 2014; 12:53.

3. Agusti A, Calverley P M, Celli B, Coxson H O, Edwards L D, Lomas D A, MacNee W, Miller B E, Rennard S, Silverman E K, Tal-Singer R, Wouters E, Yates J C, Vestbo J; Evaluation of COPD Longitudinally to Identify Predictive Surrogate Endpoints (ECLIPSE) investigators. Characterization of COPD heterogeneity in the ECLIPSE cohort. *Respir Res* 2010; 11:122.

4. Sethi S, Murphy T F. Infection in the pathogenesis and course of chronic obstructive pulmonary disease. *N Eng J Med* 2008; 359: 2355-65.

5. Bafadhel M, McKenna S, Terry S, Mistry V, Reid C, Haldar P, Kebadze T, Duvoix A, Lindblad K, Patel H, Rugman P, Dodson P, Jenkins M, Saunders M, Newbold P, Green R H, Venge P, Lomas D A, Barer M R, Johnston S L, Pavord I D, Brightling C E. Acute exacerbations of chronic obstructive pulmonary disease: identification of biological clusters and their biomarkers. *Am J Respir Crit Care Med* 2011; 184:662-671.

6. Dickson R P, Erb-Downward J R, Martinez F J, Huffnagle G B. The Microbiome and the respiratory tract. *Annu Rev Physiol* 2016; 78:481-504.

7. Erb-Downward J R, Thompson D L, Han M K, Freeman C M, McCloskey L, Schmidt, L A, Young V B, Toews G B, Curtis J L, Sundaram B, Martinez E J, Huffnagle G B. Analysis of the lung microbiome in the "healthy" smoker and in COPD. *PloS One* 2011; 6:e16384.

8. Dickson R P, Erb-Downward J R, Huffnagle G B. The role of the bacterial microbiome in lung disease. *Expert Rev of Respir Med* 2013; 7:245-257.

9. Wang Z, Bafadhel M, Haldar K, Spivak A, Mayhew D, Miller B E, Tal-Singer R, Johnston S L, Ramsheh M Y, Barer M R, Brightling C E, Brown J R. Lung microbiome dynamics in COPD exacerbations. *Eur Resp J*2016; 47:1082-1092.

10. Sze M A, Dimitriu P A, Hayashi S, Elliott W M, McDonough J E, Gosselink J V, Cooper J, Sin D D, Mohn W W, Hogg J C. The lung tissue microbiome in chronic obstructive pulmonary disease. *Am J Respir Crit Care Med* 2012; 185:1073-1080.

11. Yadava K, Pattaroni C, Sichelstiel A K, Trompette A, Gollwitzer E S, Salami O, von Garnier C, Nicod L P, Marsland B J. Microbiota promotes chronic pulmonary inflammation by enhancing IL-17A and autoantibodies. *Am J Respir Crit Care Med* 2016; 193:975-987.

12. Staples K, Taylor S, Thomas S, Leung S, Cox K, Pascal T G, Ostridge K, Welch L, Tuck A C, Clarke S C, Gorringe A, Wilkinson T M. Relationships between mucosal antibodies, non-typeable *Haemophilus influenzae* (NTHi) infection and airway inflammation in COPD. *PLoS One* 2016; 11; e0167250.

13. Bourne S, Cohet C, Kim V, Barton A, Tuck A, Aris E, Mesia-Vela S, Devaster J M, Ballou W R, Clarke S C, Wilkinson T. Acute Exacerbation and Respiratory InfectionS in COPD (AERIS): protocol for a prospective, observational cohort study. *BMJ Open* 2014; 4:e004546.

14. Zhang J, Kobert K, Flouri T, Stamatakis A. PEAR: a fast and accurate Illumina Paired-End reAd mergeR. *Bioinformatics* 2014; 30:614-620.

15. Caporaso J G, Kuczynski J, Stombaugh J, Bittenger K, Bushman F D, Costello E K, Fierer N, Pena A G, Goodrich J K, Gordon J I, Hutley G A, Kelley S T, Knights D, Koenig J E, Ley R E, Lozupone C A, McDonald D, Muegge B D, Pirrung M, Reeder J, Sevinsky J R, Turnbaugh P J, Walters W A, Widmann J, Yatsunenko T, Zaneveld J, Knight R. QIIME allows analysis of high-throughput community sequencing data. *Nat Meth* 2010; 7:335-336.

16. Galiana A, Aguirre E, Rodriguez J C, Mira A, Santibanez M, Candela I, Llavero J, Garcinuno P, Lopez F, Ruiz M, Garcia-Pachon E, Royo G. Sputum microbiota in moderate versus severe patients with COPD. *Eur Respir J* 2014; 43:1787-1790.

17. Garcia-Nuñez M, Millares L, Pomares X, Ferrari R, Perez-Brocal V, Gallego M, Espasa M, Moya A, Monso, E. Severity-related changes of bronchial microbiome in chronic obstructive pulmonary disease. *J Clin Microbiol* 2014; 52:4217-4223.

18. Pascoe S, Locanture N, Dransfield M T, Barnes N C, Pavord I D. Blood eosinophil counts, exacerbations, and response to the addition of inhaled fluticasone furoate to vilanterol in patients with chronic obstructructive pulmonary disease: a secondary analysis of data from two parallel randomised controlled trials. *Lancet Respir Med* 2015; 3:435-442.

19. Sze M A, Dimitriu P A, Suzuki M, McDonough J E, Campbell J D, Brothers J F, Erb-Downward J R, Huffnagle G B, Hayashi S, Elliott W M, Cooper J, Sin D D, Lenburg M E, Spira A, Mohn W W, Hogg J C. Host response to the lung microbiome in chronic obstructive pulmonary disease. *Am J Respir Crit Care Med* 2015; 192:438-445.

20. Avgousti D C, Herrmann C, Kulej K, Pancholi N J, Sekulic N, Petrescu J, Molden R C, Blumenthal D, Paris A J, Reyes E D, Ostapchuck P, Hearing P, Seeholzer S H, Worthen G S, Black B E, Garcia B A, Weitzman M D. A core viral protein binds host nucleosomes to sequester immune danger signals. *Nature* 2016; 535:173-177.

21. Buffie C G, Bucci V, Stein R R, McKenney P T, Ling L, Gobourne A, No D, Liu H, Kinnebrew M, Viale A, Littman E, van den Brink M R, Jenq R R, Taur Y, Sander C, Cross J R, Toussaint N C, Xavier J B, Pamer E G. Precision microbiome reconstitution restores bile acid mediated resistance to Clostridium difficile. *Nature* 2015:517; 205-208.

22. Murphy T F, Kirkham C. Biofilm formation by nontypeable *Haemophilus influenzae*: strain variability, outer membrane antigen expression and role of pili. *BMC Microbiol* 2002; 2:7.

23. Kyd J M, McGrath J, Krishnamurthy A. Mechanisms of bacterial resistance to antibiotics in infections of COPD patients. *Curr Drug Targets* 2011; 12:521-530.

24. Hillas G, Perlikos F, Tzanakis N. Acute exacerbation of COPD: is it the "stroke of the lungs"?. *Int J Chron Obstruct Pulmon Dis* 2016; 13:1579-1586.

25. Woodruff P G, Agusti A, Roche N, Singh D, Martinez F J. Current concepts in targeting chronic obstructive pulmonary disease pharmacotherapy: making progress towards personalized management. *Lancet* 2015; 385:1789-1798.

26. Bellinghausen C, Rohde G G, Savelkoul P H, Wouters E F, Stassen F R. Viral-bacterial interactions in the respiratory tract. *J Gen Virol* 2016; 97:3089-3102.

SEQUENCES:

SEQ ID NO 1: Protein D (364 amino acids)
MetLysLeuLysThrLeuAlaLeuSerLeuLeuAlaAlaGlyValLeuAlaGly
CysSerSerHisSerSerAsnMetAlaAsnThrGlnMetLysSerAspLysIle
IleIleAlaHisArgGlyAlaSerGlyTyrLeuProGluHisThrLeuGluSerLysAla
LeuAlaPheAlaGlnGlnAlaAspTyrLeuGluGlnAspLeuAlaMetThrLysAspGly
ArgLeuValValIleHisAspHisPheLeuAspGlyLeuThrAspValAlaLysLysPhe
ProHisArgHisArgLysAspGlyArgTyrTyrValIleAspPheThrLeuLysGluIle
GlnSerLeuGluMetThrGluAsnPheGluThrLysAspGlyLysGlnAlaGlnValTyr
ProAsnArgPheProLeuTrpLysSerHisPheArgIleHisThrPheGluAspGluIle
GluPheIleGlnGlyLeuGluLysSerThrGlyLysLysValGlyIleTyrProGluIle
LysAlaProTrpPheHisHisGlnAsnGlyLysAspIleAlaAlaGluThrLeuLysVal
LeuLysLysTyrGlyTyrAspLysLysThrAspMetValTyrLeuGlnThrPheAspPhe
AsnGluLeuLysArgIleLysThrGluLeuLeuProGlnMetGlyMetAspLeuLysLeu
ValGlnLeuIleAlaTyrThrAspTrpLysGluThrGlnGluLysAspProLysGlyTyr
TrpValAsnTyrAsnTyrAspTrpMetPheLysProGlyAlaMetAlaGluValValLys
TyrAlaAspGlyValGlyProGlyTrpTyrMetLeuValAsnLysGluGluSerLysPro
AspAsnIleValTyrThrProLeuValLysGluLeuAlaGlnTyrAsnValGluValHis
ProTyrThrValArgLysAspAlaLeuProGluPhePheThrAspValAsnGlnMetTyr
AspAlaLeuLeuAsnLysSerGlyAlaThrGlyValPheThrAspPheProAspThrGly
ValGluPheLeuLysGlyIleLys SEQ ID NO. 2: Protein D fragment with MDP tripeptide from NS1 (348 amino acids)
MetAspProSerSerHisSerSerAsnMetAlaAsnThrGlnMetLysSerAspLysIle
IleIleAlaHisArgGlyAlaSerGlyTyrLeuProGluHisThrLeuGluSerLysAla
LeuAlaPheAlaGlnGlnAlaAspTyrLeuGluGlnAspLeuAlaMetThrLysAspGly
ArgLeuValValIleHisAspHisPheLeuAspGlyLeuThrAspValAlaLysLysPhe
ProHisArgHisArgLysAspGlyArgTyrTyrValIleAspPheThrLeuLysGluIle
GlnSerLeuGluMetThrGluAsnPheGluThrLysAspGlyLysGlnAlaGlnValTyr
ProAsnArgPheProLeuTrpLysSerHisPheArgIleHisThrPheGluAspGluIle
GluPheIleGlnGlyLeuGluLysSerThrGlyLysLysValGlyIleTyrProGluIle
LysAlaProTrpPheHisHisGlnAsnGlyLysAspIleAlaAlaGluThrLeuLysVal
LeuLysLysTyrGlyTyrAspLysLysThrAspMetValTyrLeuGlnThrPheAspPhe
AsnGluLeuLysArgIleLysThrGluLeuLeuProGlnMetGlyMetAspLeuLysLeu
ValGlnLeuIleAlaTyrThrAspTrpLysGluThrGlnGluLysAspProLysGlyTyr
TrpValAsnTyrAsnTyrAspTrpMetPheLysProGlyAlaMetAlaGluValValLys
TyrAlaAspGlyValGlyProGlyTrpTyrMetLeuValAsnLysGluGluSerLysPro
AspAsnIleValTyrThrProLeuValLysGluLeuAlaGlnTyrAsnValGluValHis
ProTyrThrValArgLysAspAlaLeuProGluPhePheThrAspValAsnGlnMetTyr

SEQUENCES:

AspAlaLeuLeuAsnLysSerGlyAlaThrGlyValPheThrAspPheProAspThrGly
ValGluPheLeuLysGlyIleLys

SEQ ID NO. 3: SerSerHisSerSerAsnMetAlaAsnThr

SEQ ID NO. 4: Protein E from *H. influenzae*
MKKIILTLSL GLLTACSAQI QKAEQNDVKL APPTDVRSGY IRLVKNVNYY IDSESIWVDN QEPQIVH FDA
WNLDKGLYV YPEPKRYARS VRQYKILNCA NYHLTQVRTD FYDEFWGQGL RAAPKKQKKH
TLSLTPDTTL YNAAQIICAN YGEAFSVDKK SEQ ID NO. 5: Amino acids 20-160 of Protein E
I QKAEQNDVKL APPTDVRSGY IRLVKNVNYY IDSESIWVDN QEPQIVHFDA VVNLDKGLYV
YPEPKRYARS VRQYKILNCA NYHLTQVRTD FYDEFWGQGL RAAPKKQKKH TLSLTPDTTL YNAAQIICAN
YGEAFSVDKK SEQ ID NO. 6 PilA from H. influenzae
MKLTTQQTLK KGFTLIELMI VIAIIAILAT IAIPSYQNYT KKAAVSELLQ ASAPYKADVE LCVYSTNETT
NCTGGKNGIA ADITTAKGYV KSVTTSNGAI TVKGDGTLAN MEYILQATGN AATGVTWTTT
CKGTDASLFP ANFCGSVTQ SEQ ID NO. 7 Amino acids 40-149 of PilA from *H. influenzae* strain 86-028NP
T KKAAVSELLQ ASAPYKADVE LCVYSTNETT NCTGGKNGIA ADITTAKGYV KSVTTSNGAI
TVKGDGTLAN MEYILQATGN AATGVTWTTT CKGTDASLFP ANFCGSVTQ SEQ ID NO. 8: LVL735 (protein): (pelB sp)(ProtE aa 20-160)(GG)(PilA aa40-149)
MKYLLPTAAA GLLLLAAQPA MAIQKAEQND VKLAPPTDVR SGYIRLVKNV NYYIDSESIW
VDNQEPQIVH FDAVVNLDKG LYVYPEPKRY ARSVRQYKIL NCANYHLTQV RTDFYDEFWG
QGLRAAPKKQ KKHTLSLTPD TTLYNAAQII CANYGEAFSV DKKGGTKKAA VSELLQASAP
YKADVELCVY STNETTNCTG GKNGIAADIT TAKGYVKSVT TSNGAITVKG DGTLANMEYI LQATGNAATG
VTWTTTCKGT DASLFPANFC GSVTQ SEQ ID NO. 9: PE-PilA fusion protein without signal peptide
IQKAEQND VKLAPPTDVR SGYIRLVKNV NYYIDSESIW VDNQEPQIVH FDAVVNLDKG
LYVYPEPKRY ARSVRQYKIL NCANYHLTQV RTDFYDEFWG QGLRAAPKKQ KKHTLSLTPD TTLYNAAQII
CANYGEAFSV DKKGGTKKAA VSELLQASAP YKADVELCVY STNETTNCTG GKNGIAADIT TAKGYVKSVT
TSNGAITVKG DGTLANMEYI LQATGNAATG VTWTTTCKGT DASLFPANFC GSVTQ SEQ ID NO. 11: MC-001 (protein)-(M)(UspA2 amino acids 30-540)(ASHHHHHH)
MQAKNDITLEDLPYLIKKIDQNELEADIGDITALEKYLALSQYGNILALEELNKALEELDEDVGWNQNDIANLE
DDVETLTKNQNALAEQGEAIKEDLQGLADFVEGQEGKILQNETSIKKNTQRNLVNGFEIEKNKDAIAKNNESI
EDLYDFGHEVAESIGEIHAHNEAQNETLKGLITNSIENTNNITKNKADIQALENNVVEELFNLSGRLIDQKADI
DNNINNIYELAQQQDQHSSDIKTLKKNVEEGLLELSGHLIDQKTDIAQNQANIQDLATYNELQDQYAQKQTE
AIDALNKASSENTQNIEDLAAYNELQDAYAKQQTEAIDALNKASSENTQNIEDLAAYNELQDAYAKQQTEAI
DALNKASSENTQNIAKNQADIANNINNIYELAQQQDQHSSDIKTLAKASAANTDRIAKNKADADASFETLTK
NQNTLIEKDKEHDKLITANKTAIDANIKASADTKFAATADAITKNGNAITKNAKSITDLGTKVDGFDSRVTALD
TKASHHHHHH SEQ ID NO. 12 MC-002 (Protein)-(M)(UspA2 amino acids 30-540)
MQAKNDITLEDLPYLIKKIDQNELEADIGDITALEKYLALSQYGNILALEELNKALEELDEDVGWNQNDIANLE
DDVETLTKNQNALAEQGEAIKEDLQGLADFVEGQEGKILQNETSIKKNTQRNLVNGFEIEKNKDAIAKNNESI
EDLYDFGHEVAESIGEIHAHNEAQNETLKGLITNSIENTNNITKNKADIQALENNVVEELFNLSGRLIDQKADI
DNNINNIYELAQQQDQHSSDIKTLKKNVEEGLLELSGHLIDQKTDIAQNQANIQDLATYNELQDQYAQKQTE
AIDALNKASSENTQNIEDLAAYNELQD
AYAKQQTEAIDALNKASSENTQNIEDLAAYNELQDAYAKQQTEAIDALNKASSENTQNIAKNQADIANNINN
IYELAQQQDQHSSDIKTLAKASAANTDRIAKNKADADASFETLTKNQNTLIEKDKEHDKLITANKTAIDANKA
SADTKFAATADAITKNGNAITKNAKSITDLGTKVDGFDSRVTALDTK SEQ ID NO. 13 MC-003 (Protein)-(M)(UspA2 amino acids 30-540)(H)
MQAKNDITLEDLPYLIKKIDQNELEADIGDITALEKYLALSQYGNILALEELNKALEELDEDVGWNQNDIANLE
DDVETLTKNQNALAEQGEAIKEDLQGLADFVEGQEGKILQNETSIKKNTQRNLVNGFEIEKNKDAIAKNNESI
EDLYDFGHEVAESIGEIHAHNEAQNETLKGLITNSIENTNNITKNKADIQALENNVVEELFNLSGRLIDQKADI
DNNINNIYELAQQQDQHSSDIKTLKKNVEEGLLELSGHLIDQKTDIAQNQANIQDLATYNELQDQYAQKQTE
AIDALNKASSENTQNIEDLAAYNELQDAYAKQQTEAIDALNKASSENTQNIEDLAAYNELQDAYAKQQTEAI
DALNKASSENTQNIAKNQADIANNINNIYELAQQQDQHSSDIKTLAKASAANTDRIAKNKADADASFETLTK
NQNTLIEKDKEHDKLITANKTAIDANKASADTKFAATADAITKNGNAITKNAKSITDLGTKVDGFDSRVTALD
TKH SEQ ID NO. 14 MC-004 (Protein)-(M)(UspA2 amino acids 30-540)(HH)
MQAKNDITLEDLPYLIKKIDQNELEADIGDITALEKYLALSQYGNILALEELNKALEELDEDVGWNQNDIANLE
DDVETLTKNQNALAEQGEAIKEDLQGLADFVEGQEGKILQNETSIKKNTQRNLVNGFEIEKNKDAIAKNNESI
EDLYDFGHEVAESIGEIHAHNEAQNETLKGLITNSIENTNNITKNKADIQALENNVVEELFNLSGRLIDQKADI
DNNINNIYELAQQQDQHSSDIKTLKKNVEEGLLELSGHLIDQKTDIAQNQANIQDLATYNELQDQYAQKQTE
ATDALNKASSENTQNIEDLAAYNELQDAYAKQQTEAIDALNKASSENTQNIEDLAAYNELQDAYAKQQTEAI
DALNKASSENTQNIAKNQADIANNINNIYELAQQQDQHSSDIKTLAKASAANTDRIAKNKADADASFETLTK
NQNTLIEKDKEHDKLITANKTAIDANKASADTKFAATADAITKNGNAITKNAKSITDLGTKVDGFDSRVTALD
TKHH

SEQUENCES:

SEQ ID NO. 15 MC-005 (Protein)-(M)(UspA2 amino acids 30-519)(ASHHHHHH)
MQAKNDITLEDLPYLIKKIDQNELEADIGDITALEKYLALSQYGNILALEELNKALEELDEDVGWNQNDIANLE
DDVETLTKNQNALAEQGEAIKEDLQGLADFVEGQEGKILQNETSIKKNTQRNLVNGFEIEKNKDAIAKNNESI
EDLYDFGHEVAESIGEIHAHNEAQNETLKGLITNSIENTNNITKNKADIQALENNVVEELFNLSGRLIDQKADI
DNNINNIYELAQQQDQHSSDIKTLKKNVEEGLLELSGHLIDQKTDIAQNQANIQDLATYNELQDQYAQKQTE
ATDALNKASSENTQNIEDLAAYNELQDAYAKQQTEAIDALNKASSENTQNIEDLAAYNELQDAYAKQQTEAI
DALNKASSENTQNIAKNQADIANNINNIYELAQQQDQHSSDIKTLAKASAANTDRIAKNKDADASFETLTK
NQNTLIEKDKEHDKLITANKTAIDANKASADTKFAATADAITKNGNAITKNAKSASHHHHHH SEQ ID NO. 16 MC-006 (Protein)-(M)(UspA2 amino acids 30-519)
MQAKNDITLEDLPYLIKKIDQNELEADIGDITALEKYLALSQYGNILALEELNKALEELDEDVGWNQNDIANLE
DDVETLTKNQNALAEQGEAIKEDLQGLADFVEGQEGKILQNETSIKKNTQRNLVNGFEIEKNKDAIAKNNESI
EDLYDFGHEVAESIGEIHAHNEAQNETLKGLITNSIENTNNITKNKADIQALENNVVEELFNLSGRLIDQKADI
DNNINNIYELAQQQDQHSSDIKTLKKNVEEGLLELSGHLIDQKTDIAQNQANIQDLATYNELQDQYAQKQTE
ATDALNKASSENTQNIEDLAAYNELQDAYAKQQTEAIDALNKASSENTQNIEDLAAYNELQDAYAKQQTEAI
DALNKASSENTQNIAKNQADIANNINNIYELAQQQDQHSSDIKTLAKASAANTDRIAKNKADADASFETLTK
NQNTLIEKDKEHDKLITANKTAIDANKASADTKFAATADAITKNGNAITKNAKS SEQ ID NO. 17 MC-007 (Protein)-(M)(UspA2 amino acids 30-564)(ASHHHHHH)
MQAKNDITLEDLPYLIKKIDQNELEADIGDITALEKYLALSQYGNILALEELNKALEELDEDVGWNQNDIANLE
DDVETLTKNQNALAEQGEAIKEDLQGLADFVEGQEGKILQNETSIKKNTQRNLVNGFEIEKNKDAIAKNNESI
EDLYDFGHEVAESIGEIHAHNEAQNETLKGLITNSIENTNNITKNKADIQALENNVVEELFNLSGRLIDQKADI
DNNINNIYELAQQQDQHSSDIKTLKKNVEEGLLELSGHLIDQKTDIAQNQANIQDLATYNELQDQYAQKQTE
ATDALNKASSENTQNIEDLAAYNELQDAYAKQQTEAIDALNKASSENTQNIEDLAAYNELQDAYAKQQTEAI
DALNKASSENTQNIAKNQADIANNINNIYELAQQQDQHSSDIKTLAKASAANTDRIAKNKADADASFETLTK
NQNTLIEKDKEHDKLITANKTAIDANKASADTKFAATADAITKNGNAITKNAKSITDLGTKVDGFDSRVTALD
TKVNAFDGRITALDSKVENGMAAQAAASHHHHHH SEQ ID NO. 18 MC-008 (Protein)-(M)(UspA2 30-564)(HH)
MQAKNDITLEDLPYLIKKIDQNELEADIGDITALEKYLALSQYGNILALEELNKALEELDEDVGWNQNDIANLE
DDVETLTKNQNALAEQGEAIKEDLQGLADFVEGQEGKILQNETSIKKNTQRNLVNGFEIEKNKDAIAKNNESI
EDLYDFGHEVAESIGEIHAHNEAQNETLKGLITNSIENTNNITKNKADIQALENNVVEELFNLSGRLIDQKADI
DNNINNIYELAQQQDQHSSDIKTLKKNVEEGLLELSGHLIDQKTDIAQNQANIQDLATYNELQDQYAQKQTE
ATDALNKASSENTQNIEDLAAYNELQDAYAKQQTEAIDALNKASSENTQNIEDLAAYNELQDAYAKQQTEAI
DALNKASSENTQNIAKNQADIANNINNIYELAQQQDQHSSDIKTLAKASAANTDRIAKNKADADASFETLTK
NQNTLIEKDKEHDKLITANKTAIDANKASADTKFAATADAITKNGNAITKNAKSITDLGTKVDGFDSRVTALD
TKVNAFDGRITALDSWENGMAAQAAHH SEQ ID NO. 19 MC-009 (Protein)-(M)(UspA2 31-564)(HH)
MAKNDITLEDLPYLIKKIDQNELEADIGDITALEKYLALSQYGNILALEELNKALEELDEDVGWNQNDIANLED
DVETLTKNQNALAEQGEAIKEDLQGLADFVEGQEGKILQNETSIKKNTQRNLVNGFEIEKNKDAIAKNNESIE
DLYDFGHEVAESIGEIHAHNEAQNETLKGLITNSIENTNNITKNKADIQALENNVVEELFNLSGRLIDQKADID
NNINNIYELAQQQDQHSSDIKTLKKNVEEGLLELSGHLIDQKTDIAQNQANIQDLATYNELQDQYAQKQTEA
IDALNKASSENTQNIEDLAAYNELQDAYAKQQTEAIDALNKASSENTQNIEDLAAYNELQDAYAKQQTEAID
ALNKASSENTQNIAKNQADIANNINNIYELAQQQDQHSSDIKTLAKASAANTDRIAKNKADADASFETLTKN
QNTLIEKDKEHDKLITANKTAIDANKASADTKFAATADAITKNGNAITKNAKSITDLGTKVDGFDSRVTALDT
KVNAFDGRITALDSKVENGMAAQAAHH SEQ ID NO. 20 MC-010 (Protein)-(M)(UspA2 amino acids 30-564)
MQAKNDITLEDLPYLIKKIDQNELEADIGDITALEKYLALSQYGNILALEELNKALEELDEDVGWNQNDIANLE
DDVETLTKNQNALAEQGEAIKEDLQGLADFVEGQEGKILQNETSIKKNTQRNLVNGFEIEKNKDAIAKNNESI
EDLYDFGHEVAESIGEIHAHNEAQNETLKGLITNSIENTNNITKNKADIQALENNVVEELFNLSGRLIDQKADI
DNNINNIYELAQQQDQHSSDIKTLKKNVEEGLLELSGHLIDQKTDIAQNQANIQDLATYNELQDQYAQKQTE
ATDALNKASSENTQNIEDLAAYNELQDAYAKQQTEAIDALNKASSENTQNIEDLAAYNELQDAYAKQQTEAI
DALNKASSENTQNIAKNQADIANNINNIYELAQQQDQHSSDIKTLAKASAANTDRIAKNKADADASFETLTK
NQNTLIEKDKEHDKLITANKTAIDANKASADTKFAATADAITKNGNAITKNAKSITDLGTKVDGFDSRVTALD
TKVNAFDGRITALDSWENGMAAQAA SEQ ID NO. 21 MC-011 (Protein)-(M)(UspA2 amino acids 31-540)(ASHHHHHH)
MAKNDITLEDLPYLIKKIDQNELEADIGDITALEKYLALSQYGNILALEELNKALEELDEDVGWNQNDIANLED
DVETLTKNQNALAEQGEAIKEDLQGLADFVEGQEGKILQNETSIKKNTQRNLVNGFEIEKNKDAIAKNNESIE
DLYDFGHEVAESIGEIHAHNEAQNETLKGLITNSIENTNNITKNKADIQALENNVVEELFNLSGRLIDQKADID
NNINNIYELAQQQDQHSSDIKTLKKNVEEGLLELSGHLIDQKTDIAQNQANIQDLATYNELQDQYAQKQTEA
IDALNKASSENTQNIEDLAAYNELQDAYAKQQTEAIDALNKASSENTQNIEDLAAYNELQDAYAKQQTEAID
ALNKASSENTQNIAKNQADIANNINNIYELAQQQDQHSSDIKTLAKASAANTDRIAKNKADADASFETLTKN
QNTLIEKDKEHDKLITANKTAIDANKASADTKFAATADAITKNGNAITKNAKSITDLGTKVDGFDSRVTALDT
KASHHHHHH SEQ ID NO: 22 UspA2 American 2933 (613 aa)
MKTMKLLPLKIAVTSAMIIGLGAASTANAQSRDRSLEDIQDSISKLVQDDINTLKQDQQKMNKYLLLNQLAN
TLITDELNNNVIKNTNSIEALGDEIGWLENDIADLEEGVEELTKNQNTLIEKDEEHDRLIAQNQADIQTLENN
VVEELFNLSGRLIDQEADIAKNNASTEELYDFDNEVAERIGEIHAYTEEVNKTLENLITNSVKNTDNIDKNKAD
IDNNINHIYELAQQQDQHSSDIKTLKNNVEEGLLELSGHLIDQKADLTKDIKALESNVEEGLLDLSGRLLDQK
ADLTKDIKALESNVEEGLLDLSGRLLDQKADIAQNQTDIQDLAAYNELQDQYAQKQTEAIDALNKASSENTQ
NIEDLAAYNELQDAYAKQQTEAIDALNKASSENTQNIAKNQADIANNINNIYELAQQQDQHSSDIKTLAKAS
AANTNRIATAELGIAENKKDAQIAKAQANANKTAIDENKASADTKFAATADAITKNGNAITKNAKSITDLGTK

```
                                    SEQUENCES:

VDGFDGRVTALDTKVNAFDGRITALDSKVENGMAAQAALSGLFQPYSVGKFNATAALGGYGSKSAVAIGAG
YRVNPNLAFKAGAAINTSGNKKGSYNIGVNYEF

SEQ ID NO: 23 UspA2 American 2912 (644 aa)
MKTMKLLPLKIAVTSALIIGLGAASTANAQQQLQTETFLPNFLSNDNYDLTDPFYHNMILGDTALLDKQDGS
QPQLKFYSNDKDSVPDSLLFSKLLHEQQLNGFKKGDTIIPLDKDGKPVYQVDYKLDGKGKKQKRRQVYSVTT
KTATDDDVNSAYSRGILGKVDDLDDEMNFLNHDITSLYDVTANQQDAIKDLKKGVKGLNKELKELDKEVGVL
SRDIGSLNDDVAQNNESIEDLYDFSQEVADSIGEIHAHNKAQNETLQDLITNSVENTNNITKNKADIQALEN
NVVEELFNLSGRLIDQKADLTKDIKTLESNVEEGLLELSGHLIDQKADIAKNQADIAQNQANIQDLAAYNELQ
DAYAKQQTEAIDALNKASSENTQNIEDLAAYNELQDAYAKQQTEAIDALNKASSENTQNIAKNQADIANNIN
NIYELAQQQDQHSSDIKTLAKASAANTDRIAKNKADADASFETLTKNQNTLIEKDKEHDKLITANKTAIDENK
ASADTKFAATADAITKNGNAITKNAKSITDLGTKVDGFDSRVTALDTKVNAFDGRITALDSKVENGMAAQAA
LSGLFQPYSVGKFNATAALGGYGSKSAVAIGAGYRVNPNLAFKAGAAINTSGNKKGSYNIGVNYEF SEQ ID NO: 24 UspA2 American 2908 (591 aa)
MKTMKLLPLKIAVTSALIVGLGAASTANAQLVERFFPNIFLDKPLAKQHYHNVVVGDTSIVSDLQSNSDQLKF
YSDDEGLVPDSLLFNKMLHEQLLNGFKEGDTIIPLDENGKPVYWDYKLDGKEPRKVYSVTTKIATAEDVATS
SYANGIQKDIDDLYDFDHQVTERLTQHGKTIYRNGERILANEESVQYLNKEVQNNIEHIYELAQQQDQHSSD
IKTLESNVEKGLLELSGHLIDQKADLTKDIKTLESNVEEGLLDLSGRLIDQKADLTKDIKTLESNVEEGLLDLSG
RLIDQKADIAQNQANIQDLAAYNELQDQYAQKQTEAIDALNKASSENTQNIEDLAAYNELQDAYAKQQTEAI
DALNKASSENTQNIAKNQADIANNINNIYELAQQQDQHSSDIKTLAKASAANTNRIATAELGIAENKKDAQIA
KAQANANKTAIDENKASADTKFAATADAITKNGNAITKNAKSITDLGTKVDGFDSRVTALDTKVNAFDGRIT
ALDSKVENGMAAQAALSGLFQPYSVGKFNATAALGGYGSKSAVAIGAGYRVNPNLAFKAGAAINTSGNKKGS
YNIGVNYEF SEQ ID NO: 25 UspA2 Finnish 307 (687 aa)
MKTMKLLPLKIAVTSAMIIGLGAASTANAQQQQQQQQQQSRTEIFFPNIFFNENHDELDDAYHNIILGDTA
LLDKQDGSQPQLKFYSNDKDSVPDSLLFSKLLHEQQLNGFKVDLNHDGKPVYQVDYKLDGKGKKQKR
RQVYSVTTKTATDDDVNSAYSRGILGKVDDLDDEMNFLNHDITSLYDVTANQQDAIKGLKKGVKGLNKELK
ELDKEVGVLSRDIGSLNDDVAQNNESIEDLYDFSQEVADSIGEIHAHNKAQNETLQDLITNSVENTNNITKNK
ADIQALENNVVEELFNLSGRLIDQKADLTKDIKTLESNVEEGLLELSGHLIDQKADIAKNQADIAQNQANIQD
LAAYNELQDAYAKQQTEAIDALNKASSENTQNIEDLAAYNELQDAYAKQQTEAIDALNKASSENTQNIEDLA
AYNELQDAYAKQQTEAIDALNKASSENTQNIAKNQADIANNINNIYELAQQQDQHSSDIKTLAKASAANTDR
IAKNKADADASFETLTKNQNTLIEKDKEHDKLITANKTAIDENKASADTKFAATADAITKNGNAITKNAKSIT
DLGTKVDAFDGRVTALDTKVNAFDGRITALDSKVENGMAAQAALSGLFQPYSVGKFNATAALGGYGSKSAV
AIGAGYRVNPNLAFKAGAAINTSGNKKGSYNIGVNYEF SEQ ID NO: 26 UspA2 Finnish 353 (683 amino acids)
MKTMKLLPLKIAVTSAMIVGLGMASTANAQQQKSPKTETFLPNIFFNEYADDLDTLYHNMILGDTAITHDDQ
YKFYADDATEVPDSLFFNKILHDQLLYGFKEGDKIIPLDENGKPVYKLDKRLENGVQKTVYSVTTKTATADDV
NSAYSRGIQGDIDDLYEANKENVNRLIEHGDKIFANEESVQYLNREVQNNIEHIELAQQQDQHSSDIKTLK
KNVEKDLLDLSGRLIAQKEDIAQNQTDIQDLATYNELQDQYAQKQTEAIDALNKASSENTQNIAKNSNHIKT
LENNIEEGLLELSGHLIDQKADLTKDIKALESNVEEGLLDLSGRLIDQKADIAQNQANIQDLAAYNELQDAYA
KQQTEAIDALNKASSENTQNIEDLAAYNELQDAYAKQQTEAIDALNKASSENTQNIEDLAAYNELQDAYAKQ
QTEAIDALNKASSENTQNIAKNQADIANNINNIYELAQQQDQHSSDIKTLAKASAANTDRIAKNKADADASF
ETLTKNQNTLIEKDKEHDKLITANKTAIDANKASADTKFAATADAITKNGNAITKNAKSITDLGTKVDGFDGR
VTALDTKVNALDTKVNAFDGRITALDSKVENGMAAQAALSGLFQPYSVGKFNATAALGGYGSKSAVAIGAGY
RVNPNLAFKAGAAINTSGNKKGSYNIGVNYEF SEQ ID NO: 27 UspA2 Finnish 358 (684 amino acids)
MKTMKLLPLKIAVTSAMMVGLGMASTANAQQQKSPKTEIFLPNLFDNDNTELTDPLYHNMILGNTALLTQEN
QYKFYADDGNGVPDSLLFNKILHDQLLHGFKEGGTIIPLDENGKPVYKLDSIVEQGKTKTVYSVTTKTATADD
VNSAYSRGIQGDIDDLYEANKENVNRLIEHGDKIFANEESVQYLNREVQNNIENIHELAQQQDQHSSDIKTL
KKNVEKDLLDLSGRLIAQKEDIAQNQTDIQDLATYNELQDQYAQKQTEAIDALNKASSENTQNIAKNSNHIK
TLENNIEEGLLELSGHLIDQKADLTKDIKALESNVEEGLLDLSGRLIDQKADIAQNQANIQDLAAYNELQDAY
AKQQTEAIDALNKASSENTQNIEDLAAYNELQDAYAKQQTEAIDALNKASSENTQNIEDLAAYNELQDAYAK
QQTEAIDALNKASSENTQNIAKNQADIANNINNIYELAQQQDQHSSDIKTLAKASAANTDRIAKNKADADAS
FETLTKNQNTLIEKDKEHDKLITANKTAIDANKASADTKFAATADAITKNGNAITKNAKSITDLGTKVDGFDG
RVTALDTKVNALDTKVNAFDGRITALDSKVENGMAAQAALSGLFQPYSVGKFNATAALGGYGSKSAVAIGAG
YRVNPNLAFKAGAAINTSGNKKGSYNIGVNYEF SEQ ID NO: 28 UspA2 Finnish 216 (684 amino acids)
MKTMKLLPLKIAVTSAMIIGLGAASTANAQQQQKTKTEVFLPNLFDNDYYDLTDPLYHSMILGDTATLFDQQ
DNSKSQLKFYSNDKDSVPDSLLFSKLLHEQQLNGFKAGDTIIPLDKDGKPVYTQDTRTKDGKVETVYSVTTKI
ATQDDVEQSAYSRGIQGDIDDLYDINREVNEYLKATHDYNERQTEAIDALNKASSANTDRIDTAEERIDKNE
YDIKALESNVGKDLLDLSGRLIAQKEDIDNNINHIYELAQQQDQHSSDIKTLKNNVEEGLLELSGHLIDQKAD
LTKDIKTLENNIEEGLLELSGHLIDQKADLTKDIKTLENNIEEGLLELSGHLIDQKADIAQNQANIQDLAAYNEL
QDQYAQKQTEAIDALNKASSENTQNIEDLAAYNELQDAYAKQQTEAIDALNKASSENTQNIEDLAAYNELQ
DAYAKQQTEAIDALNKASSENTQNIAKNQADIANNINNIYELAQQQDQHSSDIKTLAWSAANTDRIAKNKA
DADASFETLTKNQNTLIEKDKEHDKLITANKTAIDANKASADTKFAATADAITKNGNAITKNAKSITDLGTKV
DGFDGRVTALDTKVNAFDGRITALDSKVENGMAAQAALSGLFQPYSVGKFNATAALGGYGSKSAVAIGAGY
RVNPNLAFKAGAAINTSGNKKGSYNIGVNYEF SEQ ID NO: 29 UspA2 Dutch H2 (684 amino acids)
MKTMKLLPLKIAVTSAMMVGLGMASTANAQQQKSPKTEIFLPNLFDNDNTELTDPLYHNMILGNTALLTQEN
QYKFYADDGNGVPDSLLFNKILHDQLLHGFKKGDTIIPLDENGKPVYKLDSIVEQGKTKTVYSVTTKTATADD
VNSAYSRGIQGDIDDLYEANKENVNRLIEHGDKIFANEESVQYLNREVQNNIENIYELVQQQDQHSSDIKTL
```

| SEQUENCES: |
|---|

KKNVEKDLLDLSGRLIAQKEDIAQNQTDIQDLATYNELQDQYAQKQTEAIDALNKASSENTQNIAKNSNHIK
TLENNIEEGLLELSGHLIDQKADLTKDIKALESNVEEGLLDLSGRLIDQKADIAQNQANIQDLAAYNELQDAY
AKQQTEAIDALNKASSENTQNIEDLAAYNELQDAYAKQQTEAIDALNKASSENTQNIEDLAAYNELQDAYAK
QQTEAIDALNKASSENTQNIAKNQADIANNINNIYELAQQQDQHSSDIKTLAKASAANTDRIAKNKADADAS
FETLTKNQNTLIEKDKEHDKLITANKTAIDANKASADTKFAATADAITKNGNAITKNAKSITDLGTKVDGFDG
RVTALDTKVNALDTKVNAFDGRITALDSKVENGMAAQAALSGLFQPYSVGKFNATAALGGYGSKSAVAIGAG
YRVNPNLAFKAGAAINTSGNKKGSYNIGVNYEF

SEQ ID NO: 30 UspA2 Dutch F10 (574 amino acids)
MKTMKLLPLKIAVTSAMIIGLGAASTANAQLAEQFFPNIFSNHAPVKQHYHNVVVGDTSIVENLQDSDDTQL
KFYSNDEYSVPDSLLFNKMLHEQQLNGFKKGDTIIPLDENGKPVYWDYKLDGQEPRRVYSVTTKIATQDDV
DNSPYSRGIQGDIDDLYEANKENVNRLIEHGDKIFANEESVQYLNKEVQNNIENIYELAQQQDQHSSDIKTL
KKNVEEGLLELSGHLIDQKADLTKDIKTLESNVEEGLLELSGHLIDQKADIAKNQADIAQNQANIQDLAAYNE
LQDAYAKQQTEAIDALNKASSENTQNIEDLAAYNELQDAYAKQQTEAIDALNKASSENTQNIAKNQADIANN
INNIYELAQQQDQHSSDIKTLAKASAANTDRIAKNKADADASFETLTKNQNTLIEKDKEHDKLITANKTAIDA
NKASADTKFAATADAITKNGNAITKNAKSITDLGTKVDAFDGRVTALDTKVNAFDGRITALDSKVENGMAAQ
AALSGLFQPYSVGKFNATAALGGYGSKSAVAIGAGYRVNPNLAFKAGAAINTSGNKKGSYNIGVNYEF SEQ ID NO: 31 UspA2 Norwegian 1 (678 amino acids)
MKTMKLLPLKIAVTSALIVGLGAASTANAQQQPQTETFFPNIFFNENHDALDDVYHNMILGDTAITQDNQYK
FYADAISEVPDSLLFNKILHDQQLNGFKEGDTIIPLDENGKPVYKLDEKVENGVKKSVYSVTTKTATRADVEQ
SAYSRGIQGDIDDLYEANKENVNRLIEHGDKIFANEESVQYLNKEVQNNIENIHELAQQQDQHSSDIKTLKK
NVEEGLLELSGHLIDQKADLTKDIKTLESNVEEGLLDLSGRLLDQKADIAQNQANIQDLAAYNELQDAYAKQ
QTEAIDALNKASSENTQNIEDLAAYNELQDAYAKQQTEAIDALNKASSENTQNIEDLAAYNELQDAYAKQQT
EAIDALNKASSENTQNIEDLAAYNELQDAYAKQQTEAIDALNKASSENTQNIEDLAAYNELQDAYAKQQTEA
IDALNKASSENTQNIAKNQADIANNINNIYELAQQQDQHSSDIKTLAKASAANTDRIAKNKADADASFETLTK
NQNTLIEKDKEHDKLITANKTAIDANKASADTKFAATADAITKNGNAITKNAKSITDLGTKVDAFDGRVTALD
TKVNALDTKVNAFDGRITALDSKVENGMAAQAALSGLFQPYSVGKFNATAALGGYGSKSAVAIGAGYRVNPN
LAFKAGAAINTSGNKKGSYNIGVNYEF SEQ ID NO: 32 UspA2 Norwegian 13 (678 amino acids)
MKTMKLLPLKIAVTSAMIVGLGAASTANAQQQQQPRTETFFPNIFFNENHDALDDVYHNMILGDTAITQDN
QYKFYADAISEVPDSLLFNKILHDQQLNGFKEGDTIIPLDENGKPVYKLDEKVENGVKKSVYSVTTKTATRAD
VEQSAYSRGIQGDIDDLYEANKENVNRLIEHGDKIFANEESVQYLNREVQNNIENIHELAQQQDQHSSDIKT
LKKNVEKDLLDLSGRLIAQKEDIAQNQTDIQDLATYNELQDQYAQKQTEAIDALNKASSENTQNIAKNSNHI
KTLENNIEEGLLELSGHLIDQKADLTKDIKTLENNIEEGLLELSGHLIDQKADLTKDIKALESNVEEGLLDLSGR
LLDQKADIAQNQANIQDLAAYNELQDQYAQKQTEAIDALNKASSENTQNIEDLAAYNELQDAYAKQQTEAI
DALNKASSENTQNIAKNQADIANNINNIYELAQQQDQHSSDIKTLAKASAANTDRIAKNKADADASFETLTK
NQNTLIEKDKEHDKLITANKTAIDTNKASADTKFAATADAITKNGNAITKNAKSITDLGTKVDGFDGRVTALD
TKVNALDTKVNAFDGRITALDSKVENGMAAQAALSGLFQPYSVGKFNATAALGGYGSKSAVAIGAGYRVNPN
LAFKAGAAINTSGNKKGSYNIGVNYEF SEQ ID NO: 33 UspA2 Norwegian 33 (587 amino acids)
MKTMKLLPLKIAVTSALIVGLGAASTANAQLVERFFPNIFLDKPLAKQHYHNVVVGDTSIVSDLQSNSDQLKF
YSDDEGLVPDSLLFNKMLHEQLLNGFKEGDTIIPLDENGKPVYKVDYKLDGKEPRKVYSVTTKIATAEDVATS
SYANGIQKDIDDLYDFDHQVTERLTQHGKTIYRNGERILANEESVQYLNKEVQNNIEHIYELAQQQDQHSSD
IKTLESNVEKGLLELSGHLIDQKADLTKDIKTLENNVEEGLLDLSGRLIDQKADIAQNQANIQDLAAYNELQD
QYAQKQTEAIDALNKASSENTQNIEDLAAYNELQDAYAKQQTEAIDALNKASSENTQNIAKNQADIANNINN
IYELAQQQDQHSSDIKTLAKASAANTDRIAKNKADADASFETLTKNQNTLIEKDKEHDKLITANKTAIDTNKA
SADTKFAATADAITKNGNAITKNAKSITDLGTKVDGFDSRVTALDTKVNALDTKVNALDTKVNAFDGRITAL
DSKVENGMAAQAALSGLFQPYSVGKFNATAALGGYGSKSAVAIGAGYRVNPNLAFKAGAAINTSGNKKGSY
NIGVNYEF SEQ ID NO: 34 UspA2 Norwegian 25 (678 amino acids)
MKTMKLLPLKIAVTSAMIVGLGAASTANAQQQQQPRTETFFPNIFFNENHDALDDVYHNMILGDTAITQDN
QYKFYADAISEVPDSLLFNKILHDQQLNGFKEGDTIIPLDENGKPVYKLDEKVENGVKKSVYSVTTKTATRAD
VEQSAYSRGIQGDIDDLYEANKENVNRLIEHGDKIFANEESVQYLNREVQNNIENIHELAQQQDQHSSDIKT
LKKNVEKDLLDLSGRLIAQKEDIAQNQTDIQDLATYNELQDQYAQKQTEAIDALNKASSENTQNIAKNSNHI
KTLENNIEEGLLELSGHLIDQKADLTKDIKTLENNIEEGLLELSGHLIDQKADLTKDIKALESNVEEGLLDLSGR
LLDQKADIAQNQANIQDLAAYNELQDQYAQKQTEAIDALNKASSENTQNIEDLAAYNELQDAYAKQQTEAI
DALNKASSENTQNIAKNQADIANNINNIYELAQQQDQHSSDIKTLAKASAANTDRIAKNKADADASFETLTK
NQNTLIEKDKEHDKLITANKTAIDTNKASADTKFAATADAITKNGNAITKNAKSITDLGTKVDGFDGRVTALD
TKVNALDTKVNAFDGRITALDSKVENGMAAQAALSGLFQPYSVGKFNATAALGGYGSKSAVAIGAGYRVNPN
LAFKAGAAINTSGNKKGSYNIGVNYEF SEQ ID NO: 35 UspA2 Norwegian 27 (616 amino acids)
MKTMKLLPLKIAVTSALIVGLGAASTANAQVRDKSLEDIEALLGKIDISKLEKEKKQQTELQKYLLLSQYANVL
TMEELNKNVEKNTNSIEALGYEIGWLENDIADLEEGVEELTKNQNTLIEKDEEHDRLIAQNQADIKTLENNW
EELFNLSDRLIDQEADIAKNNASTEELYDFDNEVAERIGEIHAYTEEVNKTLEKLITNSVENTDNIDKNKADIQ
ALENNVEEGLLELSGHLIDQKADLTKDIKALESNVEEGLLDLSGRLLDQKADIAKNQADIAQNQTDIQDLAAY
NELQDQYAQKQTEAIDALNKASSENTQNIEDLAAYNELQDAYAKQQTEAIDALNKASSENTQNIEDLAAYNE
LQDAYAKQQTEAIDALNKASSENTQNIAKNQADIANNINNIYELAQQQDQHSSDIKTLAWSAANTDRIAKN
KADADASFETLTKNQNTLIEKDKEHDKLITANKTAIDANKASADTKFAATADAITKNGNAITKNAKSITDLGT
KVDGFDSRVTALDTKVNAFDGRITALDSWENGMAAQAALSGLFQPYSVGKFNATAALGGYGSKSAVAIGAG
YRVNPNLAFKAGAAINTSGNKKGSYNIGVNYEF -continued

SEQUENCES:

SEQ ID NO: 36 UspA2 Norwegian 36 (676 amino acids)
MKTMKLLPLKIAVTSALIVGLGAASTANAQATETFLPNLFDNDYTETTDPLYHGMILGNTAITQDTQYKFYAE
NGNEVPDSLFFNKILHDQQLNGFKEGDTIIPLDENGKPVYKLDEITENGVKRKVYSVTTKTATREDVEQSAYS
RGIQGDIDDLYEANKENVNRLIEHGDKIFANEESVQYLNKEVQNNIENIHELAQQQDQHSSDIKTLKKNVEE
GLLELSGHLIDQKADLTKDIKALESNVEEGLLDLSGHLIDQKADLTKDIKALESNVEEGLLDLSGRLLDQKADI
AKNQADIAQNQTDIQDLAAYNELQDQYAQKQTEAIDALNKASSENTQNIEDLAAYNELQDQYAQKQTEAID
ALNKASSENTQNIEDLAAYNELQDQYAQKQTEAIDALNKASSENTQNIEDLAAYNELQDQYAQKQTEAIDAL
NKASSENTQNIAKNQADIANNINNIYELAQQQDQHSSDIKTLAKASAANTDRIAKNKADADASFETLTKNQN
TLIEKDKEHDKLITANKTAIDANKASADTKFAATADAITKNGNAITKNAKSITDLGTKVDGFDGRVTALDTKV
NALDTKVNAFDGRITALDSKVENGMAAQAALSGLFQPYSVGKFNATAALGGYGSKSAVAIGAGYRVNPNLAF
KAGAAINTSGNKKGSYNIGVNYEF SEQ ID NO: 37 UspA2 BC5SV (629 amino acids)
MKTMKLLPLKIAVTSALIVGLGAASTANAQNGTSTKLKNLKEYAQYLDNYAQYLDDDIDDLDKEVGELSQNIA
KNQANIKDLNKKLSRDIDSLREDVYDNQYEIVNNQADIEKNQDDIKELENNVGKELLNLSGRLLDQKADIDN
NINNIYELAQQQDQHSSDIKTLKKNVEEGLLELSGHLIDQKSDIAQNQTDIQDLATYNELQDQYAQKQTEAI
DALNKASSENTQNIEDLAAYNELQDAYAKQQTEAIDALNKASSENTQNIQDLAAYNELQDAYAKQQTEAIDA
LNKASSENTQNIEDLAAYNELQDAYAKQQTEAIDALNKASSENTQNIEDLAAYNELQDAYAKQQTEAIDALN
KASSENTQNIEDLAAYNELQDAYAKQQTEAIDALNKASSENTQNIAKNQADIANNINNIYELAQQQDQHSSD
IKTLAKASAANTDRIAKNKADADASFETLTKNQNTLIEKDKEHDKLITANKTAIDANKASADTKFAATADAIT
KNGNAITKNAKSITDLGTKVDAFDGRVTALDTKVNAFDGRITALDSWENGMAAQAALSGLFQPYSVGKFNA
TAALGGYGSKSAVAIGAGYRVNPNLAFKAGAAINTSGNKKGSYNIGVNYEF SEQ ID NO: 38 UspA2 Norwegian 14 (683 amino acids)
MKTMKLLPLKIAVTSAMIVGLGMASTANAQQQRSPKTETFLPNIFFNEYADDLDTLYHNMILGDTAITHDDQ
YKFYADDATEVPDSLFFNKILHDQLLYGFKEGDKIIPLDENGKPVYKLDKRLDNGVQKTVYSVTTKTATADDV
NSAYSRGIQGDIDDLYEANKENVNRLIEHGDKIFANEESVQYLNKEVQNNIENIHELAQQQDQHSSDIKTLK
KNVEEGLLELSGHLIDQKTDIAQNQTDIQDLATYNELQDQYAQKQTEAIDALNKASSENTQNIAKNSNRIKA
LENNIEEGLLELSGHLIDQKADLTKDIKALESNVEEGLLDLSGRLIDQKADIAQNQANIQDLAAYNELQDAYA
KQQTEAIDALNKASSENTQNIEDLAAYNELQDAYAKQQTEAIDALNKASSENTQNIEDLAAYNELQDAYAKQ
QTEAIDALNKASSENTQNIAKNQADIANNINNIYELAQQQDQHSSDIKTLAKASAANTDRIAKNKADADASF
ETLTKNQNTLIEKDKEHDKLITANKTAIDANKASADTKFAATADAITKNGNAITKNAKSITDLGTKVDGFDGR
VTALDTKVNALDTKVNAFDGRITALDSWENGMAAQAALSGLFQPYSVGKFNATAALGGYGSKSAVAIGAGY
RVNPNLAFKAGAAINTSGNKKGSYNIGVNYEF SEQ ID NO: 39 UspA2 Norwegian 3 (700 amino acids)
MKTMKLLPLKIAVTSAMIVGLGAASTANAQAQSNRSLDQVQALLRGIDETKIKKEIQQSQQPELNKYLTFNQL
ANALNIEELNNNVQKNTQRLDSAATLYGDLSKTVPKSIKENKESIKENKESIKENKESIKENKESIKENKESIKE
NKESITTLTRKSFQNQVDIVRNNASIEDLYAYGQEVAKSIGEIHAYTEEVNKTLENLITNSVENTNNITKNKAD
IQALENNVVEELFNLSGRLIDQKADIDNNINNIYELAQQQDQHSSDIKTLKKNVEEGLLELSGHLIDQKADLT
KDIKTLESNVEEGLLDLSGRLLDQKADIAQNQANIQDLAAYNELQDAYAKQQTEAIDALNKASSENTQNIED
LAAYNELQDAYAKQQTEAIDALNKASSENTQNIEDLAAYNELQDAYAKQQTEAIDALNKASSENTQNIEDLA
AYNELQDAYAKQQTEAIDALNKASSENTQNIAKNQADIANNINNIYELAQQQDQHSSDIKTLAKASAANTDR
IAKNKADADASFETLTKNQNTLIEKDKEHDKLITANKTVIDANKASADTKFAATADAITKNGNAITKNAKSIT
DLGTKVDGFDGRVTALDTKVNALDTKVNAFDGRITALDSKVENGMAAQAALSGLFQPYSVGKFNATAALGG
YGSKSAVAIGAGYRVNPNLAFKAGAAINTSGNKKGSYNIGVNYEF SEQ ID NO: 40 UspA2 Finnish 414 (676 amino acids)
MKTMKLLPLKIAVTSALIVGLGAASTANAQATETFLPNLFDNDYIETTDPLYHGMILGNTAITQDTQYKFYAE
NGNEVPDSLFFNKILHDQQLNGFKEGDTIIPLDENGKPVYKLDEITENGVKRIMSVTTKTATREDVEQSAYS
RGIQGDIDDLYEANKENVNRLIEHGDKIFANEESVQYLNKEVQNNIENIHELAQQQDQHSSDIKTLKKNVEE
GLLELSGHLIDQKADLTKDIKTLENNVEEGLLELSGHLIDQKADLTKDIKALESNVEEGLLDLSGRLLDQKADI
AKNQADIAQNQTDIQDLAAYNELQDQYAQKQTEAIDALNKASSENTQNIEDLAAYNELQDQYAQKQTEAID
ALNKASSENTQNIEDLAAYNELQDQYAQKQTEAIDALNKASSENTQNIEDLAAYNELQDQYAQKQTEAIDAL
NKASSENTQNIAKNQADIANNINNIYELAQQQDQHSSDIKTLAKASAANTDRIAKNKADADASFETLTKNQN
TLIEKDKEHDKLITANKTAIDANKASADTKFAATADAITKNGNAITKNAKSITDLGTKVDGFDGRVTALDTKV
NALDTKVNAFDGRITALDSKVENGMAAQAALSGLFQPYSVGKFNATAALGGYGSKSAVAIGAGYRVNPNLAF
KAGAAINTSGNKKGSYNIGVNYEF SEQ ID NO: 41 UspA2 Japanese Z7476 (678 amino acids)
MKTMKLLPLKIAVTSAMIIGLGAASTANAQLAEQFFPNIFSNHAPVKQHYHNVVVGDTSIVENLQDSDDTQL
KFYSNDEYSVPDSLLFNKMLHEQQLNGFKKGDTIIPLDENGKPVYKVDYKLDGQEPRRVYSVTTKIATQDDV
DNSPYSRGIQGDIDDLYEANKENVNRLIEHGDKIFANEESVQYLNKEVQNNIENIYELAQQQDQHSSDIKTL
KKNVEEGLLELSGRLIDQKADIAQNQANIQDLAAYNELQDQYAQKQTEAIDALNKASSENTQNIEDLAAYNE
LQDAYAKQQTEAIDALNKASSENTQNIEDLAAYNELQDAYAKQQTEAIDALNKASSENTQNIEDLAAYNELQ
DAYAKQQTEAIDALNKASSENTQNIEDLAAYNELQDAYAKQQTEAIDALNKASSENTQNIEDLAAYNELQDA
YAKQQTEAIDALNKASSENTQNIAKNQADIANNINNIYELAQQQDQHSSDIKTLAKVSAANTDRIAKNKADA
DASFETLTKNQNTLIEKDKEHDKLITANKTAIDANKASADTKFAATADAITKNGNAITKNAKSITDLGTKVDG
FDGRVTALDTKVNAFDGRITALDSKVENGMAAQAALSGLFQPYSVGKFNATAALGGYGSKSAVAIGAGYRVN
PNLAFKAGAAINTSGNKKGSYNIGVNYEF SEQ ID NO: 42 UspA2 Belgian Z7530 (613 amino acids)
MKTMKLLPLKIAVTSAMIIGLGAASTANAQSRDRSLEDIQDSISKLVQDDINTLKQDQQKMNKYLLLNQLAN
TLITDELNNNVIKNTNSIEALGDEIGWLENDIADLEEGVEELTKNQNTLIEKDEEHDRLIAQNQADIQTLENN
VVEELFNLSGRLIDQEADIAKNNASTEELYDFDNEVAERIGEIHAYTEEVNKTLENLITNSVKNTDNIDKNKAD
IDNNINHIYELAQQQDQHSSDIKTLKNNVEEGLLELSGHLIDQKADLTKDIKALESNVEEGLLDLSGRLLDQK

SEQUENCES:

ADLTKDIKALESNVEEGLLDLSGRLLDQKADIAQNQTDIQDLAAYNELQDQYAQKQTEAIDALNKASSENTQ
NIEDLAAYNELQDAYAKQQTEAIDALNKASSENTQNIAKNQADIANNINNIYELAQQQDQHSSDIKTLAKAS
AANTNRIATAELGIAENKKDAQIAKAQANANKTAIDENKASADTKFAATADAITKNGNAITKNAKSITDLGTK
VDGFDGRVTALDTKVNAFDGRITALDSKVENGMAAQAALSGLFQPYSVGKFNATAALGGYGSKSAVAIGAG
YRVNPNLAFKAGAAINTSGNKKGSYNIGVNYEF

SEQ ID NO: 43 German Z8063 (589 amino acids)
MKTMKLLPLKIAVTSALIVGLGAASTANAQATNKDITLEDVLKSIEEIDPYELRDYIEYPTAIERFLLLSQYGNT
LTLEEFDNDIELLDQDVEDLEESVTELAKNQNSLIEQGEAIKEDLQGLADFVERQEDKILQNETSIKKNTQRN
LVNGFEIEKNKDAIAKNNESIEDLYDFGHEVAKSIGEIHAHNEAQNETLKDLITNSVKNTDNITKNKADIQALE
SNVEKGLLELSGHLIDQKADIDNNINNIHELAQQQDQHSSDIKTLKKNVEEGLLELSGHLIDQKSDIAQNQAN
IQDLATYNELQDQYAQKQTEAIDALNKASSENTQNIEDLAAYNELQDAYAKQQTEAIDALNKASSENTQNIA
KNQADIANNINNIYELAQQQDQHSSDIKTLAKASAANTDRIAKNKADADASFETLTKNQNTLIEKDKEHDKLI
TANKTAIDANKASADTKFAATADAITKNGNAITKNAKSITDLGTKVDGFDSRVTALDTKVNAFDGRITALDSK
VENGMAAQAALSGLFQPYSVGKFNATAALGGYGSKSAVAIGAGYRVNPNLAFKAGAAINTSGNKKGSYNIGV
NYEF SEQ ID NO: 44 UspA2 American O12E (684 amino acids)
MKTMKLLPLKIAVTSAMMVGLGMASTANAQQQKSPKTEIFLPNLFDNDNTELTDPLYHNMILGNTALLTQEN
QYKFYADDGNGVPDSLLFNKILHDQLLHGFKEGDTIIPLDENGKPVYKLDSIVEQGKTKTVYSVTTKTATADD
VNSAYSRGIQGDIDDLYEANKENVNRLIEHGDKIFANEESVQYLNREVQNNIENIHELAQQQDQHSSDIKTL
KKNVEKDLLDLSGRLIAQKEDIAQNQTDIQDLATYNELQDQYAQKQTEAIDALNKASSENTQNIAKNSNHIK
TLENNIEEGLLELSGHLIDQKADLTKDIKALESNVEEGLLDLSGRLIDQKADIAQNQANIQDLAAYNELQDAY
AKQQTEAIDALNKASSENTQNIEDLAAYNELQDAYAKQQTEAIDALNKASSENTQNIEDLAAYNELQDAYAK
QQTEAIDALNKASSENTQNIAKNQADIANNINNIYELAQQQDQHSSDIKTLAKASAANTDRIAKNKADADAS
FETLTKNQNTLIEKDKEHDKLITANKTAIDANKASADTKFAATADAITKNGNAITKNAKSITDLGTKVDGFDG
RVTALDTKVNALDTKVNAFDGRITALDSWENGMAAQAALSGLFQPYSVGKFNATAALGGYGSKSAVAIGAG
YRVNPNLAFKAGAAINTSGNKKGSYNIGVNYEF SEQ ID NO: 45 UspA2 Greek MC317 (650 amino acids)
MKTMKLLPLKIAVTSALIVGLGAASTANAQQQQKTKTEVFLPNLFYNDYIEETDLLYHNMILGDTAALVDRQN
YSNSQLKFYSNDEESVPDSLLFSKMLNNQQLNGFKAGDIIIPVDANGQVIYQKDTRVEGGKTRTVLSVTTKIA
TQQDVDSAYSRGIQGKVNDLDDEMNFLNHDITSLYDVTANQQDDIKGLKKGVKDLKKGVKGLNKELKELDK
EVGVLSRDIGSLNDDVAQNNESIEDLYDFSQEVADSIGEIHAHNKAQNETLQDLITNSVENTNNITKNKADI
QALENNVVEELFNLSGRLIDQKADLTKDIKTLESNVEEGLLELSGHLIDQKADIAKNQADIAQNQANIQDLAA
YNELQDAYAKQQTEAIDALNKASSENTQNIEDLAAYNELQDAYAKQQTEAIDALNKASSENTQNIAKNQADI
ANNINNIYELAQQQDQHSSDIKTLAKASAANTDRIAKNKADADASFETLTKNQNTLIEKDKEHDKLITANKT
AIDENKASADTKFAATADAITKNGNAITKNAKSITDLGTKVDGFDGRVTALDTKVNAFDGRITALDSKVENG
MAAQAALSGLFQPYSVGKFNATAALGGYGSKSAVAIGAGYRVNPNLAFKAGAAINTSGNKKGSYNIGVNYEF SEQ ID NO: 46 UspA2 American V1122 (616 amino acids)
MKTMKLLPLKIAVTSALIVGLGAVSTTNAQAQSRSLDQIQTKLADLAGKIAAGKNGGGQNNQNNQNDINKYL
FLSQYANILTMEELNNNVVKNSSSIETLETDFPGWLENDVADLEDGVEELTKNQNTLIEKDEEHDRLIAQNQA
DIQTLENNVVEELFNLSDRLIDQKADIAKNQADIAQNNESIEELYDFDNEVAEKIGEIHAYTEEVNKTLQDLIT
NSVKNTDNIDKNKADIDNNINHIYELAQQQDQHSSDIKTLKNNVEEGLLELSGHLIDQKADLTKDIKTLENN
VEEGLLDLSGRLIDQKADIAKNQADIAQNQTDIQDLAAYNELQDQYAQKQTEAIDALNKASSENTQNIEDLA
AYNELQDAYAKQQTEAIDALNKASSENTQNIAKNQADIANNINNIYELAQQQDQHSSDIKTLAKASAANTDR
IAKNKADADASFETLTKNQNTLIEKDKEHDKLITANKTAIDENKASADTKFAATADAITKNGNAITKNAKSIT
DLGTKVDGFDGRVTALDTKVNAFDGRITALDSKVENGMAAQAALSGLFQPYSVGKFNATAALGGYGSKSAV
AIGAGYRVNPNLAFKAGAAINTSGNKKGSYNIGVNYEF SEQ ID NO: 47 UspA2 American P44 (668 amino acids)
MKTMKLLPLKIAVTSALIVGLGTASTANAQVASPANQKIQQKIKKVRKELRQDIKSLRNDIDSNTADIGSLND
DVADNQDDILDNQADIAKNQDDIEKNQADIKELDKEVGVLSREIGSLNDDIADNYTDIIDNYTDIIDNQANI
AKNQDDIEKNQADIKELDKEVGVLSREIGSLNDDVADNQDDIAKNQADIQTLENNVEEGLLELSGHLLDQKA
DIDNNINNIYELAQQQDQHSSDIKTLKKNVEEGLLELSGHLIDQKTDIAQNQANIQDLATYNELQDQYAQEQ
TEATDALNKASSENTQNIAKNSNRIKALESNVEEGLLELSGHLIDQKADLTKDIKALESNVEEGLLELSGHLID
QKADIAQNQANIQDLAAYNELQDQYAQKQTEAIDALNKASSENTQNIEDLAAYNELQDAYAKQQTEAIDAL
NKASSENTQNIAKNQADIANNINNIYELAQQQDQHSSDIKTLAKASAANTDRIAKNKADADASFETLTKNQN
TLIEKDKEHDKLITANKTAIDANKVSADTKFAATADAITKNGNAITKNAKSITDLGTKVDAFDSRVTALDTKV
NAFDGRITALDSKVENGMAAQAALSGLFQPYSVGKFNATAALGGYGSKSAVAIGAGYRVNPNLAFKAGAAIN
TSGNKKGSYNIGVNYEF SEQ ID NO: 48 UspA2 American V1171 (674 amino acids)
MKTMKLLPLKIAVTSAMIVGLGATSTVNAQVVEQFFPNIFFNENHDELDDAYHNMILGDTAIVSNSQDNSTQ
LKFYSNDEDSVPDSLLFSKLLHEQQLNGFKAGDTIIPLDKDGKPVYTKDTRTKDGKVETVYSVTTKIATQDDV
EQSAYSRGIQGDIDDLYDINREVNEYLKATHDYNERQTEAIDALNKASSANTDRIDTAEERIDKNEYDIKALE
SNVEEGLLELSGHLIDQKADLTKDIKALESNVEEGLLELSGHLIDQKADLTKDIKALESNVEEGLLDLSGRLID
QKADIAQNQANIQDLAAYNELQDAYAKQQTEAIDALNKASSENTQNIEDLAAYNELQDAYAKQQTEAIDAL
NKASSENTQNIEDLAAYNELQDAYAKQQTEAIDALNKASSENTQNIEDLAAYNELQDAYAKQQTEAIDALNK
ASSENTQNIAKNQADIANNINNIYELAQQQDQHSSDIKTLAKASAANTDRIAKNKADADASFETLTKNQNTL
IEKDKEHDKLITANKTAIDANKASADTKFAATADAITKNGNAITKNAKSITDLGTKVDGFDGRVTALDTKVNA
LDTKVNAFDGRITALDSWENGMAAQAALSGLFQPYSVGKFNATAALGGYGSKSAVAIGAGYRVNPNLAFKA
GAAINTSGNKKGSYNIGVNYEF

SEQUENCES:

SEQ ID NO: 49 UspA2 American T1A24 (613 amino acids)
MKTMKLLPLKIAVTSAMIIGLGAASTANAQSRDRSLEDIQDSISKLVQDDIDTLKQDQQKMNKYLLLNQLAN
TLITDELNNNVIKNTNSIEALGDEIGWLENDIADLEEGVEELTKNQNTLIEKDEEHDRLIAQNQADIQTLENN
VVEELFNLSGRLIDQEADIAKNNASTEELYDFDNEVAERIGEIHAYTEEVNKTLENLITNSVKNTDNIDKNKAD
IDNNINHIYELAQQQDQHSSDIKTLKNNVEEGLLELSGHLIDQKADLTKDIKALESNVEEGLLDLSGRLLDQK
ADLTKDIKALESNVEEGLLDLSGRLLDQKADIAQNQTDIQDLAAYNELQDQYAQKQTEAIDALNKASSENTQ
NIEDLAAYNELQDAYAKQQTEAIDALNKASSENTQNIAKNQADIANNINNIYELAQQQDQHSSDIKTLAKAS
AANTNRIATAELGIAENKKDAQIAKAQANANKTAIDENKASADTKFAATADAITKNGNAITKNAKSITDLGTK
VDGFDGRVTALDTKVNAFDGRITALDSKVENGMAAQAALSGLFQPYSVGKFNATAALGGYGSKSAVAIGAG
YRVNPNLAFKAGAAINTSGNKKGSYNIGVNYEF SEQ ID NO: 50 UspA2 American O35E (576 amino acids)
MKTMKLLPLKIAVTSAMIVGLGATSTVNAQVVEQFFPNIFFNENHDELDDAYHNMILGDTAIVSNSQDNSTQ
LKFYSNDEDSVPDSLLFSKLLHEQQLNGFKAGDTIIPLDKDGKPVYTKDTRTKDGKVETVYSVTTKIATQDDV
EQSAYSRGIQGDIDDLYDINREVNEYLKATHDYNERQTEAIDALNKASSANTDRIDTAEERIDKNEYDIKALE
SNVEEGLLELSGHLIDQKADLTKDIKALESNVEEGLLELSGHLIDQKADLTKDIKALESNVEEGLLDLSGRLLD
QKADIAKNQADIAQNQTDIQDLAAYNELQDAYAKQQTEAIDALNKASSENTQNIAKNQADIANNINNIYELA
QQQDQHSSDIKTLAKASAANTDRIAKNKADADASFETLTKNQNTLIEKDKEHDKLITANKTAIDANKASADT
KFAATADAITKNGNAITKNAKSITDLGTKVDGFDGRVTALDTKVNALDTKVNAFDGRITALDSKVENGMAAQ
AALSGLFQPYSVGKFNATAALGGYGSKSAVAIGAGYRVNPNLAFKAGAAINTSGNKKGSYNIGVNYEF SEQ ID NO: 51 UspA2 American SP12-6 (684 amino acids)
MKTMKLLPLKIAVTSAMMVGLGMASTANAQQQKSPKTEIFLPNLFDNDNTELTDPLYHNMILGNTALLTQEN
QYKFYADDGNGVPDSLLFNKILHDQLLHGFKEGDTIIPLDENGKPVYKLDSIVEQGKTKWYSVTTKTATADD
VNSAYSRGIQGDIDDLYEANKENVNRLIEHGDKIFANEESVQYLNREVQNNIENIHELAQQQDQHSSDIKTL
KKNVEKDLLDLSGRLIAQKEDIAQNQTDIQDLATYNELQDQYAQKQTEAIDALNKASSENTQNIAKNSNHIK
TLENNIEEGLLELSGHLIDQKADLTKDIKALESNVEEGLLDLSGRLLDQKADIAQNQANIQDLAAYNELQDAY
AKQQTEAIDALNKASSENTQNIEDLAAYNELQDAYAKQQTEAIDALNKASSENTQNIEDLAAYNELQDAYAK
QQTEAIDALNKASSENTQNIAKNQADIANNINNIYELAQQQDQHSSDIKTLAKASAANTDRIAKNKADADAS
FETLTKNQNTLIEKDKEHDKLITANKTAIDANKASADTKFAATADAITKNGNAITKNAKSITDLGTKVDGFDG
RVTALDTKVNALDTKVNAFDGRITALDSKVENGMAAQAALSGLFQPYSVGKFNATAALGGYGSKSAVAIGAG
YRVNPNLAFKAGAAINTSGNKKGSYNIGVNYEF SEQ ID NO: 52 UspA2 American SP12-5 (686 amino acids)
MKTMKLLPLKIAVTSAMIIGLGAASTANAQATETFLPNLFDNDYTETTDPLYHGMILGNTAITQDTQYKFYAE
NGNEVPDSLFFNKILHDQQLNGFKEGDTIIPLDENGKPVYKLDEITENGVKRKVYSVTTKTATREDVEQSAYS
RGIQGDIDDLYEANKENVNRLIEHGDKIFANEESVQYLNKEVQNNIENIHELAQQQDQHSSDIKTLKKNVEE
GLLELSGRLIAQKEDIAQNQTDIQDLATYNELQDQYAQKQTEAIDALNKASSENTQNIAKNSNHIKTLENNIE
EGLLELSGHLIDQKADLTKDIKALESNVEEGLLDLSGRLLDQKADIAKNQADIAQNQTDIQDLAAYNELQDQY
AQKQTEAIDALNKASSENTQNIEDLAAYNELQDAYAKQQTEAIDALNKASSENTQNIEDLAAYNELQDAYAK
QQTEAIDALNKASSENTQNIAKNQADIANNINNIYELAQQQDQHSSDIKTLAKASAANTDRIAKNKADADAS
FETLTKNQNTLIEKDKEHDKLITANKTAIDANKASADTKFAATADAITKNGNAITKNAKSITDLGTKVDGFDG
RVTALDTKVNALDTKVNAFDGRITALDSKVENGMAAQAALSGLFQPYSVGKFNATAALGGYGSKSAVAIGAG
YRVNPNLAFKAGAAINTSGNKKGSYNIGVNYEF SEQ ID NO: 53 UspA2 Swedish BC5 (630 amino acids)
MKTMKLLPLKIAVTSAMIIGLGAASTANAQAKNDITLEDLPYLIKKIDQNELEADIGDITALEKYLALSQYGNIL
ALEELNKALEELDEDVGWNQNDIANLEDDVETLTKNQNALAEQGEAIKEDLQGLADFVEGQEGKILQNETSI
KKNTQRNLVNGFEIEKNKDAIAKNNESIEDLYDFGHEVAESIGEIHAHNEAQNETLKGLITNSIENTNNITKNK
ADIQALENNVVEELFNLSGRLIDQKADIDNNINNIYELAQQQDQHSSDIKTLKKNVEEGLLELSGHLIDQKTD
IAQNQNANIQDLATYNELQDQYAQKQTEAIDALNKASSENTQNIEDLAAYNELQDAYAKQQTEAIDALNKASS
ENTQNIEDLAAYNELQDAYAKQQTEAIDALNKASSENTQNIAKNQADIANNINNIYELAQQQDQHSSDIKTL
AKASAANTDRIAKNKADADASFETLTKNQNTLIEKDKEHDKLITANKTAIDANKASADTKFAATADAITKNGN
AITKNAKSITDLGTKVDGFDSRVTALDTKVNAFDGRITALDSKVENGMAAQAALSGLFQPYSVGKFNATAAL
GGYGSKSAVAIGAGYRVNPNLAFKAGAAINTSGNKKGSYNIGVNYEF SEQ ID NO: 54 UspA2 American 7169 (616 amino acids)
MKTMKLLPLKIAVTSALIVGLGAASTANAQAQDRSLEQIQDKLANLVEKIEQAKSQNGQSQKDINQYLLLSQY
ANVLTMEELNNNVVKNSSSIETLDNDIAWLNDDLIDLDKEVGLSRDIGSLHDDVAQNQADIKTLKNNVVEE
LFNLSDRLIDQEADIAQNNESIEDLYDFGREVAESIGEIHAHNEAQNETLKDLITNSVKNTDNITKNKADIQAL
ENDVGKELLNLSGRLIDQKADIDNNINHIYELAQQQDQHSSDIKTLKNNVEEGLLELSGHLIDQKADLTKDIK
ALESNVEEGLLDLSGRLLDQKADIAQNQANIQDLAAYNELQDAYAKQQTEAIDALNKASSENTQNIEDLAAY
NELQDAYAKQQTEAIDALNKASSENTQNIAKNQADIANNINNIYELAQQQDQHSSDIKTLAKASAANTDRIA
KNKADADASFETLTKNQNTLIEKDKEHDKLITANKTAIDANKASADTKFAATADAITKNGNAITKNAKSITDL
GTKVDGFDSRVTALDTKVNAFDGRITALDSKVENGMAAQAALSGLFQPYSVGKFNATAALGGYGSKSAVAIG
AGYRVNPNLAFKAGAAINTSGNKKGSYNIGVNYEF SEQ ID NO: 55 UspA2 Finnish FIN2344 (614 amino acids)
MKTMKLLPLKIAVTSAMIIGLGATSTVNAQVVEQFFPNIFFNENHDELDDAYHNMILGDTAIVSNSQDNSTQL
KFYSNDEDSVPDSLLFSKLLHEQQLNGFKAGDTIIPLDKDGKPVYTKDTRTKDGKVETVYSVTTKIATQDDVE
QSAYSRGIQGDIDDLYDINREVNEYLKATHDYNERQTEAIDALNKASSANTDRIDTAEERIDKNEYDIKALES
NVGKDLLDLSGRLIAQKEDIDNNINHIYELAQQQDQHSSDIKTLKNNVEEGLLELSGHLIDQKADLTKDIKTL
ESNVEEGLLDLSGRLIDQKADIAQNQANIQDLAAYNELQDQYAQKQTEAIDALNKASSENTQNIEDLAAYNE
LQDAYAKQQTEAIDALNKASSENTQNIAKNQADIANNINNIYELAQQQDQHSSDIKTLAWSAANTDRIAKN
KADADASFETLTKNQNTLIEKDKEHDKLITANKTAIDANKASADTKFAATADAITKNGNAITKNAKSITDLGT

| SEQUENCES: |
|---|

KVDGFDGRVTALDTKVNAFDGRITALDSKVENGMAAQAALSGLFQPYSVGKFNATAALGGYGSKSAVAIGA
GYRVNPNLAFKAGAAINTSGNKKGSYNIGVNYEF

SEQ ID NO: 56 UspA2 American V1118 (679 amino acids)
MKTMKLPPLKIAVTSAMIIGLGAASTANAQTTETFLPNLFDNDYTETTDPLYHGMILGDTAITQDTQYKFYAE
NGNEVPDSLFFNKILHDQLLNGFKAGDTIIPLDENGKPVYKLDERTENGVKRKVYSVTTKTATQADVEQSAYS
RGIQGDIDDLYEANKENVNRLIEHGDKIFANEESVQYLNREVQNNIENIHELAQQQDQHSSDIKTLKKNVEK
DLLDLSGRLIAQKEDIAQNQTDIQDLATYNELQDQYAQKQTEAIDALNKASSENTQNIAKNSNHIKTLENNIE
ECLLELSGHLIDQKADLTKDIKALESNVEEGLLDLSGRLIDQKADIAQNQANIQDLAAYNELQDAYAKQQTEA
IDALNKASSENTQNIEDLAAYNELQDAYAKQQTEAIDALNKASSENTQNIEDLAAYNELQDAYAKQQTEAID
ALNKASSENTQNIAKNQADIANNINNIYELAQQQDQHSSDIKTLAKASAANTDRIAKNKADADASFETLTKN
QNTLIEKDKEHDKLITANKTAIDANKASADTKFAATADAITKNGNAITKNAKSITDLGTKVDGFDGRVTALDT
KVNALDTKVNAFDGRITALDSWENGMAAQAALSGLFQPYSVGKFNATAALGGYGSKSAVAIGAGYRVNPNL
AFKAGAAINTSGNKKGSYNIGVNYEF SEQ ID NO: 57 UspA2 American V1145 (724 amino acids)
MKTMKLLPLKIAVTSALIVGLGAASTANAQETLEEVLESIKQINEQDLQDDIGYNSALDRYLVLSQYGNLLIAK
ELNENVEKNSNSIAKNSNSIADLEADVGYLAENQNTLIEQNETINQELEGITHELESFIAYAHAQDQKNLVNE
FEIEKNKDAIAKNNESIEDLYDFGHEVAESIGEIHAYTEEVNKTLENLITNSVKNTDNITKNKADIQALESNVE
KELLNLSGRLIDQKADIDNNINHIYELAQQQDQHSSDIKTLELSGHLIDQKSDIAQNQTDIQDL
ATYNELQDQYAQKQTEAIDALNKASSENTQNIEDLAAYNELQDAYAKQQTEAIDALNKASSENTQNIEDLAA
YNELQDAYAKQQTEAIDALNKASSENTQNIEDLAAYNELQDAYAKQQTEAIDALNKASSENTQNIEDLAAYN
ELQDAYAKQQTEAIDALNKASSENTQNIEDLAAYNELQDAYAKQQTEAIDALNKASSENTQNIAKNQADIAN
NINNIYELAQQQDQHSSDIKTLAKASAANTDRIAKNKADADASFETLTKNQNTLIEKDKEHDKLITANKTAID
ANKASADTKFAATADAITKNGNAITKNAKSITDLGTKVDGFDSRVTALDTKVNAFDGRITALDSWENGMAA
QAALSGLFQPYSVGKFNATAALGGYGSKSAVAIGAGYRVNPNLAFKAGAAINTSGNKKGSYNIGVNYEF SEQ ID NO: 58 UspA2 American V1156 (611 amino acids)
MKTMKLLPLKIAVTSALIVGLGAASTANAQAQARDRSLEDIQALIGNIDVDKIRSQKQKNPEIFQYLLLNQLSN
TLITDELNNNVIKNTNSIETLDNDIAWLNDDLIDLDKEVGVLSRDIGSLHDDVAQNQADIKTLENNVVEELFN
LSDRLIDQEAEIAQNNESIEDLYDFGREVAESIGEIHAHNEAQNETLKDLITNSVKNTDNIDKNKADIQALEN
NVEEGLLELSGHLIDQKADLTKDIKALESNVEEGLLDLSGRLLDQKADIAKNQADIAQNQTDIQDLAAYNELQ
DQYAQKQTEAIDALNKASSENTQNIEDLAAYNELQDAYAKQQTEAIDALNKASSENTQNIEDLAAYNELQDA
YAKQQTEAIDALNKASSENTQNIAKNQADIANNINNIYELAQQQDQHSSDIKTLAWSAANTDRIAKNKADA
DASFETLTKNQNTLIEKDKEHDKLITANKTAIDANKASADTKFAATADAITKNGNAITKNAKSITDLGTKVDG
FDSRVTALDTKVNAFDGRITALDSKVENGMAAQAALSGLFQPYSVGKFNATAALGGYGSKSAVAIGAGYRVN
PNLAFKAGAAINTSGNKKGSYNIGVNYEF

| SEQUENCE LISTING |
|---|

<160> NUMBER OF SEQ ID NOS: 58

<210> SEQ ID NO 1
<211> LENGTH: 364
<212> TYPE: PRT
<213> ORGANISM: H. influenzae

<400> SEQUENCE: 1

```
Met Lys Leu Lys Thr Leu Ala Leu Ser Leu Leu Ala Ala Gly Val Leu
1               5                   10                  15

Ala Gly Cys Ser Ser His Ser Ser Asn Met Ala Asn Thr Gln Met Lys
            20                  25                  30

Ser Asp Lys Ile Ile Ile Ala His Arg Gly Ala Ser Gly Tyr Leu Pro
        35                  40                  45

Glu His Thr Leu Glu Ser Lys Ala Leu Ala Phe Ala Gln Gln Ala Asp
    50                  55                  60

Tyr Leu Glu Gln Asp Leu Ala Met Thr Lys Asp Gly Arg Leu Val Val
65                  70                  75                  80

Ile His Asp His Phe Leu Asp Gly Leu Thr Asp Val Ala Lys Lys Phe
                85                  90                  95

Pro His Arg His Arg Lys Asp Gly Arg Tyr Tyr Val Ile Asp Phe Thr
            100                 105                 110

Leu Lys Glu Ile Gln Ser Leu Glu Met Thr Glu Asn Phe Glu Thr Lys
        115                 120                 125
```

Asp Gly Lys Gln Ala Gln Val Tyr Pro Asn Arg Phe Pro Leu Trp Lys
    130                 135                 140

Ser His Phe Arg Ile His Thr Phe Glu Asp Glu Ile Glu Phe Ile Gln
145                 150                 155                 160

Gly Leu Glu Lys Ser Thr Gly Lys Lys Val Gly Ile Tyr Pro Glu Ile
                165                 170                 175

Lys Ala Pro Trp Phe His His Gln Asn Gly Lys Asp Ile Ala Ala Glu
            180                 185                 190

Thr Leu Lys Val Leu Lys Lys Tyr Gly Tyr Asp Lys Lys Thr Asp Met
        195                 200                 205

Val Tyr Leu Gln Thr Phe Asp Phe Asn Glu Leu Lys Arg Ile Lys Thr
    210                 215                 220

Glu Leu Leu Pro Gln Met Gly Met Asp Leu Lys Leu Val Gln Leu Ile
225                 230                 235                 240

Ala Tyr Thr Asp Trp Lys Glu Thr Gln Glu Lys Asp Pro Lys Gly Tyr
                245                 250                 255

Trp Val Asn Tyr Asn Tyr Asp Trp Met Phe Lys Pro Gly Ala Met Ala
            260                 265                 270

Glu Val Val Lys Tyr Ala Asp Gly Val Gly Pro Gly Trp Tyr Met Leu
        275                 280                 285

Val Asn Lys Glu Glu Ser Lys Pro Asp Asn Ile Val Tyr Thr Pro Leu
    290                 295                 300

Val Lys Glu Leu Ala Gln Tyr Asn Val Glu Val His Pro Tyr Thr Val
305                 310                 315                 320

Arg Lys Asp Ala Leu Pro Glu Phe Phe Thr Asp Val Asn Gln Met Tyr
                325                 330                 335

Asp Ala Leu Leu Asn Lys Ser Gly Ala Thr Gly Val Phe Thr Asp Phe
            340                 345                 350

Pro Asp Thr Gly Val Glu Phe Leu Lys Gly Ile Lys
        355                 360

<210> SEQ ID NO 2
<211> LENGTH: 348
<212> TYPE: PRT
<213> ORGANISM: Artificial
<220> FEATURE:
<223> OTHER INFORMATION: Protein D fragment with MDP tripeptide from NS1

<400> SEQUENCE: 2

Met Asp Pro Ser Ser His Ser Ser Asn Met Ala Asn Thr Gln Met Lys
1               5                   10                  15

Ser Asp Lys Ile Ile Ala His Arg Gly Ala Ser G

Ser His Phe Arg Ile His Thr Phe Glu Asp Glu Ile Glu Phe Ile Gln
            130                 135                 140

Gly Leu Glu Lys Ser Thr Gly Lys Lys Val Gly Ile Tyr Pro Glu Ile
145                 150                 155                 160

Lys Ala Pro Trp Phe His His Gln Asn Gly Lys Asp Ile Ala Ala Glu
                165                 170                 175

Thr Leu Lys Val Leu Lys Lys Tyr Gly Tyr Asp Lys Lys Thr Asp Met
            180                 185                 190

Val Tyr Leu Gln Thr Phe Asp Phe Asn Glu Leu Lys Arg Ile Lys Thr
            195                 200                 205

Glu Leu Leu Pro Gln Met Gly Met Asp Leu Lys Leu Val Gln Leu Ile
210                 215                 220

Ala Tyr Thr Asp Trp Lys Glu Thr Gln Glu Lys Asp Pro Lys Gly Tyr
225                 230                 235                 240

Trp Val Asn Tyr Asn Tyr Asp Trp Met Phe Lys Pro Gly Ala Met Ala
                245                 250                 255

Glu Val Val Lys Tyr Ala Asp Gly Val Gly Pro Gly Trp Tyr Met Leu
            260                 265                 270

Val Asn Lys Glu Glu Ser Lys Pro Asp Asn Ile Val Tyr Thr Pro Leu
            275                 280                 285

Val Lys Glu Leu Ala Gln Tyr Asn Val Glu Val His Pro Tyr Thr Val
290                 295                 300

Arg Lys Asp Ala Leu Pro Glu Phe Phe Thr Asp Val Asn Gln Met Tyr
305                 310                 315                 320

Asp Ala Leu Leu Asn Lys Ser Gly Ala Thr Gly Val Phe Thr Asp Phe
                325                 330                 335

Pro Asp Thr Gly Val Glu Phe Leu Lys Gly Ile Lys
            340                 345

<210> SEQ ID NO 3
<211> LENGTH: 10
<212> TYPE: PRT
<213> ORGANISM: H. influenzae

<400> SEQUENCE: 3

Ser Ser His Ser Ser Asn Met Ala Asn Thr
1               5                   10

<210> SEQ ID NO 4
<211> LENGTH: 160
<212> TYPE: PRT
<213> ORGANISM: H. influenzae

<400> SEQUENCE: 4

Met Lys Lys Ile Ile Leu Thr Leu Ser Leu Gly Leu Leu Thr Ala Cys
1               5                   10                  15

Ser Ala Gln Ile Gln Lys Ala Glu Gln Asn Asp Val Lys Leu Ala Pro
            20                  25                  30

Pro Thr Asp Val Arg Ser Gly Tyr Ile Arg Leu Val Lys Asn Val Asn
        35                  40                  45

Tyr Tyr Ile Asp Ser Glu Ser Ile Trp Val Asp Asn Gln Glu Pro Gln
50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
            85                  90                  95

```
Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
        115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Glu Ala Phe Ser Val Asp Lys Lys
145                 150                 155                 160

<210> SEQ ID NO 5
<211> LENGTH: 141
<212> TYPE: PRT
<213> ORGANISM: H. influenzae

<400> SEQUENCE: 5

Ile Gln Lys Ala Glu Gln Asn Asp Val Lys Leu Ala Pro Pro Thr Asp
1               5                   10                  15

Val Arg Ser Gly Tyr Ile Arg Leu Val Lys Asn Val Asn Tyr Tyr Ile
            20                  25                  30

Asp Ser Glu Ser Ile Trp Val Asp Asn Gln Glu Pro Gln Ile Val His
        35                  40                  45

Phe Asp Ala Val Val Asn Leu Asp Lys Gly Leu Tyr Val Tyr Pro Glu
    50                  55                  60

Pro Lys Arg Tyr Ala Arg Ser Val Arg Gln Tyr Lys Ile Leu Asn Cys
65                  70                  75                  80

Ala Asn Tyr His Leu Thr Gln Val Arg Thr Asp Phe Tyr Asp Glu Phe
                85                  90                  95

Trp Gly Gln Gly Leu Arg Ala Ala Pro Lys Lys Gln Lys Lys His Thr
            100                 105                 110

Leu Ser Leu Thr Pro Asp Thr Thr Leu Tyr Asn Ala Ala Gln Ile Ile
        115                 120                 125

Cys Ala Asn Tyr Gly Glu Ala Phe Ser Val Asp Lys Lys
    130                 135                 140

<210> SEQ ID NO 6
<211> LENGTH: 149
<212> TYPE: PRT
<213> ORGANISM: H. influenzae

<400> SEQUENCE: 6

Met Lys Leu Thr Thr Gln Gln Thr Leu Lys Lys Gly Phe Thr Leu Ile
1               5                   10                  15

Glu Leu Met Ile Val Ile Ala Ile Ile Ala Ile Leu Ala Thr Ile Ala
            20                  25                  30

Ile Pro Ser Tyr Gln Asn Tyr Thr Lys Lys Ala Ala Val Ser Glu Leu
        35                  40                  45

Leu Gln Ala Ser Ala Pro Tyr Lys Ala Asp Val Glu Leu Cys Val Tyr
    50                  55                  60

Ser Thr Asn Glu Thr Thr Asn Cys Thr Gly Gly Lys Asn Gly Ile Ala
65                  70                  75                  80

Ala Asp Ile Thr Thr Ala Lys Gly Tyr Val Lys Ser Val Thr Thr Ser
                85                  90                  95

Asn Gly Ala Ile Thr Val Lys Gly Asp Gly Thr Leu Ala Asn Met Glu
            100                 105                 110

Tyr Ile Leu Gln Ala Thr Gly Asn Ala Ala Thr Gly Val Thr Trp Thr
        115                 120                 125
```

```
Thr Thr Cys Lys Gly Thr Asp Ala Ser Leu Phe Pro Ala Asn Phe Cys
        130                 135                 140

Gly Ser Val Thr Gln
145

<210> SEQ ID NO 7
<211> LENGTH: 110
<212> TYPE: PRT
<213> ORGANISM: H. influenzae

<400> SEQUENCE: 7

Thr Lys Lys Ala Ala Val Ser Glu Leu Leu Gln Ala Ser Ala Pro Tyr
1               5                   10                  15

Lys Ala Asp Val Glu Leu Cys Val Tyr Ser Thr Asn Glu Thr Thr Asn
            20                  25                  30

Cys Thr Gly Gly Lys Asn Gly Ile Ala Ala Asp Ile Thr Thr Ala Lys
        35                  40                  45

Gly Tyr Val Lys Ser Val Thr Thr Ser Asn Gly Ala Ile Thr Val Lys
    50                  55                  60

Gly Asp Gly Thr Leu Ala Asn Met Glu Tyr Ile Leu Gln Ala Thr Gly
65                  70                  75                  80

Asn Ala Ala Thr Gly Val Thr Trp Thr Thr Cys Lys Gly Thr Asp
                85                  90                  95

Ala Ser Leu Phe Pro Ala Asn Phe Cys Gly Ser Val Thr Gln
            100                 105                 110

<210> SEQ ID NO 8
<211> LENGTH: 275
<212> TYPE: PRT
<213> ORGANISM: Artificial
<220> FEATURE:
<223> OTHER INFORMATION: LVL735 (protein): (pelB sp)(ProtE aa 20-160)
      (GG)(PilA aa40-149)

<400> SEQUENCE: 8

Met Lys Tyr Leu Leu Pro Thr Ala Ala Ala Gly Leu Leu Leu Leu Ala
1               5                   10                  15

Ala Gln Pro Ala Met Ala Ile Gln Lys Ala Glu Gln Asn Asp Val Lys
            20                  25                  30

Leu Ala Pro Pro Thr Asp Val Arg Ser Gly Tyr Ile Arg Leu Val Lys
        35                  40                  45

Asn Val Asn Tyr Tyr Ile Asp Ser Glu Ser Ile Trp Val Asp Asn Gln
    50                  55                  60

Glu Pro Gln Ile Val His Phe Asp Ala Val Val Asn Leu Asp Lys Gly
65                  70                  75                  80

Leu Tyr Val Tyr Pro Glu Pro Lys Arg Tyr Ala Arg Ser Val Arg Gln
                85                  90                  95

Tyr Lys Ile Leu Asn Cys Ala Asn Tyr His Leu Thr Gln Val Arg Thr
            100                 105                 110

Asp Phe Tyr Asp Glu Phe Trp Gly Gln Gly Leu Arg Ala Ala Pro Lys
        115                 120                 125

Lys Gln Lys Lys His Thr Leu Ser Leu Thr Pro Asp Thr Thr Leu Tyr
    130                 135                 140

Asn Ala Ala Gln Ile Ile Cys Ala Asn Tyr Gly Glu Ala Phe Ser Val
145                 150                 155                 160

Asp Lys Lys Gly Gly Thr Lys Lys Ala Ala Val Ser Glu Leu Leu Gln
                165                 170                 175
```

```
Ala Ser Ala Pro Tyr Lys Ala Asp Val Glu Leu Cys Val Tyr Ser Thr
            180                 185                 190

Asn Glu Thr Thr Asn Cys Thr Gly Gly Lys Asn Gly Ile Ala Ala Asp
        195                 200                 205

Ile Thr Thr Ala Lys Gly Tyr Val Lys Ser Val Thr Thr Ser Asn Gly
210                 215                 220

Ala Ile Thr Val Lys Gly Asp Gly Thr Leu Ala Asn Met Glu Tyr Ile
225                 230                 235                 240

Leu Gln Ala Thr Gly Asn Ala Ala Thr Gly Val Thr Trp Thr Thr Thr
            245                 250                 255

Cys Lys Gly Thr Asp Ala Ser Leu Phe Pro Ala Asn Phe Cys Gly Ser
        260                 265                 270

Val Thr Gln
        275

<210> SEQ ID NO 9
<211> LENGTH: 253
<212> TYPE: PRT
<213> ORGANISM: Artificial
<220> FEATURE:
<223> OTHER INFORMATION: PE-PilA fusion protein without signal peptide

<400> SEQUENCE: 9

Ile Gln Lys Ala Glu Gln Asn Asp Val Lys Leu Ala Pro Pro Thr Asp
1               5                   10                  15

Val Arg Ser Gly Tyr Ile Arg Leu Val Lys Asn Val Asn Tyr Tyr Ile
            20                  25                  30

Asp Ser Glu Ser Ile Trp Val Asp Asn Gln Pro Gln Ile Val His
        35                  40                  45

Phe Asp Ala Val Val Asn Leu Asp Lys Gly Leu Tyr Val Tyr Pro Glu
50                  55                  60

Pro Lys Arg Tyr Ala Arg Ser Val Arg Gln Tyr Lys Ile Leu Asn Cys
65                  70                  75                  80

Ala Asn Tyr His Leu Thr Gln Val Arg Thr Asp Phe Tyr Asp Glu Phe
            85                  90                  95

Trp Gly Gln Gly Leu Arg Ala Ala Pro Lys Lys Gln Lys Lys His Thr
        100                 105                 110

Leu Ser Leu Thr Pro Asp Thr Thr Leu Tyr Asn Ala Ala Gln Ile Ile
    115                 120                 125

Cys Ala Asn Tyr Gly Glu Ala Phe Ser Val Asp Lys Lys Gly Gly Thr
130                 135                 140

Lys Lys Ala Ala Val Ser Glu Leu Leu Gln Ala Ser Ala Pro Tyr Lys
145                 150                 155                 160

Ala Asp Val Glu Leu Cys Val Tyr Ser Thr Asn Glu Thr Thr Asn Cys
                165                 170                 175

Thr Gly Gly Lys Asn Gly Ile Ala Ala Asp Ile Thr Thr Ala Lys Gly
            180                 185                 190

Tyr Val Lys Ser Val Thr Thr Ser Asn Gly Ala Ile Thr Val Lys Gly
        195                 200                 205

Asp Gly Thr Leu Ala Asn Met Glu Tyr Ile Leu Gln Ala Thr Gly Asn
    210                 215                 220

Ala Ala Thr Gly Val Thr Trp Thr Thr Thr Cys Lys Gly Thr Asp Ala
225                 230                 235                 240

Ser Leu Phe Pro Ala Asn Phe Cys Gly Ser Val Thr Gln
            245                 250
```

<210> SEQ ID NO 10
<211> LENGTH: 630
<212> TYPE: PRT
<213> ORGANISM: Moraxalla catarrhalis

<400> SEQUENCE: 10

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ala Lys
            20                  25                  30

Asn Asp Ile Thr Leu Glu Asp Leu Pro Tyr Leu Ile Lys Lys Ile Asp
        35                  40                  45

Gln Asn Glu Leu Glu Ala Asp Ile Gly Asp Ile Thr Ala Leu Glu Lys
    50                  55                  60

Tyr Leu Ala Leu Ser Gln Tyr Gly Asn Ile Leu Ala Leu Glu Glu Leu
65                  70                  75                  80

Asn Lys Ala Leu Glu Glu Leu Asp Glu Asp Val Gly Trp Asn Gln Asn
                85                  90                  95

Asp Ile Ala Asn Leu Glu Asp Asp Val Glu Thr Leu Thr Lys Asn Gln
            100                 105                 110

Asn Ala Leu Ala Glu Gln Gly Glu Ala Ile Lys Glu Asp Leu Gln Gly
        115                 120                 125

Leu Ala Asp Phe Val Glu Gly Gln Glu Gly Lys Ile Leu Gln Asn Glu
    130                 135                 140

Thr Ser Ile Lys Lys Asn Thr Gln Arg Asn Leu Val Asn Gly Phe Glu
145                 150                 155                 160

Ile Glu Lys Asn Lys Asp Ala Ile Ala Lys Asn Asn Glu Ser Ile Glu
                165                 170                 175

Asp Leu Tyr Asp Phe Gly His Glu Val Ala Glu Ser Ile Gly Glu Ile
            180                 185                 190

His Ala His Asn Glu Ala Gln Asn Glu Thr Leu Lys Gly Leu Ile Thr
        195                 200                 205

Asn Ser Ile Glu Asn Thr Asn Asn Ile Thr Lys Asn Lys Ala Asp Ile
    210                 215                 220

Gln Ala Leu Glu Asn Asn Val Val Glu Glu Leu Phe Asn Leu Ser Gly
225                 230                 235                 240

Arg Leu Ile Asp Gln Lys Ala Asp Ile Asp Asn Asn Ile Asn Asn Ile
                245                 250                 255

Tyr Glu Leu Ala Gln Gln Gln Asp Gln His Ser Ser Asp Ile Lys Thr
            260                 265                 270

Leu Lys Lys Asn Val Glu Glu Gly Leu Leu Glu Leu Ser Gly His Leu
        275                 280                 285

Ile Asp Gln Lys Thr Asp Ile Ala Gln Asn Ala Asn Ile Gln Asp
    290                 295                 300

Leu Ala Thr Tyr Asn Glu Leu Gln Asp Gln Tyr Ala Gln Lys Gln Thr
305                 310                 315                 320

Glu Ala Ile Asp Ala Leu Asn Lys Ala Ser Ser Glu Asn Thr Gln Asn
                325                 330                 335

Ile Glu Asp Leu Ala Ala Tyr Asn Glu Leu Gln Asp Ala Tyr Ala Lys
            340                 345                 350

Gln Gln Thr Glu Ala Ile Asp Ala Leu Asn Lys Ala Ser Ser Glu Asn
        355                 360                 365

Thr Gln Asn Ile Glu Asp Leu Ala Ala Tyr Asn Glu Leu Gln Asp Ala
    370                 375                 380

Tyr Ala Lys Gln Gln Thr Glu Ala Ile Asp Ala Leu Asn Lys Ala Ser
385                 390                 395                 400

Ser Glu Asn Thr Gln Asn Ile Ala Lys Asn Gln Ala Asp Ile Ala Asn
            405                 410                 415

Asn Ile Asn Asn Ile Tyr Glu Leu Ala Gln Gln Asp Gln His Ser
            420                 425                 430

Ser Asp Ile Lys Thr Leu Ala Lys Ala Ser Ala Ala Asn Thr Asp Arg
            435                 440                 445

Ile Ala Lys Asn Lys Ala Asp Ala Asp Ala Ser Phe Glu Thr Leu Thr
450                 455                 460

Lys Asn Gln Asn Thr Leu Ile Glu Lys Asp Lys Glu His Asp Lys Leu
465                 470                 475                 480

Ile Thr Ala Asn Lys Thr Ala Ile Asp Ala Asn Lys Ala Ser Ala Asp
            485                 490                 495

Thr Lys Phe Ala Ala Thr Ala Asp Ala Ile Thr Lys Asn Gly Asn Ala
            500                 505                 510

Ile Thr Lys Asn Ala Lys Ser Ile Thr Asp Leu Gly Thr Lys Val Asp
            515                 520                 525

Gly Phe Asp Ser Arg Val Thr Ala Leu Asp Thr Lys Val Asn Ala Phe
530                 535                 540

Asp Gly Arg Ile Thr Ala Leu Asp Ser Lys Val Glu Asn Gly Met Ala
545                 550                 555                 560

Ala Gln Ala Ala Leu Ser Gly Leu Phe Gln Pro Tyr Ser Val Gly Lys
            565                 570                 575

Phe Asn Ala Thr Ala Ala Leu Gly Gly Tyr Gly Ser Lys Ser Ala Val
            580                 585                 590

Ala Ile Gly Ala Gly Tyr Arg Val Asn Pro Asn Leu Ala Phe Lys Ala
            595                 600                 605

Gly Ala Ala Ile Asn Thr Ser Gly Asn Lys Lys Gly Ser Tyr Asn Ile
            610                 615                 620

Gly Val Asn Tyr Glu Phe
625                 630

<210> SEQ ID NO 11
<211> LENGTH: 520
<212> TYPE: PRT
<213> ORGANISM: Artificial
<220> FEATURE:
<223> OTHER INFORMATION: MC-001 (protein) - (M)(UspA2 amino acids 30 -
      540)(ASHHHHHH)

<400> SEQUENCE: 11

Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
            35                  40                  45

Leu Glu Glu Leu Asn Lys Ala Leu Glu Glu Leu Asp Glu Asp Val Gly
        50                  55                  60

Trp Asn Gln Asn Asp Ile Ala Asn Leu Glu Asp Val Glu Thr Leu
65                  70                  75                  80

Thr Lys Asn Gln Asn Ala Leu Ala Glu Gln Gly Glu Ala Ile Lys Glu
            85                  90                  95

Asp Leu Gln Gly Leu Ala Asp Phe Val Glu Gly Gln Glu Gly Lys Ile

```
                100             105             110
Leu Gln Asn Glu Thr Ser Ile Lys Lys Asn Thr Gln Arg Asn Leu Val
            115             120             125
Asn Gly Phe Glu Ile Glu Lys Asn Lys Asp Ala Ile Ala Lys Asn Asn
        130             135             140
Glu Ser Ile Glu Asp Leu Tyr Asp Phe Gly His Glu Val Ala Glu Ser
145             150             155             160
Ile Gly Glu Ile His Ala His Asn Glu Ala Gln Asn Glu Thr Leu Lys
                165             170             175
Gly Leu Ile Thr Asn Ser Ile Glu Asn Thr Asn Asn Ile Thr Lys Asn
            180             185             190
Lys Ala Asp Ile Gln Ala Leu Glu Asn Asn Val Val Glu Glu Leu Phe
        195             200             205
Asn Leu Ser Gly Arg Leu Ile Asp Gln Lys Ala Asp Ile Asp Asn Asn
210             215             220
Ile Asn Asn Ile Tyr Glu Leu Ala Gln Gln Gln Asp Gln His Ser Ser
225             230             235             240
Asp Ile Lys Thr Leu Lys Lys Asn Val Glu Glu Gly Leu Leu Glu Leu
            245             250             255
Ser Gly His Leu Ile Asp Gln Lys Thr Asp Ile Ala Gln Asn Gln Ala
        260             265             270
Asn Ile Gln Asp Leu Ala Thr Tyr Asn Glu Leu Gln Asp Gln Tyr Ala
    275             280             285
Gln Lys Gln Thr Glu Ala Ile Asp Ala Leu Asn Lys Ala Ser Ser Glu
290             295             300
Asn Thr Gln Asn Ile Glu Asp Leu Ala Ala Tyr Asn Glu Leu Gln Asp
305             310             315             320
Ala Tyr Ala Lys Gln Gln Thr Glu Ala Ile Asp Ala Leu Asn Lys Ala
            325             330             335
Ser Ser Glu Asn Thr Gln Asn Ile Glu Asp Leu Ala Ala Tyr Asn Glu
        340             345             350
Leu Gln Asp Ala Tyr Ala Lys Gln Gln Thr Glu Ala Ile Asp Ala Leu
    355             360             365
Asn Lys Ala Ser Ser Glu Asn Thr Gln Asn Ile Ala Lys Asn Gln Ala
370             375             380
Asp Ile Ala Asn Asn Ile Asn Asn Ile Tyr Glu Leu Ala Gln Gln Gln
385             390             395             400
Asp Gln His Ser Ser Asp Ile Lys Thr Leu Ala Lys Ala Ser Ala Ala
            405             410             415
Asn Thr Asp Arg Ile Ala Lys Asn Lys Ala Asp Ala Asp Ala Ser Phe
        420             425             430
Glu Thr Leu Thr Lys Asn Gln Asn Thr Leu Ile Glu Lys Asp Lys Glu
    435             440             445
His Asp Lys Leu Ile Thr Ala Asn Lys Thr Ala Ile Asp Ala Asn Lys
450             455             460
Ala Ser Ala Asp Thr Lys Phe Ala Thr Ala Asp Ala Ile Thr Lys
465             470             475             480
Asn Gly Asn Ala Ile Thr Lys Asn Ala Lys Ser Ile Thr Asp Leu Gly
            485             490             495
Thr Lys Val Asp Gly Phe Asp Ser Arg Val Thr Ala Leu Asp Thr Lys
        500             505             510
Ala Ser His His His His His His
    515             520
```

<210> SEQ ID NO 12
<211> LENGTH: 512
<212> TYPE: PRT
<213> ORGANISM: Moraxalla catarrhalis

<400> SEQUENCE: 12

Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala

```
                370              375              380
Asp Ile Ala Asn Asn Ile Asn Asn Ile Tyr Glu Leu Ala Gln Gln Gln
385              390              395              400

Asp Gln His Ser Ser Asp Ile Lys Thr Leu Ala Lys Ala Ser Ala Ala
            405              410              415

Asn Thr Asp Arg Ile Ala Lys Asn Lys Ala Asp Ala Asp Ala Ser Phe
            420              425              430

Glu Thr Leu Thr Lys Asn Gln Asn Thr Leu Ile Glu Lys Asp Lys Glu
            435              440              445

His Asp Lys Leu Ile Thr Ala Asn Lys Thr Ala Ile Asp Ala Asn Lys
        450              455              460

Ala Ser Ala Asp Thr Lys Phe Ala Ala Thr Ala Asp Ala Ile Thr Lys
465              470              475              480

Asn Gly Asn Ala Ile Thr Lys Asn Ala Lys Ser Ile Thr Asp Leu Gly
                485              490              495

Thr Lys Val Asp Gly Phe Asp Ser Arg Val Thr Ala Leu Asp Thr Lys
            500              505              510
```

<210> SEQ ID NO 13
<211> LENGTH: 513
<212> TYPE: PRT
<213> ORGANISM: Artificial
<220> FEATURE:
<223> OTHER INFORMATION: MC-003 (Protein) - (M)(UspA2 amino acids 30-540)(H)

<400> SEQUENCE: 13

```
Met Gln Ala Lys Asn Asp Ile Thr Leu Glu Asp Leu Pro Tyr Leu Ile
1               5                  10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220
```

```
Ile Asn Asn Ile Tyr Glu Leu Ala Gln Gln Gln Asp Gln His Ser Ser
225                 230                 235                 240

Asp Ile Lys Thr Leu Lys Lys Asn Val Glu Glu Gly Leu Leu Glu Leu
            245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
            275                 280                 285

Gln Lys Gln Thr Glu Ala Ile Asp Ala Leu Asn Lys Ala Ser Ser Glu
            290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
            325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
            355                 360                 365

Asn Lys Ala Ser Ser Glu Asn Thr Gln Asn Ile Ala Lys Asn Gln Ala
370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
            405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
            435                 440                 445

His Asp Lys Leu Ile Thr Ala Asn Lys Thr Ala Ile Asp Ala Asn Lys
            450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
            485                 490                 495

Thr Lys Val Asp Gly Phe Asp Ser Arg Val Thr Ala Leu Asp Thr Lys
            500                 505                 510

His
```

<210> SEQ ID NO 14
<211> LENGTH: 514
<212> TYPE: PRT
<213> ORGANISM: Artificial
<220> FEATURE:
<223> OTHER INFORMATION: MC-004 (Protein) - (M)(UspA2 amino acids 30-540)(HH)

<400> SEQUENCE: 14

```
Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60
```

```
Trp Asn Gln Asn Asp Ile Ala Asn Leu Glu Asp Val Glu Thr Leu
 65                  70                  75                  80

Thr Lys Asn Gln Asn Ala Leu Ala Glu Gln Gly Glu Ala Ile Lys Glu
                 85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala
    370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
        435                 440                 445

His Asp Lys Leu Ile Thr Ala Asn Lys Thr Ala Ile Asp Ala Asn Lys
    450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
```

```
                    485                 490                 495
Thr Lys Val Asp Gly Phe Asp Ser Arg Val Thr Ala Leu Asp Thr Lys
                500                 505                 510

His His

<210> SEQ ID NO 15
<211> LENGTH: 499
<212> TYPE: PRT
<213> ORGANISM: Artificial
<220> FEATURE:
<223> OTHER INFORMATION: MC-005 (Protein) - (M)(UspA2 amino acids
      30-519)(ASHHHHHH)

<400> SEQUENCE: 15

Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
```

```
                    325                 330                 335
Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
            355                 360                 365

Asn Lys Ala Ser Ser Glu Asn Thr Gln Asn Ile Ala Lys Asn Gln Ala
            370                 375                 380

Asp Ile Ala Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
            405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
            435                 440                 445

His Asp Lys Leu Ile Thr Ala Asn Lys Thr Ala Ile Asp Ala Asn Lys
            450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ala Ser His His His
            485                 490                 495

His His His

<210> SEQ ID NO 16
<211> LENGTH: 491
<212> TYPE: PRT
<213> ORGANISM: Moraxalla catarrhalis

<400> SEQUENCE: 16

Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
                20                  25                  30

Ala Leu Glu Lys Tyr Leu Ala Leu Ser Gln Tyr Gly Asn Ile Leu Ala
            35                  40                  45

Leu Glu Glu Leu Asn Lys Ala Leu Glu Glu Leu Asp Glu Asp Val Gly
        50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
```

|  | 195 |  |  |  | 200 |  |  |  | 205 |  |  |
|---|---|---|---|---|---|---|---|---|---|---|---|

Asn Leu Ser Gly Arg Leu Ile Asp Gln Lys Ala Asp Ile Asp Asn Asn
210 215 220

Ile Asn Asn Ile Tyr Glu Leu Ala Gln Gln Asp Gln His Ser Ser
225 230 235 240

Asp Ile Lys Thr Leu Lys Lys Asn Val Glu Glu Gly Leu Leu Glu Leu
245 250 255

Ser Gly His Leu Ile Asp Gln Lys Thr Asp Ile Ala Gln Asn Gln Ala
260 265 270

Asn Ile Gln Asp Leu Ala Thr Tyr Asn Glu Leu Gln Asp Gln Tyr Ala
275 280 285

Gln Lys Gln Thr Glu Ala Ile Asp Ala Leu Asn Lys Ala Ser Ser Glu
290 295 300

Asn Thr Gln Asn Ile Glu Asp Leu Ala Ala Tyr Asn Glu Leu Gln Asp
305 310 315 320

Ala Tyr Ala Lys Gln Gln Thr Glu Ala Ile Asp Ala Leu Asn Lys Ala
325 330 335

Ser Ser Glu Asn Thr Gln Asn Ile Glu Asp Leu Ala Ala Tyr Asn Glu
340 345 350

Leu Gln Asp Ala Tyr Ala Lys Gln Gln Thr Glu Ala Ile Asp Ala Leu
355 360 365

Asn Lys Ala Ser Ser Glu Asn Thr Gln Asn Ile Ala Lys Asn Gln Ala
370 375 380

Asp Ile Ala Asn Asn Ile Asn Asn Ile Tyr Glu Leu Ala Gln Gln Gln
385 390 395 400

Asp Gln His Ser Ser Asp Ile Lys Thr Leu Ala Lys Ala Ser Ala Ala
405 410 415

Asn Thr Asp Arg Ile Ala Lys Asn Lys Ala Asp Ala Asp Ala Ser Phe
420 425 430

Glu Thr Leu Thr Lys Asn Gln Asn Thr Leu Ile Glu Lys Asp Lys Glu
435 440 445

His Asp Lys Leu Ile Thr Ala Asn Lys Thr Ala Ile Asp Ala Asn Lys
450 455 460

Ala Ser Ala Asp Thr Lys Phe Ala Ala Thr Ala Asp Ala Ile Thr Lys
465 470 475 480

Asn Gly Asn Ala Ile Thr Lys Asn Ala Lys Ser
485 490

<210> SEQ ID NO 17
<211> LENGTH: 544
<212> TYPE: PRT
<213> ORGANISM: Artificial
<220> FEATURE:
<223> OTHER INFORMATION: MC-007 (Protein) - (M)(UspA2 amino acids 30-564)(ASHHHHHH)

<400> SEQUENCE: 17

Met Gln Ala Lys Asn Asp Ile Thr Leu Glu Asp Leu Pro Tyr Leu Ile
1 5 10 15

Lys Lys Ile Asp Gln Asn Glu Leu Glu Ala Asp Ile Gly Asp Ile Thr
20 25 30

Ala Leu Glu Lys Tyr Leu Ala Leu Ser Gln Tyr Gly Asn Ile Leu Ala
35 40 45

Leu Glu Glu Leu Asn Lys Ala Leu Glu Glu Leu Asp Glu Asp Val Gly
50 55 60

-continued

```
Trp Asn Gln Asn Asp Ile Ala Asn Leu Glu Asp Val Glu Thr Leu
 65                  70                  75                  80

Thr Lys Asn Gln Asn Ala Leu Ala Glu Gln Gly Glu Ala Ile Lys Glu
                 85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala
    370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
            420                 425                 430

Glu Thr Leu Thr Lys Asn Gln Asn Thr Leu Ile Glu Lys Asp Lys Glu
        435                 440                 445

His Asp Lys Leu Ile Thr Ala Asn Lys Thr Ala Ile Asp Ala Asn Lys
    450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
```

```
                        485                 490                 495
Thr Lys Val Asp Gly Phe Asp Ser Arg Val Thr Ala Leu Asp Thr Lys
                    500                 505                 510

Val Asn Ala Phe Asp Gly Arg Ile Thr Ala Leu Asp Ser Lys Val Glu
                515                 520                 525

Asn Gly Met Ala Ala Gln Ala Ala Ser His His His His His His
            530                 535                 540

<210> SEQ ID NO 18
<211> LENGTH: 538
<212> TYPE: PRT
<213> ORGANISM: Artificial
<220> FEATURE:
<223> OTHER INFORMATION: MC-008 (Protein) - (M)(UspA2 30-564)(HH)

<400> SEQUENCE: 18

Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Gly Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
```

```
            305                 310                 315                 320
Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
                340                 345                 350

Leu Gln Asp Ala Tyr Ala Lys Gln Thr Glu Ala Ile Asp Ala Leu
                355                 360                 365

Asn Lys Ala Ser Ser Glu Asn Thr Gln Asn Ile Ala Lys Asn Gln Ala
    370                 375                 380

Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
                405                 410                 415

Asn Thr Asp Arg Ile Ala Lys Asn Lys Ala Asp Ala Asp Ala Ser Phe
                420                 425                 430

Glu Thr Leu Thr Lys Asn Gln Asn Thr Leu Ile Glu Lys Asp Lys Glu
                435                 440                 445

His Asp Lys Leu Ile Thr Ala Asn Lys Thr Ala Ile Asp Ala Asn Lys
    450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
                485                 490                 495

Thr Lys Val Asp Gly Phe Asp Ser Arg Val Thr Ala Leu Asp Thr Lys
                500                 505                 510

Val Asn Ala Phe Asp Gly Arg Ile Thr Ala Leu Asp Ser Lys Val Glu
                515                 520                 525

Asn Gly Met Ala Ala Gln Ala Ala His His
    530                 535

<210> SEQ ID NO 19
<211> LENGTH: 537
<212> TYPE: PRT
<213> ORGANISM: Artificial
<220> FEATURE:
<223> OTHER INFORMATION: MC-009 (Protein) - (M)(UspA2 31-564)(HH)

<400> SEQUENCE: 19

Met Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
                20                  25                  30

Leu Glu Lys Tyr Leu Ala Leu Ser Gln Tyr Gly Asn Ile Leu Ala Leu
                35                  40                  45

Glu Glu Leu Asn Lys Ala Leu Glu Glu Leu Asp Glu Asp Val Gly Trp
    50                  55                  60

Asn Gln Asn Asp Ile Ala Asn Leu Glu Asp Asp Val Glu Thr Leu Thr
65                  70                  75                  80

Lys Asn Gln Asn Ala Leu Ala Glu Gln Gly Glu Ala Ile Lys Glu Asp
                85                  90                  95

Leu Gln Gly Leu Ala Asp Phe Val Glu Gly Gln Glu Gly Lys Ile Leu
                100                 105                 110

Gln Asn Glu Thr Ser Ile Lys Lys Asn Thr Gln Arg Asn Leu Val Asn
                115                 120                 125

Gly Phe Glu Ile Glu Lys Asn Lys Asp Ala Ile Ala Lys Asn Asn Glu
```

```
            130                 135                 140
Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
                165                 170                 175

Leu Ile Thr Asn Ser Ile Glu Asn Thr Asn Asn Ile Thr Lys Asn Lys
                180                 185                 190

Ala Asp Ile Gln Ala Leu Glu Asn Asn Val Val Glu Glu Leu Phe Asn
                195                 200                 205

Leu Ser Gly Arg Leu Ile Asp Gln Lys Ala Asp Ile Asp Asn Asn Ile
210                 215                 220

Asn Asn Ile Tyr Glu Leu Ala Gln Gln Gln Asp Gln His Ser Ser Asp
225                 230                 235                 240

Ile Lys Thr Leu Lys Lys Asn Val Glu Glu Gly Leu Leu Glu Leu Ser
                245                 250                 255

Gly His Leu Ile Asp Gln Lys Thr Asp Ile Ala Gln Asn Gln Ala Asn
                260                 265                 270

Ile Gln Asp Leu Ala Thr Tyr Asn Glu Leu Gln Asp Gln Tyr Ala Gln
                275                 280                 285

Lys Gln Thr Glu Ala Ile Asp Ala Leu Asn Lys Ala Ser Ser Glu Asn
290                 295                 300

Thr Gln Asn Ile Glu Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
                325                 330                 335

Ser Glu Asn Thr Gln Asn Ile Glu Asp Leu Ala Ala Tyr Asn Glu Leu
                340                 345                 350

Gln Asp Ala Tyr Ala Lys Gln Gln Thr Glu Ala Ile Asp Ala Leu Asn
                355                 360                 365

Lys Ala Ser Ser Glu Asn Thr Gln Asn Ile Ala Lys Asn Gln Ala Asp
                370                 375                 380

Ile Ala Asn Asn Ile Asn Asn Ile Tyr Glu Leu Ala Gln Gln Gln Asp
385                 390                 395                 400

Gln His Ser Ser Asp Ile Lys Thr Leu Ala Lys Ala Ser Ala Ala Asn
                405                 410                 415

Thr Asp Arg Ile Ala Lys Asn Lys Ala Asp Ala Asp Ala Ser Phe Glu
                420                 425                 430

Thr Leu Thr Lys Asn Gln Asn Thr Leu Ile Glu Lys Asp Lys Glu His
                435                 440                 445

Asp Lys Leu Ile Thr Ala Asn Lys Thr Ala Ile Asp Ala Asn Lys Ala
                450                 455                 460

Ser Ala Asp Thr Lys Phe Ala Ala Thr Ala Asp Ala Ile Thr Lys Asn
465                 470                 475                 480

Gly Asn Ala Ile Thr Lys Asn Ala Lys Ser Ile Thr Asp Leu Gly Thr
                485                 490                 495

Lys Val Asp Gly Phe Asp Ser Arg Val Thr Ala Leu Asp Thr Lys Val
                500                 505                 510

Asn Ala Phe Asp Gly Arg Ile Thr Ala Leu Asp Ser Lys Val Glu Asn
                515                 520                 525

Gly Met Ala Ala Gln Ala Ala His His
530                 535
```

<210> SEQ ID NO 20

<211> LENGTH: 536
<212> TYPE: PRT
<213> ORGANISM: Moraxalla catarrhalis

<400> SEQUENCE: 20

```
Met Gln Ala Lys Asn Asp Ile Thr Leu Glu Asp Leu Pro Tyr Leu Ile
1               5                   10                  15

Lys Lys Ile Asp Gln Asn Glu Leu Glu Ala Asp Ile Gly Asp Ile Thr
            20                  25                  30

Ala Leu Glu Lys Tyr Leu Ala Leu Ser Gln Tyr Gly Asn Ile Leu Ala
        35                  40                  45

Leu Glu Glu Leu Asn Lys Ala Leu Glu Glu Leu Asp Glu Asp Val Gly
    50                  55                  60

Trp Asn Gln Asn Asp Ile Ala Asn Leu Glu Asp Asp Val Glu Thr Leu
65                  70                  75                  80

Thr Lys Asn Gln Asn Ala Leu Ala Glu Gln Gly Glu Ala Ile Lys Glu
                85                  90                  95

Asp Leu Gln Gly Leu Ala Asp Phe Val Glu Gly Gln Glu Gly Lys Ile
            100                 105                 110

Leu Gln Asn Glu Thr Ser Ile Lys Lys Asn Thr Gln Arg Asn Leu Val
        115                 120                 125

Asn Gly Phe Glu Ile Glu Lys Asn Lys Asp Ala Ile Ala Lys Asn Asn
    130                 135                 140

Glu Ser Ile Glu Asp Leu Tyr Asp Phe Gly His Glu Val Ala Glu Ser
145                 150                 155                 160

Ile Gly Glu Ile His Ala His Asn Glu Ala Gln Asn Glu Thr Leu Lys
                165                 170                 175

Gly Leu Ile Thr Asn Ser Ile Glu Asn Thr Asn Asn Ile Thr Lys Asn
            180                 185                 190

Lys Ala Asp Ile Gln Ala Leu Glu Asn Asn Val Val Glu Glu Leu Phe
        195                 200                 205

Asn Leu Ser Gly Arg Leu Ile Asp Gln Lys Ala Asp Ile Asp Asn Asn
    210                 215                 220

Ile Asn Asn Ile Tyr Glu Leu Ala Gln Gln Asp Gln His Ser Ser
225                 230                 235                 240

Asp Ile Lys Thr Leu Lys Lys Asn Val Glu Glu Gly Leu Leu Glu Leu
                245                 250                 255

Ser Gly His Leu Ile Asp Gln Lys Thr Asp Ile Ala Gln Asn Gln Ala
            260                 265                 270

Asn Ile Gln Asp Leu Ala Thr Tyr Asn Glu Leu Gln Asp Gln Tyr Ala
        275                 280                 285

Gln Lys Gln Thr Glu Ala Ile Asp Ala Leu Asn Lys Ala Ser Ser Glu
    290                 295                 300

Asn Thr Gln Asn Ile Glu Asp Leu Ala Ala Tyr Asn Glu Leu Gln Asp
305                 310                 315                 320

Ala Tyr Ala Lys Gln Gln Thr Glu Ala Ile Asp Ala Leu Asn Lys Ala
                325                 330                 335

Ser Ser Glu Asn Thr Gln Asn Ile Glu Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Ala Lys Asn Gln Ala
    370                 375                 380

Asp Ile Ala Asn Asn Ile Asn Asn Ile Tyr Glu Leu Ala Gln Gln Gln
```

```
                385                 390                 395                 400
Asp Gln His Ser Ser Asp Ile Lys Thr Leu Ala Lys Ala Ser Ala Ala
                    405                 410                 415

Asn Thr Asp Arg Ile Ala Lys Asn Lys Ala Asp Ala Asp Ala Ser Phe
                420                 425                 430

Glu Thr Leu Thr Lys Asn Gln Asn Thr Leu Ile Glu Lys Asp Lys Glu
                435                 440                 445

His Asp Lys Leu Ile Thr Ala Asn Lys Thr Ala Ile Asp Ala Asn Lys
450                 455                 460

Ala Ser Ala Asp Thr Lys Phe Ala Ala Thr Ala Asp Ala Ile Thr Lys
465                 470                 475                 480

Asn Gly Asn Ala Ile Thr Lys Asn Ala Lys Ser Ile Thr Asp Leu Gly
                    485                 490                 495

Thr Lys Val Asp Gly Phe Asp Ser Arg Val Thr Ala Leu Asp Thr Lys
                500                 505                 510

Val Asn Ala Phe Asp Gly Arg Ile Thr Ala Leu Asp Ser Lys Val Glu
            515                 520                 525

Asn Gly Met Ala Ala Gln Ala Ala
530                 535

<210> SEQ ID NO 21
<211> LENGTH: 519
<212> TYPE: PRT
<213> ORGANISM: Artificial
<220> FEATURE:
<223> OTHER INFORMATION: MC-011 (Protein) - (M)(UspA2 amino acids
      31-540)(ASHHHHHH)

<400> SEQUENCE: 21

Met Ala Lys Asn Asp Ile Thr Leu Glu Asp Leu Pro Tyr Leu Ile Lys
1               5                   10                  15

Lys Ile Asp Gln Asn Glu Leu Glu Ala Asp Ile Gly Asp Ile Thr Ala
                20                  25                  30

Leu Glu Lys Tyr Leu Ala Leu Ser Gln Tyr Gly Asn Ile Leu Ala Leu
            35                  40                  45

Glu Glu Leu Asn Lys Ala Leu Glu Glu Leu Asp Glu Asp Val Gly Trp
        50                  55                  60

Asn Gln Asn Asp Ile Ala Asn Leu Glu Asp Asp Val Glu Thr Leu Thr
65                  70                  75                  80

Lys Asn Gln Asn Ala Leu Ala Glu Gln Gly Glu Ala Ile Lys Glu Asp
                85                  90                  95

Leu Gln Gly Leu Ala Asp Phe Val Glu Gly Gln Gly Lys Ile Leu
            100                 105                 110

Gln Asn Glu Thr Ser Ile Lys Lys Asn Thr Gln Arg Asn Leu Val Asn
        115                 120                 125

Gly Phe Glu Ile Glu Lys Asn Lys Asp Ala Ile Ala Lys Asn Asn Glu
130                 135                 140

Ser Ile Glu Asp Leu Tyr Asp Phe Gly His Glu Val Ala Glu Ser Ile
145                 150                 155                 160

Gly Glu Ile His Ala His Asn Glu Ala Gln Asn Glu Thr Leu Lys Gly
                165                 170                 175

Leu Ile Thr Asn Ser Ile Glu Asn Thr Asn Asn Ile Thr Lys Asn Lys
            180                 185                 190

Ala Asp Ile Gln Ala Leu Glu Asn Asn Val Val Glu Glu Leu Phe Asn
        195                 200                 205
```

```
Leu Ser Gly Arg Leu Ile Asp Gln Lys Ala Asp Ile Asp Asn Asn Ile
    210                 215                 220

Asn Asn Ile Tyr Glu Leu Ala Gln Gln Gln Asp Gln His Ser Ser Asp
225                 230                 235                 240

Ile Lys Thr Leu Lys Lys Asn Val Glu Glu Gly Leu Leu Glu Leu Ser
                245                 250                 255

Gly His Leu Ile Asp Gln Lys Thr Asp Ile Ala Gln Asn Gln Ala Asn
            260                 265                 270

Ile Gln Asp Leu Ala Thr Tyr Asn Glu Leu Gln Asp Gln Tyr Ala Gln
        275                 280                 285

Lys Gln Thr Glu Ala Ile Asp Ala Leu Asn Lys Ala Ser Ser Glu Asn
    290                 295                 300

Thr Gln Asn Ile Glu Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
                325                 330                 335

Ser Glu Asn Thr Gln Asn Ile Glu Asp Leu Ala Ala Tyr Asn Glu Leu
            340                 345                 350

Gln Asp Ala Tyr Ala Lys Gln Gln Thr Glu Ala Ile Asp Ala Leu Asn
        355                 360                 365

Lys Ala Ser Ser Glu Asn Thr Gln Asn Ile Ala Lys Asn Gln Ala Asp
    370                 375                 380

Ile Ala Asn Asn Ile Asn Asn Ile Tyr Glu Leu Ala Gln Gln Gln Asp
385                 390                 395                 400

Gln His Ser Ser Asp Ile Lys Thr Leu Ala Lys Ala Ser Ala Ala Asn
                405                 410                 415

Thr Asp Arg Ile Ala Lys Asn Lys Ala Asp Ala Asp Ala Ser Phe Glu
            420                 425                 430

Thr Leu Thr Lys Asn Gln Asn Thr Leu Ile Glu Lys Asp Lys Glu His
        435                 440                 445

Asp Lys Leu Ile Thr Ala Asn Lys Thr Ala Ile Asp Ala Asn Lys Ala
    450                 455                 460

Ser Ala Asp Thr Lys Phe Ala Ala Thr Ala Asp Ala Ile Thr Lys Asn
465                 470                 475                 480

Gly Asn Ala Ile Thr Lys Asn Ala Lys Ser Ile Thr Asp Leu Gly Thr
                485                 490                 495

Lys Val Asp Gly Phe Asp Ser Arg Val Thr Ala Leu Asp Thr Lys Ala
            500                 505                 510

Ser His His His His His
    515

<210> SEQ ID NO 22
<211> LENGTH: 613
<212> TYPE: PRT
<213> ORGANISM: Moraxalla catarrhalis

<400> SEQUENCE: 22

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ser Arg
            20                  25                  30

Asp Arg Ser Leu Glu Asp Ile Gln Asp Ser Ile Ser Lys Leu Val Gln
        35                  40                  45

Asp Asp Ile Asn Thr Leu Lys Gln Asp Gln Gln Lys Met Asn Lys Tyr
    50                  55                  60
```

```
Leu Leu Leu Asn Gln Leu Ala Asn Thr Leu Ile Thr Asp Glu Leu Asn
 65                  70                  75                  80

Asn Asn Val Ile Lys Asn Thr Asn Ser Ile Glu Ala Leu Gly Asp Glu
                 85                  90                  95

Ile Gly Trp Leu Glu Asn Asp Ile Ala Asp Leu Glu Glu Gly Val Glu
                100                 105                 110

Glu Leu Thr Lys Asn Gln Asn Thr Leu Ile Glu Lys Asp Glu Glu His
            115                 120                 125

Asp Arg Leu Ile Ala Gln Asn Gln Ala Asp Ile Gln Thr Leu Glu Asn
130                 135                 140

Asn Val Val Glu Glu Leu Phe Asn Leu Ser Gly Arg Leu Ile Asp Gln
145                 150                 155                 160

Glu Ala Asp Ile Ala Lys Asn Asn Ala Ser Ile Glu Glu Leu Tyr Asp
                165                 170                 175

Phe Asp Asn Glu Val Ala Glu Arg Ile Gly Glu Ile His Ala Tyr Thr
                180                 185                 190

Glu Glu Val Asn Lys Thr Leu Glu Asn Leu Ile Thr Asn Ser Val Lys
            195                 200                 205

Asn Thr Asp Asn Ile Asp Lys Asn Lys Ala Asp Ile Asp Asn Asn Ile
210                 215                 220

Asn His Ile Tyr Glu Leu Ala Gln Gln Gln Asp Gln His Ser Ser Asp
225                 230                 235                 240

Ile Lys Thr Leu Lys Asn Asn Val Glu Glu Gly Leu Leu Glu Leu Ser
                245                 250                 255

Gly His Leu Ile Asp Gln Lys Ala Asp Leu Thr Lys Asp Ile Lys Ala
                260                 265                 270

Leu Glu Ser Asn Val Glu Glu Gly Leu Leu Asp Leu Ser Gly Arg Leu
            275                 280                 285

Leu Asp Gln Lys Ala Asp Leu Thr Lys Asp Ile Lys Ala Leu Glu Ser
290                 295                 300

Asn Val Glu Glu Gly Leu Leu Asp Leu Ser Gly Arg Leu Leu Asp Gln
305                 310                 315                 320

Lys Ala Asp Ile Ala Gln Asn Gln Thr Asp Ile Gln Asp Leu Ala Ala
                325                 330                 335

Tyr Asn Glu Leu Gln Asp Gln Tyr Ala Gln Lys Gln Thr Glu Ala Ile
                340                 345                 350

Asp Ala Leu Asn Lys Ala Ser Ser Glu Asn Thr Gln Asn Ile Glu Asp
            355                 360                 365

Leu Ala Ala Tyr Asn Glu Leu Gln Asp Ala Tyr Ala Lys Gln Gln Thr
370                 375                 380

Glu Ala Ile Asp Ala Leu Asn Lys Ala Ser Ser Glu Asn Thr Gln Asn
385                 390                 395                 400

Ile Ala Lys Asn Gln Ala Asp Ile Ala Asn Asn Ile Asn Asn Ile Tyr
                405                 410                 415

Glu Leu Ala Gln Gln Gln Asp Gln His Ser Ser Asp Ile Lys Thr Leu
                420                 425                 430

Ala Lys Ala Ser Ala Ala Asn Thr Asn Arg Ile Ala Thr Ala Glu Leu
            435                 440                 445

Gly Ile Ala Glu Asn Lys Lys Asp Ala Gln Ile Ala Lys Ala Gln Ala
            450                 455                 460

Asn Ala Asn Lys Thr Ala Ile Asp Glu Asn Lys Ala Ser Ala Asp Thr
465                 470                 475                 480
```

```
Lys Phe Ala Ala Thr Ala Asp Ala Ile Thr Lys Asn Gly Asn Ala Ile
                485                 490                 495

Thr Lys Asn Ala Lys Ser Ile Thr Asp Leu Gly Thr Lys Val Asp Gly
            500                 505                 510

Phe Asp Gly Arg Val Thr Ala Leu Asp Thr Lys Val Asn Ala Phe Asp
        515                 520                 525

Gly Arg Ile Thr Ala Leu Asp Ser Lys Val Glu Asn Gly Met Ala Ala
    530                 535                 540

Gln Ala Ala Leu Ser Gly Leu Phe Gln Pro Tyr Ser Val Gly Lys Phe
545                 550                 555                 560

Asn Ala Thr Ala Ala Leu Gly Gly Tyr Gly Ser Lys Ser Ala Val Ala
                565                 570                 575

Ile Gly Ala Gly Tyr Arg Val Asn Pro Asn Leu Ala Phe Lys Ala Gly
            580                 585                 590

Ala Ala Ile Asn Thr Ser Gly Asn Lys Lys Gly Ser Tyr Asn Ile Gly
        595                 600                 605

Val Asn Tyr Glu Phe
    610

<210> SEQ ID NO 23
<211> LENGTH: 644
<212> TYPE: PRT
<213> ORGANISM: Moraxalla catarrhalis

<400> SEQUENCE: 23

Met Lys Thr Met Lys Leu Leu Pro Leu Lys Ile Ala Val Thr Ser Ala
1               5                   10                  15

Leu Ile Ile Gly Leu Gly Ala Ala Ser Thr Ala Asn Ala Gln Gln Gln
                20                  25                  30

Leu Gln Thr Glu Thr Phe Leu Pro Asn Phe Leu Ser Asn Asp Asn Tyr
            35                  40                  45

Asp Leu Thr Asp Pro Phe Tyr His Asn Met Ile Leu Gly Asp Thr Ala
        50                  55                  60

Leu Leu Asp Lys Gln Asp Gly Ser Gln Pro Gln Leu Lys Phe Tyr Ser
65                  70                  75                  80

Asn Asp Lys Asp Ser Val Pro Asp Ser Leu Leu Phe Ser Lys Leu Leu
                85                  90                  95

His Glu Gln Gln Leu Asn Gly Phe Lys Lys Gly Asp Thr Ile Ile Pro
            100                 105                 110

Leu Asp Lys Asp Gly Lys Pro Val Tyr Gln Val Asp Tyr Lys Leu Asp
        115                 120                 125

Gly Lys Gly Lys Lys Gln Lys Arg Arg Gln Val Tyr Ser Val Thr Thr
    130                 135                 140

Lys Thr Ala Thr Asp Asp Val Asn Ser Ala Tyr Ser Arg Gly Ile
145                 150                 155                 160

Leu Gly Lys Val Asp Asp Leu Asp Asp Glu Met Asn Phe Leu Asn His
                165                 170                 175

Asp Ile Thr Ser Leu Tyr Asp Val Thr Ala Asn Gln Gln Asp Ala Ile
            180                 185                 190

Lys Asp Leu Lys Lys Gly Val Lys Gly Leu Asn Lys Glu Leu Lys Glu
        195                 200                 205

Leu Asp Lys Glu Val Gly Val Leu Ser Arg Asp Ile Gly Ser Leu Asn
    210                 215                 220

Asp Asp Val Ala Gln Asn Asn Glu Ser Ile Glu Asp Leu Tyr Asp Phe
225                 230                 235                 240
```

```
Ser Gln Glu Val Ala Asp Ser Ile Gly Glu Ile His Ala His Asn Lys
                245                 250                 255

Ala Gln Asn Glu Thr Leu Gln Asp Leu Ile Thr Asn Ser Val Glu Asn
            260                 265                 270

Thr Asn Asn Ile Thr Lys Asn Lys Ala Asp Ile Gln Ala Leu Glu Asn
        275                 280                 285

Asn Val Val Glu Glu Leu Phe Asn Leu Ser Gly Arg Leu Ile Asp Gln
    290                 295                 300

Lys Ala Asp Leu Thr Lys Asp Ile Lys Thr Leu Glu Ser Asn Val Glu
305                 310                 315                 320

Glu Gly Leu Leu Glu Leu Ser Gly His Leu Ile Asp Gln Lys Ala Asp
                325                 330                 335

Ile Ala Lys Asn Gln Ala Asp Ile Ala Gln Asn Gln Ala Asn Ile Gln
            340                 345                 350

Asp Leu Ala Ala Tyr Asn Glu Leu Gln Asp Ala Tyr Ala Lys Gln Gln
        355                 360                 365

Thr Glu Ala Ile Asp Ala Leu Asn Lys Ala Ser Ser Glu Asn Thr Gln
    370                 375                 380

Asn Ile Glu Asp Leu Ala Ala Tyr Asn Glu Leu Gln Asp Ala Tyr Ala
385                 390                 395                 400

Lys Gln Gln Thr Glu Ala Ile Asp Ala Leu Asn Lys Ala Ser Ser Glu
                405                 410                 415

Asn Thr Gln Asn Ile Ala Lys Asn Gln Ala Asp Ile Ala Asn Asn Ile
            420                 425                 430

Asn Asn Ile Tyr Glu Leu Ala Gln Gln Gln Asp Gln His Ser Ser Asp
        435                 440                 445

Ile Lys Thr Leu Ala Lys Ala Ser Ala Ala Asn Thr Asp Arg Ile Ala
    450                 455                 460

Lys Asn Lys Ala Asp Ala Asp Ala Ser Phe Glu Thr Leu Thr Lys Asn
465                 470                 475                 480

Gln Asn Thr Leu Ile Glu Lys Asp Lys Glu His Asp Lys Leu Ile Thr
                485                 490                 495

Ala Asn Lys Thr Ala Ile Asp Glu Asn Lys Ala Ser Ala Asp Thr Lys
            500                 505                 510

Phe Ala Ala Thr Ala Asp Ala Ile Thr Lys Asn Gly Asn Ala Ile Thr
        515                 520                 525

Lys Asn Ala Lys Ser Ile Thr Asp Leu Gly Thr Lys Val Asp Gly Phe
    530                 535                 540

Asp Ser Arg Val Thr Ala Leu Asp Thr Lys Val Asn Ala Phe Asp Gly
545                 550                 555                 560

Arg Ile Thr Ala Leu Asp Ser Lys Val Glu Asn Gly Met Ala Ala Gln
                565                 570                 575

Ala Ala Leu Ser Gly Leu Phe Gln Pro Tyr Ser Val Gly Lys Phe Asn
            580                 585                 590

Ala Thr Ala Ala Leu Gly Gly Tyr Gly Ser Lys Ser Ala Val Ala Ile
        595                 600                 605

Gly Ala Gly Tyr Arg Val Asn Pro Asn Leu Ala Phe Lys Ala Gly Ala
    610                 615                 620

Ala Ile Asn Thr Ser Gly Asn Lys Lys Gly Ser Tyr Asn Ile Gly Val
625                 630                 635                 640

Asn Tyr Glu Phe
```

-continued

```
<210> SEQ ID NO 24
<211> LENGTH: 591
<212> TYPE: PRT
<213> ORGANISM: Moraxalla catarrhalis

<400> SEQUENCE: 24
```

| | | | | | | | | | | | | | | |
|---|---|---|---|---|---|---|---|---|---|---|---|---|---|---|
| Met | Lys | Thr | Met | Lys | Leu | Leu | Pro | Leu | Lys | Ile | Ala | Val | Thr | Ser | Ala |
| 1 | | | | 5 | | | | | 10 | | | | | 15 | |
| Leu | Ile | Val | Gly | Leu | Gly | Ala | Ala | Ser | Thr | Ala | Asn | Ala | Gln | Leu | Val |
| | | | 20 | | | | | 25 | | | | | 30 | | |
| Glu | Arg | Phe | Phe | Pro | Asn | Ile | Phe | Leu | Asp | Lys | Pro | Leu | Ala | Lys | Gln |
| | | | 35 | | | | | 40 | | | | | 45 | | |
| His | Tyr | His | Asn | Val | Val | Gly | Asp | Thr | Ser | Ile | Val | Ser | Asp | Leu | |
| | 50 | | | | | 55 | | | | | 60 | | | | |
| Gln | Ser | Asn | Ser | Asp | Gln | Leu | Lys | Phe | Tyr | Ser | Asp | Glu | Gly | Leu | |
| 65 | | | | | 70 | | | | | 75 | | | | | 80 |
| Val | Pro | Asp | Ser | Leu | Leu | Phe | Asn | Lys | Met | Leu | His | Glu | Gln | Leu | Leu |
| | | | | 85 | | | | | 90 | | | | | 95 | |
| Asn | Gly | Phe | Lys | Glu | Gly | Asp | Thr | Ile | Ile | Pro | Leu | Asp | Glu | Asn | Gly |
| | | | 100 | | | | | 105 | | | | | 110 | | |
| Lys | Pro | Val | Tyr | Lys | Val | Asp | Tyr | Lys | Leu | Asp | Gly | Lys | Glu | Pro | Arg |
| | | | 115 | | | | | 120 | | | | | 125 | | |
| Lys | Val | Tyr | Ser | Val | Thr | Thr | Lys | Ile | Ala | Thr | Ala | Glu | Asp | Val | Ala |
| | 130 | | | | | 135 | | | | | 140 | | | | |
| Thr | Ser | Ser | Tyr | Ala | Asn | Gly | Ile | Gln | Lys | Asp | Ile | Asp | Leu | Tyr | |
| 145 | | | | | 150 | | | | | 155 | | | | | 160 |
| Asp | Phe | Asp | His | Gln | Val | Thr | Glu | Arg | Leu | Thr | Gln | His | Gly | Lys | Thr |
| | | | | 165 | | | | | 170 | | | | | 175 | |
| Ile | Tyr | Arg | Asn | Gly | Glu | Arg | Ile | Leu | Ala | Asn | Glu | Glu | Ser | Val | Gln |
| | | | 180 | | | | | 185 | | | | | 190 | | |
| Tyr | Leu | Asn | Lys | Glu | Val | Gln | Asn | Asn | Ile | Glu | His | Ile | Tyr | Glu | Leu |
| | | | 195 | | | | | 200 | | | | | 205 | | |
| Ala | Gln | Gln | Gln | Asp | Gln | His | Ser | Ser | Asp | Ile | Lys | Thr | Leu | Glu | Ser |
| | 210 | | | | | 215 | | | | | 220 | | | | |
| Asn | Val | Glu | Lys | Gly | Leu | Leu | Glu | Leu | Ser | Gly | His | Leu | Ile | Asp | Gln |
| 225 | | | | | 230 | | | | | 235 | | | | | 240 |
| Lys | Ala | Asp | Leu | Thr | Lys | Asp | Ile | Lys | Thr | Leu | Glu | Ser | Asn | Val | Glu |
| | | | | 245 | | | | | 250 | | | | | 255 | |
| Glu | Gly | Leu | Leu | Asp | Leu | Ser | Gly | Arg | Leu | Ile | Asp | Gln | Lys | Ala | Asp |
| | | | 260 | | | | | 265 | | | | | 270 | | |
| Leu | Thr | Lys | Asp | Ile | Lys | Thr | Leu | Glu | Ser | Asn | Val | Glu | Glu | Gly | Leu |
| | | | 275 | | | | | 280 | | | | | 285 | | |
| Leu | Asp | Leu | Ser | Gly | Arg | Leu | Ile | Asp | Gln | Lys | Ala | Asp | Ile | Ala | Gln |
| | 290 | | | | | 295 | | | | | 300 | | | | |
| Asn | Gln | Ala | Asn | Ile | Gln | Asp | Leu | Ala | Ala | Tyr | Asn | Glu | Leu | Gln | Asp |
| 305 | | | | | 310 | | | | | 315 | | | | | 320 |
| Gln | Tyr | Ala | Gln | Lys | Gln | Thr | Glu | Ala | Ile | Asp | Ala | Leu | Asn | Lys | Ala |
| | | | | 325 | | | | | 330 | | | | | 335 | |
| Ser | Ser | Glu | Asn | Thr | Gln | Asn | Ile | Glu | Asp | Leu | Ala | Ala | Tyr | Asn | Glu |
| | | | 340 | | | | | 345 | | | | | 350 | | |
| Leu | Gln | Asp | Ala | Tyr | Ala | Lys | Gln | Gln | Thr | Glu | Ala | Ile | Asp | Ala | Leu |
| | | | 355 | | | | | 360 | | | | | 365 | | |
| Asn | Lys | Ala | Ser | Ser | Glu | Asn | Thr | Gln | Asn | Ile | Ala | Lys | Asn | Gln | Ala |
| | 370 | | | | | 375 | | | | | 380 | | | | |

```
Asp Ile Ala Asn Asn Ile Asn Asn Ile Tyr Glu Leu Ala Gln Gln Gln
385                 390                 395                 400

Asp Gln His Ser Ser Asp Ile Lys Thr Leu Ala Lys Ala Ser Ala Ala
            405                 410                 415

Asn Thr Asn Arg Ile Ala Thr Ala Glu Leu Gly Ile Ala Glu Asn Lys
        420                 425                 430

Lys Asp Ala Gln Ile Ala Lys Ala Gln Ala Asn Ala Asn Lys Thr Ala
    435                 440                 445

Ile Asp Glu Asn Lys Ala Ser Ala Asp Thr Lys Phe Ala Ala Thr Ala
    450                 455                 460

Asp Ala Ile Thr Lys Asn Gly Asn Ala Ile Thr Lys Asn Ala Lys Ser
465                 470                 475                 480

Ile Thr Asp Leu Gly Thr Lys Val Asp Gly Phe Asp Ser Arg Val Thr
            485                 490                 495

Ala Leu Asp Thr Lys Val Asn Ala Phe Asp Gly Arg Ile Thr Ala Leu
            500                 505                 510

Asp Ser Lys Val Glu Asn Gly Met Ala Ala Gln Ala Ala Leu Ser Gly
        515                 520                 525

Leu Phe Gln Pro Tyr Ser Val Gly Lys Phe Asn Ala Thr Ala Ala Leu
530                 535                 540

Gly Gly Tyr Gly Ser Lys Ser Ala Val Ala Ile Gly Ala Gly Tyr Arg
545                 550                 555                 560

Val Asn Pro Asn Leu Ala Phe Lys Ala Gly Ala Ala Ile Asn Thr Ser
            565                 570                 575

Gly Asn Lys Lys Gly Ser Tyr Asn Ile Gly Val Asn Tyr Glu Phe
        580                 585                 590

<210> SEQ ID NO 25
<211> LENGTH: 687
<212> TYPE: PRT
<213> ORGANISM: Moraxalla catarrhalis

<400> SEQUENCE: 25

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Gln Gln
            20                  25                  30

Gln Gln Gln Gln Gln Gln Gln Ser Arg Thr Glu Ile Phe Phe Pro
        35                  40                  45

Asn Ile Phe Phe Asn Glu Asn His Asp Glu Leu Asp Asp Ala Tyr His
    50                  55                  60

Asn Ile Ile Leu Gly Asp Thr Ala Leu Leu Asp Lys Gln Asp Gly Ser
65                  70                  75                  80

Gln Pro Gln Leu Lys Phe Tyr Ser Asn Asp Lys Asp Ser Val Pro Asp
            85                  90                  95

Ser Leu Leu Phe Ser Lys Leu Leu His Glu Gln Gln Leu Asn Gly Phe
            100                 105                 110

Lys Lys Gly Asp Thr Ile Ile Pro Leu Asp Lys Asp Gly Lys Pro Val
        115                 120                 125

Tyr Gln Val Asp Tyr Lys Leu Asp Gly Lys Gly Lys Gln Lys Arg
130                 135                 140

Arg Gln Val Tyr Ser Val Thr Thr Lys Thr Ala Thr Asp Asp Val
145                 150                 155                 160

Asn Ser Ala Tyr Ser Arg Gly Ile Leu Gly Lys Val Asp Asp Leu Asp
            165                 170                 175
```

```
Asp Glu Met Asn Phe Leu Asn His Asp Ile Thr Ser Leu Tyr Asp Val
            180                 185                 190

Thr Ala Asn Gln Gln Asp Ala Ile Lys Gly Leu Lys Lys Gly Val Lys
        195                 200                 205

Gly Leu Asn Lys Glu Leu Lys Glu Leu Asp Lys Glu Val Gly Val Leu
    210                 215                 220

Ser Arg Asp Ile Gly Ser Leu Asn Asp Asp Val Ala Gln Asn Asn Glu
225                 230                 235                 240

Ser Ile Glu Asp Leu Tyr Asp Phe Ser Gln Glu Val Ala Asp Ser Ile
                245                 250                 255

Gly Glu Ile His Ala His Asn Lys Ala Gln Asn Glu Thr Leu Gln Asp
                260                 265                 270

Leu Ile Thr Asn Ser Val Glu Asn Thr Asn Ile Thr Lys Asn Lys
                275                 280                 285

Ala Asp Ile Gln Ala Leu Glu Asn Asn Val Val Glu Glu Leu Phe Asn
    290                 295                 300

Leu Ser Gly Arg Leu Ile Asp Gln Lys Ala Asp Leu Thr Lys Asp Ile
305                 310                 315                 320

Lys Thr Leu Glu Ser Asn Val Glu Glu Gly Leu Leu Glu Leu Ser Gly
                325                 330                 335

His Leu Ile Asp Gln Lys Ala Asp Ile Ala Lys Asn Gln Ala Asp Ile
                340                 345                 350

Ala Gln Asn Gln Ala Asn Ile Gln Asp Leu Ala Ala Tyr Asn Glu Leu
            355                 360                 365

Gln Asp Ala Tyr Ala Lys Gln Thr Glu Ala Ile Asp Ala Leu Asn
    370                 375                 380

Lys Ala Ser Ser Glu Asn Thr Gln Asn Ile Glu Asp Leu Ala Ala Tyr
385                 390                 395                 400

Asn Glu Leu Gln Asp Ala Tyr Ala Lys Gln Gln Thr Glu Ala Ile Asp
                405                 410                 415

Ala Leu Asn Lys Ala Ser Ser Glu Asn Thr Gln Asn Ile Glu Asp Leu
                420                 425                 430

Ala Ala Tyr Asn Glu Leu Gln Asp Ala Tyr Ala Lys Gln Gln Thr Glu
                435                 440                 445

Ala Ile Asp Ala Leu Asn Lys Ala Ser Ser Glu Asn Thr Gln Asn Ile
    450                 455                 460

Ala Lys Asn Gln Ala Asp Ile Ala Asn Ile Asn Asn Ile Tyr Glu
465                 470                 475                 480

Leu Ala Gln Gln Gln Asp Gln His Ser Ser Asp Ile Lys Thr Leu Ala
                485                 490                 495

Lys Ala Ser Ala Ala Asn Thr Asp Arg Ile Ala Lys Asn Lys Ala Asp
            500                 505                 510

Ala Asp Ala Ser Phe Glu Thr Leu Thr Lys Asn Gln Asn Thr Leu Ile
            515                 520                 525

Glu Lys Asp Lys Glu His Asp Lys Leu Ile Thr Ala Asn Lys Thr Ala
                530                 535                 540

Ile Asp Glu Asn Lys Ala Ser Ala Asp Thr Lys Phe Ala Ala Thr Ala
545                 550                 555                 560

Asp Ala Ile Thr Lys Asn Gly Asn Ala Ile Thr Lys Asn Ala Lys Ser
                565                 570                 575

Ile Thr Asp Leu Gly Thr Lys Val Asp Ala Phe Asp Gly Arg Val Thr
                580                 585                 590
```

-continued

```
Ala Leu Asp Thr Lys Val Asn Ala Phe Asp Gly Arg Ile Thr Ala Leu
            595                 600                 605

Asp Ser Lys Val Glu Asn Gly Met Ala Ala Gln Ala Ala Leu Ser Gly
    610                 615                 620

Leu Phe Gln Pro Tyr Ser Val Gly Lys Phe Asn Ala Thr Ala Ala Leu
625                 630                 635                 640

Gly Gly Tyr Gly Ser Lys Ser Ala Val Ala Ile Gly Ala Gly Tyr Arg
                645                 650                 655

Val Asn Pro Asn Leu Ala Phe Lys Ala Gly Ala Ala Ile Asn Thr Ser
            660                 665                 670

Gly Asn Lys Lys Gly Ser Tyr Asn Ile Gly Val Asn Tyr Glu Phe
            675                 680                 685
```

<210> SEQ ID NO 26
<211> LENGTH: 683
<212> TYPE: PRT
<213> ORGANISM: Moraxalla catarrhalis

<400> SEQUENCE: 26

```
Met Lys Thr Met Lys Leu Leu Pro Leu Lys Ile Ala Val Thr Ser Ala
1               5                   10                  15

Met Ile Val Gly Leu Gly Met Ala Ser Thr Ala Asn Ala Gln Gln Gln
                20                  25                  30

Lys Ser Pro Lys Thr Glu Thr Phe Leu Pro Asn Ile Phe Phe Asn Glu
            35                  40                  45

Tyr Ala Asp Asp Leu Asp Thr Leu Tyr His Asn Met Ile Leu Gly Asp
        50                  55                  60

Thr Ala Ile Thr His Asp Asp Gln Tyr Lys Phe Tyr Ala Asp Asp Ala
65                  70                  75                  80

Thr Glu Val Pro Asp Ser Leu Phe Phe Asn Lys Ile Leu His Asp Gln
                85                  90                  95

Leu Leu Tyr Gly Phe Lys Glu Gly Asp Lys Ile Ile Pro Leu Asp Glu
            100                 105                 110

Asn Gly Lys Pro Val Tyr Lys Leu Asp Lys Arg Leu Glu Asn Gly Val
        115                 120                 125

Gln Lys Thr Val Tyr Ser Val Thr Thr Lys Thr Ala Thr Ala Asp Asp
130                 135                 140

Val Asn Ser Ala Tyr Ser Arg Gly Ile Gln Gly Asp Ile Asp Asp Leu
145                 150                 155                 160

Tyr Glu Ala Asn Lys Glu Asn Val Asn Arg Leu Ile Glu His Gly Asp
                165                 170                 175

Lys Ile Phe Ala Asn Glu Glu Ser Val Gln Tyr Leu Asn Arg Glu Val
            180                 185                 190

Gln Asn Asn Ile Glu Asn Ile His Glu Leu Ala Gln Gln Gln Asp Gln
        195                 200                 205

His Ser Ser Asp Ile Lys Thr Leu Lys Lys Asn Val Glu Lys Asp Leu
    210                 215                 220

Leu Asp Leu Ser Gly Arg Leu Ile Ala Gln Lys Glu Asp Ile Ala Gln
225                 230                 235                 240

Asn Gln Thr Asp Ile Gln Asp Leu Ala Thr Tyr Asn Glu Leu Gln Asp
                245                 250                 255

Gln Tyr Ala Gln Lys Gln Thr Glu Ala Ile Asp Ala Leu Asn Lys Ala
            260                 265                 270

Ser Ser Glu Asn Thr Gln Asn Ile Ala Lys Asn Ser Asn His Ile Lys
        275                 280                 285
```

-continued

Thr Leu Glu Asn Asn Ile Glu Glu Gly Leu Leu Glu Leu Ser Gly His
    290                 295                 300

Leu Ile Asp Gln Lys Ala Asp Leu Thr Lys Asp Ile Lys Ala Leu Glu
305                 310                 315                 320

Ser Asn Val Glu Glu Gly Leu Leu Asp Leu Ser Gly Arg Leu Ile Asp
                325                 330                 335

Gln Lys Ala Asp Ile Ala Gln Asn Gln Ala Asn Ile Gln Asp Leu Ala
            340                 345                 350

Ala Tyr Asn Glu Leu Gln Asp Ala Tyr Ala Lys Gln Gln Thr Glu Ala
        355                 360                 365

Ile Asp Ala Leu Asn Lys Ala Ser Ser Glu Asn Thr Gln Asn Ile Glu
370                 375                 380

Asp Leu Ala Ala Tyr Asn Glu Leu Gln Asp Ala Tyr Ala Lys Gln Gln
385                 390                 395                 400

Thr Glu Ala Ile Asp Ala Leu Asn Lys Ala Ser Ser Glu Asn Thr Gln
                405                 410                 415

Asn Ile Glu Asp Leu Ala Ala Tyr Asn Glu Leu Gln Asp Ala Tyr Ala
            420                 425                 430

Lys Gln Gln Thr Glu Ala Ile Asp Ala Leu Asn Lys Ala Ser Ser Glu
        435                 440                 445

Asn Thr Gln Asn Ile Ala Lys Asn Gln Ala Asp Ile Ala Asn Asn Ile
450                 455                 460

Asn Asn Ile Tyr Glu Leu Ala Gln Gln Gln Asp Gln His Ser Ser Asp
465                 470                 475                 480

Ile Lys Thr Leu Ala Lys Ala Ser Ala Ala Asn Thr Asp Arg Ile Ala
                485                 490                 495

Lys Asn Lys Ala Asp Ala Asp Ala Ser Phe Glu Thr Leu Thr Lys Asn
            500                 505                 510

Gln Asn Thr Leu Ile Glu Lys Asp Lys Glu His Asp Lys Leu Ile Thr
        515                 520                 525

Ala Asn Lys Thr Ala Ile Asp Ala Asn Lys Ala Ser Ala Asp Thr Lys
530                 535                 540

Phe Ala Ala Thr Ala Asp Ala Ile Thr Lys Asn Gly Asn Ala Ile Thr
545                 550                 555                 560

Lys Asn Ala Lys Ser Ile Thr Asp Leu Gly Thr Lys Val Asp Gly Phe
                565                 570                 575

Asp Gly Arg Val Thr Ala Leu Asp Thr Lys Val Asn Ala Leu Asp Thr
            580                 585                 590

Lys Val Asn Ala Phe Asp Gly Arg Ile Thr Ala Leu Asp Ser Lys Val
        595                 600                 605

Glu Asn Gly Met Ala Ala Gln Ala Ala Leu Ser Gly Leu Phe Gln Pro
610                 615                 620

Tyr Ser Val Gly Lys Phe Asn Ala Thr Ala Ala Leu Gly Gly Tyr Gly
625                 630                 635                 640

Ser Lys Ser Ala Val Ala Ile Gly Ala Gly Tyr Arg Val Asn Pro Asn
                645                 650                 655

Leu Ala Phe Lys Ala Gly Ala Ala Ile Asn Thr Ser Gly Asn Lys Lys
            660                 665                 670

Gly Ser Tyr Asn Ile Gly Val Asn Tyr Glu Phe
        675                 680

<210> SEQ ID NO 27
<211> LENGTH: 684

<212> TYPE: PRT
<213> ORGANISM: Moraxalla catarrhalis

<400> SEQUENCE: 27

```
Met Lys Thr Met Lys Leu Leu Pro Leu Lys Ile Ala Val Thr Ser Ala
1               5                   10                  15

Met Met Val Gly Leu Gly Met Ala Ser Thr Ala Asn Ala Gln Gln Gln
            20                  25                  30

Lys Ser Pro Lys Thr Glu Ile Phe Leu Pro Asn Leu Phe Asp Asn Asp
        35                  40                  45

Asn Thr Glu Leu Thr Asp Pro Leu Tyr His Asn Met Ile Leu Gly Asn
    50                  55                  60

Thr Ala Leu Leu Thr Gln Glu Asn Gln Tyr Lys Phe Tyr Ala Asp Asp
65                  70                  75                  80

Gly Asn Gly Val Pro Asp Ser Leu Leu Phe Asn Lys Ile Leu His Asp
                85                  90                  95

Gln Leu Leu His Gly Phe Lys Glu Gly Gly Thr Ile Ile Pro Leu Asp
            100                 105                 110

Glu Asn Gly Lys Pro Val Tyr Lys Leu Asp Ser Ile Val Glu Gln Gly
        115                 120                 125

Lys Thr Lys Thr Val Tyr Ser Val Thr Thr Lys Thr Ala Thr Ala Asp
    130                 135                 140

Asp Val Asn Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
                165                 170                 175

Asp Lys Ile Phe Ala Asn Glu Ser Val Gln Tyr Leu Asn Arg Glu
            180                 185                 190

Val Gln Asn Asn Ile Glu Asn Ile His Glu Leu Ala Gln Gln Gln Asp
        195                 200                 205

Gln His Ser Ser Asp Ile Lys Thr Leu Lys Lys Asn Val Glu Lys Asp
    210                 215                 220

Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
                245                 250                 255

Asp Gln Tyr Ala Gln Lys Gln Thr Glu Ala Ile Asp Ala Leu Asn Lys
            260                 265                 270

Ala Ser Ser Glu Asn Thr Gln Asn Ile Ala Lys Asn Ser Asn His Ile
        275                 280                 285

Lys Thr Leu Glu Asn Asn Ile Glu Glu Gly Leu Leu Glu Leu Ser Gly
    290                 295                 300

His Leu Ile Asp Gln Lys Ala Asp Leu Thr Lys Asp Ile Lys Ala Leu
305                 310                 315                 320

Glu Ser Asn Val Glu Glu Gly Leu Leu Asp Leu Ser Gly Arg Leu Ile
                325                 330                 335

Asp Gln Lys Ala Asp Ile Ala Gln Asn Gln Ala Asn Ile Gln Asp Leu
            340                 345                 350

Ala Ala Tyr Asn Glu Leu Gln Asp Ala Tyr Ala Lys Gln Gln Thr Glu
        355                 360                 365

Ala Ile Asp Ala Leu Asn Lys Ala Ser Ser Glu Asn Thr Gln Asn Ile
    370                 375                 380

Glu Asp Leu Ala Ala Tyr Asn Glu Leu Gln Asp Ala Tyr Ala Lys Gln
385                 390                 395                 400
```

```
Gln Thr Glu Ala Ile Asp Ala Leu Asn Lys Ala Ser Ser Glu Asn Thr
                405                 410                 415

Gln Asn Ile Glu Asp Leu Ala Ala Tyr Asn Glu Leu Gln Asp Ala Tyr
            420                 425                 430

Ala Lys Gln Gln Thr Glu Ala Ile Asp Ala Leu Asn Lys Ala Ser Ser
        435                 440                 445

Glu Asn Thr Gln Asn Ile Ala Lys Asn Gln Ala Asp Ile Ala Asn Asn
    450                 455                 460

Ile Asn Asn Ile Tyr Glu Leu Ala Gln Gln Asp Gln His Ser Ser
465                 470                 475                 480

Asp Ile Lys Thr Leu Ala Lys Ala Ser Ala Ala Asn Thr Asp Arg Ile
                485                 490                 495

Ala Lys Asn Lys Ala Asp Ala Asp Ala Ser Phe Glu Thr Leu Thr Lys
            500                 505                 510

Asn Gln Asn Thr Leu Ile Glu Lys Asp Lys Glu His Asp Lys Leu Ile
        515                 520                 525

Thr Ala Asn Lys Thr Ala Ile Asp Ala Asn Lys Ala Ser Ala Asp Thr
    530                 535                 540

Lys Phe Ala Ala Thr Ala Asp Ala Ile Thr Lys Asn Gly Asn Ala Ile
545                 550                 555                 560

Thr Lys Asn Ala Lys Ser Ile Thr Asp Leu Gly Thr Lys Val Asp Gly
                565                 570                 575

Phe Asp Gly Arg Val Thr Ala Leu Asp Thr Lys Val Asn Ala Leu Asp
            580                 585                 590

Thr Lys Val Asn Ala Phe Asp Gly Arg Ile Thr Ala Leu Asp Ser Lys
        595                 600                 605

Val Glu Asn Gly Met Ala Ala Gln Ala Ala Leu Ser Gly Leu Phe Gln
    610                 615                 620

Pro Tyr Ser Val Gly Lys Phe Asn Ala Thr Ala Ala Leu Gly Gly Tyr
625                 630                 635                 640

Gly Ser Lys Ser Ala Val Ala Ile Gly Ala Gly Tyr Arg Val Asn Pro
                645                 650                 655

Asn Leu Ala Phe Lys Ala Gly Ala Ala Ile Asn Thr Ser Gly Asn Lys
            660                 665                 670

Lys Gly Ser Tyr Asn Ile Gly Val Asn Tyr Glu Phe
        675                 680

<210> SEQ ID NO 28
<211> LENGTH: 684
<212> TYPE: PRT
<213> ORGANISM: Moraxalla catarrhalis

<400> SEQUENCE: 28

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Gln Gln
            20                  25                  30

Gln Lys Thr Lys Thr Glu Val Phe Leu Pro Asn Leu Phe Asp Asn Asp
        35                  40                  45

Tyr Tyr Asp Leu Thr Asp Pro Leu Tyr His Ser Met Ile Leu Gly Asp
    50                  55                  60

Thr Ala Thr Leu Phe Asp Gln Gln Asp Asn Ser Lys Ser Gln Leu Lys
65                  70                  75                  80

Phe Tyr Ser Asn Asp Lys Asp Ser Val Pro Asp Ser Leu Leu Phe Ser
```

```
                85                  90                  95
Lys Leu Leu His Glu Gln Gln Leu Asn Gly Phe Lys Ala Gly Asp Thr
                100                 105                 110

Ile Ile Pro Leu Asp Lys Asp Gly Lys Pro Val Tyr Thr Gln Asp Thr
                115                 120                 125

Arg Thr Lys Asp Gly Lys Val Glu Thr Val Tyr Ser Val Thr Thr Lys
                130                 135                 140

Ile Ala Thr Gln Asp Asp Val Glu Gln Ser Ala Tyr Ser Arg Gly Ile
145                 150                 155                 160

Gln Gly Asp Ile Asp Asp Leu Tyr Asp Ile Asn Arg Glu Val Asn Glu
                165                 170                 175

Tyr Leu Lys Ala Thr His Asp Tyr Asn Glu Arg Gln Thr Glu Ala Ile
                180                 185                 190

Asp Ala Leu Asn Lys Ala Ser Ser Ala Asn Thr Asp Arg Ile Asp Thr
                195                 200                 205

Ala Glu Glu Arg Ile Asp Lys Asn Glu Tyr Asp Ile Lys Ala Leu Glu
                210                 215                 220

Ser Asn Val Gly Lys Asp Leu Leu Asp Leu Ser Gly Arg Leu Ile Ala
225                 230                 235                 240

Gln Lys Glu Asp Ile Asp Asn Asn Ile Asn His Ile Tyr Glu Leu Ala
                245                 250                 255

Gln Gln Gln Asp Gln His Ser Ser Asp Ile Lys Thr Leu Lys Asn Asn
                260                 265                 270

Val Glu Glu Gly Leu Leu Glu Leu Ser Gly His Leu Ile Asp Gln Lys
                275                 280                 285

Ala Asp Leu Thr Lys Asp Ile Lys Thr Leu Glu Asn Asn Ile Glu Glu
                290                 295                 300

Gly Leu Leu Glu Leu Ser Gly His Leu Ile Asp Gln Lys Ala Asp Leu
305                 310                 315                 320

Thr Lys Asp Ile Lys Thr Leu Glu Asn Asn Ile Glu Glu Gly Leu Leu
                325                 330                 335

Glu Leu Ser Gly His Leu Ile Asp Gln Lys Ala Asp Ile Ala Gln Asn
                340                 345                 350

Gln Ala Asn Ile Gln Asp Leu Ala Ala Tyr Asn Glu Leu Gln Asp Gln
                355                 360                 365

Tyr Ala Gln Lys Gln Thr Glu Ala Ile Asp Ala Leu Asn Lys Ala Ser
                370                 375                 380

Ser Glu Asn Thr Gln Asn Ile Glu Asp Leu Ala Ala Tyr Asn Glu Leu
385                 390                 395                 400

Gln Asp Ala Tyr Ala Lys Gln Thr Glu Ala Ile Asp Ala Leu Asn
                405                 410                 415

Lys Ala Ser Ser Glu Asn Thr Gln Asn Ile Glu Asp Leu Ala Ala Tyr
                420                 425                 430

Asn Glu Leu Gln Asp Ala Tyr Ala Lys Gln Thr Glu Ala Ile Asp
                435                 440                 445

Ala Leu Asn Lys Ala Ser Ser Glu Asn Thr Gln Asn Ile Ala Lys Asn
                450                 455                 460

Gln Ala Asp Ile Ala Asn Asn Ile Asn Asn Ile Tyr Glu Leu Ala Gln
465                 470                 475                 480

Gln Gln Asp Gln His Ser Ser Asp Ile Lys Thr Leu Ala Lys Val Ser
                485                 490                 495

Ala Ala Asn Thr Asp Arg Ile Ala Lys Asn Lys Ala Asp Ala Asp Ala
                500                 505                 510
```

```
Ser Phe Glu Thr Leu Thr Lys Asn Gln Asn Thr Leu Ile Glu Lys Asp
            515                 520                 525

Lys Glu His Asp Lys Leu Ile Thr Ala Asn Lys Thr Ala Ile Asp Ala
        530                 535                 540

Asn Lys Ala Ser Ala Asp Thr Lys Phe Ala Ala Thr Ala Asp Ala Ile
545                 550                 555                 560

Thr Lys Asn Gly Asn Ala Ile Thr Lys Asn Ala Lys Ser Ile Thr Asp
                565                 570                 575

Leu Gly Thr Lys Val Asp Gly Phe Asp Gly Arg Val Thr Ala Leu Asp
            580                 585                 590

Thr Lys Val Asn Ala Phe Asp Gly Arg Ile Thr Ala Leu Asp Ser Lys
            595                 600                 605

Val Glu Asn Gly Met Ala Ala Gln Ala Ala Leu Ser Gly Leu Phe Gln
            610                 615                 620

Pro Tyr Ser Val Gly Lys Phe Asn Ala Thr Ala Ala Leu Gly Gly Tyr
625                 630                 635                 640

Gly Ser Lys Ser Ala Val Ala Ile Gly Ala Gly Tyr Arg Val Asn Pro
                645                 650                 655

Asn Leu Ala Phe Lys Ala Gly Ala Ala Ile Asn Thr Ser Gly Asn Lys
                660                 665                 670

Lys Gly Ser Tyr Asn Ile Gly Val Asn Tyr Glu Phe
            675                 680

<210> SEQ ID NO 29
<211> LENGTH: 684
<212> TYPE: PRT
<213> ORGANISM: Moraxalla catarrhalis

<400> SEQUENCE: 29

Met Lys Thr Met Lys Leu Leu Pro Leu Lys Ile Ala Val Thr Ser Ala
1               5                   10                  15

Met Met Val Gly Leu Gly Met Ala Ser Thr Ala Asn Ala Gln Gln Gln
            20                  25                  30

Lys Ser Pro Lys Thr Glu Ile Phe Leu Pro Asn Leu Phe Asp Asn Asp
        35                  40                  45

Asn Thr Glu Leu Thr Asp Pro Leu Tyr His Asn Met Ile Leu Gly Asn
    50                  55                  60

Thr Ala Leu Leu Thr Gln Glu Asn Gln Tyr Lys Phe Tyr Ala Asp Asp
65              70                  75                  80

Gly Asn Gly Val Pro Asp Ser Leu Leu Phe Asn Lys Ile Leu His Asp
                85                  90                  95

Gln Leu Leu His Gly Phe Lys Lys Gly Asp Thr Ile Ile Pro Leu Asp
            100                 105                 110

Glu Asn Gly Lys Pro Val Tyr Lys Leu Asp Ser Ile Val Glu Gln Gly
        115                 120                 125

Lys Thr Lys Thr Val Tyr Ser Val Thr Thr Lys Thr Ala Thr Ala Asp
    130                 135                 140

Asp Val Asn Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
                165                 170                 175

Asp Lys Ile Phe Ala Asn Glu Glu Ser Val Gln Tyr Leu Asn Arg Glu
            180                 185                 190

Val Gln Asn Asn Ile Glu Asn Ile Tyr Glu Leu Val Gln Gln Gln Asp
```

```
            195                 200                 205
Gln His Ser Ser Asp Ile Lys Thr Leu Lys Lys Asn Val Glu Lys Asp
210                 215                 220
Leu Leu Asp Leu Ser Gly Arg Leu Ile Ala Gln Lys Glu Asp Ile Ala
225                 230                 235                 240
Gln Asn Gln Thr Asp Ile Gln Asp Leu Ala Thr Tyr Asn Glu Leu Gln
            245                 250                 255
Asp Gln Tyr Ala Gln Lys Gln Thr Glu Ala Ile Asp Ala Leu Asn Lys
            260                 265                 270
Ala Ser Ser Glu Asn Thr Gln Asn Ile Ala Lys Asn Ser Asn His Ile
            275                 280                 285
Lys Thr Leu Glu Asn Asn Ile Glu Glu Gly Leu Leu Glu Leu Ser Gly
            290                 295                 300
His Leu Ile Asp Gln Lys Ala Asp Leu Thr Lys Asp Ile Lys Ala Leu
305                 310                 315                 320
Glu Ser Asn Val Glu Glu Gly Leu Leu Asp Leu Ser Gly Arg Leu Ile
            325                 330                 335
Asp Gln Lys Ala Asp Ile Ala Gln Asn Gln Ala Asn Ile Gln Asp Leu
            340                 345                 350
Ala Ala Tyr Asn Glu Leu Gln Asp Ala Tyr Ala Lys Gln Gln Thr Glu
            355                 360                 365
Ala Ile Asp Ala Leu Asn Lys Ala Ser Ser Glu Asn Thr Gln Asn Ile
            370                 375                 380
Glu Asp Leu Ala Ala Tyr Asn Glu Leu Gln Asp Ala Tyr Ala Lys Gln
385                 390                 395                 400
Gln Thr Glu Ala Ile Asp Ala Leu Asn Lys Ala Ser Ser Glu Asn Thr
            405                 410                 415
Gln Asn Ile Glu Asp Leu Ala Ala Tyr Asn Glu Leu Gln Asp Ala Tyr
            420                 425                 430
Ala Lys Gln Gln Thr Glu Ala Ile Asp Ala Leu Asn Lys Ala Ser Ser
            435                 440                 445
Glu Asn Thr Gln Asn Ile Ala Lys Asn Gln Ala Asp Ile Ala Asn Asn
            450                 455                 460
Ile Asn Asn Ile Tyr Glu Leu Ala Gln Gln Gln Asp Gln His Ser Ser
465                 470                 475                 480
Asp Ile Lys Thr Leu Ala Lys Ala Ser Ala Ala Asn Thr Asp Arg Ile
            485                 490                 495
Ala Lys Asn Lys Ala Asp Ala Asp Ala Ser Phe Glu Thr Leu Thr Lys
            500                 505                 510
Asn Gln Asn Thr Leu Ile Glu Lys Asp Lys Glu His Asp Lys Leu Ile
            515                 520                 525
Thr Ala Asn Lys Thr Ala Ile Asp Ala Asn Lys Ala Ser Ala Asp Thr
            530                 535                 540
Lys Phe Ala Ala Thr Ala Asp Ala Ile Thr Lys Asn Gly Asn Ala Ile
545                 550                 555                 560
Thr Lys Asn Ala Lys Ser Ile Thr Asp Leu Gly Thr Lys Val Asp Gly
            565                 570                 575
Phe Asp Gly Arg Val Thr Ala Leu Asp Thr Lys Val Asn Ala Leu Asp
            580                 585                 590
Thr Lys Val Asn Ala Phe Asp Gly Arg Ile Thr Ala Leu Asp Ser Lys
            595                 600                 605
Val Glu Asn Gly Met Ala Ala Gln Ala Ala Leu Ser Gly Leu Phe Gln
610                 615                 620
```

```
Pro Tyr Ser Val Gly Lys Phe Asn Ala Thr Ala Ala Leu Gly Gly Tyr
625                 630                 635                 640

Gly Ser Lys Ser Ala Val Ala Ile Gly Ala Gly Tyr Arg Val Asn Pro
            645                 650                 655

Asn Leu Ala Phe Lys Ala Gly Ala Ala Ile Asn Thr Ser Gly Asn Lys
        660                 665                 670

Lys Gly Ser Tyr Asn Ile Gly Val Asn Tyr Glu Phe
        675                 680

<210> SEQ ID NO 30
<211> LENGTH: 574
<212> TYPE: PRT
<213> ORGANISM: Moraxalla catarrhalis

<400> SEQUENCE: 30

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Leu Ala
            20                  25                  30

Glu Gln Phe Phe Pro Asn Ile Phe Ser Asn His Ala Pro Val Lys Gln
        35                  40                  45

His Tyr His Asn Val Val Gly Asp Thr Ser Ile Val Glu Asn Leu
50                  55                  60

Gln Asp Ser Asp Asp Thr Gln Leu Lys Phe Tyr Ser Asn Asp Glu Tyr
65                  70                  75                  80

Ser Val Pro Asp Ser Leu Leu Phe Asn Lys Met Leu His Glu Gln Gln
                85                  90                  95

Leu Asn Gly Phe Lys Lys Gly Asp Thr Ile Ile Pro Leu Asp Glu Asn
            100                 105                 110

Gly Lys Pro Val Tyr Lys Val Asp Tyr Lys Leu Asp Gly Gln Glu Pro
        115                 120                 125

Arg Arg Val Tyr Ser Val Thr Thr Lys Ile Ala Thr Gln Asp Asp Val
130                 135                 140

Asp Asn Ser Pro Tyr Ser Arg Gly Ile Gln Gly Asp Ile Asp Asp Leu
145                 150                 155                 160

Tyr Glu Ala Asn Lys Glu Asn Val Asn Arg Leu Ile Glu His Gly Asp
                165                 170                 175

Lys Ile Phe Ala Asn Glu Glu Ser Val Gln Tyr Leu Asn Lys Glu Val
            180                 185                 190

Gln Asn Asn Ile Glu Asn Ile Tyr Glu Leu Ala Gln Gln Gln Asp Gln
        195                 200                 205

His Ser Ser Asp Ile Lys Thr Leu Lys Lys Asn Val Glu Glu Gly Leu
210                 215                 220

Leu Glu Leu Ser Gly His Leu Ile Asp Gln Lys Ala Asp Leu Thr Lys
225                 230                 235                 240

Asp Ile Lys Thr Leu Glu Ser Asn Val Glu Glu Gly Leu Leu Glu Leu
                245                 250                 255

Ser Gly His Leu Ile Asp Gln Lys Ala Asp Ile Ala Lys Asn Gln Ala
            260                 265                 270

Asp Ile Ala Gln Asn Gln Ala Asn Ile Gln Asp Leu Ala Ala Tyr Asn
        275                 280                 285

Glu Leu Gln Asp Ala Tyr Ala Lys Gln Thr Glu Ala Ile Asp Ala
290                 295                 300

Leu Asn Lys Ala Ser Ser Glu Asn Thr Gln Asn Ile Glu Asp Leu Ala
```

```
            305                 310                 315                 320
Ala Tyr Asn Glu Leu Gln Asp Ala Tyr Ala Lys Gln Gln Thr Glu Ala
                325                 330                 335

Ile Asp Ala Leu Asn Lys Ala Ser Ser Glu Asn Thr Gln Asn Ile Ala
                340                 345                 350

Lys Asn Gln Ala Asp Ile Ala Asn Asn Ile Asn Asn Ile Tyr Glu Leu
                355                 360                 365

Ala Gln Gln Gln Asp Gln His Ser Ser Asp Ile Lys Thr Leu Ala Lys
        370                 375                 380

Ala Ser Ala Ala Asn Thr Asp Arg Ile Ala Lys Asn Lys Ala Asp Ala
385                 390                 395                 400

Asp Ala Ser Phe Glu Thr Leu Thr Lys Asn Gln Asn Thr Leu Ile Glu
                405                 410                 415

Lys Asp Lys Glu His Asp Lys Leu Ile Thr Ala Asn Lys Thr Ala Ile
                420                 425                 430

Asp Ala Asn Lys Ala Ser Ala Asp Thr Lys Phe Ala Ala Thr Ala Asp
                435                 440                 445

Ala Ile Thr Lys Asn Gly Asn Ala Ile Thr Lys Asn Ala Lys Ser Ile
        450                 455                 460

Thr Asp Leu Gly Thr Lys Val Asp Ala Phe Asp Gly Arg Val Thr Ala
465                 470                 475                 480

Leu Asp Thr Lys Val Asn Ala Phe Asp Gly Arg Ile Thr Ala Leu Asp
                485                 490                 495

Ser Lys Val Glu Asn Gly Met Ala Ala Gln Ala Ala Leu Ser Gly Leu
                500                 505                 510

Phe Gln Pro Tyr Ser Val Gly Lys Phe Asn Ala Thr Ala Ala Leu Gly
                515                 520                 525

Gly Tyr Gly Ser Lys Ser Ala Val Ala Ile Gly Ala Gly Tyr Arg Val
        530                 535                 540

Asn Pro Asn Leu Ala Phe Lys Ala Gly Ala Ala Ile Asn Thr Ser Gly
545                 550                 555                 560

Asn Lys Lys Gly Ser Tyr Asn Ile Gly Val Asn Tyr Glu Phe
                565                 570

<210> SEQ ID NO 31
<211> LENGTH: 678
<212> TYPE: PRT
<213> ORGANISM: Moraxalla catarrhalis

<400> SEQUENCE: 31

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Gln Gln
                20                  25                  30

Pro Gln Thr Glu Thr Phe Phe Pro Asn Ile Phe Phe Asn Glu Asn His
                35                  40                  45

Asp Ala Leu Asp Asp Val Tyr His Asn Met Ile Leu Gly Asp Thr Ala
                50                  55                  60

Ile Thr Gln Asp Asn Gln Tyr Lys Phe Tyr Ala Asp Ala Ile Ser Glu
65                  70                  75                  80

Val Pro Asp Ser Leu Leu Phe Asn Lys Ile Leu His Asp Gln Gln Leu
                85                  90                  95

Asn Gly Phe Lys Glu Gly Asp Thr Ile Ile Pro Leu Asp Glu Asn Gly
                100                 105                 110
```

```
Lys Pro Val Tyr Lys Leu Asp Glu Lys Val Glu Asn Gly Val Lys Lys
            115                 120                 125
Ser Val Tyr Ser Val Thr Thr Lys Thr Ala Thr Arg Ala Asp Val Glu
130                 135                 140
Gln Ser Ala Tyr Ser Arg Gly Ile Gln Gly Asp Ile Asp Asp Leu Tyr
145                 150                 155                 160
Glu Ala Asn Lys Glu Asn Val Asn Arg Leu Ile Glu His Gly Asp Lys
                165                 170                 175
Ile Phe Ala Asn Glu Glu Ser Val Gln Tyr Leu Asn Lys Glu Val Gln
            180                 185                 190
Asn Asn Ile Glu Asn Ile His Glu Leu Ala Gln Gln Asp Gln His
            195                 200                 205
Ser Ser Asp Ile Lys Thr Leu Lys Lys Asn Val Glu Glu Gly Leu Leu
210                 215                 220
Glu Leu Ser Gly His Leu Ile Asp Gln Lys Ala Asp Leu Thr Lys Asp
225                 230                 235                 240
Ile Lys Thr Leu Glu Ser Asn Val Glu Glu Gly Leu Leu Asp Leu Ser
                245                 250                 255
Gly Arg Leu Leu Asp Gln Lys Ala Asp Ile Ala Gln Asn Gln Ala Asn
            260                 265                 270
Ile Gln Asp Leu Ala Ala Tyr Asn Glu Leu Gln Asp Ala Tyr Ala Lys
            275                 280                 285
Gln Gln Thr Glu Ala Ile Asp Ala Leu Asn Lys Ala Ser Ser Glu Asn
            290                 295                 300
Thr Gln Asn Ile Glu Asp Leu Ala Ala Tyr Asn Glu Leu Gln Asp Ala
305                 310                 315                 320
Tyr Ala Lys Gln Gln Thr Glu Ala Ile Asp Ala Leu Asn Lys Ala Ser
                325                 330                 335
Ser Glu Asn Thr Gln Asn Ile Glu Asp Leu Ala Ala Tyr Asn Glu Leu
            340                 345                 350
Gln Asp Ala Tyr Ala Lys Gln Gln Thr Glu Ala Ile Asp Ala Leu Asn
            355                 360                 365
Lys Ala Ser Ser Glu Asn Thr Gln Asn Ile Glu Asp Leu Ala Ala Tyr
            370                 375                 380
Asn Glu Leu Gln Asp Ala Tyr Ala Lys Gln Gln Thr Glu Ala Ile Asp
385                 390                 395                 400
Ala Leu Asn Lys Ala Ser Ser Glu Asn Thr Gln Asn Ile Glu Asp Leu
                405                 410                 415
Ala Ala Tyr Asn Glu Leu Gln Asp Ala Tyr Ala Lys Gln Gln Thr Glu
            420                 425                 430
Ala Ile Asp Ala Leu Asn Lys Ala Ser Ser Glu Asn Thr Gln Asn Ile
            435                 440                 445
Ala Lys Asn Gln Ala Asp Ile Ala Asn Asn Ile Asn Asn Ile Tyr Glu
            450                 455                 460
Leu Ala Gln Gln Gln Asp Gln His Ser Ser Asp Ile Lys Thr Leu Ala
465                 470                 475                 480
Lys Ala Ser Ala Ala Asn Thr Asp Arg Ile Ala Lys Asn Lys Ala Asp
                485                 490                 495
Ala Asp Ala Ser Phe Glu Thr Leu Thr Lys Asn Gln Asn Thr Leu Ile
            500                 505                 510
Glu Lys Asp Lys Glu His Asp Lys Leu Ile Thr Ala Asn Lys Thr Ala
            515                 520                 525
Ile Asp Ala Asn Lys Ala Ser Ala Asp Thr Lys Phe Ala Ala Thr Ala
```

-continued

```
                530                 535                 540
Asp Ala Ile Thr Lys Asn Gly Asn Ala Ile Thr Lys Asn Ala Lys Ser
545                 550                 555                 560

Ile Thr Asp Leu Gly Thr Lys Val Asp Ala Phe Asp Gly Arg Val Thr
                565                 570                 575

Ala Leu Asp Thr Lys Val Asn Ala Leu Asp Thr Lys Val Asn Ala Phe
                580                 585                 590

Asp Gly Arg Ile Thr Ala Leu Asp Ser Lys Val Glu Asn Gly Met Ala
            595                 600                 605

Ala Gln Ala Ala Leu Ser Gly Leu Phe Gln Pro Tyr Ser Val Gly Lys
        610                 615                 620

Phe Asn Ala Thr Ala Ala Leu Gly Gly Tyr Gly Ser Lys Ser Ala Val
625                 630                 635                 640

Ala Ile Gly Ala Gly Tyr Arg Val Asn Pro Asn Leu Ala Phe Lys Ala
                645                 650                 655

Gly Ala Ala Ile Asn Thr Ser Gly Asn Lys Lys Gly Ser Tyr Asn Ile
                660                 665                 670

Gly Val Asn Tyr Glu Phe
            675

<210> SEQ ID NO 32
<211> LENGTH: 678
<212> TYPE: PRT
<213> ORGANISM: Moraxalla catarrhalis

<400> SEQUENCE: 32

Met Lys Thr Met Lys Leu Leu Pro Leu Lys Ile Ala Val Thr Ser Ala
1               5                   10                  15

Met Ile Val Gly Leu Gly Ala Ala Ser Thr Ala Asn Ala Gln Gln Gln
            20                  25                  30

Gln Gln Pro Arg Thr Glu Thr Phe Phe Pro Asn Ile Phe Phe Asn Glu
        35                  40                  45

Asn His Asp Ala Leu Asp Asp Val Tyr His Asn Met Ile Leu Gly Asp
    50                  55                  60

Thr Ala Ile Thr Gln Asp Asn Gln Tyr Lys Phe Tyr Ala Asp Ala Ile
65                  70                  75                  80

Ser Glu Val Pro Asp Ser Leu Leu Phe Asn Lys Ile Leu His Asp Gln
                85                  90                  95

Gln Leu Asn Gly Phe Lys Glu Gly Asp Thr Ile Ile Pro Leu Asp Glu
            100                 105                 110

Asn Gly Lys Pro Val Tyr Lys Leu Asp Glu Lys Val Glu Asn Gly Val
        115                 120                 125

Lys Lys Ser Val Tyr Ser Val Thr Thr Lys Thr Ala Thr Arg Ala Asp
    130                 135                 140

Val Glu Gln Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
                165                 170                 175

Asp Lys Ile Phe Ala Asn Glu Glu Ser Val Gln Tyr Leu Asn Arg Glu
            180                 185                 190

Val Gln Asn Asn Ile Glu Asn Ile His Glu Leu Ala Gln Gln Gln Asp
        195                 200                 205

Gln His Ser Ser Asp Ile Lys Thr Leu Lys Lys Asn Val Glu Lys Asp
    210                 215                 220
```

```
Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
            245                 250                 255

Asp Gln Tyr Ala Gln Lys Gln Thr Glu Ala Ile Asp Ala Leu Asn Lys
        260                 265                 270

Ala Ser Ser Glu Asn Thr Gln Asn Ile Ala Lys Asn Ser Asn His Ile
    275                 280                 285

Lys Thr Leu Glu Asn Asn Ile Glu Glu Gly Leu Leu Glu Leu Ser Gly
290                 295                 300

His Leu Ile Asp Gln Lys Ala Asp Leu Thr Lys Asp Ile Lys Thr Leu
305                 310                 315                 320

Glu Asn Asn Ile Glu Glu Gly Leu Leu Glu Leu Ser Gly His Leu Ile
            325                 330                 335

Asp Gln Lys Ala Asp Leu Thr Lys Asp Ile Lys Ala Leu Glu Ser Asn
        340                 345                 350

Val Glu Glu Gly Leu Leu Asp Leu Ser Gly Arg Leu Leu Asp Gln Lys
    355                 360                 365

Ala Asp Ile Ala Gln Asn Gln Ala Asn Ile Gln Asp Leu Ala Ala Tyr
370                 375                 380

Asn Glu Leu Gln Asp Gln Tyr Ala Gln Lys Gln Thr Glu Ala Ile Asp
385                 390                 395                 400

Ala Leu Asn Lys Ala Ser Ser Glu Asn Thr Gln Asn Ile Glu Asp Leu
            405                 410                 415

Ala Ala Tyr Asn Glu Leu Gln Asp Ala Tyr Ala Lys Gln Gln Thr Glu
        420                 425                 430

Ala Ile Asp Ala Leu Asn Lys Ala Ser Ser Glu Asn Thr Gln Asn Ile
    435                 440                 445

Ala Lys Asn Gln Ala Asp Ile Ala Asn Asn Ile Asn Asn Ile Tyr Glu
450                 455                 460

Leu Ala Gln Gln Gln Asp Gln His Ser Ser Asp Ile Lys Thr Leu Ala
465                 470                 475                 480

Lys Ala Ser Ala Ala Asn Thr Asp Arg Ile Ala Lys Asn Lys Ala Asp
            485                 490                 495

Ala Asp Ala Ser Phe Glu Thr Leu Thr Lys Asn Gln Asn Thr Leu Ile
        500                 505                 510

Glu Lys Asp Lys Glu His Asp Lys Leu Ile Thr Ala Asn Lys Thr Ala
    515                 520                 525

Ile Asp Thr Asn Lys Ala Ser Ala Asp Thr Lys Phe Ala Ala Thr Ala
530                 535                 540

Asp Ala Ile Thr Lys Asn Gly Asn Ala Ile Thr Lys Asn Ala Lys Ser
545                 550                 555                 560

Ile Thr Asp Leu Gly Thr Lys Val Asp Gly Phe Asp Gly Arg Val Thr
            565                 570                 575

Ala Leu Asp Thr Lys Val Asn Ala Leu Asp Thr Lys Val Asn Ala Phe
        580                 585                 590

Asp Gly Arg Ile Thr Ala Leu Asp Ser Lys Val Glu Asn Gly Met Ala
    595                 600                 605

Ala Gln Ala Ala Leu Ser Gly Leu Phe Gln Pro Tyr Ser Val Gly Lys
610                 615                 620

Phe Asn Ala Thr Ala Ala Leu Gly Gly Tyr Gly Ser Lys Ser Ala Val
625                 630                 635                 640

Ala Ile Gly Ala Gly Tyr Arg Val Asn Pro Asn Leu Ala Phe Lys Ala
```

```
                    645                 650                 655
Gly Ala Ala Ile Asn Thr Ser Gly Asn Lys Lys Gly Ser Tyr Asn Ile
                660                 665                 670
Gly Val Asn Tyr Glu Phe
            675

<210> SEQ ID NO 33
<211> LENGTH: 587
<212> TYPE: PRT
<213> ORGANISM: Moraxalla catarrhalis

<400> SEQUENCE: 33

Met Lys Thr Met Lys Leu Leu Pro Leu Lys Ile Ala Val Thr Ser Ala
1               5                   10                  15
Leu Ile Val Gly Leu Gly Ala Ala Ser Thr Ala Asn Ala Gln Leu Val
                20                  25                  30
Glu Arg Phe Phe Pro Asn Ile Phe Leu Asp Lys Pro Leu Ala Lys Gln
            35                  40                  45
His Tyr His Asn Val Val Gly Asp Thr Ser Ile Val Ser Asp Leu
        50                  55                  60
Gln Ser Asn Ser Asp Gln Leu Lys Phe Tyr Ser Asp Glu Gly Leu
65                  70                  75                  80
Val Pro Asp Ser Leu Leu Phe Asn Lys Met Leu His Glu Gln Leu Leu
                85                  90                  95
Asn Gly Phe Lys Glu Gly Asp Thr Ile Ile Pro Leu Asp Glu Asn Gly
            100                 105                 110
Lys Pro Val Tyr Lys Val Asp Tyr Lys Leu Asp Gly Lys Glu Pro Arg
        115                 120                 125
Lys Val Tyr Ser Val Thr Thr Lys Ile Ala Thr Ala Glu Asp Val Ala
130                 135                 140
Thr Ser Ser Tyr Ala Asn Gly Ile Gln Lys Asp Ile Asp Leu Tyr
145                 150                 155                 160
Asp Phe Asp His Gln Val Thr Glu Arg Leu Thr Gln His Gly Lys Thr
                165                 170                 175
Ile Tyr Arg Asn Gly Glu Arg Ile Leu Ala Asn Glu Glu Ser Val Gln
            180                 185                 190
Tyr Leu Asn Lys Glu Val Gln Asn Asn Ile Glu His Ile Tyr Glu Leu
        195                 200                 205
Ala Gln Gln Gln Asp Gln His Ser Ser Asp Ile Lys Thr Leu Glu Ser
    210                 215                 220
Asn Val Glu Lys Gly Leu Leu Glu Leu Ser Gly His Leu Ile Asp Gln
225                 230                 235                 240
Lys Ala Asp Leu Thr Lys Asp Ile Lys Thr Leu Glu Asn Asn Val Glu
                245                 250                 255
Glu Gly Leu Leu Asp Leu Ser Gly Arg Leu Ile Asp Gln Lys Ala Asp
            260                 265                 270
Ile Ala Gln Asn Gln Ala Asn Ile Gln Asp Leu Ala Ala Tyr Asn Glu
        275                 280                 285
Leu Gln Asp Gln Tyr Ala Gln Lys Gln Thr Glu Ala Ile Asp Ala Leu
    290                 295                 300
Asn Lys Ala Ser Ser Glu Asn Thr Gln Asn Ile Glu Asp Leu Ala Ala
305                 310                 315                 320
Tyr Asn Glu Leu Gln Asp Ala Tyr Ala Lys Gln Gln Thr Glu Ala Ile
                325                 330                 335
```

```
Asp Ala Leu Asn Lys Ala Ser Ser Glu Asn Thr Gln Asn Ile Ala Lys
                340                 345                 350

Asn Gln Ala Asp Ile Ala Asn Asn Ile Asn Asn Ile Tyr Glu Leu Ala
            355                 360                 365

Gln Gln Gln Asp Gln His Ser Ser Asp Ile Lys Thr Leu Ala Lys Ala
        370                 375                 380

Ser Ala Ala Asn Thr Asp Arg Ile Ala Lys Asn Lys Ala Asp Ala Asp
385                 390                 395                 400

Ala Ser Phe Glu Thr Leu Thr Lys Asn Gln Asn Thr Leu Ile Glu Lys
                405                 410                 415

Asp Lys Glu His Asp Lys Leu Ile Thr Ala Asn Lys Thr Ala Ile Asp
            420                 425                 430

Thr Asn Lys Ala Ser Ala Asp Thr Lys Phe Ala Ala Thr Ala Asp Ala
        435                 440                 445

Ile Thr Lys Asn Gly Asn Ala Ile Thr Lys Asn Ala Lys Ser Ile Thr
    450                 455                 460

Asp Leu Gly Thr Lys Val Asp Gly Phe Asp Ser Arg Val Thr Ala Leu
465                 470                 475                 480

Asp Thr Lys Val Asn Ala Leu Asp Thr Lys Val Asn Ala Leu Asp Thr
                485                 490                 495

Lys Val Asn Ala Phe Asp Gly Arg Ile Thr Ala Leu Asp Ser Lys Val
            500                 505                 510

Glu Asn Gly Met Ala Ala Gln Ala Leu Ser Gly Leu Phe Gln Pro
        515                 520                 525

Tyr Ser Val Gly Lys Phe Asn Ala Thr Ala Ala Leu Gly Gly Tyr Gly
    530                 535                 540

Ser Lys Ser Ala Val Ala Ile Gly Ala Gly Tyr Arg Val Asn Pro Asn
545                 550                 555                 560

Leu Ala Phe Lys Ala Gly Ala Ala Ile Asn Thr Ser Gly Asn Lys Lys
                565                 570                 575

Gly Ser Tyr Asn Ile Gly Val Asn Tyr Glu Phe
            580                 585

<210> SEQ ID NO 34
<211> LENGTH: 678
<212> TYPE: PRT
<213> ORGANISM: Moraxalla catarrhalis

<400> SEQUENCE: 34

Met Lys Thr Met Lys Leu Leu Pro Leu Lys Ile Ala Val Thr Ser Ala
1               5                   10                  15

Met Ile Val Gly Leu Gly Ala Ala Ser Thr Ala Asn Ala Gln Gln Gln
            20                  25                  30

Gln Gln Pro Arg Thr Glu Thr Phe Phe Pro Asn Ile Phe Phe Asn Glu
        35                  40                  45

Asn His Asp Ala Leu Asp Asp Val Tyr His Asn Met Ile Leu Gly Asp
    50                  55                  60

Thr Ala Ile Thr Gln Asp Asn Gln Tyr Lys Phe Tyr Ala Asp Ala Ile
65                  70                  75                  80

Ser Glu Val Pro Asp Ser Leu Leu Phe Asn Lys Ile Leu His Asp Gln
                85                  90                  95

Gln Leu Asn Gly Phe Lys Glu Gly Asp Thr Ile Ile Pro Leu Asp Glu
            100                 105                 110

Asn Gly Lys Pro Val Tyr Lys Leu Asp Glu Lys Val Glu Asn Gly Val
        115                 120                 125
```

```
Lys Lys Ser Val Tyr Ser Val Thr Lys Thr Ala Thr Arg Ala Asp
    130             135             140

Val Glu Gln Ser Ala Tyr Ser Arg Gly Ile Gln Gly Asp Ile Asp Asp
145             150             155             160

Leu Tyr Glu Ala Asn Lys Glu Asn Val Asn Arg Leu Ile Glu His Gly
                165             170             175

Asp Lys Ile Phe Ala Asn Glu Glu Ser Val Gln Tyr Leu Asn Arg Glu
            180             185             190

Val Gln Asn Asn Ile Glu Asn Ile His Glu Leu Ala Gln Gln Gln Asp
        195             200             205

Gln His Ser Ser Asp Ile Lys Thr Leu Lys Lys Asn Val Glu Lys Asp
    210             215             220

Leu Leu Asp Leu Ser Gly Arg Leu Ile Ala Gln Lys Glu Asp Ile Ala
225             230             235             240

Gln Asn Gln Thr Asp Ile Gln Asp Leu Ala Thr Tyr Asn Glu Leu Gln
                245             250             255

Asp Gln Tyr Ala Gln Lys Gln Thr Glu Ala Ile Asp Ala Leu Asn Lys
            260             265             270

Ala Ser Ser Glu Asn Thr Gln Asn Ile Ala Lys Asn Ser Asn His Ile
        275             280             285

Lys Thr Leu Glu Asn Asn Ile Glu Glu Gly Leu Leu Glu Leu Ser Gly
    290             295             300

His Leu Ile Asp Gln Lys Ala Asp Leu Thr Lys Asp Ile Lys Thr Leu
305             310             315             320

Glu Asn Asn Ile Glu Glu Gly Leu Leu Glu Leu Ser Gly His Leu Ile
                325             330             335

Asp Gln Lys Ala Asp Leu Thr Lys Asp Ile Lys Ala Leu Glu Ser Asn
            340             345             350

Val Glu Glu Gly Leu Leu Asp Leu Ser Gly Arg Leu Leu Asp Gln Lys
        355             360             365

Ala Asp Ile Ala Gln Asn Gln Ala Asn Ile Gln Asp Leu Ala Ala Tyr
    370             375             380

Asn Glu Leu Gln Asp Gln Tyr Ala Gln Lys Gln Thr Glu Ala Ile Asp
385             390             395             400

Ala Leu Asn Lys Ala Ser Ser Glu Asn Thr Gln Asn Ile Glu Asp Leu
                405             410             415

Ala Ala Tyr Asn Glu Leu Gln Asp Ala Tyr Ala Lys Gln Gln Thr Glu
            420             425             430

Ala Ile Asp Ala Leu Asn Lys Ala Ser Ser Glu Asn Thr Gln Asn Ile
        435             440             445

Ala Lys Asn Gln Ala Asp Ile Ala Asn Asn Ile Asn Asn Ile Tyr Glu
    450             455             460

Leu Ala Gln Gln Gln Asp Gln His Ser Ser Asp Ile Lys Thr Leu Ala
465             470             475             480

Lys Ala Ser Ala Ala Asn Thr Asp Arg Ile Ala Lys Asn Lys Ala Asp
                485             490             495

Ala Asp Ala Ser Phe Glu Thr Leu Thr Lys Asn Gln Asn Thr Leu Ile
            500             505             510

Glu Lys Asp Lys Glu His Asp Lys Leu Ile Thr Ala Asn Lys Thr Ala
        515             520             525

Ile Asp Thr Asn Lys Ala Ser Ala Asp Thr Lys Phe Ala Ala Thr Ala
    530             535             540
```

```
Asp Ala Ile Thr Lys Asn Gly Asn Ala Ile Thr Lys Asn Ala Lys Ser
545                 550                 555                 560

Ile Thr Asp Leu Gly Thr Lys Val Asp Gly Phe Asp Gly Arg Val Thr
                565                 570                 575

Ala Leu Asp Thr Lys Val Asn Ala Leu Asp Thr Lys Val Asn Ala Phe
                580                 585                 590

Asp Gly Arg Ile Thr Ala Leu Asp Ser Lys Val Glu Asn Gly Met Ala
                595                 600                 605

Ala Gln Ala Ala Leu Ser Gly Leu Phe Gln Pro Tyr Ser Val Gly Lys
        610                 615                 620

Phe Asn Ala Thr Ala Ala Leu Gly Gly Tyr Gly Ser Lys Ser Ala Val
625                 630                 635                 640

Ala Ile Gly Ala Gly Tyr Arg Val Asn Pro Asn Leu Ala Phe Lys Ala
                645                 650                 655

Gly Ala Ala Ile Asn Thr Ser Gly Asn Lys Lys Gly Ser Tyr Asn Ile
                660                 665                 670

Gly Val Asn Tyr Glu Phe
        675

<210> SEQ ID NO 35
<211> LENGTH: 616
<212> TYPE: PRT
<213> ORGANISM: Moraxalla catarrhalis

<400> SEQUENCE: 35

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Val Arg
                20                  25                  30

Asp Lys Ser Leu Glu Asp Ile Glu Ala Leu Leu Gly Lys Ile Asp Ile
                35                  40                  45

Ser Lys Leu Glu Lys Glu Lys Lys Gln Gln Thr Glu Leu Gln Lys Tyr
        50                  55                  60

Leu Leu Leu Ser Gln Tyr Ala Asn Val Leu Thr Met Glu Glu Leu Asn
65                  70                  75                  80

Lys Asn Val Glu Lys Asn Thr Asn Ser Ile Glu Ala Leu Gly Tyr Glu
                85                  90                  95

Ile Gly Trp Leu Glu Asn Asp Ile Ala Asp Leu Glu Glu Gly Val Glu
                100                 105                 110

Glu Leu Thr Lys Asn Gln Asn Thr Leu Ile Glu Lys Asp Glu Glu His
        115                 120                 125

Asp Arg Leu Ile Ala Gln Asn Ala Asp Ile Lys Thr Leu Glu Asn
        130                 135                 140

Asn Val Val Glu Glu Leu Phe Asn Leu Ser Asp Arg Leu Ile Asp Gln
145                 150                 155                 160

Glu Ala Asp Ile Ala Lys Asn Asn Ala Ser Ile Glu Glu Leu Tyr Asp
                165                 170                 175

Phe Asp Asn Glu Val Ala Glu Arg Ile Gly Glu Ile His Ala Tyr Thr
                180                 185                 190

Glu Glu Val Asn Lys Thr Leu Glu Lys Leu Ile Thr Asn Ser Val Lys
        195                 200                 205

Asn Thr Asp Asn Ile Asp Lys Asn Lys Ala Asp Ile Gln Ala Leu Glu
        210                 215                 220

Asn Asn Val Glu Glu Gly Leu Leu Glu Leu Ser Gly His Leu Ile Asp
225                 230                 235                 240
```

```
Gln Lys Ala Asp Leu Thr Lys Asp Ile Lys Ala Leu Glu Ser Asn Val
                245                 250                 255

Glu Glu Gly Leu Leu Asp Leu Ser Gly Arg Leu Leu Asp Gln Lys Ala
            260                 265                 270

Asp Ile Ala Lys Asn Gln Ala Asp Ile Ala Gln Asn Gln Thr Asp Ile
        275                 280                 285

Gln Asp Leu Ala Ala Tyr Asn Glu Leu Gln Asp Gln Tyr Ala Gln Lys
    290                 295                 300

Gln Thr Glu Ala Ile Asp Ala Leu Asn Lys Ala Ser Ser Glu Asn Thr
305                 310                 315                 320

Gln Asn Ile Glu Asp Leu Ala Ala Tyr Asn Glu Leu Gln Asp Ala Tyr
                325                 330                 335

Ala Lys Gln Gln Thr Glu Ala Ile Asp Ala Leu Asn Lys Ala Ser Ser
            340                 345                 350

Glu Asn Thr Gln Asn Ile Glu Asp Leu Ala Ala Tyr Asn Glu Leu Gln
        355                 360                 365

Asp Ala Tyr Ala Lys Gln Gln Thr Glu Ala Ile Asp Ala Leu Asn Lys
    370                 375                 380

Ala Ser Ser Glu Asn Thr Gln Asn Ile Ala Lys Asn Gln Ala Asp Ile
385                 390                 395                 400

Ala Asn Asn Ile Asn Asn Ile Tyr Glu Leu Ala Gln Gln Gln Asp Gln
                405                 410                 415

His Ser Ser Asp Ile Lys Thr Leu Ala Lys Val Ser Ala Ala Asn Thr
            420                 425                 430

Asp Arg Ile Ala Lys Asn Lys Ala Asp Ala Ser Phe Glu Thr
        435                 440                 445

Leu Thr Lys Asn Gln Asn Thr Leu Ile Glu Lys Asp Lys Glu His Asp
    450                 455                 460

Lys Leu Ile Thr Ala Asn Lys Thr Ala Ile Asp Ala Asn Lys Ala Ser
465                 470                 475                 480

Ala Asp Thr Lys Phe Ala Ala Thr Ala Asp Ala Ile Thr Lys Asn Gly
                485                 490                 495

Asn Ala Ile Thr Lys Asn Ala Lys Ser Ile Thr Asp Leu Gly Thr Lys
            500                 505                 510

Val Asp Gly Phe Asp Ser Arg Val Thr Ala Leu Asp Thr Lys Val Asn
        515                 520                 525

Ala Phe Asp Gly Arg Ile Thr Ala Leu Asp Ser Lys Val Glu Asn Gly
    530                 535                 540

Met Ala Ala Gln Ala Ala Leu Ser Gly Leu Phe Gln Pro Tyr Ser Val
545                 550                 555                 560

Gly Lys Phe Asn Ala Thr Ala Ala Leu Gly Gly Tyr Gly Ser Lys Ser
                565                 570                 575

Ala Val Ala Ile Gly Ala Gly Tyr Arg Val Asn Pro Asn Leu Ala Phe
            580                 585                 590

Lys Ala Gly Ala Ala Ile Asn Thr Ser Gly Asn Lys Lys Gly Ser Tyr
        595                 600                 605

Asn Ile Gly Val Asn Tyr Glu Phe
    610                 615

<210> SEQ ID NO 36
<211> LENGTH: 676
<212> TYPE: PRT
<213> ORGANISM: Moraxalla catarrhalis
```

```
<400> SEQUENCE: 36

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Thr
            20                  25                  30

Glu Thr Phe Leu Pro Asn Leu Phe Asp Asn Asp Tyr Thr Glu Thr Thr
        35                  40                  45

Asp Pro Leu Tyr His Gly Met Ile Leu Gly Asn Thr Ala Ile Thr Gln
    50                  55                  60

Asp Thr Gln Tyr Lys Phe Tyr Ala Glu Asn Gly Asn Glu Val Pro Asp
65                  70                  75                  80

Ser Leu Phe Phe Asn Lys Ile Leu His Asp Gln Leu Asn Gly Phe
                85                  90                  95

Lys Glu Gly Asp Thr Ile Ile Pro Leu Asp Glu Asn Gly Lys Pro Val
                100                 105                 110

Tyr Lys Leu Asp Glu Ile Thr Glu Asn Gly Val Lys Arg Lys Val Tyr
            115                 120                 125

Ser Val Thr Thr Lys Thr Ala Thr Arg Glu Asp Val Glu Gln Ser Ala
        130                 135                 140

Tyr Ser Arg Gly Ile Gln Gly Asp Ile Asp Asp Leu Tyr Glu Ala Asn
145                 150                 155                 160

Lys Glu Asn Val Asn Arg Leu Ile Glu His Gly Asp Lys Ile Phe Ala
                165                 170                 175

Asn Glu Glu Ser Val Gln Tyr Leu Asn Lys Glu Val Gln Asn Asn Ile
                180                 185                 190

Glu Asn Ile His Glu Leu Ala Gln Gln Gln Asp Gln His Ser Ser Asp
            195                 200                 205

Ile Lys Thr Leu Lys Lys Asn Val Glu Glu Gly Leu Leu Glu Leu Ser
        210                 215                 220

Gly His Leu Ile Asp Gln Lys Ala Asp Leu Thr Lys Asp Ile Lys Ala
225                 230                 235                 240

Leu Glu Ser Asn Val Glu Glu Gly Leu Leu Asp Leu Ser Gly His Leu
                245                 250                 255

Ile Asp Gln Lys Ala Asp Leu Thr Lys Asp Ile Lys Ala Leu Glu Ser
                260                 265                 270

Asn Val Glu Glu Gly Leu Leu Asp Leu Ser Gly Arg Leu Leu Asp Gln
            275                 280                 285

Lys Ala Asp Ile Ala Lys Asn Gln Ala Asp Ile Ala Gln Asn Gln Thr
        290                 295                 300

Asp Ile Gln Asp Leu Ala Ala Tyr Asn Glu Leu Gln Asp Gln Tyr Ala
305                 310                 315                 320

Gln Lys Gln Thr Glu Ala Ile Asp Ala Leu Asn Lys Ala Ser Ser Glu
                325                 330                 335

Asn Thr Gln Asn Ile Glu Asp Leu Ala Ala Tyr Asn Glu Leu Gln Asp
            340                 345                 350

Gln Tyr Ala Gln Lys Gln Thr Glu Ala Ile Asp Ala Leu Asn Lys Ala
        355                 360                 365

Ser Ser Glu Asn Thr Gln Asn Ile Glu Asp Leu Ala Ala Tyr Asn Glu
    370                 375                 380

Leu Gln Asp Gln Tyr Ala Gln Lys Gln Thr Glu Ala Ile Asp Ala Leu
385                 390                 395                 400

Asn Lys Ala Ser Ser Glu Asn Thr Gln Asn Ile Glu Asp Leu Ala Ala
                405                 410                 415
```

-continued

Tyr Asn Glu Leu Gln Asp Gln Tyr Ala Gln Lys Gln Thr Glu Ala Ile
              420                 425                 430

Asp Ala Leu Asn Lys Ala Ser Ser Glu Asn Thr Gln Asn Ile Ala Lys
              435                 440                 445

Asn Gln Ala Asp Ile Ala Asn Asn Ile Asn Asn Ile Tyr Glu Leu Ala
          450                 455                 460

Gln Gln Gln Asp Gln His Ser Ser Asp Ile Lys Thr Leu Ala Lys Ala
465                 470                 475                 480

Ser Ala Ala Asn Thr Asp Arg Ile Ala Lys Asn Lys Ala Asp Ala Asp
              485                 490                 495

Ala Ser Phe Glu Thr Leu Thr Lys Asn Gln Asn Thr Leu Ile Glu Lys
              500                 505                 510

Asp Lys Glu His Asp Lys Leu Ile Thr Ala Asn Lys Thr Ala Ile Asp
              515                 520                 525

Ala Asn Lys Ala Ser Ala Asp Thr Lys Phe Ala Ala Thr Ala Asp Ala
          530                 535                 540

Ile Thr Lys Asn Gly Asn Ala Ile Thr Lys Asn Ala Lys Ser Ile Thr
545                 550                 555                 560

Asp Leu Gly Thr Lys Val Asp Gly Phe Asp Gly Arg Val Thr Ala Leu
              565                 570                 575

Asp Thr Lys Val Asn Ala Leu Asp Thr Lys Val Asn Ala Phe Asp Gly
              580                 585                 590

Arg Ile Thr Ala Leu Asp Ser Lys Val Glu Asn Gly Met Ala Ala Gln
              595                 600                 605

Ala Ala Leu Ser Gly Leu Phe Gln Pro Tyr Ser Val Gly Lys Phe Asn
          610                 615                 620

Ala Thr Ala Ala Leu Gly Gly Tyr Gly Ser Lys Ser Ala Val Ala Ile
625                 630                 635                 640

Gly Ala Gly Tyr Arg Val Asn Pro Asn Leu Ala Phe Lys Ala Gly Ala
              645                 650                 655

Ala Ile Asn Thr Ser Gly Asn Lys Lys Gly Ser Tyr Asn Ile Gly Val
              660                 665                 670

Asn Tyr Glu Phe
              675

<210> SEQ ID NO 37
<211> LENGTH: 629
<212> TYPE: PRT
<213> ORGANISM: Moraxalla catarrhalis

<400> SEQUENCE: 37

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Asn Gly
              20                  25                  30

Thr Ser Thr Lys Leu Lys Asn Leu Lys Glu Tyr Ala Gln Tyr Leu Asp
          35                  40                  45

Asn Tyr Ala Gln Tyr Leu Asp Asp Ile Asp Asp Leu Asp Lys Glu
      50                  55                  60

Val Gly Glu Leu Ser Gln Asn Ile Ala Lys Gln Ala Asn Ile Lys
65                  70                  75                  80

Asp Leu Asn Lys Lys Leu Ser Arg Asp Ile Asp Ser Leu Arg Glu Asp
              85                  90                  95

Val Tyr Asp Asn Gln Tyr Glu Ile Val Asn Asn Gln Ala Asp Ile Glu

-continued

```
              100                 105                 110
Lys Asn Gln Asp Asp Ile Lys Glu Leu Glu Asn Asn Val Gly Lys Glu
              115                 120                 125
Leu Leu Asn Leu Ser Gly Arg Leu Leu Asp Gln Lys Ala Asp Ile Asp
              130                 135                 140
Asn Asn Ile Asn Asn Ile Tyr Glu Leu Ala Gln Gln Gln Asp Gln His
145                 150                 155                 160
Ser Ser Asp Ile Lys Thr Leu Lys Lys Asn Val Glu Glu Gly Leu Leu
                  165                 170                 175
Glu Leu Ser Gly His Leu Ile Asp Gln Lys Ser Asp Ile Ala Gln Asn
              180                 185                 190
Gln Thr Asp Ile Gln Asp Leu Ala Thr Tyr Asn Glu Leu Gln Asp Gln
              195                 200                 205
Tyr Ala Gln Lys Gln Thr Glu Ala Ile Asp Ala Leu Asn Lys Ala Ser
              210                 215                 220
Ser Glu Asn Thr Gln Asn Ile Glu Asp Leu Ala Ala Tyr Asn Glu Leu
225                 230                 235                 240
Gln Asp Ala Tyr Ala Lys Gln Gln Thr Glu Ala Ile Asp Ala Leu Asn
                  245                 250                 255
Lys Ala Ser Ser Glu Asn Thr Gln Asn Ile Gln Asp Leu Ala Ala Tyr
              260                 265                 270
Asn Glu Leu Gln Asp Ala Tyr Ala Lys Gln Gln Thr Glu Ala Ile Asp
              275                 280                 285
Ala Leu Asn Lys Ala Ser Ser Glu Asn Thr Gln Asn Ile Glu Asp Leu
              290                 295                 300
Ala Ala Tyr Asn Glu Leu Gln Asp Ala Tyr Ala Lys Gln Gln Thr Glu
305                 310                 315                 320
Ala Ile Asp Ala Leu Asn Lys Ala Ser Ser Glu Asn Thr Gln Asn Ile
                  325                 330                 335
Glu Asp Leu Ala Ala Tyr Asn Glu Leu Gln Asp Ala Tyr Ala Lys Gln
              340                 345                 350
Gln Thr Glu Ala Ile Asp Ala Leu Asn Lys Ala Ser Ser Glu Asn Thr
              355                 360                 365
Gln Asn Ile Glu Asp Leu Ala Ala Tyr Asn Glu Leu Gln Asp Ala Tyr
              370                 375                 380
Ala Lys Gln Gln Thr Glu Ala Ile Asp Ala Leu Asn Lys Ala Ser Ser
385                 390                 395                 400
Glu Asn Thr Gln Asn Ile Ala Lys Asn Gln Ala Asp Ile Ala Asn Asn
                  405                 410                 415
Ile Asn Asn Ile Tyr Glu Leu Ala Gln Gln Gln Asp Gln His Ser Ser
              420                 425                 430
Asp Ile Lys Thr Leu Ala Lys Ala Ser Ala Ala Asn Thr Asp Arg Ile
              435                 440                 445
Ala Lys Asn Lys Ala Asp Ala Asp Ala Ser Phe Glu Thr Leu Thr Lys
              450                 455                 460
Asn Gln Asn Thr Leu Ile Glu Lys Asp Lys Glu His Asp Lys Leu Ile
465                 470                 475                 480
Thr Ala Asn Lys Thr Ala Ile Asp Ala Asn Lys Ala Ser Ala Asp Thr
                  485                 490                 495
Lys Phe Ala Ala Thr Ala Asp Ala Ile Thr Lys Asn Gly Asn Ala Ile
              500                 505                 510
Thr Lys Asn Ala Lys Ser Ile Thr Asp Leu Gly Thr Lys Val Asp Ala
              515                 520                 525
```

```
Phe Asp Gly Arg Val Thr Ala Leu Asp Thr Lys Val Asn Ala Phe Asp
        530                 535                 540

Gly Arg Ile Thr Ala Leu Asp Ser Lys Val Glu Asn Gly Met Ala Ala
545                 550                 555                 560

Gln Ala Ala Leu Ser Gly Leu Phe Gln Pro Tyr Ser Val Gly Lys Phe
                565                 570                 575

Asn Ala Thr Ala Ala Leu Gly Gly Tyr Gly Ser Lys Ser Ala Val Ala
            580                 585                 590

Ile Gly Ala Gly Tyr Arg Val Asn Pro Asn Leu Ala Phe Lys Ala Gly
        595                 600                 605

Ala Ala Ile Asn Thr Ser Gly Asn Lys Lys Gly Ser Tyr Asn Ile Gly
    610                 615                 620

Val Asn Tyr Glu Phe
625

<210> SEQ ID NO 38
<211> LENGTH: 683
<212> TYPE: PRT
<213> ORGANISM: Moraxalla catarrhalis

<400> SEQUENCE: 38

Met Lys Thr Met Lys Leu Leu Pro Leu Lys Ile Ala Val Thr Ser Ala
1               5                   10                  15

Met Ile Val Gly Leu Gly Met Ala Ser Thr Ala Asn Ala Gln Gln Gln
            20                  25                  30

Arg Ser Pro Lys Thr Glu Thr Phe Leu Pro Asn Ile Phe Phe Asn Glu
        35                  40                  45

Tyr Ala Asp Asp Leu Asp Thr Leu Tyr His Asn Met Ile Leu Gly Asp
    50                  55                  60

Thr Ala Ile Thr His Asp Asp Gln Tyr Lys Phe Tyr Ala Asp Asp Ala
65                  70                  75                  80

Thr Glu Val Pro Asp Ser Leu Phe Phe Asn Lys Ile Leu His Asp Gln
                85                  90                  95

Leu Leu Tyr Gly Phe Lys Glu Gly Asp Lys Ile Ile Pro Leu Asp Glu
            100                 105                 110

Asn Gly Lys Pro Val Tyr Lys Leu Asp Lys Arg Leu Asp Asn Gly Val
        115                 120                 125

Gln Lys Thr Val Tyr Ser Val Thr Thr Lys Thr Ala Thr Ala Asp Asp
    130                 135                 140

Val Asn Ser Ala Tyr Ser Arg Gly Ile Gln Gly Asp Ile Asp Asp Leu
145                 150                 155                 160

Tyr Glu Ala Asn Lys Glu Asn Val Asn Arg Leu Ile Glu His Gly Asp
                165                 170                 175

Lys Ile Phe Ala Asn Glu Glu Ser Val Gln Tyr Leu Asn Lys Glu Val
            180                 185                 190

Gln Asn Asn Ile Glu Asn Ile His Glu Leu Ala Gln Gln Gln Asp Gln
        195                 200                 205

His Ser Ser Asp Ile Lys Thr Leu Lys Lys Asn Val Glu Glu Gly Leu
    210                 215                 220

Leu Glu Leu Ser Gly His Leu Ile Asp Gln Lys Thr Asp Ile Ala Gln
225                 230                 235                 240

Asn Gln Thr Asp Ile Gln Asp Leu Ala Thr Tyr Asn Glu Leu Gln Asp
                245                 250                 255

Gln Tyr Ala Gln Lys Gln Thr Glu Ala Ile Asp Ala Leu Asn Lys Ala
```

```
                260                 265                 270
Ser Ser Glu Asn Thr Gln Asn Ile Ala Lys Asn Ser Asn Arg Ile Lys
            275                 280                 285
Ala Leu Glu Asn Asn Ile Glu Glu Gly Leu Leu Glu Leu Ser Gly His
            290                 295                 300
Leu Ile Asp Gln Lys Ala Asp Leu Thr Lys Asp Ile Lys Ala Leu Glu
305                 310                 315                 320
Ser Asn Val Glu Glu Gly Leu Leu Asp Leu Ser Gly Arg Leu Ile Asp
            325                 330                 335
Gln Lys Ala Asp Ile Ala Gln Asn Gln Ala Asn Ile Gln Asp Leu Ala
            340                 345                 350
Ala Tyr Asn Glu Leu Gln Asp Ala Tyr Ala Lys Gln Gln Thr Glu Ala
            355                 360                 365
Ile Asp Ala Leu Asn Lys Ala Ser Ser Glu Asn Thr Gln Asn Ile Glu
            370                 375                 380
Asp Leu Ala Ala Tyr Asn Glu Leu Gln Asp Ala Tyr Ala Lys Gln Gln
385                 390                 395                 400
Thr Glu Ala Ile Asp Ala Leu Asn Lys Ala Ser Ser Glu Asn Thr Gln
            405                 410                 415
Asn Ile Glu Asp Leu Ala Ala Tyr Asn Glu Leu Gln Asp Ala Tyr Ala
            420                 425                 430
Lys Gln Gln Thr Glu Ala Ile Asp Ala Leu Asn Lys Ala Ser Ser Glu
            435                 440                 445
Asn Thr Gln Asn Ile Ala Lys Asn Gln Ala Asp Ile Ala Asn Asn Ile
            450                 455                 460
Asn Asn Ile Tyr Glu Leu Ala Gln Gln Gln Asp Gln His Ser Ser Asp
465                 470                 475                 480
Ile Lys Thr Leu Ala Lys Ala Ser Ala Ala Asn Thr Asp Arg Ile Ala
            485                 490                 495
Lys Asn Lys Ala Asp Ala Asp Ala Ser Phe Glu Thr Leu Thr Lys Asn
            500                 505                 510
Gln Asn Thr Leu Ile Glu Lys Asp Lys Glu His Asp Lys Leu Ile Thr
            515                 520                 525
Ala Asn Lys Thr Ala Ile Asp Ala Asn Lys Ala Ser Ala Asp Thr Lys
            530                 535                 540
Phe Ala Ala Thr Ala Asp Ala Ile Thr Lys Asn Gly Asn Ala Ile Thr
545                 550                 555                 560
Lys Asn Ala Lys Ser Ile Thr Asp Leu Gly Thr Lys Val Asp Gly Phe
            565                 570                 575
Asp Gly Arg Val Thr Ala Leu Asp Thr Lys Val Asn Ala Leu Asp Thr
            580                 585                 590
Lys Val Asn Ala Phe Asp Gly Arg Ile Thr Ala Leu Asp Ser Lys Val
            595                 600                 605
Glu Asn Gly Met Ala Ala Gln Ala Ala Leu Ser Gly Leu Phe Gln Pro
            610                 615                 620
Tyr Ser Val Gly Lys Phe Asn Ala Thr Ala Ala Leu Gly Gly Tyr Gly
625                 630                 635                 640
Ser Lys Ser Ala Val Ala Ile Gly Ala Gly Tyr Arg Val Asn Pro Asn
            645                 650                 655
Leu Ala Phe Lys Ala Gly Ala Ala Ile Asn Thr Ser Gly Asn Lys Lys
            660                 665                 670
Gly Ser Tyr Asn Ile Gly Val Asn Tyr Glu Phe
            675                 680
```

<210> SEQ ID NO 39
<211> LENGTH: 700
<212> TYPE: PRT
<213> ORGANISM: Moraxalla catarrhalis

<400> SEQUENCE: 39

```
Met Lys Thr Met Lys Leu Leu Pro Leu Lys Ile Ala Val Thr Ser Ala
1               5                   10                  15

Met Ile Val Gly Leu Gly Ala Ala Ser Thr Ala Asn Ala Gln Ala Gln
            20                  25                  30

Ser Asn Arg Ser Leu Asp Gln Val Gln Ala Leu Leu Arg Gly Ile Asp
        35                  40                  45

Glu Thr Lys Ile Lys Lys Glu Ile Gln Gln Ser Gln Gln Pro Glu Leu
    50                  55                  60

Asn Lys Tyr Leu Thr Phe Asn Gln Leu Ala Asn Ala Leu Asn Ile Glu
65                  70                  75                  80

Glu Leu Asn Asn Asn Val Gln Lys Asn Thr Gln Arg Leu Asp Ser Ala
                85                  90                  95

Ala Thr Leu Tyr Gly Asp Leu Ser Lys Thr Val Pro Lys Ser Ile Lys
            100                 105                 110

Glu Asn Lys Glu Ser Ile Lys Glu Asn Lys Glu Ser Ile Lys Glu Asn
        115                 120                 125

Lys Glu Ser Ile Lys Glu Asn Lys Glu Ser Ile Lys Glu Asn Lys Glu
    130                 135                 140

Ser Ile Lys Glu Asn Lys Glu Ser Ile Thr Thr Leu Thr Arg Lys Ser
145                 150                 155                 160

Phe Gln Asn Gln Val Asp Ile Val Arg Asn Asn Ala Ser Ile Glu Asp
                165                 170                 175

Leu Tyr Ala Tyr Gly Gln Glu Val Ala Lys Ser Ile Gly Glu Ile His
            180                 185                 190

Ala Tyr Thr Glu Glu Val Asn Lys Thr Leu Glu Asn Leu Ile Thr Asn
        195                 200                 205

Ser Val Glu Asn Thr Asn Asn Ile Thr Lys Asn Lys Ala Asp Ile Gln
    210                 215                 220

Ala Leu Glu Asn Asn Val Val Glu Glu Leu Phe Asn Leu Ser Gly Arg
225                 230                 235                 240

Leu Ile Asp Gln Lys Ala Ile Asp Asn Asn Ile Asn Asn Ile Tyr
                245                 250                 255

Glu Leu Ala Gln Gln Gln Asp Gln His Ser Ser Asp Ile Lys Thr Leu
            260                 265                 270

Lys Lys Asn Val Glu Glu Gly Leu Leu Glu Leu Ser Gly His Leu Ile
        275                 280                 285

Asp Gln Lys Ala Asp Leu Thr Lys Asp Ile Lys Thr Leu Glu Ser Asn
    290                 295                 300

Val Glu Glu Gly Leu Leu Asp Leu Ser Gly Arg Leu Leu Asp Gln Lys
305                 310                 315                 320

Ala Asp Ile Ala Gln Asn Gln Ala Asn Ile Gln Asp Leu Ala Ala Tyr
                325                 330                 335

Asn Glu Leu Gln Asp Ala Tyr Ala Lys Gln Gln Thr Glu Ala Ile Asp
            340                 345                 350

Ala Leu Asn Lys Ala Ser Ser Glu Asn Thr Gln Asn Ile Glu Asp Leu
        355                 360                 365

Ala Ala Tyr Asn Glu Leu Gln Asp Ala Tyr Ala Lys Gln Gln Thr Glu
```

```
                    370                 375                 380
Ala Ile Asp Ala Leu Asn Lys Ala Ser Ser Glu Asn Thr Gln Asn Ile
385                 390                 395                 400

Glu Asp Leu Ala Ala Tyr Asn Glu Leu Gln Asp Ala Tyr Ala Lys Gln
                    405                 410                 415

Gln Thr Glu Ala Ile Asp Ala Leu Asn Lys Ala Ser Ser Glu Asn Thr
                    420                 425                 430

Gln Asn Ile Glu Asp Leu Ala Ala Tyr Asn Glu Leu Gln Asp Ala Tyr
                    435                 440                 445

Ala Lys Gln Gln Thr Glu Ala Ile Asp Ala Leu Asn Lys Ala Ser Ser
450                 455                 460

Glu Asn Thr Gln Asn Ile Ala Lys Asn Gln Ala Asp Ile Ala Asn Asn
465                 470                 475                 480

Ile Asn Asn Ile Tyr Glu Leu Ala Gln Gln Asp Gln His Ser Ser
                    485                 490                 495

Asp Ile Lys Thr Leu Ala Lys Ala Ser Ala Ala Asn Thr Asp Arg Ile
                    500                 505                 510

Ala Lys Asn Lys Ala Asp Ala Asp Ala Ser Phe Glu Thr Leu Thr Lys
                    515                 520                 525

Asn Gln Asn Thr Leu Ile Glu Lys Asp Lys Glu His Asp Lys Leu Ile
530                 535                 540

Thr Ala Asn Lys Thr Val Ile Asp Ala Asn Lys Ala Ser Ala Asp Thr
545                 550                 555                 560

Lys Phe Ala Ala Thr Ala Asp Ala Ile Thr Lys Asn Gly Asn Ala Ile
                    565                 570                 575

Thr Lys Asn Ala Lys Ser Ile Thr Asp Leu Gly Thr Lys Val Asp Gly
                    580                 585                 590

Phe Asp Gly Arg Val Thr Ala Leu Asp Thr Lys Val Asn Ala Leu Asp
                    595                 600                 605

Thr Lys Val Asn Ala Phe Asp Gly Arg Ile Thr Ala Leu Asp Ser Lys
                    610                 615                 620

Val Glu Asn Gly Met Ala Ala Gln Ala Ala Leu Ser Gly Leu Phe Gln
625                 630                 635                 640

Pro Tyr Ser Val Gly Lys Phe Asn Ala Thr Ala Ala Leu Gly Gly Tyr
                    645                 650                 655

Gly Ser Lys Ser Ala Val Ala Ile Gly Ala Gly Tyr Arg Val Asn Pro
                    660                 665                 670

Asn Leu Ala Phe Lys Ala Gly Ala Ala Ile Asn Thr Ser Gly Asn Lys
                    675                 680                 685

Lys Gly Ser Tyr Asn Ile Gly Val Asn Tyr Glu Phe
690                 695                 700

<210> SEQ ID NO 40
<211> LENGTH: 676
<212> TYPE: PRT
<213> ORGANISM: Moraxalla catarrhalis

<400> SEQUENCE: 40

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Thr
                20                  25                  30

Glu Thr Phe Leu Pro Asn Leu Phe Asp Asn Asp Tyr Ile Glu Thr Thr
                35                  40                  45
```

```
Asp Pro Leu Tyr His Gly Met Ile Leu Gly Asn Thr Ala Ile Thr Gln
 50                  55                  60

Asp Thr Gln Tyr Lys Phe Tyr Ala Glu Asn Gly Asn Glu Val Pro Asp
 65                  70                  75                  80

Ser Leu Phe Phe Asn Lys Ile Leu His Asp Gln Gln Leu Asn Gly Phe
                 85                  90                  95

Lys Glu Gly Asp Thr Ile Ile Pro Leu Asp Glu Asn Gly Lys Pro Val
            100                 105                 110

Tyr Lys Leu Asp Glu Ile Thr Glu Asn Gly Val Lys Arg Lys Val Tyr
        115                 120                 125

Ser Val Thr Thr Lys Thr Ala Thr Arg Glu Asp Val Glu Gln Ser Ala
130                 135                 140

Tyr Ser Arg Gly Ile Gln Gly Asp Ile Asp Asp Leu Tyr Glu Ala Asn
145                 150                 155                 160

Lys Glu Asn Val Asn Arg Leu Ile Glu His Gly Asp Lys Ile Phe Ala
                165                 170                 175

Asn Glu Glu Ser Val Gln Tyr Leu Asn Lys Glu Val Gln Asn Asn Ile
            180                 185                 190

Glu Asn Ile His Glu Leu Ala Gln Gln Gln Asp Gln His Ser Ser Asp
        195                 200                 205

Ile Lys Thr Leu Lys Lys Asn Val Glu Glu Gly Leu Leu Glu Leu Ser
210                 215                 220

Gly His Leu Ile Asp Gln Lys Ala Asp Leu Thr Lys Asp Ile Lys Thr
225                 230                 235                 240

Leu Glu Asn Asn Val Glu Glu Gly Leu Leu Glu Leu Ser Gly His Leu
                245                 250                 255

Ile Asp Gln Lys Ala Asp Leu Thr Lys Asp Ile Lys Ala Leu Glu Ser
            260                 265                 270

Asn Val Glu Glu Gly Leu Leu Asp Leu Ser Gly Arg Leu Leu Asp Gln
        275                 280                 285

Lys Ala Asp Ile Ala Lys Asn Gln Ala Asp Ile Ala Gln Asn Gln Thr
290                 295                 300

Asp Ile Gln Asp Leu Ala Ala Tyr Asn Glu Leu Gln Asp Gln Tyr Ala
305                 310                 315                 320

Gln Lys Gln Thr Glu Ala Ile Asp Ala Leu Asn Lys Ala Ser Ser Glu
                325                 330                 335

Asn Thr Gln Asn Ile Glu Asp Leu Ala Ala Tyr Asn Glu Leu Gln Asp
            340                 345                 350

Gln Tyr Ala Gln Lys Gln Thr Glu Ala Ile Asp Ala Leu Asn Lys Ala
        355                 360                 365

Ser Ser Glu Asn Thr Gln Asn Ile Glu Asp Leu Ala Ala Tyr Asn Glu
370                 375                 380

Leu Gln Asp Gln Tyr Ala Gln Lys Gln Thr Glu Ala Ile Asp Ala Leu
385                 390                 395                 400

Asn Lys Ala Ser Ser Glu Asn Thr Gln Asn Ile Glu Asp Leu Ala Ala
                405                 410                 415

Tyr Asn Glu Leu Gln Asp Gln Tyr Ala Gln Lys Gln Thr Glu Ala Ile
            420                 425                 430

Asp Ala Leu Asn Lys Ala Ser Ser Glu Asn Thr Gln Asn Ile Ala Lys
        435                 440                 445

Asn Gln Ala Asp Ile Ala Asn Asn Ile Asn Asn Ile Tyr Glu Leu Ala
450                 455                 460

Gln Gln Gln Asp Gln His Ser Ser Asp Ile Lys Thr Leu Ala Lys Ala
```

```
                465                 470                 475                 480
        Ser Ala Ala Asn Thr Asp Arg Ile Ala Lys Asn Lys Ala Asp Ala Asp
                            485                 490                 495

Ala Ser Phe Glu Thr Leu Thr Lys Asn Gln Asn Thr Leu Ile Glu Lys
                        500                 505                 510

Asp Lys Glu His Asp Lys Leu Ile Thr Ala Asn Lys Thr Ala Ile Asp
                    515                 520                 525

Ala Asn Lys Ala Ser Ala Asp Thr Lys Phe Ala Ala Thr Ala Asp Ala
                530                 535                 540

Ile Thr Lys Asn Gly Asn Ala Ile Thr Lys Asn Ala Lys Ser Ile Thr
        545                 550                 555                 560

Asp Leu Gly Thr Lys Val Asp Gly Phe Asp Gly Arg Val Thr Ala Leu
                            565                 570                 575

Asp Thr Lys Val Asn Ala Leu Asp Thr Lys Val Asn Ala Phe Asp Gly
                        580                 585                 590

Arg Ile Thr Ala Leu Asp Ser Lys Val Glu Asn Gly Met Ala Ala Gln
                    595                 600                 605

Ala Ala Leu Ser Gly Leu Phe Gln Pro Tyr Ser Val Gly Lys Phe Asn
                610                 615                 620

Ala Thr Ala Ala Leu Gly Gly Tyr Gly Ser Lys Ser Ala Val Ala Ile
        625                 630                 635                 640

Gly Ala Gly Tyr Arg Val Asn Pro Asn Leu Ala Phe Lys Ala Gly Ala
                            645                 650                 655

Ala Ile Asn Thr Ser Gly Asn Lys Lys Gly Ser Tyr Asn Ile Gly Val
                        660                 665                 670

Asn Tyr Glu Phe
                675

<210> SEQ ID NO 41
<211> LENGTH: 678
<212> TYPE: PRT
<213> ORGANISM: Moraxalla catarrhalis

<400> SEQUENCE: 41

Met Lys Thr Met Lys Leu Leu Pro Leu Lys Ile Ala Val Thr Ser Ala
        1               5                   10                  15

Met Ile Ile Gly Leu Gly Ala Ala Ser Thr Ala Asn Ala Gln Leu Ala
                    20                  25                  30

Glu Gln Phe Phe Pro Asn Ile Phe Ser Asn His Ala Pro Val Lys Gln
                35                  40                  45

His Tyr His Asn Val Val Gly Asp Thr Ser Ile Val Glu Asn Leu
            50                  55                  60

Gln Asp Ser Asp Asp Thr Gln Leu Lys Phe Tyr Ser Asn Asp Glu Tyr
        65                  70                  75                  80

Ser Val Pro Asp Ser Leu Leu Phe Asn Lys Met Leu His Glu Gln Gln
                        85                  90                  95

Leu Asn Gly Phe Lys Lys Gly Asp Thr Ile Ile Pro Leu Asp Glu Asn
                    100                 105                 110

Gly Lys Pro Val Tyr Lys Val Asp Tyr Lys Leu Asp Gly Gln Glu Pro
                115                 120                 125

Arg Arg Val Tyr Ser Val Thr Thr Lys Ile Ala Thr Gln Asp Asp Val
            130                 135                 140

Asp Asn Ser Pro Tyr Ser Arg Gly Ile Gln Gly Asp Ile Asp Asp Leu
        145                 150                 155                 160
```

```
Tyr Glu Ala Asn Lys Glu Asn Val Asn Arg Leu Ile Glu His Gly Asp
                165                 170                 175
Lys Ile Phe Ala Asn Glu Glu Ser Val Gln Tyr Leu Asn Lys Glu Val
            180                 185                 190
Gln Asn Asn Ile Glu Asn Ile Tyr Glu Leu Ala Gln Gln Gln Asp Gln
        195                 200                 205
His Ser Ser Asp Ile Lys Thr Leu Lys Lys Asn Val Glu Glu Gly Leu
    210                 215                 220
Leu Glu Leu Ser Gly Arg Leu Ile Asp Gln Lys Ala Asp Ile Ala Gln
225                 230                 235                 240
Asn Gln Ala Asn Ile Gln Asp Leu Ala Ala Tyr Asn Glu Leu Gln Asp
                245                 250                 255
Gln Tyr Ala Gln Lys Gln Thr Glu Ala Ile Asp Ala Leu Asn Lys Ala
            260                 265                 270
Ser Ser Glu Asn Thr Gln Asn Ile Glu Asp Leu Ala Ala Tyr Asn Glu
        275                 280                 285
Leu Gln Asp Ala Tyr Ala Lys Gln Gln Thr Glu Ala Ile Asp Ala Leu
    290                 295                 300
Asn Lys Ala Ser Ser Glu Asn Thr Gln Asn Ile Glu Asp Leu Ala Ala
305                 310                 315                 320
Tyr Asn Glu Leu Gln Asp Ala Tyr Ala Lys Gln Gln Thr Glu Ala Ile
                325                 330                 335
Asp Ala Leu Asn Lys Ala Ser Ser Glu Asn Thr Gln Asn Ile Glu Asp
            340                 345                 350
Leu Ala Ala Tyr Asn Glu Leu Gln Asp Ala Tyr Ala Lys Gln Gln Thr
        355                 360                 365
Glu Ala Ile Asp Ala Leu Asn Lys Ala Ser Ser Glu Asn Thr Gln Asn
    370                 375                 380
Ile Glu Asp Leu Ala Ala Tyr Asn Glu Leu Gln Asp Ala Tyr Ala Lys
385                 390                 395                 400
Gln Gln Thr Glu Ala Ile Asp Ala Leu Asn Lys Ala Ser Ser Glu Asn
                405                 410                 415
Thr Gln Asn Ile Glu Asp Leu Ala Ala Tyr Asn Glu Leu Gln Asp Ala
            420                 425                 430
Tyr Ala Lys Gln Gln Thr Glu Ala Ile Asp Ala Leu Asn Lys Ala Ser
        435                 440                 445
Ser Glu Asn Thr Gln Asn Ile Ala Lys Asn Gln Ala Asp Ile Ala Asn
    450                 455                 460
Asn Ile Asn Asn Ile Tyr Glu Leu Ala Gln Gln Gln Asp Gln His Ser
465                 470                 475                 480
Ser Asp Ile Lys Thr Leu Ala Lys Val Ser Ala Ala Asn Thr Asp Arg
                485                 490                 495
Ile Ala Lys Asn Lys Ala Asp Ala Asp Ala Ser Phe Glu Thr Leu Thr
            500                 505                 510
Lys Asn Gln Asn Thr Leu Ile Glu Lys Asp Lys Glu His Asp Lys Leu
        515                 520                 525
Ile Thr Ala Asn Lys Thr Ala Ile Asp Ala Asn Lys Ala Ser Ala Asp
    530                 535                 540
Thr Lys Phe Ala Ala Thr Ala Asp Ala Ile Thr Lys Asn Gly Asn Ala
545                 550                 555                 560
Ile Thr Lys Asn Ala Lys Ser Ile Thr Asp Leu Gly Thr Lys Val Asp
                565                 570                 575
Gly Phe Asp Gly Arg Val Thr Ala Leu Asp Thr Lys Val Asn Ala Phe
```

-continued

```
                580             585               590
Asp Gly Arg Ile Thr Ala Leu Asp Ser Lys Val Glu Asn Gly Met Ala
            595                 600                 605

Ala Gln Ala Ala Leu Ser Gly Leu Phe Gln Pro Tyr Ser Val Gly Lys
    610                 615                 620

Phe Asn Ala Thr Ala Ala Leu Gly Gly Tyr Gly Ser Lys Ser Ala Val
625                 630                 635                 640

Ala Ile Gly Ala Gly Tyr Arg Val Asn Pro Asn Leu Ala Phe Lys Ala
                645                 650                 655

Gly Ala Ala Ile Asn Thr Ser Gly Asn Lys Lys Gly Ser Tyr Asn Ile
            660                 665                 670

Gly Val Asn Tyr Glu Phe
            675

<210> SEQ ID NO 42
<211> LENGTH: 613
<212> TYPE: PRT
<213> ORGANISM: Moraxalla catarrhalis

<400> SEQUENCE: 42

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ser Arg
            20                  25                  30

Asp Arg Ser Leu Glu Asp Ile Gln Asp Ser Ile Ser Lys Leu Val Gln
        35                  40                  45

Asp Asp Ile Asn Thr Leu Lys Gln Asp Gln Gln Lys Met Asn Lys Tyr
    50                  55                  60

Leu Leu Leu Asn Gln Leu Ala Asn Thr Leu Ile Thr Asp Glu Leu Asn
65                  70                  75                  80

Asn Asn Val Ile Lys Asn Thr Asn Ser Ile Glu Ala Leu Gly Asp Glu
                85                  90                  95

Ile Gly Trp Leu Glu Asn Asp Ile Ala Asp Leu Glu Glu Gly Val Glu
            100                 105                 110

Glu Leu Thr Lys Asn Gln Asn Thr Leu Ile Glu Lys Asp Glu Glu His
        115                 120                 125

Asp Arg Leu Ile Ala Gln Asn Gln Ala Asp Ile Gln Thr Leu Glu Asn
    130                 135                 140

Asn Val Val Glu Glu Leu Phe Asn Leu Ser Gly Arg Leu Ile Asp Gln
145                 150                 155                 160

Glu Ala Asp Ile Ala Lys Asn Asn Ala Ser Ile Glu Glu Leu Tyr Asp
                165                 170                 175

Phe Asp Asn Glu Val Ala Glu Arg Ile Gly Glu Ile His Ala Tyr Thr
            180                 185                 190

Glu Glu Val Asn Lys Thr Leu Glu Asn Leu Ile Thr Asn Ser Val Lys
        195                 200                 205

Asn Thr Asp Asn Ile Asp Lys Asn Lys Ala Asp Ile Asp Asn Asn Ile
    210                 215                 220

Asn His Ile Tyr Glu Leu Ala Gln Gln Gln Asp Gln His Ser Ser Asp
225                 230                 235                 240

Ile Lys Thr Leu Lys Asn Asn Val Glu Glu Gly Leu Leu Glu Leu Ser
                245                 250                 255

Gly His Leu Ile Asp Gln Lys Ala Asp Leu Thr Lys Asp Ile Lys Ala
            260                 265                 270
```

```
Leu Glu Ser Asn Val Glu Gly Leu Leu Asp Leu Ser Gly Arg Leu
            275                 280                 285

Leu Asp Gln Lys Ala Asp Leu Thr Lys Asp Ile Lys Ala Leu Glu Ser
290                 295                 300

Asn Val Glu Glu Gly Leu Leu Asp Leu Ser Gly Arg Leu Leu Asp Gln
305                 310                 315                 320

Lys Ala Asp Ile Ala Gln Asn Gln Thr Asp Ile Gln Asp Leu Ala Ala
                325                 330                 335

Tyr Asn Glu Leu Gln Asp Gln Tyr Ala Gln Lys Gln Thr Glu Ala Ile
            340                 345                 350

Asp Ala Leu Asn Lys Ala Ser Ser Glu Asn Thr Gln Asn Ile Glu Asp
        355                 360                 365

Leu Ala Ala Tyr Asn Glu Leu Gln Asp Ala Tyr Ala Lys Gln Gln Thr
    370                 375                 380

Glu Ala Ile Asp Ala Leu Asn Lys Ala Ser Ser Glu Asn Thr Gln Asn
385                 390                 395                 400

Ile Ala Lys Asn Gln Ala Asp Ile Ala Asn Asn Ile Asn Asn Ile Tyr
                405                 410                 415

Glu Leu Ala Gln Gln Gln Asp Gln His Ser Ser Asp Ile Lys Thr Leu
            420                 425                 430

Ala Lys Ala Ser Ala Ala Asn Thr Asn Arg Ile Ala Thr Ala Glu Leu
        435                 440                 445

Gly Ile Ala Glu Asn Lys Lys Asp Ala Gln Ile Ala Lys Ala Gln Ala
    450                 455                 460

Asn Ala Asn Lys Thr Ala Ile Asp Glu Asn Lys Ala Ser Ala Asp Thr
465                 470                 475                 480

Lys Phe Ala Ala Thr Ala Asp Ala Ile Thr Lys Asn Gly Asn Ala Ile
                485                 490                 495

Thr Lys Asn Ala Lys Ser Ile Thr Asp Leu Gly Thr Lys Val Asp Gly
            500                 505                 510

Phe Asp Gly Arg Val Thr Ala Leu Asp Thr Lys Val Asn Ala Phe Asp
        515                 520                 525

Gly Arg Ile Thr Ala Leu Asp Ser Lys Val Glu Asn Gly Met Ala Ala
    530                 535                 540

Gln Ala Ala Leu Ser Gly Leu Phe Gln Pro Tyr Ser Val Gly Lys Phe
545                 550                 555                 560

Asn Ala Thr Ala Ala Leu Gly Gly Tyr Gly Ser Lys Ser Ala Val Ala
                565                 570                 575

Ile Gly Ala Gly Tyr Arg Val Asn Pro Asn Leu Ala Phe Lys Ala Gly
            580                 585                 590

Ala Ala Ile Asn Thr Ser Gly Asn Lys Lys Gly Ser Tyr Asn Ile Gly
        595                 600                 605

Val Asn Tyr Glu Phe
610

<210> SEQ ID NO 43
<211> LENGTH: 589
<212> TYPE: PRT
<213> ORGANISM: Moraxalla catarrhalis

<400> SEQUENCE: 43

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Thr
            20                  25                  30
```

```
Asn Lys Asp Ile Thr Leu Glu Asp Val Leu Lys Ser Ile Glu Glu Ile
        35                  40                  45

Asp Pro Tyr Glu Leu Arg Asp Tyr Ile Glu Tyr Pro Thr Ala Ile Glu
    50                  55                  60

Arg Phe Leu Leu Leu Ser Gln Tyr Gly Asn Thr Leu Thr Leu Glu Glu
65                  70                  75                  80

Phe Asp Asn Asp Ile Glu Leu Leu Asp Gln Asp Val Glu Asp Leu Glu
                85                  90                  95

Glu Ser Val Thr Glu Leu Ala Lys Asn Gln Asn Ser Leu Ile Glu Gln
            100                 105                 110

Gly Glu Ala Ile Lys Glu Asp Leu Gln Gly Leu Ala Asp Phe Val Glu
        115                 120                 125

Arg Gln Glu Asp Lys Ile Leu Gln Asn Glu Thr Ser Ile Lys Lys Asn
    130                 135                 140

Thr Gln Arg Asn Leu Val Asn Gly Phe Glu Ile Glu Lys Asn Lys Asp
145                 150                 155                 160

Ala Ile Ala Lys Asn Asn Glu Ser Ile Glu Asp Leu Tyr Asp Phe Gly
                165                 170                 175

His Glu Val Ala Lys Ser Ile Gly Glu Ile His Ala His Asn Glu Ala
            180                 185                 190

Gln Asn Glu Thr Leu Lys Asp Leu Ile Thr Asn Ser Val Lys Asn Thr
        195                 200                 205

Asp Asn Ile Thr Lys Asn Lys Ala Asp Ile Gln Ala Leu Glu Ser Asn
    210                 215                 220

Val Glu Lys Gly Leu Leu Glu Leu Ser Gly His Leu Ile Asp Gln Lys
225                 230                 235                 240

Ala Asp Ile Asp Asn Asn Ile Asn Asn Ile His Glu Leu Ala Gln Gln
                245                 250                 255

Gln Asp Gln His Ser Ser Asp Ile Lys Thr Leu Lys Lys Asn Val Glu
            260                 265                 270

Glu Gly Leu Leu Glu Leu Ser Gly His Leu Ile Asp Gln Lys Ser Asp
        275                 280                 285

Ile Ala Gln Asn Gln Ala Asn Ile Gln Asp Leu Ala Thr Tyr Asn Glu
    290                 295                 300

Leu Gln Asp Gln Tyr Ala Gln Lys Gln Thr Glu Ala Ile Asp Ala Leu
305                 310                 315                 320

Asn Lys Ala Ser Ser Glu Asn Thr Gln Asn Ile Glu Asp Leu Ala Ala
                325                 330                 335

Tyr Asn Glu Leu Gln Asp Ala Tyr Ala Lys Gln Gln Thr Glu Ala Ile
            340                 345                 350

Asp Ala Leu Asn Lys Ala Ser Ser Glu Asn Thr Gln Asn Ile Ala Lys
        355                 360                 365

Asn Gln Ala Asp Ile Ala Asn Asn Ile Asn Asn Ile Tyr Glu Leu Ala
    370                 375                 380

Gln Gln Gln Asp Gln His Ser Ser Asp Ile Lys Thr Leu Ala Lys Ala
385                 390                 395                 400

Ser Ala Ala Asn Thr Asp Arg Ile Ala Lys Asn Lys Ala Asp Ala Asp
                405                 410                 415

Ala Ser Phe Glu Thr Leu Thr Lys Asn Gln Asn Thr Leu Ile Glu Lys
            420                 425                 430

Asp Lys Glu His Asp Lys Leu Ile Thr Ala Asn Lys Thr Ala Ile Asp
        435                 440                 445
```

```
Ala Asn Lys Ala Ser Ala Asp Thr Lys Phe Ala Ala Thr Ala Asp Ala
    450                 455                 460

Ile Thr Lys Asn Gly Asn Ala Ile Thr Lys Asn Ala Lys Ser Ile Thr
465                 470                 475                 480

Asp Leu Gly Thr Lys Val Asp Gly Phe Asp Ser Arg Val Thr Ala Leu
                485                 490                 495

Asp Thr Lys Val Asn Ala Phe Asp Gly Arg Ile Thr Ala Leu Asp Ser
            500                 505                 510

Lys Val Glu Asn Gly Met Ala Ala Gln Ala Ala Leu Ser Gly Leu Phe
        515                 520                 525

Gln Pro Tyr Ser Val Gly Lys Phe Asn Ala Thr Ala Ala Leu Gly Gly
    530                 535                 540

Tyr Gly Ser Lys Ser Ala Val Ala Ile Gly Ala Gly Tyr Arg Val Asn
545                 550                 555                 560

Pro Asn Leu Ala Phe Lys Ala Gly Ala Ala Ile Asn Thr Ser Gly Asn
                565                 570                 575

Lys Lys Gly Ser Tyr Asn Ile Gly Val Asn Tyr Glu Phe
            580                 585
```

<210> SEQ ID NO 44
<211> LENGTH: 684
<212> TYPE: PRT
<213> ORGANISM: Moraxalla catarrhalis

<400> SEQUENCE: 44

```
Met Lys Thr Met Lys Leu Leu Pro Leu Lys Ile Ala Val Thr Ser Ala
1               5                   10                  15

Met Met Val Gly Leu Gly Met Ala Ser Thr Ala Asn Ala Gln Gln Gln
            20                  25                  30

Lys Ser Pro Lys Thr Glu Ile Phe Leu Pro Asn Leu Phe Asp Asn Asp
        35                  40                  45

Asn Thr Glu Leu Thr Asp Pro Leu Tyr His Asn Met Ile Leu Gly Asn
    50                  55                  60

Thr Ala Leu Leu Thr Gln Glu Asn Gln Tyr Lys Phe Tyr Ala Asp Asp
65                  70                  75                  80

Gly Asn Gly Val Pro Asp Ser Leu Leu Phe Asn Lys Ile Leu His Asp
                85                  90                  95

Gln Leu Leu His Gly Phe Lys Glu Gly Asp Thr Ile Ile Pro Leu Asp
                100                 105                 110

Glu Asn Gly Lys Pro Val Tyr Lys Leu Asp Ser Ile Val Glu Gln Gly
            115                 120                 125

Lys Thr Lys Thr Val Tyr Ser Val Thr Thr Lys Thr Ala Thr Ala Asp
130                 135                 140

Asp Val Asn Ser Ala Tyr Ser Arg Gly Ile Gln Gly Asp Ile Asp Asp
145                 150                 155                 160

Leu Tyr Glu Ala Asn Lys Glu Asn Val Asn Arg Leu Ile Glu His Gly
                165                 170                 175

Asp Lys Ile Phe Ala Asn Glu Glu Ser Val Gln Tyr Leu Asn Arg Glu
            180                 185                 190

Val Gln Asn Asn Ile Glu Asn Ile His Glu Leu Ala Gln Gln Gln Asp
        195                 200                 205

Gln His Ser Ser Asp Ile Lys Thr Leu Lys Lys Asn Val Glu Lys Asp
    210                 215                 220

Leu Leu Asp Leu Ser Gly Arg Leu Ile Ala Gln Lys Glu Asp Ile Ala
225                 230                 235                 240
```

```
Gln Asn Gln Thr Asp Ile Gln Asp Leu Ala Thr Tyr Asn Glu Leu Gln
                245                 250                 255

Asp Gln Tyr Ala Gln Lys Gln Thr Glu Ala Ile Asp Ala Leu Asn Lys
            260                 265                 270

Ala Ser Ser Glu Asn Thr Gln Asn Ile Ala Lys Asn Ser Asn His Ile
        275                 280                 285

Lys Thr Leu Glu Asn Asn Ile Glu Glu Gly Leu Leu Glu Leu Ser Gly
    290                 295                 300

His Leu Ile Asp Gln Lys Ala Asp Leu Thr Lys Asp Ile Lys Ala Leu
305                 310                 315                 320

Glu Ser Asn Val Glu Glu Gly Leu Leu Asp Leu Ser Gly Arg Leu Ile
                325                 330                 335

Asp Gln Lys Ala Asp Ile Ala Gln Asn Gln Ala Asn Ile Gln Asp Leu
            340                 345                 350

Ala Ala Tyr Asn Glu Leu Gln Asp Ala Tyr Ala Lys Gln Gln Thr Glu
        355                 360                 365

Ala Ile Asp Ala Leu Asn Lys Ala Ser Ser Glu Asn Thr Gln Asn Ile
    370                 375                 380

Glu Asp Leu Ala Ala Tyr Asn Glu Leu Gln Asp Ala Tyr Ala Lys Gln
385                 390                 395                 400

Gln Thr Glu Ala Ile Asp Ala Leu Asn Lys Ala Ser Ser Glu Asn Thr
                405                 410                 415

Gln Asn Ile Glu Asp Leu Ala Ala Tyr Asn Glu Leu Gln Asp Ala Tyr
            420                 425                 430

Ala Lys Gln Gln Thr Glu Ala Ile Asp Ala Leu Asn Lys Ala Ser Ser
        435                 440                 445

Glu Asn Thr Gln Asn Ile Ala Lys Asn Gln Ala Asp Ile Ala Asn Asn
    450                 455                 460

Ile Asn Asn Ile Tyr Glu Leu Ala Gln Gln Gln Asp Gln His Ser Ser
465                 470                 475                 480

Asp Ile Lys Thr Leu Ala Lys Ala Ser Ala Ala Asn Thr Asp Arg Ile
                485                 490                 495

Ala Lys Asn Lys Ala Asp Ala Asp Ala Ser Phe Glu Thr Leu Thr Lys
            500                 505                 510

Asn Gln Asn Thr Leu Ile Glu Lys Asp Lys Glu His Asp Lys Leu Ile
        515                 520                 525

Thr Ala Asn Lys Thr Ala Ile Asp Ala Asn Lys Ala Ser Ala Asp Thr
    530                 535                 540

Lys Phe Ala Ala Thr Ala Asp Ala Ile Thr Lys Asn Gly Asn Ala Ile
545                 550                 555                 560

Thr Lys Asn Ala Lys Ser Ile Thr Asp Leu Gly Thr Lys Val Asp Gly
                565                 570                 575

Phe Asp Gly Arg Val Thr Ala Leu Asp Thr Lys Val Asn Ala Leu Asp
            580                 585                 590

Thr Lys Val Asn Ala Phe Asp Gly Arg Ile Thr Ala Leu Asp Ser Lys
        595                 600                 605

Val Glu Asn Gly Met Ala Ala Gln Ala Ala Leu Ser Gly Leu Phe Gln
    610                 615                 620

Pro Tyr Ser Val Gly Lys Phe Asn Ala Thr Ala Ala Leu Gly Gly Tyr
625                 630                 635                 640

Gly Ser Lys Ser Ala Val Ala Ile Gly Ala Gly Tyr Arg Val Asn Pro
                645                 650                 655
```

```
Asn Leu Ala Phe Lys Ala Gly Ala Ala Ile Asn Thr Ser Gly Asn Lys
            660                 665                 670

Lys Gly Ser Tyr Asn Ile Gly Val Asn Tyr Glu Phe
        675                 680

<210> SEQ ID NO 45
<211> LENGTH: 650
<212> TYPE: PRT
<213> ORGANISM: Moraxalla catarrhalis

<400> SEQUENCE: 45

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Gln Gln
            20                  25                  30

Gln Lys Thr Lys Thr Glu Val Phe Leu Pro Asn Leu Phe Tyr Asn Asp
        35                  40                  45

Tyr Ile Glu Glu Thr Asp Leu Leu Tyr His Asn Met Ile Leu Gly Asp
50                  55                  60

Thr Ala Ala Leu Val Asp Arg Gln Asn Tyr Ser Asn Ser Gln Leu Lys
65                  70                  75                  80

Phe Tyr Ser Asn Asp Glu Gly Ser Val Pro Asp Ser Leu Leu Phe Ser
                85                  90                  95

Lys Met Leu Asn Asn Gln Gln Leu Asn Gly Phe Lys Ala Gly Asp Ile
            100                 105                 110

Ile Ile Pro Val Asp Ala Asn Gly Gln Val Ile Tyr Gln Lys Asp Thr
        115                 120                 125

Arg Val Glu Gly Gly Lys Thr Arg Thr Val Leu Ser Val Thr Thr Lys
130                 135                 140

Ile Ala Thr Gln Gln Asp Val Asp Ser Ala Tyr Ser Arg Gly Ile Gln
145                 150                 155                 160

Gly Lys Val Asn Asp Leu Asp Asp Glu Met Asn Phe Leu Asn His Asp
                165                 170                 175

Ile Thr Ser Leu Tyr Asp Val Thr Ala Asn Gln Gln Asp Asp Ile Lys
            180                 185                 190

Gly Leu Lys Lys Gly Val Lys Asp Leu Lys Lys Gly Val Lys Gly Leu
        195                 200                 205

Asn Lys Glu Leu Lys Glu Leu Asp Lys Glu Val Gly Val Leu Ser Arg
210                 215                 220

Asp Ile Gly Ser Leu Asn Asp Asp Val Ala Gln Asn Asn Glu Ser Ile
225                 230                 235                 240

Glu Asp Leu Tyr Asp Phe Ser Gln Glu Val Ala Asp Ser Ile Gly Glu
                245                 250                 255

Ile His Ala His Asn Lys Ala Gln Asn Glu Thr Leu Gln Asp Leu Ile
            260                 265                 270

Thr Asn Ser Val Glu Asn Thr Asn Asn Ile Thr Lys Asn Lys Ala Asp
        275                 280                 285

Ile Gln Ala Leu Glu Asn Asn Val Val Glu Glu Leu Phe Asn Leu Ser
290                 295                 300

Gly Arg Leu Ile Asp Gln Lys Ala Asp Leu Thr Lys Asp Ile Lys Thr
305                 310                 315                 320

Leu Glu Ser Asn Val Glu Glu Gly Leu Leu Glu Leu Ser Gly His Leu
                325                 330                 335

Ile Asp Gln Lys Ala Asp Ile Ala Lys Asn Gln Ala Asp Ile Ala Gln
            340                 345                 350
```

```
Asn Gln Ala Asn Ile Gln Asp Leu Ala Ala Tyr Asn Glu Leu Gln Asp
            355                 360                 365

Ala Tyr Ala Lys Gln Gln Thr Glu Ala Ile Asp Ala Leu Asn Lys Ala
        370                 375                 380

Ser Ser Glu Asn Thr Gln Asn Ile Glu Asp Leu Ala Ala Tyr Asn Glu
385                 390                 395                 400

Leu Gln Asp Ala Tyr Ala Lys Gln Gln Thr Glu Ala Ile Asp Ala Leu
                405                 410                 415

Asn Lys Ala Ser Ser Glu Asn Thr Gln Asn Ile Ala Lys Asn Gln Ala
            420                 425                 430

Asp Ile Ala Asn Asn Ile Asn Ile Tyr Glu Leu Ala Gln Gln Gln
            435                 440                 445

Asp Gln His Ser Ser Asp Ile Lys Thr Leu Ala Lys Ala Ser Ala Ala
        450                 455                 460

Asn Thr Asp Arg Ile Ala Lys Asn Lys Ala Asp Ala Asp Ala Ser Phe
465                 470                 475                 480

Glu Thr Leu Thr Lys Asn Gln Asn Thr Leu Ile Glu Lys Asp Lys Glu
                485                 490                 495

His Asp Lys Leu Ile Thr Ala Asn Lys Thr Ala Ile Asp Glu Asn Lys
            500                 505                 510

Ala Ser Ala Asp Thr Lys Phe Ala Ala Thr Ala Asp Ala Ile Thr Lys
        515                 520                 525

Asn Gly Asn Ala Ile Thr Lys Asn Ala Lys Ser Ile Thr Asp Leu Gly
530                 535                 540

Thr Lys Val Asp Gly Phe Asp Gly Arg Val Thr Ala Leu Asp Thr Lys
545                 550                 555                 560

Val Asn Ala Phe Asp Gly Arg Ile Thr Ala Leu Asp Ser Lys Val Glu
                565                 570                 575

Asn Gly Met Ala Ala Gln Ala Ala Leu Ser Gly Leu Phe Gln Pro Tyr
            580                 585                 590

Ser Val Gly Lys Phe Asn Ala Thr Ala Ala Leu Gly Gly Tyr Gly Ser
        595                 600                 605

Lys Ser Ala Val Ala Ile Gly Ala Gly Tyr Arg Val Asn Pro Asn Leu
610                 615                 620

Ala Phe Lys Ala Gly Ala Ala Ile Asn Thr Ser Gly Asn Lys Lys Gly
625                 630                 635                 640

Ser Tyr Asn Ile Gly Val Asn Tyr Glu Phe
                645                 650

<210> SEQ ID NO 46
<211> LENGTH: 616
<212> TYPE: PRT
<213> ORGANISM: Moraxalla catarrhalis

<400> SEQUENCE: 46

Met Lys Thr Met Lys Leu Leu Pro Leu Lys Ile Ala Val Thr Ser Ala
1               5                   10                  15

Leu Ile Val Gly Leu Gly Ala Val Ser Thr Thr Asn Ala Gln Ala Gln
            20                  25                  30

Ser Arg Ser Leu Asp Gln Ile Gln Thr Lys Leu Ala Asp Leu Ala Gly
        35                  40                  45

Lys Ile Ala Ala Gly Lys Asn Gly Gly Gln Asn Asn Gln Asn Asn
    50                  55                  60

Gln Asn Asp Ile Asn Lys Tyr Leu Phe Leu Ser Gln Tyr Ala Asn Ile
```

```
              65                  70                  75                  80
Leu Thr Met Glu Glu Leu Asn Asn Val Val Lys Asn Ser Ser Ser
                        85                  90                  95
Ile Glu Thr Leu Glu Thr Asp Phe Gly Trp Leu Glu Asn Asp Val Ala
                100                 105                 110
Asp Leu Glu Asp Gly Val Glu Leu Thr Lys Asn Gln Asn Thr Leu
            115                 120                 125
Ile Glu Lys Asp Glu Glu His Asp Arg Leu Ile Ala Gln Asn Gln Ala
130                 135                 140
Asp Ile Gln Thr Leu Glu Asn Asn Val Val Glu Glu Leu Phe Asn Leu
145                 150                 155                 160
Ser Asp Arg Leu Ile Asp Gln Lys Ala Asp Ile Ala Lys Asn Gln Ala
                165                 170                 175
Asp Ile Ala Gln Asn Asn Glu Ser Ile Glu Glu Leu Tyr Asp Phe Asp
                180                 185                 190
Asn Glu Val Ala Glu Lys Ile Gly Glu Ile His Ala Tyr Thr Glu Glu
            195                 200                 205
Val Asn Lys Thr Leu Gln Asp Leu Ile Thr Asn Ser Val Lys Asn Thr
            210                 215                 220
Asp Asn Ile Asp Lys Asn Lys Ala Asp Ile Asp Asn Asn Ile Asn His
225                 230                 235                 240
Ile Tyr Glu Leu Ala Gln Gln Asp Gln His Ser Ser Asp Ile Lys
                245                 250                 255
Thr Leu Lys Asn Asn Val Glu Glu Gly Leu Leu Glu Leu Ser Gly His
                260                 265                 270
Leu Ile Asp Gln Lys Ala Asp Leu Thr Lys Asp Ile Lys Thr Leu Glu
            275                 280                 285
Asn Asn Val Glu Glu Gly Leu Leu Asp Leu Ser Gly Arg Leu Ile Asp
            290                 295                 300
Gln Lys Ala Asp Ile Ala Lys Asn Gln Ala Asp Ile Ala Gln Asn Gln
305                 310                 315                 320
Thr Asp Ile Gln Asp Leu Ala Ala Tyr Asn Glu Leu Gln Asp Gln Tyr
                325                 330                 335
Ala Gln Lys Gln Thr Glu Ala Ile Asp Ala Leu Asn Lys Ala Ser Ser
                340                 345                 350
Glu Asn Thr Gln Asn Ile Glu Asp Leu Ala Ala Tyr Asn Glu Leu Gln
            355                 360                 365
Asp Ala Tyr Ala Lys Gln Gln Thr Glu Ala Ile Asp Ala Leu Asn Lys
            370                 375                 380
Ala Ser Ser Glu Asn Thr Gln Asn Ile Ala Lys Asn Gln Ala Asp Ile
385                 390                 395                 400
Ala Asn Asn Ile Asn Ile Tyr Glu Leu Ala Gln Gln Asp Gln
                405                 410                 415
His Ser Ser Asp Ile Lys Thr Leu Ala Lys Ala Ser Ala Ala Asn Thr
                420                 425                 430
Asp Arg Ile Ala Lys Asn Lys Ala Asp Ala Asp Ala Ser Phe Glu Thr
            435                 440                 445
Leu Thr Lys Asn Gln Asn Thr Leu Ile Glu Lys Asp Lys Glu His Asp
            450                 455                 460
Lys Leu Ile Thr Ala Asn Lys Thr Ala Ile Asp Glu Asn Lys Ala Ser
465                 470                 475                 480
Ala Asp Thr Lys Phe Ala Ala Thr Ala Asp Ala Ile Thr Lys Asn Gly
                485                 490                 495
```

```
Asn Ala Ile Thr Lys Asn Ala Lys Ser Ile Thr Asp Leu Gly Thr Lys
                500                 505                 510

Val Asp Gly Phe Asp Gly Arg Val Thr Ala Leu Asp Thr Lys Val Asn
            515                 520                 525

Ala Phe Asp Gly Arg Ile Thr Ala Leu Asp Ser Lys Val Glu Asn Gly
        530                 535                 540

Met Ala Gln Ala Ala Leu Ser Gly Leu Phe Gln Pro Tyr Ser Val
545                 550                 555                 560

Gly Lys Phe Asn Ala Thr Ala Ala Leu Gly Gly Tyr Gly Ser Lys Ser
                565                 570                 575

Ala Val Ala Ile Gly Ala Gly Tyr Arg Val Asn Pro Asn Leu Ala Phe
            580                 585                 590

Lys Ala Gly Ala Ala Ile Asn Thr Ser Gly Asn Lys Lys Gly Ser Tyr
        595                 600                 605

Asn Ile Gly Val Asn Tyr Glu Phe
    610                 615

<210> SEQ ID NO 47
<211> LENGTH: 668
<212> TYPE: PRT
<213> ORGANISM: Moraxalla catarrhalis

<400> SEQUENCE: 47

Met Lys Thr Met Lys Leu Leu Pro Leu Lys Ile Ala Val Thr Ser Ala
1               5                   10                  15

Leu Ile Val Gly Leu Gly Thr Ala Ser Thr Ala Asn Ala Gln Val Ala
            20                  25                  30

Ser Pro Ala Asn Gln Lys Ile Gln Gln Lys Ile Lys Lys Val Arg Lys
        35                  40                  45

Glu Leu Arg Gln Asp Ile Lys Ser Leu Arg Asn Asp Ile Asp Ser Asn
    50                  55                  60

Thr Ala Asp Ile Gly Ser Leu Asn Asp Val Ala Asp Asn Gln Asp
65                  70                  75                  80

Asp Ile Leu Asp Asn Gln Ala Asp Ile Ala Lys Asn Gln Asp Asp Ile
                85                  90                  95

Glu Lys Asn Gln Ala Asp Ile Lys Glu Leu Asp Lys Glu Val Gly Val
            100                 105                 110

Leu Ser Arg Glu Ile Gly Ser Leu Asn Asp Asp Ile Ala Asp Asn Tyr
        115                 120                 125

Thr Asp Ile Ile Asp Asn Tyr Thr Asp Ile Ile Asp Asn Gln Ala Asn
    130                 135                 140

Ile Ala Lys Asn Gln Asp Asp Ile Glu Lys Asn Gln Ala Asp Ile Lys
145                 150                 155                 160

Glu Leu Asp Lys Glu Val Gly Val Leu Ser Arg Glu Ile Gly Ser Leu
                165                 170                 175

Asn Asp Asp Val Ala Asn Gln Asp Asp Ile Ala Lys Asn Gln Ala
            180                 185                 190

Asp Ile Gln Thr Leu Glu Asn Val Glu Glu Gly Leu Leu Glu Leu
        195                 200                 205

Ser Gly His Leu Leu Asp Gln Lys Ala Asp Ile Asp Asn Asn Ile Asn
    210                 215                 220

Asn Ile Tyr Glu Leu Ala Gln Gln Asp Gln His Ser Ser Asp Ile
225                 230                 235                 240

Lys Thr Leu Lys Lys Asn Val Glu Glu Gly Leu Leu Glu Leu Ser Gly
```

-continued

```
                245                 250                 255
His Leu Ile Asp Gln Lys Thr Asp Ile Ala Gln Asn Gln Ala Asn Ile
            260                 265                 270

Gln Asp Leu Ala Thr Tyr Asn Glu Leu Gln Asp Gln Tyr Ala Gln Glu
        275                 280                 285

Gln Thr Glu Ala Ile Asp Ala Leu Asn Lys Ala Ser Ser Glu Asn Thr
    290                 295                 300

Gln Asn Ile Ala Lys Asn Ser Asn Arg Ile Lys Ala Leu Glu Ser Asn
305                 310                 315                 320

Val Glu Glu Gly Leu Leu Glu Leu Ser Gly His Leu Ile Asp Gln Lys
                325                 330                 335

Ala Asp Leu Thr Lys Asp Ile Lys Ala Leu Glu Ser Asn Val Glu Glu
            340                 345                 350

Gly Leu Leu Glu Leu Ser Gly His Leu Ile Asp Gln Lys Ala Asp Ile
        355                 360                 365

Ala Gln Asn Gln Ala Asn Ile Gln Asp Leu Ala Ala Tyr Asn Glu Leu
    370                 375                 380

Gln Asp Gln Tyr Ala Gln Lys Gln Thr Glu Ala Ile Asp Ala Leu Asn
385                 390                 395                 400

Lys Ala Ser Ser Glu Asn Thr Gln Asn Ile Glu Asp Leu Ala Ala Tyr
                405                 410                 415

Asn Glu Leu Gln Asp Ala Tyr Ala Lys Gln Gln Thr Glu Ala Ile Asp
            420                 425                 430

Ala Leu Asn Lys Ala Ser Ser Glu Asn Thr Gln Asn Ile Ala Lys Asn
        435                 440                 445

Gln Ala Asp Ile Ala Asn Asn Ile Asn Asn Ile Tyr Glu Leu Ala Gln
    450                 455                 460

Gln Gln Asp Gln His Ser Ser Asp Ile Lys Thr Leu Ala Lys Ala Ser
465                 470                 475                 480

Ala Ala Asn Thr Asp Arg Ile Ala Lys Asn Lys Ala Asp Ala Asp Ala
                485                 490                 495

Ser Phe Glu Thr Leu Thr Lys Asn Gln Asn Thr Leu Ile Glu Lys Asp
            500                 505                 510

Lys Glu His Asp Lys Leu Ile Thr Ala Asn Lys Thr Ala Ile Asp Ala
        515                 520                 525

Asn Lys Val Ser Ala Asp Thr Lys Phe Ala Ala Thr Ala Asp Ala Ile
    530                 535                 540

Thr Lys Asn Gly Asn Ala Ile Thr Lys Asn Ala Lys Ser Ile Thr Asp
545                 550                 555                 560

Leu Gly Thr Lys Val Asp Ala Phe Asp Ser Arg Val Thr Ala Leu Asp
                565                 570                 575

Thr Lys Val Asn Ala Phe Asp Gly Arg Ile Thr Ala Leu Asp Ser Lys
            580                 585                 590

Val Glu Asn Gly Met Ala Ala Gln Ala Ala Leu Ser Gly Leu Phe Gln
        595                 600                 605

Pro Tyr Ser Val Gly Lys Phe Asn Ala Thr Ala Ala Leu Gly Gly Tyr
    610                 615                 620

Gly Ser Lys Ser Ala Val Ala Ile Gly Ala Gly Tyr Arg Val Asn Pro
625                 630                 635                 640

Asn Leu Ala Phe Lys Ala Gly Ala Ala Ile Asn Thr Ser Gly Asn Lys
                645                 650                 655

Lys Gly Ser Tyr Asn Ile Gly Val Asn Tyr Glu Phe
            660                 665
```

<210> SEQ ID NO 48
<211> LENGTH: 674
<212> TYPE: PRT
<213> ORGANISM: Moraxalla catarrhalis

<400> SEQUENCE: 48

```
Met Lys Thr Met Lys Leu Leu Pro Leu Lys Ile Ala Val Thr Ser Ala
1               5                   10                  15

Met Ile Val Gly Leu Gly Ala Thr Ser Thr Val Asn Ala Gln Val Val
            20                  25                  30

Glu Gln Phe Phe Pro Asn Ile Phe Phe Asn Glu Asn His Asp Glu Leu
        35                  40                  45

Asp Asp Ala Tyr His Asn Met Ile Leu Gly Asp Thr Ala Ile Val Ser
    50                  55                  60

Asn Ser Gln Asp Asn Ser Thr Gln Leu Lys Phe Tyr Ser Asn Asp Glu
65                  70                  75                  80

Asp Ser Val Pro Asp Ser Leu Leu Phe Ser Lys Leu Leu His Glu Gln
                85                  90                  95

Gln Leu Asn Gly Phe Lys Ala Gly Asp Thr Ile Ile Pro Leu Asp Lys
            100                 105                 110

Asp Gly Lys Pro Val Tyr Thr Lys Asp Thr Arg Thr Lys Asp Gly Lys
        115                 120                 125

Val Glu Thr Val Tyr Ser Val Thr Thr Lys Ile Ala Thr Gln Asp Asp
    130                 135                 140

Val Glu Gln Ser Ala Tyr Ser Arg Gly Ile Gln Gly Asp Ile Asp Asp
145                 150                 155                 160

Leu Tyr Asp Ile Asn Arg Glu Val Asn Glu Tyr Leu Lys Ala Thr His
                165                 170                 175

Asp Tyr Asn Glu Arg Gln Thr Glu Ala Ile Asp Ala Leu Asn Lys Ala
            180                 185                 190

Ser Ser Ala Asn Thr Asp Arg Ile Asp Thr Ala Glu Glu Arg Ile Asp
        195                 200                 205

Lys Asn Glu Tyr Asp Ile Lys Ala Leu Glu Ser Asn Val Glu Glu Gly
    210                 215                 220

Leu Leu Glu Leu Ser Gly His Leu Ile Asp Gln Lys Ala Asp Leu Thr
225                 230                 235                 240

Lys Asp Ile Lys Ala Leu Glu Ser Asn Val Glu Glu Gly Leu Leu Glu
                245                 250                 255

Leu Ser Gly His Leu Ile Asp Gln Lys Ala Asp Leu Thr Lys Asp Ile
            260                 265                 270

Lys Ala Leu Glu Ser Asn Val Glu Glu Gly Leu Leu Asp Leu Ser Gly
        275                 280                 285

Arg Leu Ile Asp Gln Lys Ala Asp Ile Ala Gln Asn Gln Ala Asn Ile
    290                 295                 300

Gln Asp Leu Ala Ala Tyr Asn Glu Leu Gln Asp Ala Tyr Ala Lys Gln
305                 310                 315                 320

Gln Thr Glu Ala Ile Asp Ala Leu Asn Lys Ala Ser Ser Glu Asn Thr
                325                 330                 335

Gln Asn Ile Glu Asp Leu Ala Ala Tyr Asn Glu Leu Gln Asp Ala Tyr
            340                 345                 350

Ala Lys Gln Gln Thr Glu Ala Ile Asp Ala Leu Asn Lys Ala Ser Ser
        355                 360                 365

Glu Asn Thr Gln Asn Ile Glu Asp Leu Ala Ala Tyr Asn Glu Leu Gln
```

```
                370               375               380
Asp Ala Tyr Ala Lys Gln Gln Thr Glu Ala Ile Asp Ala Leu Asn Lys
385                 390                 395                 400

Ala Ser Ser Glu Asn Thr Gln Asn Ile Glu Asp Leu Ala Ala Tyr Asn
                405                 410                 415

Glu Leu Gln Asp Ala Tyr Ala Lys Gln Gln Thr Glu Ala Ile Asp Ala
            420                 425                 430

Leu Asn Lys Ala Ser Ser Glu Asn Thr Gln Asn Ile Ala Lys Asn Gln
        435                 440                 445

Ala Asp Ile Ala Asn Asn Ile Asn Asn Ile Tyr Glu Leu Ala Gln Gln
450                 455                 460

Gln Asp Gln His Ser Ser Asp Ile Lys Thr Leu Ala Lys Ala Ser Ala
465                 470                 475                 480

Ala Asn Thr Asp Arg Ile Ala Lys Asn Lys Ala Asp Ala Asp Ala Ser
                485                 490                 495

Phe Glu Thr Leu Thr Lys Asn Gln Asn Thr Leu Ile Glu Lys Asp Lys
            500                 505                 510

Glu His Asp Lys Leu Ile Thr Ala Asn Lys Thr Ala Ile Asp Ala Asn
        515                 520                 525

Lys Ala Ser Ala Asp Thr Lys Phe Ala Ala Thr Ala Asp Ala Ile Thr
530                 535                 540

Lys Asn Gly Asn Ala Ile Thr Lys Asn Ala Lys Ser Ile Thr Asp Leu
545                 550                 555                 560

Gly Thr Lys Val Asp Gly Phe Asp Gly Arg Val Thr Ala Leu Asp Thr
                565                 570                 575

Lys Val Asn Ala Leu Asp Thr Lys Val Asn Ala Phe Asp Gly Arg Ile
            580                 585                 590

Thr Ala Leu Asp Ser Lys Val Glu Asn Gly Met Ala Ala Gln Ala Ala
        595                 600                 605

Leu Ser Gly Leu Phe Gln Pro Tyr Ser Val Gly Lys Phe Asn Ala Thr
610                 615                 620

Ala Ala Leu Gly Gly Tyr Gly Ser Lys Ser Ala Val Ala Ile Gly Ala
625                 630                 635                 640

Gly Tyr Arg Val Asn Pro Asn Leu Ala Phe Lys Ala Gly Ala Ala Ile
                645                 650                 655

Asn Thr Ser Gly Asn Lys Lys Gly Ser Tyr Asn Ile Gly Val Asn Tyr
            660                 665                 670

Glu Phe

<210> SEQ ID NO 49
<211> LENGTH: 613
<212> TYPE: PRT
<213> ORGANISM: Moraxalla catarrhalis

<400> SEQUENCE: 49

Met Lys Thr Met Lys Leu Leu Pro Leu Lys Ile Ala Val Thr Ser Ala
1               5                   10                  15

Met Ile Ile Gly Leu Gly Ala Ala Ser Thr Ala Asn Ala Gln Ser Arg
            20                  25                  30

Asp Arg Ser Leu Glu Asp Ile Gln Asp Ser Ile Ser Lys Leu Val Gln
        35                  40                  45

Asp Asp Ile Asp Thr Leu Lys Gln Asp Gln Gln Lys Met Asn Lys Tyr
    50                  55                  60

Leu Leu Leu Asn Gln Leu Ala Asn Thr Leu Ile Thr Asp Glu Leu Asn
```

```
                65                  70                  75                  80
Asn Asn Val Ile Lys Asn Thr Asn Ser Ile Glu Ala Leu Gly Asp Glu
                    85                  90                  95
Ile Gly Trp Leu Glu Asn Asp Ile Ala Asp Leu Glu Glu Gly Val Glu
                    100                 105                 110
Glu Leu Thr Lys Asn Gln Asn Thr Leu Ile Glu Lys Asp Glu Glu His
                    115                 120                 125
Asp Arg Leu Ile Ala Gln Asn Gln Ala Asp Ile Gln Thr Leu Glu Asn
                    130                 135                 140
Asn Val Val Glu Glu Leu Phe Asn Leu Ser Gly Arg Leu Ile Asp Gln
145                 150                 155                 160
Glu Ala Asp Ile Ala Lys Asn Asn Ala Ser Ile Glu Glu Leu Tyr Asp
                    165                 170                 175
Phe Asp Asn Glu Val Ala Glu Arg Ile Gly Glu Ile His Ala Tyr Thr
                    180                 185                 190
Glu Glu Val Asn Lys Thr Leu Glu Asn Leu Ile Thr Asn Ser Val Lys
                    195                 200                 205
Asn Thr Asp Asn Ile Asp Lys Asn Lys Ala Asp Ile Asp Asn Asn Ile
                    210                 215                 220
Asn His Ile Tyr Glu Leu Ala Gln Gln Gln Asp Gln His Ser Ser Asp
225                 230                 235                 240
Ile Lys Thr Leu Lys Asn Asn Val Glu Glu Gly Leu Leu Glu Leu Ser
                    245                 250                 255
Gly His Leu Ile Asp Gln Lys Ala Asp Leu Thr Lys Asp Ile Lys Ala
                    260                 265                 270
Leu Glu Ser Asn Val Glu Glu Gly Leu Leu Asp Leu Ser Gly Arg Leu
                    275                 280                 285
Leu Asp Gln Lys Ala Asp Leu Thr Lys Asp Ile Lys Ala Leu Glu Ser
                    290                 295                 300
Asn Val Glu Glu Gly Leu Leu Asp Leu Ser Gly Arg Leu Leu Asp Gln
305                 310                 315                 320
Lys Ala Asp Ile Ala Gln Asn Gln Thr Asp Ile Gln Asp Leu Ala Ala
                    325                 330                 335
Tyr Asn Glu Leu Gln Asp Gln Tyr Ala Gln Lys Gln Thr Glu Ala Ile
                    340                 345                 350
Asp Ala Leu Asn Lys Ala Ser Ser Glu Asn Thr Gln Asn Ile Glu Asp
                    355                 360                 365
Leu Ala Ala Tyr Asn Glu Leu Gln Asp Ala Tyr Ala Lys Gln Gln Thr
                    370                 375                 380
Glu Ala Ile Asp Ala Leu Asn Lys Ala Ser Ser Glu Asn Thr Gln Asn
385                 390                 395                 400
Ile Ala Lys Asn Gln Ala Asp Ile Ala Asn Ile Asn Asn Ile Tyr
                    405                 410                 415
Glu Leu Ala Gln Gln Gln Asp Gln His Ser Ser Asp Ile Lys Thr Leu
                    420                 425                 430
Ala Lys Ala Ser Ala Ala Asn Thr Asn Arg Ile Ala Thr Ala Glu Leu
                    435                 440                 445
Gly Ile Ala Glu Asn Lys Lys Asp Ala Gln Ile Ala Lys Ala Gln Ala
                    450                 455                 460
Asn Ala Asn Lys Thr Ala Ile Asp Glu Asn Lys Ala Ser Ala Asp Thr
465                 470                 475                 480
Lys Phe Ala Ala Thr Ala Asp Ala Ile Thr Lys Asn Gly Asn Ala Ile
                    485                 490                 495
```

```
Thr Lys Asn Ala Lys Ser Ile Thr Asp Leu Gly Thr Lys Val Asp Gly
                500                 505                 510

Phe Asp Gly Arg Val Thr Ala Leu Asp Thr Lys Val Asn Ala Phe Asp
            515                 520                 525

Gly Arg Ile Thr Ala Leu Asp Ser Lys Val Glu Asn Gly Met Ala Ala
        530                 535                 540

Gln Ala Ala Leu Ser Gly Leu Phe Gln Pro Tyr Ser Val Gly Lys Phe
545                 550                 555                 560

Asn Ala Thr Ala Ala Leu Gly Gly Tyr Gly Ser Lys Ser Ala Val Ala
                565                 570                 575

Ile Gly Ala Gly Tyr Arg Val Asn Pro Asn Leu Ala Phe Lys Ala Gly
            580                 585                 590

Ala Ala Ile Asn Thr Ser Gly Asn Lys Lys Gly Ser Tyr Asn Ile Gly
        595                 600                 605

Val Asn Tyr Glu Phe
    610

<210> SEQ ID NO 50
<211> LENGTH: 576
<212> TYPE: PRT
<213> ORGANISM: Moraxalla catarrhalis

<400> SEQUENCE: 50

Met Lys Thr Met Lys Leu Leu Pro Leu Lys Ile Ala Val Thr Ser Ala
1               5                   10                  15

Met Ile Val Gly Leu Gly Ala Thr Ser Thr Val Asn Ala Gln Val Val
            20                  25                  30

Glu Gln Phe Phe Pro Asn Ile Phe Asn Glu Asn His Asp Glu Leu
        35                  40                  45

Asp Asp Ala Tyr His Asn Met Ile Leu Gly Asp Thr Ala Ile Val Ser
    50                  55                  60

Asn Ser Gln Asp Asn Ser Thr Gln Leu Lys Phe Tyr Ser Asn Asp Glu
65                  70                  75                  80

Asp Ser Val Pro Asp Ser Leu Leu Phe Ser Lys Leu Leu His Glu Gln
                85                  90                  95

Gln Leu Asn Gly Phe Lys Ala Gly Asp Thr Ile Ile Pro Leu Asp Lys
            100                 105                 110

Asp Gly Lys Pro Val Tyr Thr Lys Asp Thr Arg Thr Lys Asp Gly Lys
        115                 120                 125

Val Glu Thr Val Tyr Ser Val Thr Thr Lys Ile Ala Thr Gln Asp Asp
    130                 135                 140

Val Glu Gln Ser Ala Tyr Ser Arg Gly Ile Gln Gly Asp Ile Asp Asp
145                 150                 155                 160

Leu Tyr Asp Ile Asn Arg Glu Val Asn Glu Tyr Leu Lys Ala Thr His
                165                 170                 175

Asp Tyr Asn Glu Arg Gln Thr Glu Ala Ile Ala Leu Asn Lys Ala
            180                 185                 190

Ser Ser Ala Asn Thr Asp Arg Ile Asp Thr Ala Glu Glu Arg Ile Asp
        195                 200                 205

Lys Asn Glu Tyr Asp Ile Lys Ala Leu Glu Ser Asn Val Glu Glu Gly
    210                 215                 220

Leu Leu Glu Leu Ser Gly His Leu Ile Asp Gln Lys Ala Asp Leu Thr
225                 230                 235                 240

Lys Asp Ile Lys Ala Leu Glu Ser Asn Val Glu Glu Gly Leu Leu Glu
```

Leu Ser Gly His Leu Ile Asp Gln Lys Ala Asp Leu Thr Lys Asp Ile
                260                 265                 270

Lys Ala Leu Glu Ser Asn Val Glu Glu Gly Leu Leu Asp Leu Ser Gly
                275                 280                 285

Arg Leu Leu Asp Gln Lys Ala Asp Ile Ala Lys Asn Gln Ala Asp Ile
            290                 295                 300

Ala Gln Asn Gln Thr Asp Ile Gln Asp Leu Ala Ala Tyr Asn Glu Leu
305                 310                 315                 320

Gln Asp Ala Tyr Ala Lys Gln Gln Thr Glu Ala Ile Asp Ala Leu Asn
                325                 330                 335

Lys Ala Ser Ser Glu Asn Thr Gln Asn Ile Ala Lys Asn Gln Ala Asp
                340                 345                 350

Ile Ala Asn Asn Ile Asn Asn Ile Tyr Glu Leu Ala Gln Gln Gln Asp
                355                 360                 365

Gln His Ser Ser Asp Ile Lys Thr Leu Ala Lys Ala Ser Ala Ala Asn
            370                 375                 380

Thr Asp Arg Ile Ala Lys Asn Lys Ala Asp Ala Asp Ala Ser Phe Glu
385                 390                 395                 400

Thr Leu Thr Lys Asn Gln Asn Thr Leu Ile Glu Lys Asp Lys Glu His
                405                 410                 415

Asp Lys Leu Ile Thr Ala Asn Lys Thr Ala Ile Asp Ala Asn Lys Ala
                420                 425                 430

Ser Ala Asp Thr Lys Phe Ala Ala Thr Ala Asp Ala Ile Thr Lys Asn
            435                 440                 445

Gly Asn Ala Ile Thr Lys Asn Ala Lys Ser Ile Thr Asp Leu Gly Thr
450                 455                 460

Lys Val Asp Gly Phe Asp Gly Arg Val Thr Ala Leu Asp Thr Lys Val
465                 470                 475                 480

Asn Ala Leu Asp Thr Lys Val Asn Ala Phe Asp Gly Arg Ile Thr Ala
                485                 490                 495

Leu Asp Ser Lys Val Glu Asn Gly Met Ala Ala Gln Ala Ala Leu Ser
                500                 505                 510

Gly Leu Phe Gln Pro Tyr Ser Val Gly Lys Phe Asn Ala Thr Ala Ala
            515                 520                 525

Leu Gly Gly Tyr Gly Ser Lys Ser Ala Val Ala Ile Gly Ala Gly Tyr
            530                 535                 540

Arg Val Asn Pro Asn Leu Ala Phe Lys Ala Gly Ala Ala Ile Asn Thr
545                 550                 555                 560

Ser Gly Asn Lys Lys Gly Ser Tyr Asn Ile Gly Val Asn Tyr Glu Phe
                565                 570                 575

<210> SEQ ID NO 51
<211> LENGTH: 684
<212> TYPE: PRT
<213> ORGANISM: Moraxalla catarrhalis

<400> SEQUENCE: 51

Met Lys Thr Met Lys Leu Leu Pro Leu Lys Ile Ala Val Thr Ser Ala
1               5                   10                  15

Met Met Val Gly Leu Gly Met Ala Ser Thr Ala Asn Ala Gln Gln Gln
                20                  25                  30

Lys Ser Pro Lys Thr Glu Ile Phe Leu Pro Asn Leu Phe Asp Asn Asp
            35                  40                  45

```
Asn Thr Glu Leu Thr Asp Pro Leu Tyr His Asn Met Ile Leu Gly Asn
    50              55                  60

Thr Ala Leu Leu Thr Gln Glu Asn Gln Tyr Lys Phe Tyr Ala Asp Asp
65              70                  75                  80

Gly Asn Gly Val Pro Asp Ser Leu Leu Phe Asn Lys Ile Leu His Asp
                85                  90                  95

Gln Leu Leu His Gly Phe Lys Glu Gly Asp Thr Ile Ile Pro Leu Asp
            100             105                 110

Glu Asn Gly Lys Pro Val Tyr Lys Leu Asp Ser Ile Val Glu Gln Gly
            115             120                 125

Lys Thr Lys Thr Val Tyr Ser Val Thr Thr Lys Thr Ala Thr Ala Asp
130             135                 140

Asp Val Asn Ser Ala Tyr Ser Arg Gly Ile Gln Gly Asp Ile Asp Asp
145             150                 155                 160

Leu Tyr Glu Ala Asn Lys Glu Asn Val Asn Arg Leu Ile Glu His Gly
                165                 170                 175

Asp Lys Ile Phe Ala Asn Glu Glu Ser Val Gln Tyr Leu Asn Arg Glu
            180                 185                 190

Val Gln Asn Asn Ile Glu Asn Ile His Glu Leu Ala Gln Gln Gln Asp
            195                 200                 205

Gln His Ser Ser Asp Ile Lys Thr Leu Lys Lys Asn Val Glu Lys Asp
            210                 215                 220

Leu Leu Asp Leu Ser Gly Arg Leu Ile Ala Gln Lys Glu Asp Ile Ala
225                 230                 235                 240

Gln Asn Gln Thr Asp Ile Gln Asp Leu Ala Thr Tyr Asn Glu Leu Gln
                245                 250                 255

Asp Gln Tyr Ala Gln Lys Gln Thr Glu Ala Ile Asp Ala Leu Asn Lys
                260                 265                 270

Ala Ser Ser Glu Asn Thr Gln Asn Ile Ala Lys Asn Ser Asn His Ile
            275                 280                 285

Lys Thr Leu Glu Asn Asn Ile Glu Glu Gly Leu Leu Glu Leu Ser Gly
            290                 295                 300

His Leu Ile Asp Gln Lys Ala Asp Leu Thr Lys Asp Ile Lys Ala Leu
305                 310                 315                 320

Glu Ser Asn Val Glu Glu Gly Leu Leu Asp Leu Ser Gly Arg Leu Ile
                325                 330                 335

Asp Gln Lys Ala Asp Ile Ala Gln Asn Gln Ala Asn Ile Gln Asp Leu
            340                 345                 350

Ala Ala Tyr Asn Glu Leu Gln Asp Ala Tyr Ala Lys Gln Gln Thr Glu
            355                 360                 365

Ala Ile Asp Ala Leu Asn Lys Ala Ser Ser Glu Asn Thr Gln Asn Ile
370                 375                 380

Glu Asp Leu Ala Ala Tyr Asn Glu Leu Gln Asp Ala Tyr Ala Lys Gln
385                 390                 395                 400

Gln Thr Glu Ala Ile Asp Ala Leu Asn Lys Ala Ser Ser Glu Asn Thr
                405                 410                 415

Gln Asn Ile Glu Asp Leu Ala Ala Tyr Asn Glu Leu Gln Asp Ala Tyr
            420                 425                 430

Ala Lys Gln Gln Thr Glu Ala Ile Asp Ala Leu Asn Lys Ala Ser Ser
            435                 440                 445

Glu Asn Thr Gln Asn Ile Ala Lys Asn Gln Ala Asp Ile Ala Asn Asn
450                 455                 460

Ile Asn Asn Ile Tyr Glu Leu Ala Gln Gln Gln Asp Gln His Ser Ser
```

-continued

```
                465                 470                 475                 480
        Asp Ile Lys Thr Leu Ala Lys Ala Ser Ala Ala Asn Thr Asp Arg Ile
                        485                 490                 495

Ala Lys Asn Lys Ala Asp Ala Asp Ala Ser Phe Glu Thr Leu Thr Lys
                        500                 505                 510

Asn Gln Asn Thr Leu Ile Glu Lys Asp Lys His Asp Lys Leu Ile
                        515                 520                 525

Thr Ala Asn Lys Thr Ala Ile Asp Ala Asn Lys Ala Ser Ala Asp Thr
                530                 535                 540

Lys Phe Ala Ala Thr Ala Asp Ala Ile Thr Lys Asn Gly Asn Ala Ile
        545                 550                 555                 560

Thr Lys Asn Ala Lys Ser Ile Thr Asp Leu Gly Thr Lys Val Asp Gly
                        565                 570                 575

Phe Asp Gly Arg Val Thr Ala Leu Asp Thr Lys Val Asn Ala Leu Asp
                        580                 585                 590

Thr Lys Val Asn Ala Phe Asp Gly Arg Ile Thr Ala Leu Asp Ser Lys
                        595                 600                 605

Val Glu Asn Gly Met Ala Ala Gln Ala Ala Leu Ser Gly Leu Phe Gln
                        610                 615                 620

Pro Tyr Ser Val Gly Lys Phe Asn Ala Thr Ala Ala Leu Gly Gly Tyr
        625                 630                 635                 640

Gly Ser Lys Ser Ala Val Ala Ile Gly Ala Gly Tyr Arg Val Asn Pro
                        645                 650                 655

Asn Leu Ala Phe Lys Ala Gly Ala Ala Ile Asn Thr Ser Gly Asn Lys
                        660                 665                 670

Lys Gly Ser Tyr Asn Ile Gly Val Asn Tyr Glu Phe
                        675                 680

<210> SEQ ID NO 52
<211> LENGTH: 686
<212> TYPE: PRT
<213> ORGANISM: Moraxalla catarrhalis

<400> SEQUENCE: 52

Met Lys Thr Met Lys Leu Leu Pro Leu Lys Ile Ala Val Thr Ser Ala
        1               5                   10                  15

Met Ile Ile Gly Leu Gly Ala Ala Ser Thr Ala Asn Ala Gln Ala Thr
                        20                  25                  30

Glu Thr Phe Leu Pro Asn Leu Phe Asp Asn Asp Tyr Thr Glu Thr Thr
                        35                  40                  45

Asp Pro Leu Tyr His Gly Met Ile Leu Gly Asn Thr Ala Ile Thr Gln
                50                  55                  60

Asp Thr Gln Tyr Lys Phe Tyr Ala Glu Asn Gly Asn Glu Val Pro Asp
        65                  70                  75                  80

Ser Leu Phe Phe Asn Lys Ile Leu His Asp Gln Gln Leu Asn Gly Phe
                        85                  90                  95

Lys Glu Gly Asp Thr Ile Ile Pro Leu Asp Glu Asn Gly Lys Pro Val
                        100                 105                 110

Tyr Lys Leu Asp Glu Ile Thr Glu Asn Gly Val Lys Arg Lys Val Tyr
                        115                 120                 125

Ser Val Thr Thr Lys Thr Ala Thr Arg Glu Asp Val Glu Gln Ser Ala
                        130                 135                 140

Tyr Ser Arg Gly Ile Gln Gly Asp Ile Asp Asp Leu Tyr Glu Ala Asn
        145                 150                 155                 160
```

```
Lys Glu Asn Val Asn Arg Leu Ile Glu His Gly Asp Lys Ile Phe Ala
                165                 170                 175
Asn Glu Glu Ser Val Gln Tyr Leu Asn Lys Glu Val Gln Asn Asn Ile
            180                 185                 190
Glu Asn Ile His Glu Leu Ala Gln Gln Gln Asp Gln His Ser Ser Asp
            195                 200                 205
Ile Lys Thr Leu Lys Lys Asn Val Glu Glu Gly Leu Leu Glu Leu Ser
        210                 215                 220
Gly Arg Leu Ile Ala Gln Lys Glu Asp Ile Ala Gln Asn Gln Thr Asp
225                 230                 235                 240
Ile Gln Asp Leu Ala Thr Tyr Asn Glu Leu Gln Asp Gln Tyr Ala Gln
                245                 250                 255
Lys Gln Thr Glu Ala Ile Asp Ala Leu Asn Lys Ala Ser Ser Glu Asn
            260                 265                 270
Thr Gln Asn Ile Ala Lys Asn Ser Asn His Ile Lys Thr Leu Glu Asn
            275                 280                 285
Asn Ile Glu Glu Gly Leu Leu Glu Leu Ser Gly His Leu Ile Asp Gln
        290                 295                 300
Lys Ala Asp Leu Thr Lys Asp Ile Lys Ala Leu Glu Ser Asn Val Glu
305                 310                 315                 320
Glu Gly Leu Leu Asp Leu Ser Gly Arg Leu Leu Asp Gln Lys Ala Asp
                325                 330                 335
Ile Ala Lys Asn Gln Ala Asp Ile Ala Gln Asn Gln Thr Asp Ile Gln
            340                 345                 350
Asp Leu Ala Ala Tyr Asn Glu Leu Gln Asp Gln Tyr Ala Gln Lys Gln
            355                 360                 365
Thr Glu Ala Ile Asp Ala Leu Asn Lys Ala Ser Ser Glu Asn Thr Gln
        370                 375                 380
Asn Ile Glu Asp Leu Ala Ala Tyr Asn Glu Leu Gln Asp Ala Tyr Ala
385                 390                 395                 400
Lys Gln Gln Thr Glu Ala Ile Asp Ala Leu Asn Lys Ala Ser Ser Glu
                405                 410                 415
Asn Thr Gln Asn Ile Glu Asp Leu Ala Ala Tyr Asn Glu Leu Gln Asp
            420                 425                 430
Ala Tyr Ala Lys Gln Gln Thr Glu Ala Ile Asp Ala Leu Asn Lys Ala
            435                 440                 445
Ser Ser Glu Asn Thr Gln Asn Ile Ala Lys Asn Gln Ala Asp Ile Ala
        450                 455                 460
Asn Asn Ile Asn Asn Ile Tyr Glu Leu Ala Gln Gln Gln Asp Gln His
465                 470                 475                 480
Ser Ser Asp Ile Lys Thr Leu Ala Lys Ala Ser Ala Ala Asn Thr Asp
                485                 490                 495
Arg Ile Ala Lys Asn Lys Ala Asp Ala Asp Ala Ser Phe Glu Thr Leu
            500                 505                 510
Thr Lys Asn Gln Asn Thr Leu Ile Glu Lys Asp Lys Glu His Asp Lys
            515                 520                 525
Leu Ile Thr Ala Asn Lys Thr Ala Ile Asp Ala Asn Lys Ala Ser Ala
        530                 535                 540
Asp Thr Lys Phe Ala Ala Thr Ala Asp Ala Ile Thr Lys Asn Gly Asn
545                 550                 555                 560
Ala Ile Thr Lys Asn Ala Lys Ser Ile Thr Asp Leu Gly Thr Lys Val
                565                 570                 575
Asp Gly Phe Asp Gly Arg Val Thr Ala Leu Asp Thr Lys Val Asn Ala
```

```
                      580                 585                 590
Leu Asp Thr Lys Val Asn Ala Phe Asp Gly Arg Ile Thr Ala Leu Asp
                595                 600                 605

Ser Lys Val Glu Asn Gly Met Ala Ala Gln Ala Ala Leu Ser Gly Leu
            610                 615                 620

Phe Gln Pro Tyr Ser Val Gly Lys Phe Asn Ala Thr Ala Ala Leu Gly
625                 630                 635                 640

Gly Tyr Gly Ser Lys Ser Ala Val Ala Ile Gly Ala Gly Tyr Arg Val
                645                 650                 655

Asn Pro Asn Leu Ala Phe Lys Ala Gly Ala Ala Ile Asn Thr Ser Gly
            660                 665                 670

Asn Lys Lys Gly Ser Tyr Asn Ile Gly Val Asn Tyr Glu Phe
            675                 680                 685

<210> SEQ ID NO 53
<211> LENGTH: 630
<212> TYPE: PRT
<213> ORGANISM: Moraxalla catarrhalis

<400> SEQUENCE: 53

Met Lys Thr Met Lys Leu Leu Pro Leu Lys Ile Ala Val Thr Ser Ala
1               5                  10                  15

Met Ile Ile Gly Leu Gly Ala Ala Ser Thr Ala Asn Ala Gln Ala Lys
            20                  25                  30

Asn Asp Ile Thr Leu Glu Asp Leu Pro Tyr Leu Ile Lys Lys Ile Asp
        35                  40                  45

Gln Asn Glu Leu Glu Ala Asp Ile Gly Asp Ile Thr Ala Leu Glu Lys
    50                  55                  60

Tyr Leu Ala Leu Ser Gln Tyr Gly Asn Ile Leu Ala Leu Glu Glu Leu
65                  70                  75                  80

Asn Lys Ala Leu Glu Glu Leu Asp Glu Asp Val Gly Trp Asn Gln Asn
                85                  90                  95

Asp Ile Ala Asn Leu Glu Asp Val Glu Thr Leu Thr Lys Asn Gln
            100                 105                 110

Asn Ala Leu Ala Glu Gln Gly Glu Ala Ile Lys Glu Asp Leu Gln Gly
        115                 120                 125

Leu Ala Asp Phe Val Glu Gly Gln Gly Lys Ile Leu Gln Asn Glu
130                 135                 140

Thr Ser Ile Lys Lys Asn Thr Gln Arg Asn Leu Val Asn Gly Phe Glu
145                 150                 155                 160

Ile Glu Lys Asn Lys Asp Ala Ile Ala Lys Asn Asn Glu Ser Ile Glu
                165                 170                 175

Asp Leu Tyr Asp Phe Gly His Glu Val Ala Glu Ser Ile Gly Glu Ile
            180                 185                 190

His Ala His Asn Glu Ala Gln Asn Glu Thr Leu Lys Gly Leu Ile Thr
        195                 200                 205

Asn Ser Ile Glu Asn Thr Asn Asn Ile Thr Lys Asn Lys Ala Asp Ile
    210                 215                 220

Gln Ala Leu Glu Asn Asn Val Val Glu Leu Phe Asn Leu Ser Gly
225                 230                 235                 240

Arg Leu Ile Asp Gln Lys Ala Asp Ile Asp Asn Asn Ile Asn Asn Ile
                245                 250                 255

Tyr Glu Leu Ala Gln Gln Gln Asp Gln His Ser Ser Asp Ile Lys Thr
            260                 265                 270
```

Leu Lys Lys Asn Val Glu Glu Gly Leu Leu Glu Leu Ser Gly His Leu
            275                 280                 285

Ile Asp Gln Lys Thr Asp Ile Ala Gln Asn Gln Ala Asn Ile Gln Asp
290                 295                 300

Leu Ala Thr Tyr Asn Glu Leu Gln Asp Gln Tyr Ala Gln Lys Gln Thr
305                 310                 315                 320

Glu Ala Ile Asp Ala Leu Asn Lys Ala Ser Ser Glu Asn Thr Gln Asn
            325                 330                 335

Ile Glu Asp Leu Ala Ala Tyr Asn Glu Leu Gln Asp Ala Tyr Ala Lys
            340                 345                 350

Gln Gln Thr Glu Ala Ile Asp Ala Leu Asn Lys Ala Ser Ser Glu Asn
            355                 360                 365

Thr Gln Asn Ile Glu Asp Leu Ala Ala Tyr Asn Glu Leu Gln Asp Ala
370                 375                 380

Tyr Ala Lys Gln Gln Thr Glu Ala Ile Asp Ala Leu Asn Lys Ala Ser
385                 390                 395                 400

Ser Glu Asn Thr Gln Asn Ile Ala Lys Asn Gln Ala Asp Ile Ala Asn
            405                 410                 415

Asn Ile Asn Asn Ile Tyr Glu Leu Ala Gln Gln Gln Asp Gln His Ser
            420                 425                 430

Ser Asp Ile Lys Thr Leu Ala Lys Ala Ser Ala Ala Asn Thr Asp Arg
            435                 440                 445

Ile Ala Lys Asn Lys Ala Asp Ala Asp Ala Ser Phe Glu Thr Leu Thr
            450                 455                 460

Lys Asn Gln Asn Thr Leu Ile Glu Lys Asp Lys Glu His Asp Lys Leu
465                 470                 475                 480

Ile Thr Ala Asn Lys Thr Ala Ile Asp Ala Asn Lys Ala Ser Ala Asp
            485                 490                 495

Thr Lys Phe Ala Ala Thr Ala Asp Ala Ile Thr Lys Asn Gly Asn Ala
            500                 505                 510

Ile Thr Lys Asn Ala Lys Ser Ile Thr Asp Leu Gly Thr Lys Val Asp
            515                 520                 525

Gly Phe Asp Ser Arg Val Thr Ala Leu Asp Thr Lys Val Asn Ala Phe
530                 535                 540

Asp Gly Arg Ile Thr Ala Leu Asp Ser Lys Val Glu Asn Gly Met Ala
545                 550                 555                 560

Ala Gln Ala Ala Leu Ser Gly Leu Phe Gln Pro Tyr Ser Val Gly Lys
            565                 570                 575

Phe Asn Ala Thr Ala Ala Leu Gly Gly Tyr Gly Ser Lys Ser Ala Val
            580                 585                 590

Ala Ile Gly Ala Gly Tyr Arg Val Asn Pro Asn Leu Ala Phe Lys Ala
            595                 600                 605

Gly Ala Ala Ile Asn Thr Ser Gly Asn Lys Lys Gly Ser Tyr Asn Ile
            610                 615                 620

Gly Val Asn Tyr Glu Phe
625                 630

<210> SEQ ID NO 54
<211> LENGTH: 616
<212> TYPE: PRT
<213> ORGANISM: Moraxalla catarrhalis

<400> SEQUENCE: 54

Met Lys Thr Met Lys Leu Leu Pro Leu Lys Ile Ala Val Thr Ser Ala
1               5                   10                  15

```
Leu Ile Val Gly Leu Gly Ala Ala Ser Thr Ala Asn Ala Gln Ala Gln
            20                  25                  30

Asp Arg Ser Leu Glu Gln Ile Gln Asp Lys Leu Ala Asn Leu Val Glu
        35                  40                  45

Lys Ile Glu Gln Ala Lys Ser Gln Asn Gly Gln Ser Gln Lys Asp Ile
50                  55                  60

Asn Gln Tyr Leu Leu Leu Ser Gln Tyr Ala Asn Val Leu Thr Met Glu
65                  70                  75                  80

Glu Leu Asn Asn Asn Val Val Lys Asn Ser Ser Ile Glu Thr Leu
            85                  90                  95

Asp Asn Asp Ile Ala Trp Leu Asn Asp Leu Ile Asp Leu Asp Lys
            100                 105                 110

Glu Val Gly Val Leu Ser Arg Asp Ile Gly Ser Leu His Asp Asp Val
            115                 120                 125

Ala Gln Asn Gln Ala Asp Ile Lys Thr Leu Lys Asn Asn Val Val Glu
        130                 135                 140

Glu Leu Phe Asn Leu Ser Asp Arg Leu Ile Asp Gln Glu Ala Asp Ile
145                 150                 155                 160

Ala Gln Asn Asn Glu Ser Ile Glu Asp Leu Tyr Asp Phe Gly Arg Glu
                165                 170                 175

Val Ala Glu Ser Ile Gly Glu Ile His Ala His Asn Glu Ala Gln Asn
            180                 185                 190

Glu Thr Leu Lys Asp Leu Ile Thr Asn Ser Val Lys Asn Thr Asp Asn
        195                 200                 205

Ile Thr Lys Asn Lys Ala Asp Ile Gln Ala Leu Glu Asn Asp Val Gly
        210                 215                 220

Lys Glu Leu Leu Asn Leu Ser Gly Arg Leu Ile Asp Gln Lys Ala Asp
225                 230                 235                 240

Ile Asp Asn Asn Ile Asn His Ile Tyr Glu Leu Ala Gln Gln Gln Asp
                245                 250                 255

Gln His Ser Ser Asp Ile Lys Thr Leu Lys Asn Asn Val Glu Glu Gly
            260                 265                 270

Leu Leu Glu Leu Ser Gly His Leu Ile Asp Gln Lys Ala Asp Leu Thr
        275                 280                 285

Lys Asp Ile Lys Ala Leu Glu Ser Asn Val Glu Glu Gly Leu Leu Asp
        290                 295                 300

Leu Ser Gly Arg Leu Leu Asp Gln Lys Ala Asp Ile Ala Gln Asn Gln
305                 310                 315                 320

Ala Asn Ile Gln Asp Leu Ala Ala Tyr Asn Glu Leu Gln Asp Ala Tyr
                325                 330                 335

Ala Lys Gln Gln Thr Glu Ala Ile Asp Ala Leu Asn Lys Ala Ser Ser
            340                 345                 350

Glu Asn Thr Gln Asn Ile Glu Asp Leu Ala Ala Tyr Asn Glu Leu Gln
        355                 360                 365

Asp Ala Tyr Ala Lys Gln Gln Thr Glu Ala Ile Asp Ala Leu Asn Lys
        370                 375                 380

Ala Ser Ser Glu Asn Thr Gln Asn Ile Ala Lys Asn Gln Ala Asp Ile
385                 390                 395                 400

Ala Asn Asn Ile Asn Asn Ile Tyr Glu Leu Ala Gln Gln Gln Asp Gln
                405                 410                 415

His Ser Ser Asp Ile Lys Thr Leu Ala Lys Ala Ser Ala Ala Asn Thr
            420                 425                 430
```

Asp Arg Ile Ala Lys Asn Lys Ala Asp Ala Asp Ala Ser Phe Glu Thr
            435                 440                 445

Leu Thr Lys Asn Gln Asn Thr Leu Ile Glu Lys Asp Lys Glu His Asp
    450                 455                 460

Lys Leu Ile Thr Ala Asn Lys Thr Ala Ile Asp Ala Asn Lys Ala Ser
465                 470                 475                 480

Ala Asp Thr Lys Phe Ala Ala Thr Ala Asp Ala Ile Thr Lys Asn Gly
                485                 490                 495

Asn Ala Ile Thr Lys Asn Ala Lys Ser Ile Thr Asp Leu Gly Thr Lys
                500                 505                 510

Val Asp Gly Phe Asp Ser Arg Val Thr Ala Leu Asp Thr Lys Val Asn
            515                 520                 525

Ala Phe Asp Gly Arg Ile Thr Ala Leu Asp Ser Lys Val Glu Asn Gly
            530                 535                 540

Met Ala Ala Gln Ala Ala Leu Ser Gly Leu Phe Gln Pro Tyr Ser Val
545                 550                 555                 560

Gly Lys Phe Asn Ala Thr Ala Ala Leu Gly Gly Tyr Gly Ser Lys Ser
                565                 570                 575

Ala Val Ala Ile Gly Ala Gly Tyr Arg Val Asn Pro Asn Leu Ala Phe
            580                 585                 590

Lys Ala Gly Ala Ala Ile Asn Thr Ser Gly Asn Lys Lys Gly Ser Tyr
            595                 600                 605

Asn Ile Gly Val Asn Tyr Glu Phe
        610                 615

<210> SEQ ID NO 55
<211> LENGTH: 614
<212> TYPE: PRT
<213> ORGANISM: Moraxalla catarrhalis

<400> SEQUENCE: 55

Met Lys Thr Met Lys Leu Leu Pro Leu Lys Ile Ala Val Thr Ser Ala
1               5                   10                  15

Met Ile Ile Gly Leu Gly Ala Thr Ser Thr Val Asn Ala Gln Val Val
            20                  25                  30

Glu Gln Phe Phe Pro Asn Ile Phe Asn Glu Asn His Asp Glu Leu
        35                  40                  45

Asp Asp Ala Tyr His Asn Met Ile Leu Gly Asp Thr Ala Ile Val Ser
    50                  55                  60

Asn Ser Gln Asp Asn Ser Thr Gln Leu Lys Phe Tyr Ser Asn Asp Glu
65                  70                  75                  80

Asp Ser Val Pro Asp Ser Leu Leu Phe Ser Lys Leu Leu His Glu Gln
                85                  90                  95

Gln Leu Asn Gly Phe Lys Ala Gly Asp Thr Ile Ile Pro Leu Asp Lys
            100                 105                 110

Asp Gly Lys Pro Val Tyr Thr Lys Asp Thr Arg Thr Lys Asp Gly Lys
            115                 120                 125

Val Glu Thr Val Tyr Ser Val Thr Lys Ile Ala Thr Gln Asp Asp
    130                 135                 140

Val Glu Gln Ser Ala Tyr Ser Arg Gly Ile Gln Gly Asp Ile Asp Asp
145                 150                 155                 160

Leu Tyr Asp Ile Asn Arg Glu Val Asn Glu Tyr Leu Lys Ala Thr His
                165                 170                 175

Asp Tyr Asn Glu Arg Gln Thr Glu Ala Ile Asp Ala Leu Asn Lys Ala
            180                 185                 190

```
Ser Ser Ala Asn Thr Asp Arg Ile Asp Thr Ala Glu Glu Arg Ile Asp
        195                 200                 205

Lys Asn Glu Tyr Asp Ile Lys Ala Leu Glu Ser Asn Val Gly Lys Asp
        210                 215                 220

Leu Leu Asp Leu Ser Gly Arg Leu Ile Ala Gln Lys Glu Asp Ile Asp
225                 230                 235                 240

Asn Asn Ile Asn His Ile Tyr Glu Leu Ala Gln Gln Gln Asp Gln His
                245                 250                 255

Ser Ser Asp Ile Lys Thr Leu Lys Asn Asn Val Glu Glu Gly Leu Leu
            260                 265                 270

Glu Leu Ser Gly His Leu Ile Asp Gln Lys Ala Asp Leu Thr Lys Asp
        275                 280                 285

Ile Lys Thr Leu Glu Ser Asn Val Glu Glu Gly Leu Leu Asp Leu Ser
        290                 295                 300

Gly Arg Leu Ile Asp Gln Lys Ala Asp Ile Ala Gln Asn Gln Ala Asn
305                 310                 315                 320

Ile Gln Asp Leu Ala Ala Tyr Asn Glu Leu Gln Asp Gln Tyr Ala Gln
                325                 330                 335

Lys Gln Thr Glu Ala Ile Asp Ala Leu Asn Lys Ala Ser Ser Glu Asn
            340                 345                 350

Thr Gln Asn Ile Glu Asp Leu Ala Ala Tyr Asn Glu Leu Gln Asp Ala
        355                 360                 365

Tyr Ala Lys Gln Gln Thr Glu Ala Ile Asp Ala Leu Asn Lys Ala Ser
        370                 375                 380

Ser Glu Asn Thr Gln Asn Ile Ala Lys Asn Gln Ala Asp Ile Ala Asn
385                 390                 395                 400

Asn Ile Asn Asn Ile Tyr Glu Leu Ala Gln Gln Gln Asp Gln His Ser
                405                 410                 415

Ser Asp Ile Lys Thr Leu Ala Lys Val Ser Ala Ala Asn Thr Asp Arg
            420                 425                 430

Ile Ala Lys Asn Lys Ala Asp Ala Asp Ala Ser Phe Glu Thr Leu Thr
        435                 440                 445

Lys Asn Gln Asn Thr Leu Ile Glu Lys Asp Lys Glu His Asp Lys Leu
        450                 455                 460

Ile Thr Ala Asn Lys Thr Ala Ile Asp Ala Asn Lys Ala Ser Ala Asp
465                 470                 475                 480

Thr Lys Phe Ala Ala Thr Ala Asp Ala Ile Thr Lys Asn Gly Asn Ala
                485                 490                 495

Ile Thr Lys Asn Ala Lys Ser Ile Thr Asp Leu Gly Thr Lys Val Asp
            500                 505                 510

Gly Phe Asp Gly Arg Val Thr Ala Leu Asp Thr Lys Val Asn Ala Phe
        515                 520                 525

Asp Gly Arg Ile Thr Ala Leu Asp Ser Lys Val Glu Asn Gly Met Ala
        530                 535                 540

Ala Gln Ala Ala Leu Ser Gly Leu Phe Gln Pro Tyr Ser Val Gly Lys
545                 550                 555                 560

Phe Asn Ala Thr Ala Ala Leu Gly Gly Tyr Gly Ser Lys Ser Ala Val
                565                 570                 575

Ala Ile Gly Ala Gly Tyr Arg Val Asn Pro Asn Leu Ala Phe Lys Ala
            580                 585                 590

Gly Ala Ala Ile Asn Thr Ser Gly Asn Lys Lys Gly Ser Tyr Asn Ile
        595                 600                 605
```

Gly Val Asn Tyr Glu Phe
        610

<210> SEQ ID NO 56
<211> LENGTH: 679
<212> TYPE: PRT
<213> ORGANISM: Moraxalla catarrhalis

<400> SEQUENCE: 56

Met Lys Thr Met Lys Leu Pro Pro Leu Lys Ile Ala Val Thr Ser Ala
1               5                   10                  15

Met Ile Ile Gly Leu Gly Ala Ala Ser Thr Ala Asn Ala Gln Thr Thr
            20                  25                  30

Glu Thr Phe Leu Pro Asn Leu Phe Asp Asn Asp Tyr Thr Glu Thr Thr
        35                  40                  45

Asp Pro Leu Tyr His Gly Met Ile Leu Gly Asp Thr Ala Ile Thr Gln
    50                  55                  60

Asp Thr Gln Tyr Lys Phe Tyr Ala Glu Asn Gly Asn Glu Val Pro Asp
65                  70                  75                  80

Ser Leu Phe Phe Asn Lys Ile Leu His Asp Gln Leu Leu Asn Gly Phe
                85                  90                  95

Lys Ala Gly Asp Thr Ile Ile Pro Leu Asp Glu Asn Gly Lys Pro Val
            100                 105                 110

Tyr Lys Leu Asp Glu Arg Thr Glu Asn Gly Val Lys Arg Lys Val Tyr
        115                 120                 125

Ser Val Thr Thr Lys Thr Ala Thr Gln Ala Asp Val Glu Gln Ser Ala
    130                 135                 140

Tyr Ser Arg Gly Ile Gln Gly Asp Ile Asp Asp Leu Tyr Glu Ala Asn
145                 150                 155                 160

Lys Glu Asn Val Asn Arg Leu Ile Glu His Gly Asp Lys Ile Phe Ala
                165                 170                 175

Asn Glu Glu Ser Val Gln Tyr Leu Asn Arg Glu Val Gln Asn Asn Ile
            180                 185                 190

Glu Asn Ile His Glu Leu Ala Gln Gln Asp Gln His Ser Ser Asp
        195                 200                 205

Ile Lys Thr Leu Lys Lys Asn Val Glu Lys Asp Leu Leu Asp Leu Ser
    210                 215                 220

Gly Arg Leu Ile Ala Gln Lys Glu Asp Ile Ala Gln Asn Gln Thr Asp
225                 230                 235                 240

Ile Gln Asp Leu Ala Thr Tyr Asn Glu Leu Gln Asp Gln Tyr Ala Gln
                245                 250                 255

Lys Gln Thr Glu Ala Ile Asp Ala Leu Asn Lys Ala Ser Ser Glu Asn
            260                 265                 270

Thr Gln Asn Ile Ala Lys Asn Ser Asn His Ile Lys Thr Leu Glu Asn
        275                 280                 285

Asn Ile Glu Glu Cys Leu Leu Glu Leu Ser Gly His Leu Ile Asp Gln
    290                 295                 300

Lys Ala Asp Leu Thr Lys Asp Ile Lys Ala Leu Glu Ser Asn Val Glu
305                 310                 315                 320

Glu Gly Leu Leu Asp Leu Ser Gly Arg Leu Ile Asp Gln Lys Ala Asp
                325                 330                 335

Ile Ala Gln Asn Gln Ala Asn Ile Gln Asp Leu Ala Ala Tyr Asn Glu
            340                 345                 350

Leu Gln Asp Ala Tyr Ala Lys Gln Gln Thr Glu Ala Ile Asp Ala Leu
        355                 360                 365

Asn Lys Ala Ser Ser Glu Asn Thr Gln Asn Ile Glu Asp Leu Ala Ala
    370                 375                 380

Tyr Asn Glu Leu Gln Asp Ala Tyr Ala Lys Gln Gln Thr Glu Ala Ile
385                 390                 395                 400

Asp Ala Leu Asn Lys Ala Ser Ser Glu Asn Thr Gln Asn Ile Glu Asp
            405                 410                 415

Leu Ala Ala Tyr Asn Glu Leu Gln Asp Ala Tyr Ala Lys Gln Gln Thr
        420                 425                 430

Glu Ala Ile Asp Ala Leu Asn Lys Ala Ser Ser Glu Asn Thr Gln Asn
    435                 440                 445

Ile Ala Lys Asn Gln Ala Asp Ile Ala Asn Asn Ile Asn Asn Ile Tyr
450                 455                 460

Glu Leu Ala Gln Gln Asp Gln His Ser Ser Asp Ile Lys Thr Leu
465                 470                 475                 480

Ala Lys Ala Ser Ala Ala Asn Thr Asp Arg Ile Ala Lys Asn Lys Ala
            485                 490                 495

Asp Ala Asp Ala Ser Phe Glu Thr Leu Thr Lys Asn Gln Asn Thr Leu
        500                 505                 510

Ile Glu Lys Asp Lys Glu His Asp Lys Leu Ile Thr Ala Asn Lys Thr
    515                 520                 525

Ala Ile Asp Ala Asn Lys Ala Ser Ala Asp Thr Lys Phe Ala Ala Thr
530                 535                 540

Ala Asp Ala Ile Thr Lys Asn Gly Asn Ala Ile Thr Lys Asn Ala Lys
545                 550                 555                 560

Ser Ile Thr Asp Leu Gly Thr Lys Val Asp Gly Phe Asp Gly Arg Val
            565                 570                 575

Thr Ala Leu Asp Thr Lys Val Asn Ala Leu Asp Thr Lys Val Asn Ala
        580                 585                 590

Phe Asp Gly Arg Ile Thr Ala Leu Asp Ser Lys Val Glu Asn Gly Met
    595                 600                 605

Ala Ala Gln Ala Ala Leu Ser Gly Leu Phe Gln Pro Tyr Ser Val Gly
610                 615                 620

Lys Phe Asn Ala Thr Ala Ala Leu Gly Gly Tyr Gly Ser Lys Ser Ala
625                 630                 635                 640

Val Ala Ile Gly Ala Gly Tyr Arg Val Asn Pro Asn Leu Ala Phe Lys
            645                 650                 655

Ala Gly Ala Ala Ile Asn Thr Ser Gly Asn Lys Lys Gly Ser Tyr Asn
        660                 665                 670

Ile Gly Val Asn Tyr Glu Phe
        675

<210> SEQ ID NO 57
<211> LENGTH: 724
<212> TYPE: PRT
<213> ORGANISM: Moraxalla catarrhalis

<400> SEQUENCE: 57

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Glu Thr
            20                  25                  30

Leu Glu Glu Val Leu Glu Ser Ile Lys Gln Ile Asn Glu Gln Asp Leu
        35                  40                  45

Gln Asp Asp Ile Gly Tyr Asn Ser Ala Leu Asp Arg Tyr Leu Val Leu

```
            50                  55                  60
Ser Gln Tyr Gly Asn Leu Leu Ile Ala Lys Glu Leu Asn Glu Asn Val
 65                  70                  75                  80

Glu Lys Asn Ser Asn Ser Ile Ala Lys Asn Ser Asn Ser Ile Ala Asp
                 85                  90                  95

Leu Glu Ala Asp Val Gly Tyr Leu Ala Glu Asn Gln Asn Thr Leu Ile
                100                 105                 110

Glu Gln Asn Glu Thr Ile Asn Gln Gln Leu Glu Gly Ile Thr His Glu
                115                 120                 125

Leu Glu Ser Phe Ile Ala Tyr Ala His Ala Gln Asp Gln Lys Asn Leu
130                 135                 140

Val Asn Glu Phe Glu Ile Glu Lys Asn Lys Asp Ala Ile Ala Lys Asn
145                 150                 155                 160

Asn Glu Ser Ile Glu Asp Leu Tyr Asp Phe Gly His Glu Val Ala Glu
                165                 170                 175

Ser Ile Gly Glu Ile His Ala Tyr Thr Glu Glu Val Asn Lys Thr Leu
                180                 185                 190

Glu Asn Leu Ile Thr Asn Ser Val Lys Asn Thr Asp Asn Ile Thr Lys
                195                 200                 205

Asn Lys Ala Asp Ile Gln Ala Leu Glu Ser Asn Val Glu Lys Glu Leu
210                 215                 220

Leu Asn Leu Ser Gly Arg Leu Ile Asp Gln Lys Ala Asp Ile Asp Asn
225                 230                 235                 240

Asn Ile Asn His Ile Tyr Glu Leu Ala Gln Gln Gln Asp Gln His Ser
                245                 250                 255

Ser Asp Ile Lys Thr Leu Lys Lys Asn Val Glu Glu Gly Leu Leu Glu
                260                 265                 270

Leu Ser Gly His Leu Ile Asp Gln Lys Ser Asp Ile Ala Gln Asn Gln
                275                 280                 285

Thr Asp Ile Gln Asp Leu Ala Thr Tyr Asn Glu Leu Gln Asp Gln Tyr
                290                 295                 300

Ala Gln Lys Gln Thr Glu Ala Ile Asp Ala Leu Asn Lys Ala Ser Ser
305                 310                 315                 320

Glu Asn Thr Gln Asn Ile Glu Asp Leu Ala Ala Tyr Asn Glu Leu Gln
                325                 330                 335

Asp Ala Tyr Ala Lys Gln Gln Thr Glu Ala Ile Asp Ala Leu Asn Lys
                340                 345                 350

Ala Ser Ser Glu Asn Thr Gln Asn Ile Glu Asp Leu Ala Ala Tyr Asn
                355                 360                 365

Glu Leu Gln Asp Ala Tyr Ala Lys Gln Gln Thr Glu Ala Ile Asp Ala
                370                 375                 380

Leu Asn Lys Ala Ser Ser Glu Asn Thr Gln Asn Ile Glu Asp Leu Ala
385                 390                 395                 400

Ala Tyr Asn Glu Leu Gln Asp Ala Tyr Ala Lys Gln Gln Thr Glu Ala
                405                 410                 415

Ile Asp Ala Leu Asn Lys Ala Ser Ser Glu Asn Thr Gln Asn Ile Glu
                420                 425                 430

Asp Leu Ala Ala Tyr Asn Glu Leu Gln Asp Ala Tyr Ala Lys Gln Gln
                435                 440                 445

Thr Glu Ala Ile Asp Ala Leu Asn Lys Ala Ser Ser Glu Asn Thr Gln
                450                 455                 460

Asn Ile Glu Asp Leu Ala Ala Tyr Asn Glu Leu Gln Asp Ala Tyr Ala
465                 470                 475                 480
```

Lys Gln Gln Thr Glu Ala Ile Asp Ala Leu Asn Lys Ala Ser Ser Glu
            485                 490                 495

Asn Thr Gln Asn Ile Ala Lys Asn Gln Ala Asp Ile Ala Asn Asn Ile
            500                 505                 510

Asn Asn Ile Tyr Glu Leu Ala Gln Gln Asp Gln His Ser Ser Asp
            515                 520                 525

Ile Lys Thr Leu Ala Lys Ala Ser Ala Ala Asn Thr Asp Arg Ile Ala
530                 535                 540

Lys Asn Lys Ala Asp Ala Asp Ala Ser Phe Glu Thr Leu Thr Lys Asn
545                 550                 555                 560

Gln Asn Thr Leu Ile Glu Lys Asp Lys Glu His Asp Lys Leu Ile Thr
            565                 570                 575

Ala Asn Lys Thr Ala Ile Asp Ala Asn Lys Ala Ser Ala Asp Thr Lys
            580                 585                 590

Phe Ala Ala Thr Ala Asp Ala Ile Thr Lys Asn Gly Asn Ala Ile Thr
            595                 600                 605

Lys Asn Ala Lys Ser Ile Thr Asp Leu Gly Thr Lys Val Asp Gly Phe
            610                 615                 620

Asp Ser Arg Val Thr Ala Leu Asp Thr Lys Val Asn Ala Phe Asp Gly
625                 630                 635                 640

Arg Ile Thr Ala Leu Asp Ser Lys Val Glu Asn Gly Met Ala Ala Gln
            645                 650                 655

Ala Ala Leu Ser Gly Leu Phe Gln Pro Tyr Ser Val Gly Lys Phe Asn
            660                 665                 670

Ala Thr Ala Ala Leu Gly Gly Tyr Gly Ser Lys Ser Ala Val Ala Ile
            675                 680                 685

Gly Ala Gly Tyr Arg Val Asn Pro Asn Leu Ala Phe Lys Ala Gly Ala
            690                 695                 700

Ala Ile Asn Thr Ser Gly Asn Lys Lys Gly Ser Tyr Asn Ile Gly Val
705                 710                 715                 720

Asn Tyr Glu Phe

<210> SEQ ID NO 58
<211> LENGTH: 611
<212> TYPE: PRT
<213> ORGANISM: Moraxalla catarrhalis

<400> SEQUENCE: 58

Met Lys Thr Met Lys Leu Leu Pro Leu Lys Ile Ala Val Thr Ser Ala
1               5                   10                  15

Leu Ile Val Gly Leu Gly Ala Ala Ser Thr Ala Asn Ala Gln Ala Gln
            20                  25                  30

Ala Arg Asp Arg Ser Leu Glu Asp Ile Gln Ala Leu Ile Gly Asn Ile
            35                  40                  45

Asp Val Asp Lys Ile Arg Ser Gln Lys Gln Lys Asn Pro Glu Ile Phe
            50                  55                  60

Gln Tyr Leu Leu Leu Asn Gln Leu Ser Asn Thr Leu Ile Thr Asp Glu
65                  70                  75                  80

Leu Asn Asn Asn Val Ile Lys Asn Thr Asn Ser Ile Glu Thr Leu Asp
            85                  90                  95

Asn Asp Ile Ala Trp Leu Asn Asp Leu Ile Asp Leu Asp Lys Glu
            100                 105                 110

Val Gly Val Leu Ser Arg Asp Ile Gly Ser Leu His Asp Asp Val Ala
            115                 120                 125

```
Gln Asn Gln Ala Asp Ile Lys Thr Leu Glu Asn Asn Val Glu Glu
    130                 135                 140

Leu Phe Asn Leu Ser Asp Arg Leu Ile Asp Gln Glu Ala Glu Ile Ala
145                 150                 155                 160

Gln Asn Asn Glu Ser Ile Glu Asp Leu Tyr Asp Phe Gly Arg Glu Val
                165                 170                 175

Ala Glu Ser Ile Gly Glu Ile His Ala His Asn Glu Ala Gln Asn Glu
            180                 185                 190

Thr Leu Lys Asp Leu Ile Thr Asn Ser Val Lys Asn Thr Asp Asn Ile
        195                 200                 205

Asp Lys Asn Lys Ala Asp Ile Gln Ala Leu Glu Asn Asn Val Glu Glu
210                 215                 220

Gly Leu Leu Glu Leu Ser Gly His Leu Ile Asp Gln Lys Ala Asp Leu
225                 230                 235                 240

Thr Lys Asp Ile Lys Ala Leu Glu Ser Asn Val Glu Glu Gly Leu Leu
                245                 250                 255

Asp Leu Ser Gly Arg Leu Leu Asp Gln Lys Ala Asp Ile Ala Lys Asn
            260                 265                 270

Gln Ala Asp Ile Ala Gln Asn Gln Thr Asp Ile Gln Asp Leu Ala Ala
        275                 280                 285

Tyr Asn Glu Leu Gln Asp Gln Tyr Ala Gln Lys Gln Thr Glu Ala Ile
    290                 295                 300

Asp Ala Leu Asn Lys Ala Ser Ser Glu Asn Thr Gln Asn Ile Glu Asp
305                 310                 315                 320

Leu Ala Ala Tyr Asn Glu Leu Gln Asp Ala Tyr Ala Lys Gln Gln Thr
                325                 330                 335

Glu Ala Ile Asp Ala Leu Asn Lys Ala Ser Ser Glu Asn Thr Gln Asn
            340                 345                 350

Ile Glu Asp Leu Ala Ala Tyr Asn Glu Leu Gln Asp Ala Tyr Ala Lys
        355                 360                 365

Gln Gln Thr Glu Ala Ile Asp Ala Leu Asn Lys Ala Ser Ser Glu Asn
    370                 375                 380

Thr Gln Asn Ile Ala Lys Asn Gln Ala Asp Ile Ala Asn Asn Ile Asn
385                 390                 395                 400

Asn Ile Tyr Glu Leu Ala Gln Gln Gln Asp Gln His Ser Ser Asp Ile
                405                 410                 415

Lys Thr Leu Ala Lys Val Ser Ala Ala Asn Thr Asp Arg Ile Ala Lys
            420                 425                 430

Asn Lys Ala Asp Ala Asp Ala Ser Phe Glu Thr Leu Thr Lys Asn Gln
        435                 440                 445

Asn Thr Leu Ile Glu Lys Asp Lys Glu His Asp Lys Leu Ile Thr Ala
    450                 455                 460

Asn Lys Thr Ala Ile Asp Ala Asn Lys Ala Ser Ala Asp Thr Lys Phe
465                 470                 475                 480

Ala Ala Thr Ala Asp Ala Ile Thr Lys Asn Gly Asn Ala Ile Thr Lys
                485                 490                 495

Asn Ala Lys Ser Ile Thr Asp Leu Gly Thr Lys Val Asp Gly Phe Asp
            500                 505                 510

Ser Arg Val Thr Ala Leu Asp Thr Lys Val Asn Ala Phe Asp Gly Arg
        515                 520                 525

Ile Thr Ala Leu Asp Ser Lys Val Glu Asn Gly Met Ala Ala Gln Ala
530                 535                 540
```

-continued

```
Ala Leu Ser Gly Leu Phe Gln Pro Tyr Ser Val Gly Lys Phe Asn Ala
545                 550                 555                 560

Thr Ala Ala Leu Gly Gly Tyr Gly Ser Lys Ser Ala Val Ala Ile Gly
            565                 570                 575

Ala Gly Tyr Arg Val Asn Pro Asn Leu Ala Phe Lys Ala Gly Ala Ala
                580                 585                 590

Ile Asn Thr Ser Gly Asn Lys Lys Gly Ser Tyr Asn Ile Gly Val Asn
        595                 600                 605

Tyr Glu Phe
    610
```

The invention claimed is:

1. A method of reducing the frequency of acute exacerbations of chronic obstructive pulmonary disease (AECOPD) associated with a bacterial infection in a subject at risk of developing an acute exacerbation of chronic obstructive pulmonary disease (AECOPD) recurrence, said method comprising administering to said subject a therapeutically effective amount of an immunogenic composition comprising an immunogenic polypeptide from *Haemophilus influenzae* capable of eliciting a humoral and/or cellular immune response in a host animal, wherein the immunogenic polypeptide from *Haemophilus influenzae* is an amino acid sequence at least 96% identical to a reference sequence selected from SEQ ID NO: 2, SEQ ID NO: 5, SEQ ID NO: 7 and SEQ ID NO: 9.

2. The method according to claim 1, wherein the method further comprises identifying that the subject has previously had an acute exacerbation of chronic obstructive pulmonary disease (AECOPD) associated with a bacterial infection before administering the immunogenic composition to the subject.

3. The method according to claim 1, wherein the acute exacerbation of chronic obstructive pulmonary disease (AECOPD) associated with a bacterial infection is defined by:
   a) a positive bacterial pathogen on culture of an induced or spontaneous sputum sample obtained from a subject; and/or
   b) a total aerobic CFU count greater than or equal to $10^7$ cells; and/or
   c) the presence of increased sputum purulence.

4. The method according to claim 1, wherein the acute exacerbation of chronic obstructive pulmonary disease (AECOPD) associated with a bacterial infection is defined by:
   a) a positive bacterial pathogen on culture of an induced or spontaneous sputum sample obtained from a subject; and/or
   b) the presence of an increased sputum purulence.

5. The method according to claim 1, wherein the bacterial infection occurred in the presence of *Haemophilus* influenza or *Moraxella catarrhalis*.

6. The method according to claim 1, wherein the subject has GOLD 2 (moderate), GOLD 3 (severe) or GOLD 4 (very severe) COPD status.

7. The method according to claim 1, wherein the subject has experienced at least one (e.g. 2 or more, 3 or more) episodes of acute exacerbation in chronic obstructive pulmonary disease (AECOPD) resulting from a bacterial infection within a period of 12 months.

8. The method according to claim 1, wherein the subject has experienced at least one (e.g. 2 or more, 3 or more) episodes of acute exacerbation in chronic obstructive pulmonary disease (AECOPD) resulting from a bacterial infection in the preceding 12 months.

9. The method according to claim 1, wherein the subject has bronchiectasis.

10. The method according to claim 1, wherein the subject has experienced an acute exacerbation of chronic obstructive pulmonary disease (AECOPD) resulting from a bacterial infection and failed to achieve resolution of symptoms after antibiotic therapy.

11. The method according to claim 1, wherein the subject is taking one or more other therapeutic agents for COPD selected from the group consisting of beta2-agonists, anticholinergics, methylxanthines, phosphodiesterase-4 (PDE-4) inhibitors and inhaled corticosteroids.

12. The method according to claim 2, wherein the subject is a human.

13. The method according to claim 1 wherein (a) the immunogenic polypeptide from *Haemophilus influenzae* is selected from (i) Protein D with at least 96% sequence identity to SEQ ID NO: 2, (ii) Protein E with at least 96% sequence identity to SEQ ID NO: 5, (iii) PilA with at least 96% sequence identity to SEQ ID NO: 7, or (iv) Protein E and PilA as a fusion protein with at least 96% sequence identity to SEQ ID NO: 9.

14. The method according to claim 5 wherein the bacterial infection occurred in the presence of *Haemophilus* influenza.

15. The method according to claim 14 wherein the wherein the bacterial infection occurred in the presence of non-typeable *Haemophilus influenzae* (NTHi)).

16. The method according to claim 1 wherein the immunogenic composition further comprises an immunogenic polypeptide from *Moraxella catarrhalis* capable of eliciting a humoral and/or cellular immune response in a host animal, wherein the immunogenic polypeptide from *Moraxella catarrhalis* is an amino acid sequence at least 96% identical to a reference sequence selected from MC-009 (SEQ ID NO. 19), MC-010 (SEQ ID NO. 20) or MC-011 (SEQ ID NO. 21).

17. The method according to claim 16 wherein the immunogenic polypeptide from *Moraxella catarrhalis* is an amino acid sequence at least 96% identical to SEQ ID NO. 19.

* * * * *